(12) United States Patent
Kim et al.

(10) Patent No.: US 11,957,714 B2
(45) Date of Patent: Apr. 16, 2024

(54) NON-NATURAL NKG2D RECEPTORS THAT DO NOT DIRECTLY SIGNAL THE CELLS TO WHICH THEY ARE ATTACHED

(71) Applicant: XYPHOS BIOSCIENCES INC., South San Francisco, CA (US)

(72) Inventors: Kaman C. Kim, San Bruno, CA (US); David W. Martin, Jr., Mill Valley, CA (US); Steven Williams, San Francisco, CA (US)

(73) Assignee: XYPHOS BIOSCIENCES INC., South San Francisco, CA (US)

( * ) Notice: Subject to any disclaimer, the term of this patent is extended or adjusted under 35 U.S.C. 154(b) by 970 days.

(21) Appl. No.: 16/674,705

(22) Filed: Nov. 5, 2019

(65) Prior Publication Data

US 2020/0138866 A1 May 7, 2020

Related U.S. Application Data

(60) Provisional application No. 62/755,776, filed on Nov. 5, 2018.

(51) Int. Cl.
*C07K 14/705* (2006.01)
*A61K 35/17* (2015.01)
*A61K 47/64* (2017.01)
*C07K 19/00* (2006.01)
*C12N 5/07* (2010.01)
*C12N 5/078* (2010.01)

(52) U.S. Cl.
CPC .......... *A61K 35/17* (2013.01); *A61K 47/6425* (2017.08); *C07K 14/705* (2013.01); *C07K 14/7056* (2013.01); *C07K 14/70596* (2013.01); *C07K 19/00* (2013.01); *C12N 5/06* (2013.01); *C12N 5/0634* (2013.01); *C07K 2319/02* (2013.01); *C07K 2319/03* (2013.01); *C07K 2319/75* (2013.01)

(58) Field of Classification Search
CPC .. A61K 35/17; A61K 38/177; A61K 47/6425; C07K 2319/00; C07K 14/705; C07K 19/00; C07K 2319/03; C07K 2319/75
See application file for complete search history.

(56) References Cited

U.S. PATENT DOCUMENTS

2017/0204372 A1 7/2017 Mohler et al.
2018/0134765 A1 5/2018 Landgraf et al.

FOREIGN PATENT DOCUMENTS

WO 2007/066109 A1 6/2007
WO WO-2017024131 A1 * 2/2017

OTHER PUBLICATIONS

Bhattacharya et al. Impact of genetic variation on three dimensional structure and function of proteins. PLoS ONE 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Culpepper et al. Synthetic mutation and thermodynamic analysis of central tyrosine pairs in polyspecific NKG2D receptor interactions. Mol Immunol 48: 516-523, 2011.*
Doerks et al. Protein annotation: detective work for function prediction. Trends in Genetics 14:248-250, 1998.*
Fenton et al. Rheostat positions: a new classification of protein positions relevant to pharmacogenomics. Medicinal Chem Res 29: 1133-1146, 2020.*
Guo et al. Protein tolerance to random amino acid change. Proc Natl Acad Sci USA 101(25): 9205-9210, 2004.*
Ngo et al. "Computational complexity, protein structure prediction, and the Levinthal paradox" in The Protein Folding Problem and Tertiary Structure Prediction, pp. 492-495, 1994.*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Strong et al. NKG2D and related immunoreceptors. Adv Protein Chem 68: 281-313, 2004.*
Tokuriki et al. Stability effects of mutations and protein evolvability. Curr Opin Structural Biol 19: 596-604, 2009.*
Wells, J.A. Additivity of mutational effects in proteins. Biochemistry 29(37): 8509-8517, 1990.*
Wensveen et al. NKG2D: a master regulator of immune cell responsiveness. Front Immunol 9: 441, Mar. 2017 (8 total pages).*
Hermanson et al. "Design and evaluation of novel natural killer cell chimeric antigen receptors," Cancer Immunology Research, vol. 4, Issue 1, Supplement; Jan. 2018.
Communication, dated Jan. 30, 2020, issued by International Searching Authority in International Application No. PCT/US 19/59846.
Abakushina et al., Inhibition of the NKG2D activating receptor expression on NK-cells by recombinant MICA protein, Medical Immunology, vol. 19, No. 1, pp. 81-88 (2017).

(Continued)

*Primary Examiner* — Bridget E Bunner
(74) *Attorney, Agent, or Firm* — MARSHALL, GERSTEIN & BORUN LLP

(57) ABSTRACT

The present disclosure relates to non-natural NKG2D receptors attached to mammalian cell surfaces wherein the non-natural receptors do not directly signal or directly activate the cell when the receptor is bound by cognate non-natural α1-α2 domains of NKG2D ligands mod

(56) References Cited

OTHER PUBLICATIONS

Bridgeman, et al., CD3-zeta based chimeric antigen receptors mediate T cell activation via cis-and trans-signalling mechanisms: implications for optimization of receptor structure for adoptive cell therapy, Clin. Exp. Immunol., vol. 175, No. 2, pp. 258-267 (2014).
Kriegsmann et al., NKT cells—New players in CAR cell immunotherapy?, Eur J. Haematol., vol. 101, i. 6, pp. 750-757 (2018).
Pakula, et al., Genetic analysis of protein stability and function, Anna. Rev. Genet., vol. 23, pp. 289-310 (1989).
Sadelain et al., The basic principles of chimeric antigen receptor design, Cancer Discov., vol. 4, No. 3, pp. 1-21 (2013).

* cited by examiner

FIG.1A

```
NKG2D.wt   FLNSLFNQEVQIPLTESYCGPCPKNWICYKNNCYQFFDESKNWYESQASCMSQNASLLKV
NKG2D.YA   FLNSLFNQEVQIPLTESYCGPCPKNWICYKNNCYQFFDESKNWYESQASCMSQNASLLKV
NKG2D.AF   FLNSLFNQEVQIPLTESYCGPCPKNWICYKNNCYQFFDESKNWYESQASCMSQNASLLKV
                                         Y152
                                          |
NKG2D.wt   YSKEDQDLLKLVKSYHWMGLVHIPTNGSWQWEDGSILSPNLLTIIEMQKGDCALYASSFK
NKG2D.YA   YSKEDQDLLKLVKSAHWMGLVHIPTNGSWQWEDGSILSPNLLTIIEMQKGDCALYASSFK
NKG2D.AF   YSKEDQDLLKLVKSAHWMGLVHIPTNGSWQWEDGSILSPNLLTIIEMQKGDCALYASSFK
            Y199
             |
NKG2D.wt   GYIENCSTPNTYICMQRTV
NKG2D.YA   GYIENCSTPNTYICMQRTV
NKG2D.AF   GFIENCSTPNTYICMQRTV
```

FIG.1B

```
ULBP2α1α2  DPHSLCYDITVIPKFRPGPRWCAVQGQVDEKTFLHYDCGNKTVTPVSPLGKKLNVTTAWK
ULBP2.R80W EPHSLSYDITVIPKFRPGPRWCAVQGQVDEKTFLHYDCGNKTVTPVSPLGKKLNVTTAWK
ULBP2.S3   EPHSLSYDITVIPKFRPGPRWCAVQGQVDEKTFLHYDCGNKTVTPVSPLGKKLNVTTAWK
ULBP2.C    EPHSLSYDITVIPKFRPGPRWCAVQGQVDEKTFLHYDCGNKTVTPVSPLGKKLNVTTAWK
ULBP2.R    EPHSLSYDITVIPKFRPGPRWCAVQGQVDEKTFLHYDCGNKTVTPVSPLGKKLNVTTAWK
ULBP2.AA   EPHSLSYDITVIPKFRPGPRWCAVQGQVDEKTFLHYDCGNKTVTPVSPLGKKLNVTTAWK
ULBP2.AB   EPHSLSYDITVIPKFRPGPRWCAVQGQVDEKTFLHYDCGNKTVTPVSPLGKKLNVTTAWK
                                 R80
                                  |
ULBP2α1α2  AQNPVLREVVDILTEQLRDIQLENYTPKEPLTLQARMSCEQKAEGHSSGSWQFSFDGQIF
ULBP2.R80W AQNPVLREVVDILTEQLWDIQLENYTPKEPLTLQARMSCEQKAEGHSSGSWQFSFDGQIF
ULBP2.S3   AQNPVLREVVDILTEQLWDIQLENYTPKEPLTLQARMSCEQKAEGHSSGSWQFSFDGQIF
ULBP2.C    AQNPVLREVVDILTEQLWDIQLENYTPKEPLTLQARMSCEQKAEGHSSGSWQFSFDGQIF
ULBP2.R    AQNPVLREVVDILTEQLWDIQLENYTPKEPLTLQARMSCEQKAEGHSSGSWQFSFDGQIF
ULBP2.AA   AQNPVLREVVDILTEQLWDIQLENYTPKEPLTLQARMSCEQKAEGHSSGSWQFSFDGQIF
ULBP2.AB   AQNPVLREVVDILTEQLWDIQLENYTPKEPLTLQARMSCEQKAEGHSSGSWQFSFDGQIF
                                          M154
                                           |
ULBP2α1α2  LLFDSEKRMWTTVHPGARKMKEKWENDKVVAMSFHYFSMGDCIGWLEDFLMGMDSTLEPS
ULBP2.R80W LLFDSEKRMWTTVHPGARKMKEKWENDKVVAMSFHYFSMGDCIGWLEDFLMGMDSTLEPS
ULBP2.S3   LLFDSEKRMWTTVHPGARKMKEKWENDKVVATKLYLWSMGDCIGWLEDFLMGMDSTLEPS
ULBP2.C    LLFDSEKRMWTTVHPGARKMKEKWENDKVVATILWQTSMGDCIGWLEDFLMGMDSTLEPS
ULBP2.R    LLFDSEKRMWTTVHPGARKMKEKWENDKVVATLLWGWSMGDCIGWLEDFLMGMDSTLEPS
ULBP2.AA   LLFDSEKRMWTTVHPGARKMKEKWENDKVVATMFWSWSMGDCIGWLEDFLMGMDSTLEPS
ULBP2.AB   LLFDSEKRMWTTVHPGARKMKEKWENDKVVATLMWQWSMGDCIGWLEDFLMGMDSTLEPS
```

| | Pos | A0101 | A0201 | A0301 | A2402 | A2601 | B0702 | B0801 | B1501 | B2705 | B3901 | B4001 | B5801 |
|---|---|---|---|---|---|---|---|---|---|---|---|---|---|
| | | | | | | MHCI HLA supertype representative | | | | | | | |
| ULBP2 wild-type | 0 | 48 | 75 | 75 | 23 | 95 | 35 | 49 | 38 | 36 | 55 | 28 | 50 |
| | 1 | 14 | 34 | 46 | 55 | 6.5 | 12 | 5.5 | 3.5 | 20 | 0.7 | 0.15 | 29 |
| | 2 | 34 | 60 | 95 | 80 | 36 | 47 | 46 | 90 | 60 | 24 | 55 | 75 |
| | 3 | 16 | 44 | 40 | 13 | 11 | 25 | 16 | 9.5 | 32 | 22 | 17 | 49 |
| | 4 | 29 | 70 | 70 | 85 | 6.5 | 40 | 70 | 75 | 29 | 22 | 48 | 65 |
| | 5 | 4 | 21 | 0.7 | 12 | 2.5 | 17 | 46 | 0.5 | 8.5 | 19 | 18 | 0.08 |
| | 6 | 1.7 | 13 | 9.5 | 0.7 | 1.9 | 6 | 6.5 | 0.6 | 24 | 14 | 9 | 0.9 |
| | 7 | 8 | 11 | 21 | 10 | 23 | 19 | 14 | 34 | 29 | 20 | 25 | 8.5 |
| | 8 | 4 | 0.6 | 4.5 | 2.5 | 4 | 4.5 | 0.8 | 0.7 | 9.5 | 2.5 | 6 | 4 |
| | 9 | 5.5 | 21 | 13 | 19 | 9 | 29 | 7 | 6 | 29 | 14 | 15 | 6.5 |
| | 10 | 34 | 55 | 42 | 19 | 22 | 46 | 70 | 55 | 55 | 20 | 20 | 47 |
| | 11 | 12 | 39 | 36 | 40 | 10 | 43 | 70 | 65 | 55 | 3 | 17 | 42 |
| | 12 | 13 | 37 | 42 | 0.4 | 28 | 24 | 39 | 24 | 16 | 1.6 | 9.5 | 26 |
| | 13 | 15 | 50 | 70 | 14 | 35 | 49 | 24 | 17 | 75 | 24 | 38 | 21 |
| | 14 | 14 | 16 | 30 | 8.5 | 4.5 | 22 | 37 | 8.5 | 21 | 6 | 21 | 0.15 |
| | 15 | 14 | 0.8 | 18 | 18 | 15 | 12 | 12 | 8 | 13 | 11 | 12 | 28 |
| ULBP2.C | 0 | 48 | 75 | 75 | 23 | 95 | 35 | 49 | 38 | 36 | 55 | 28 | 50 |
| | 1 | 26 | 50 | 70 | 85 | 26 | 36 | 28 | 24 | 39 | 6 | 1.9 | 45 |
| | 2 | 17 | 37 | 65 | 20 | 28 | 29 | 21 | 60 | 34 | 1.9 | 22 | 28 |
| | 3 | 19 | 41 | 50 | 37 | 26 | 24 | 9.5 | 31 | 43 | 10 | 11 | 45 |
| | 4 | 26 | 39 | 60 | 21 | 10 | 32 | 55 | 70 | 29 | 7 | 60 | 7.5 |
| | 5 | 27 | 20 | 8 | 50 | 11 | 17 | 80 | 19 | 16 | 25 | 18 | 5 |
| | 6 | 12 | 4 | 26 | 19 | 20 | 24 | 45 | 55 | 28 | 24 | 21 | 5.5 |
| | 7 | 19 | 34 | 70 | 28 | 41 | 27 | 70 | 55 | 49 | 34 | 36 | 12 |
| | 8 | 7 | 8.5 | 14 | 18 | 0.8 | 4.5 | 30 | 2 | 9.5 | 3 | 11 | 1 |
| | 9 | 39 | 40 | 23 | 29 | 16 | 24 | 30 | 32 | 55 | 15 | 55 | 70 |
| | 10 | 34 | 14 | 17 | 37 | 29 | 29 | 75 | 27 | 40 | 34 | 25 | 24 |
| | 11 | 24 | 75 | 75 | 16 | 33 | 70 | 60 | 44 | 47 | 70 | 27 | 43 |
| | 12 | 6.5 | 19 | 65 | 8.5 | 19 | 25 | 22 | 7 | 5.5 | 0.9 | 2.5 | 20 |
| | 13 | 9.5 | 70 | 65 | 70 | 27 | 42 | 33 | 18 | 70 | 24 | 44 | 11 |
| | 14 | 22 | 35 | 32 | 8.5 | 7 | 21 | 55 | 14 | 31 | 8.5 | 29 | 0.3 |
| | 15 | 14 | 0.8 | 18 | 18 | 15 | 12 | 12 | 8 | 13 | 11 | 12 | 28 |
| ULBP2.R | 0 | 48 | 75 | 75 | 23 | 95 | 35 | 49 | 38 | 36 | 55 | 28 | 50 |
| | 1 | 26 | 50 | 70 | 85 | 26 | 36 | 28 | 24 | 39 | 6 | 1.9 | 45 |
| | 2 | 14 | 35 | 60 | 28 | 20 | 21 | 12 | 55 | 35 | 0.6 | 14 | 34 |
| | 3 | 15 | 36 | 42 | 29 | 20 | 27 | 13 | 34 | 34 | 15 | 15 | 42 |
| | 4 | 24 | 40 | 60 | 14 | 9 | 30 | 49 | 70 | 27 | 8.5 | 55 | 4 |
| | 5 | 31 | 16 | 12 | 40 | 20 | 23 | 75 | 19 | 20 | 34 | 25 | 5 |
| | 6 | 8 | 17 | 17 | 3 | 8.5 | 23 | 48 | 24 | 20 | 15 | 20 | 0.05 | to FIG. 8B

FIG. 8A from FIG. 8A

| | | | | | | | | | | | | |
|---|---|---|---|---|---|---|---|---|---|---|---|---|
| ULBP2.R | 7 | 24 | 37 | 55 | 60 | 20 | 27 | 70 | 65 | 47 | 60 | 34 | 20 |
| | 8 | 8 | 4.5 | 18 | 6.5 | 4 | 5.5 | 19 | 6.5 | 5.5 | 1.2 | 6 | 1.7 |
| | 9 | 19 | 13 | 15 | 16 | 19 | 27 | 37 | 30 | 42 | 14 | 38 | 60 |
| | 10 | 28 | 8.5 | 16 | 31 | 21 | 29 | 70 | 27 | 24 | 17 | 35 | 27 |
| | 11 | 32 | 65 | 65 | 14 | 36 | 65 | 65 | 60 | 55 | 65 | 25 | 46 |
| | 12 | 8 | 26 | 70 | 16 | 46 | 19 | 23 | 21 | 14 | 10 | 17 | 14 |
| | 13 | 47 | 75 | 85 | 28 | 65 | 60 | 55 | 22 | 60 | 55 | 43 | 26 |
| | 14 | 10 | 27 | 38 | 9.5 | 6.5 | 20 | 35 | 8.5 | 20 | 8 | 19 | 0.175 |
| | 15 | 14 | 0.8 | 18 | 18 | 15 | 12 | 12 | 8 | 13 | 11 | 12 | 28 |
| ULBP2.AA | 0 | 48 | 75 | 75 | 23 | 95 | 35 | 49 | 38 | 36 | 55 | 28 | 50 |
| | 1 | 26 | 50 | 70 | 85 | 26 | 36 | 28 | 24 | 39 | 6 | 1.9 | 45 |
| | 2 | 15 | 41 | 65 | 38 | 8 | 18 | 15 | 44 | 34 | 1.6 | 20 | 27 |
| | 3 | 16 | 44 | 45 | 14 | 12 | 29 | 25 | 17 | 32 | 33 | 20 | 50 |
| | 4 | 24 | 42 | 60 | 19 | 7 | 32 | 49 | 65 | 35 | 9 | 55 | 6 |
| | 5 | 25 | 9.5 | 10 | 42 | 11 | 21 | 85 | 34 | 18 | 32 | 26 | 5 |
| | 6 | 6.5 | 18 | 14 | 0.4 | 9 | 13 | 12 | 6.5 | 21 | 8.5 | 17 | 0.04 |
| | 7 | 12 | 29 | 43 | 43 | 25 | 31 | 43 | 55 | 42 | 50 | 32 | 20 |
| | 8 | 3 | 0.5 | 7.5 | 1.5 | 0.5 | 3 | 5.5 | 0.9 | 5 | 0.4 | 5 | 0.5 |
| | 9 | 11 | 12 | 7.5 | 8.5 | 17 | 26 | 28 | 9.5 | 26 | 6 | 21 | 33 |
| | 10 | 23 | 30 | 29 | 9 | 21 | 38 | 85 | 55 | 35 | 13 | 23 | 20 |
| | 11 | 22 | 42 | 55 | 13 | 18 | 65 | 70 | 47 | 42 | 27 | 14 | 24 |
| | 12 | 3 | 15 | 60 | 11 | 19 | 16 | 24 | 10 | 10 | 5.5 | 9.5 | 3 |
| | 13 | 40 | 75 | 85 | 16 | 65 | 45 | 45 | 18 | 65 | 37 | 48 | 29 |
| | 14 | 10 | 27 | 38 | 9.5 | 6.5 | 20 | 35 | 8.5 | 20 | 8 | 19 | 0.175 |
| | 15 | 14 | 0.8 | 18 | 18 | 15 | 12 | 12 | 8 | 13 | 11 | 12 | 28 |
| ULBP2.AB | 0 | 48 | 75 | 75 | 23 | 95 | 35 | 49 | 38 | 36 | 55 | 28 | 50 |
| | 1 | 26 | 50 | 70 | 85 | 26 | 36 | 28 | 24 | 39 | 6 | 1.9 | 45 |
| | 2 | 14 | 35 | 60 | 28 | 20 | 21 | 12 | 55 | 35 | 0.6 | 14 | 34 |
| | 3 | 18 | 40 | 45 | 40 | 12 | 22 | 17 | 26 | 34 | 24 | 22 | 35 |
| | 4 | 30 | 41 | 70 | 19 | 11 | 31 | 55 | 70 | 28 | 8.5 | 55 | 7.5 |
| | 5 | 28 | 21 | 7 | 60 | 9.5 | 14 | 80 | 23 | 19 | 24 | 16 | 5.5 |
| | 6 | 8 | 20 | 18 | 1.4 | 8 | 21 | 48 | 23 | 26 | 13 | 23 | 0.01 |
| | 7 | 19 | 36 | 65 | 36 | 31 | 29 | 60 | 55 | 43 | 47 | 35 | 17 |
| | 8 | 5 | 1.8 | 16 | 6 | 3.5 | 8.5 | 9.5 | 7.5 | 6 | 2 | 12 | 0.6 |
| | 9 | 14 | 13 | 13 | 9.5 | 12 | 20 | 13 | 18 | 32 | 11 | 35 | 55 |
| | 10 | 23 | 11 | 17 | 20 | 28 | 31 | 55 | 15 | 14 | 12 | 27 | 14 |
| | 11 | 34 | 50 | 55 | 11 | 19 | 60 | 70 | 46 | 40 | 30 | 16 | 45 |
| | 12 | 7.5 | 5 | 55 | 6.5 | 20 | 19 | 20 | 3 | 1.8 | 0.8 | 2.5 | 22 |
| | 13 | 35 | 80 | 85 | 21 | 60 | 55 | 45 | 20 | 60 | 38 | 48 | 29 |
| | 14 | 10 | 27 | 38 | 9.5 | 6.5 | 20 | 35 | 8.5 | 20 | 8 | 19 | 0.175 |
| | 15 | 14 | 0.8 | 18 | 18 | 15 | 12 | 12 | 8 | 13 | 11 | 12 | 28 |

FIG. 8B

| | MHCII alleles | | | | | | | | | | | | | | | | | | | |
|---|---|---|---|---|---|---|---|---|---|---|---|---|---|---|---|---|---|---|---|---|
| | HLA-DP | | | | | | | | | HLA-DQ | | | | | | | | | | |
| pos | DPA10103_DPB10301 | DPA10103_DPB10401 | DPA10103_DPB10402 | DPA10103_DPB10601 | DPA10201_DPB10101 | DPA10201_DPB10501 | DPA10201_DPB11401 | DPA10301_DPB10402 | DPA10103_DPB10201 | DQA10101_DQB10501 | DQA10102_DQB10501 | DQA10102_DQB10502 | DQA10102_DQB10602 | DQA10103_DQB10603 | DQA10104_DQB10603 | DQA10201_DQB10202 | DQA10103_DQB10301 | DQA10201_DQB10303 | DQA10201_DQB10402 | DQA10301_DQB10301 |

ULBP2_wt

| pos | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 | | | | | | | | | | | | | | | | | | | | |
| 2 | | | | | | | | | | | | | | | | | | | | |
| 3 | | | | | | | | | | | | | | | | | | | | |
| 4 | | | | | | | | | | | | | | | | | | | | |
| 5 | | | | | | | | | | | | | | | | | | | | |
| 6 | | | | | | | | | | | | | | | | | | | | |
| 7 | | | | | | | | | | | | | | | | | | | | |
| 8 | | | | | | | | | | | | | | | | | | | | |
| 9 | WB | | | | WB | | | | | | | | | | | | | | | WB |
| 10 | WB | | WB | | WB | | | | | | | | | | WB | | | | WB | WB |
| 11 | WB | | WB | | WB | | | | | | | | | | SB | | | | WB | WB |
| 12 | WB | | WB | | WB | | | | | | | WB | | | SB | | | | WB | WB |
| 13 | WB | | | | WB | WB | | WB | | | | | | | SB | | | | WB | WB |
| 14 | WB | WB | | | WB | WB | | | | | | | | | SB | | | | WB | WB |
| 15 | | WB | | | WB | WB | | | | | | | | | SB | | | | WB | |
| 16 | | WB | | | WB | | | | | | | | | | | | | | | |
| 17 | | WB | | | WB | | | | | | | | | | | | | | | |
| 18 | | WB | | | | | | | | | | | | | | | | | | |
| 19 | | | | | WB | | | | | | | | | | | | | | | |
| 20 | | WB | | | | | | | | SB | | WB | | | WB | | | | | |
| 21 | | SB | | | | | | | | SB | | WB | | | WB | | | | | |
| 22 | | SB | | | | | | | | WB | SB | WB | | | SB | | | | | |

ULBP2_C

| pos | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 | | | | | | | | | | | | | | | | | | | | |
| 2 | | | | | | | | | | | | | | | | | | | | |
| 3 | | | | | | | | | | | | | | | | | | | | |
| 4 | | | | | | | | | | | | | | | | | | | | |
| 5 | | | | | | | | | | | | | | | | | | | | |
| 6 | | | | | | | | | | | | | | | | | | | | |
| 7 | | | | | | | | | | | | | | | | | | | | |
| 8 | | | | | | | | | | | WB | | | | | | | | | |
| 9 | WB | | | | WB | | | | | | WB | | | | | | | | | |
| 10 | WB | | | | WB | | | | | | WB | WB | | | | | WB | | | |
| 11 | WB | | | | WB | | | | | | WB | WB | | | | | WB | | | | to FIG. 9D
to FIG. 9B

FIG. 9A

| MHCII alleles | | | | | | | | | | | | | | | | | | | | | |
|---|---|---|---|---|---|---|---|---|---|---|---|---|---|---|---|---|---|---|---|---|---|
| HLA-DQ | | | | | | | | | | HLA-DR | | | | | | | | | | | |
| DQA10301_DQB10302 | DQA10303_DQB10402 | DQA10401_DQB10402 | DQA10501_DQB10201 | DQA10501_DQB10301 | DQA10501_DQB10302 | DQA10501_DQB10303 | DQA10501_DQB10402 | DQA10601_DQB10402 | DRB1_0101 | DRB1_0103 | DRB1_0301 | DRB1_0401 | DRB1_0402 | DRB1_0403 | DRB1_0404 | DRB1_0405 | DRB1_0701 | DRB1_0801 | DRB1_0802 | DRB1_0901 | |
| | | | | | | | | | | | | | | | | | | | | | |
| | | | | | | | | | | | | | | | | | | | | | |
| WB | | | | | | | | | | | | | | | | | | | | | |
| WB | | | | | | | | | | | | | | | | | | | | | |
| WH | | | | | | | | | | | | | | | | | | | | | |
| | | | | | | | | | | | | | | | | | | | | | |
| | | | | | | | | | | | | | | WB | | | | | | | |
| | | | | | | | WB | | | | | | | WB | | | | | | | |
| | | | WB | | | | WB | | | | | | | WB | | | | | | | |
| | | | WB | | WB | WB | | | | | | | | WB | | | | | | | |
| | | | WB | | WB | SB | | | | | | | | SB | | | | | | WB | |
| | | | WB | | WB | SB | | | | | | | | SB | | | | | | WB | |
| | | | WB | | WB | WB | | | | | | | | SB | | | | | | WB | |
| | | | WB | | WB | WB | | | | | | | | WB | | | | | | WB | |
| | | | WB | | | | | | | | | | | WB | | | | | | WB | |
| | | | | | | | | | | | | | | WB | | | | | | WB | |
| | | WB | | | | | | | | | | | | | | | | | | | |
| | | WB | | | | | | | | | | | | | | | | | | | |
| | | WB | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | WB | | | | | | | | | | | | | | |
| | | | | | | | WB | | | | | | WB | | | | | | | | |

FIG. 9B

| MHCII alleles | | | | | | | | | | | | |
|---|---|---|---|---|---|---|---|---|---|---|---|---|
| HLA-DR | | | | | | | | | | | | |
| DRB1_1001 | DRB1_1101 | DRB1_1201 | DRB1_1301 | DRB1_1302 | DRB1_1501 | DRB1_1602 | DRB3_0101 | DRB3_0202 | DRB3_0301 | DRB4_0101 | DRB4_0103 | DRB5_0101 |
|  |  |  |  |  |  |  | WB |  |  |  |  |  |
|  |  |  |  |  |  |  | WB |  |  |  |  |  |
|  |  |  |  |  |  |  | SB |  |  |  |  |  |
|  |  |  |  |  |  |  | WB |  |  |  |  |  |
|  |  | WB |  |  |  |  | WB |  |  |  |  |  |
|  |  | SB |  |  |  |  | WB |  |  |  |  |  |
|  |  | WB |  |  |  |  |  |  |  | WB |  |  |
|  |  | WB |  |  |  |  |  |  |  | WB |  |  |
|  |  | WB |  |  |  |  |  |  |  | WB |  |  |
|  |  | WB |  |  |  |  |  |  |  | WB |  |  |
|  |  | WB |  |  |  |  |  |  |  |  |  |  |
|  |  |  |  |  |  |  | WB |  |  |  |  |  |
|  |  |  |  |  |  |  | WB |  |  |  |  |  |
|  |  |  |  |  |  |  | WB |  |  |  |  |  |
|  |  |  |  |  |  |  | WB |  |  |  |  |  | from FIG. 9B to FIG. 9F

FIG. 9C from FIG. 9A

| | | | | | | | | | | | | | | | | |
|---|---|---|---|---|---|---|---|---|---|---|---|---|---|---|---|---|
| ULBP2_C | 12 | WB | | | | | | | WB | | | WB | | | | |
| | 13 | | | | | | | | WB | | WB | WB | | | | |
| | 14 | | | | | | | | WB | | WB | WB | | | | |
| | 15 | | | | | | | | WB | | | WB | | | | |
| | 16 | WB | | | | | | | | | | | | | | |
| | 17 | | | | | | | | | | | | | | | |
| | 18 | | | | | | | | | | | | | | | |
| | 19 | | | | | | | | | | | | | | | |
| | 20 | WB | | | | | | SB | WB | | WB | | | | | |
| | 21 | WB | | | | | | SB | WB | | WB | | | | | |
| | 22 | SB | | | | | WB | SB | WB | | SB | | | | | |
| ULBP2_R | 1 | | | | | | | | | | | | | | | |
| | 2 | | | | | | | | | | | | | | | |
| | 3 | | | | | | | | | | | | | | | |
| | 4 | | | | | | | | | | | | | | | |
| | 5 | | | | | | | | | | | | | | | |
| | 6 | | | | | | | | | | | | | | | |
| | 7 | | | | | | | | | | | | | | | |
| | 8 | | | | | | | | | | | | | | | |
| | 9 | | | | | | | | | | | | | | | |
| | 10 | | | | | | | | | | | | | | | |
| | 11 | | | | | | | | | | | | | | | |
| | 12 | | | | | | | | | | | | | | | WB |
| | 13 | | | | | | | | WB | | | | | | | WB |
| | 14 | WB | | | | | | | WB | | | | | | | WB |
| | 15 | WB | | | | | | | WB | | | | | | | WB |
| | 16 | WB | | | | | | | WB | | | | | | | |
| | 17 | WB | | | | | | | WB | | | | | | | |
| | 18 | WB | | | | | | | WB | | | | | | | |
| | 19 | | | | | | | | WB | | | | | | | |
| | 20 | WB | | | | | | SB | WB | | WB | | | | | |
| | 21 | WB | | | | | WB | SB | WB | | WB | | | | | |
| | 22 | SB | | | | | WB | SB | WB | | SB | | | | | |
| ULBP2_AA | 1 | | | | | | | | | | | | | | | |
| | 2 | | | | | | | | | | | | | | | |
| | 3 | | | | | | | | | | | | | | | |
| | 4 | | | | | | | | | | | | | | | |
| | 5 | | | | | | | | | | | | | | | |
| | 6 | | | | | | | | | | | | | | | | to FIG. 9E to FIG. 9G

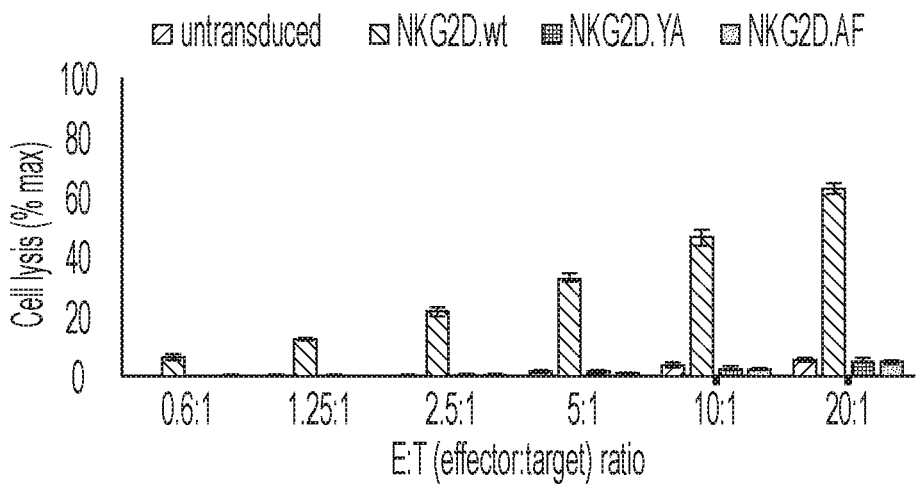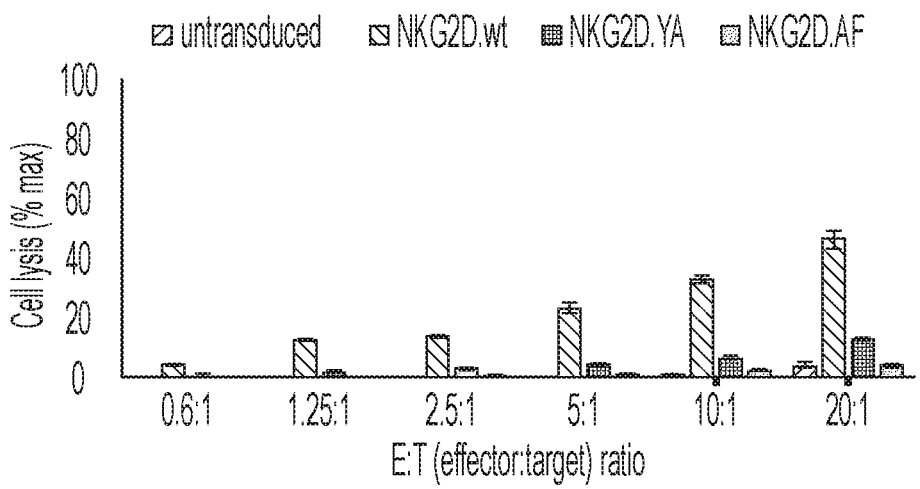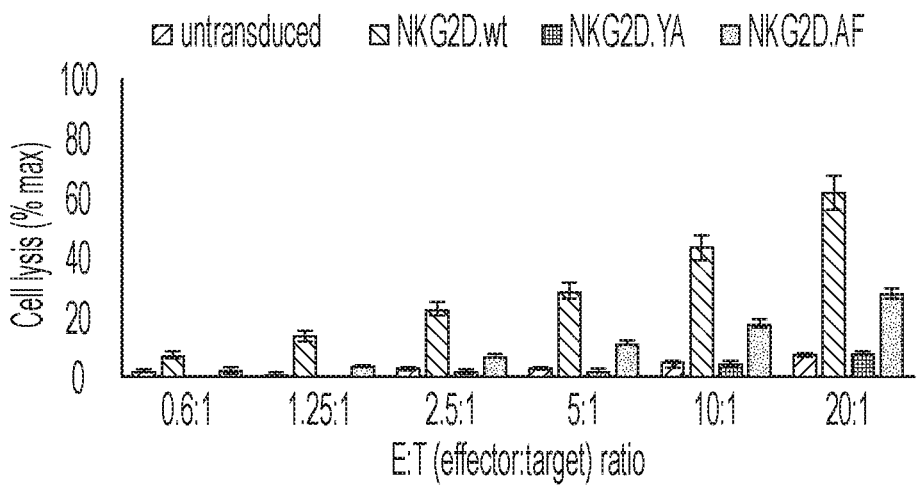

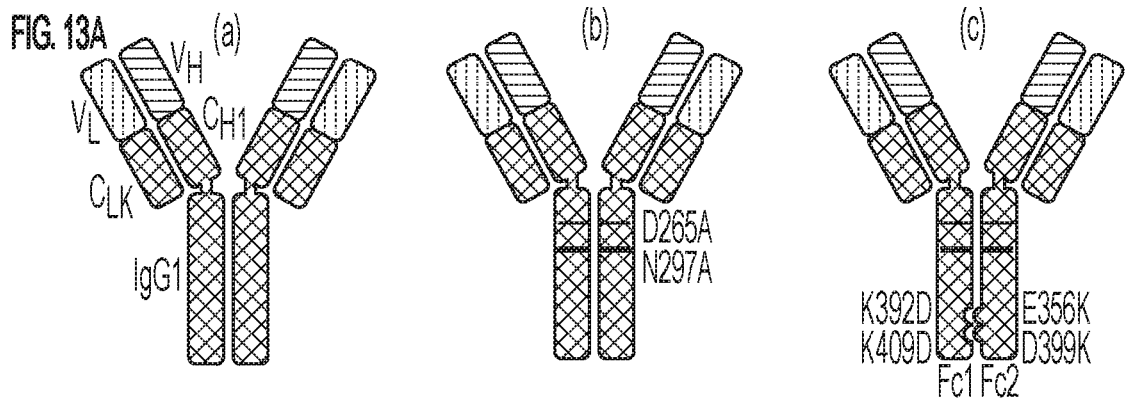
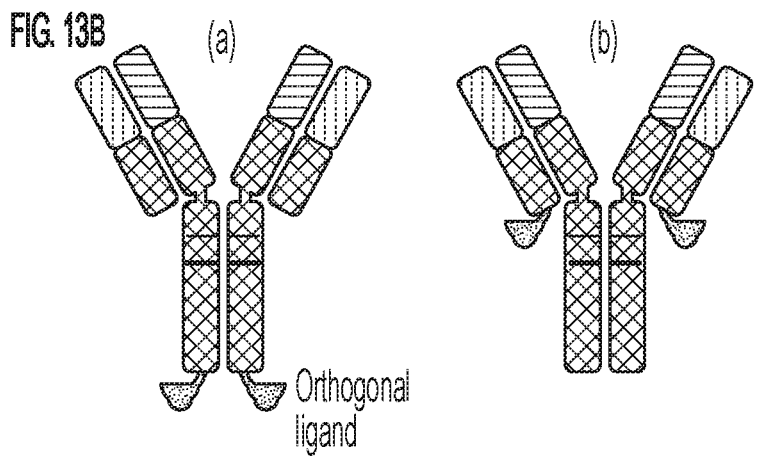
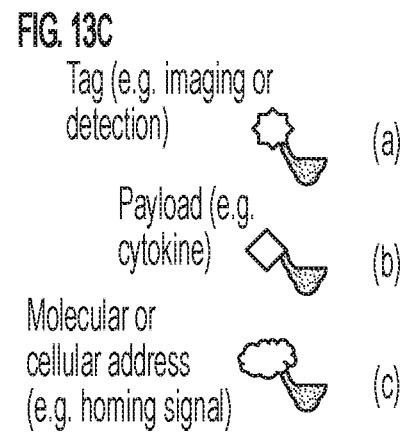
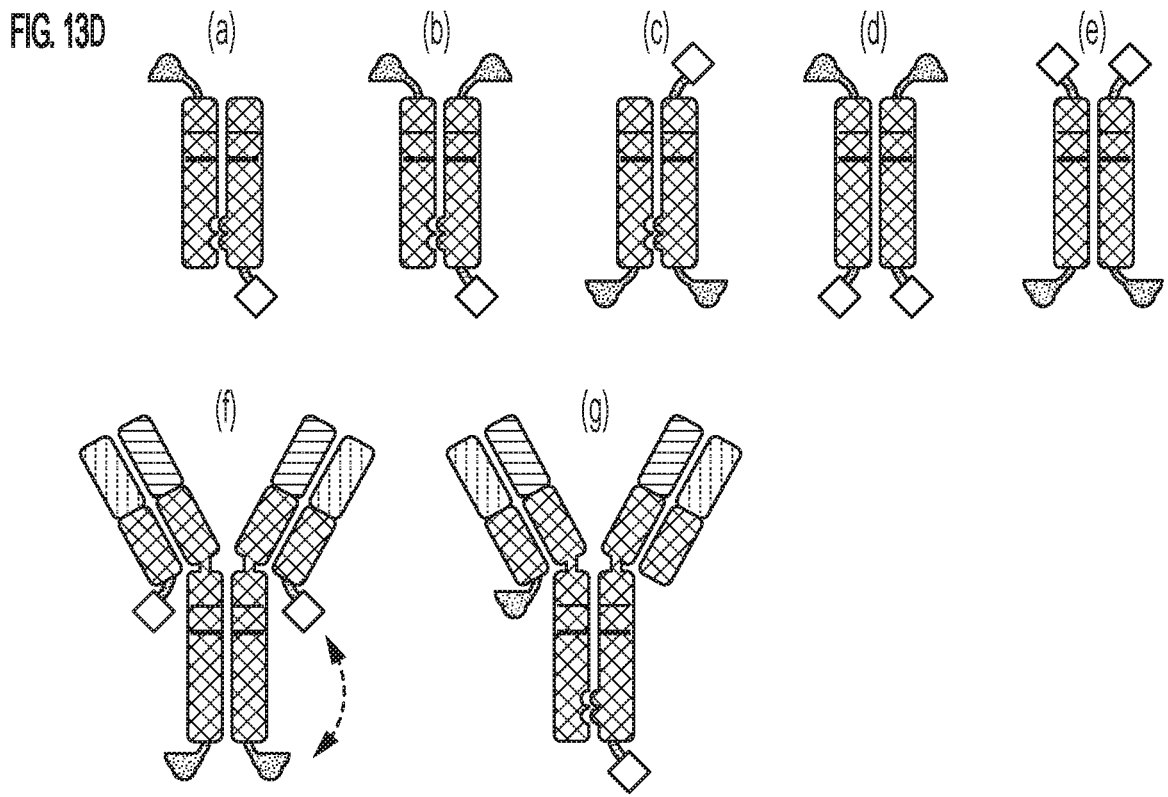

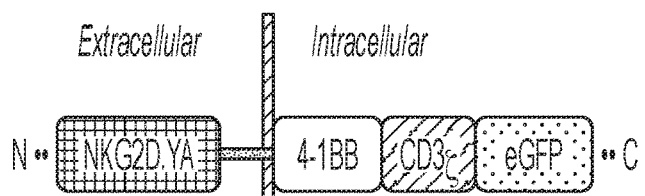
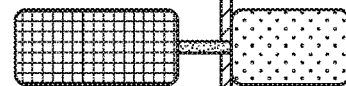
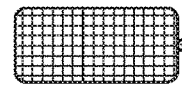
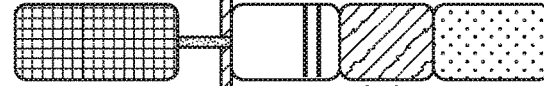
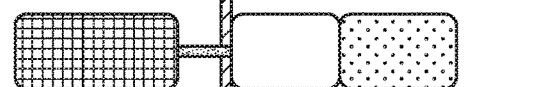
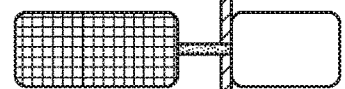
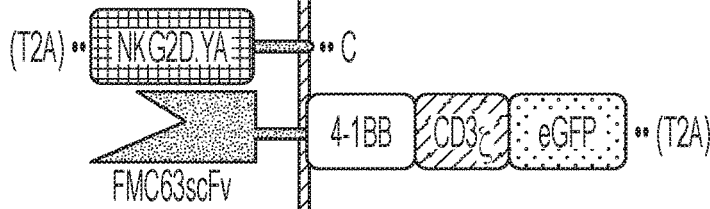
FIG. 14

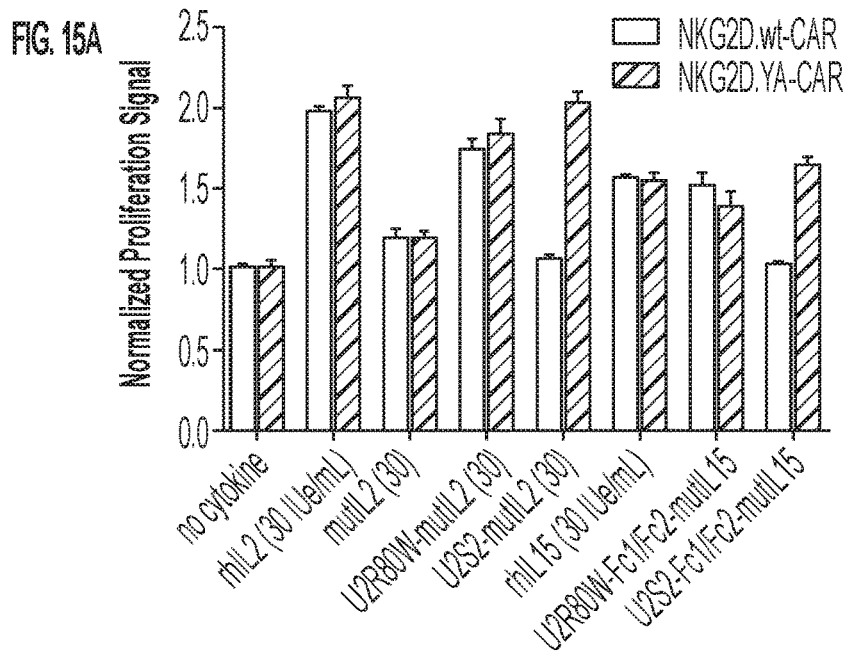
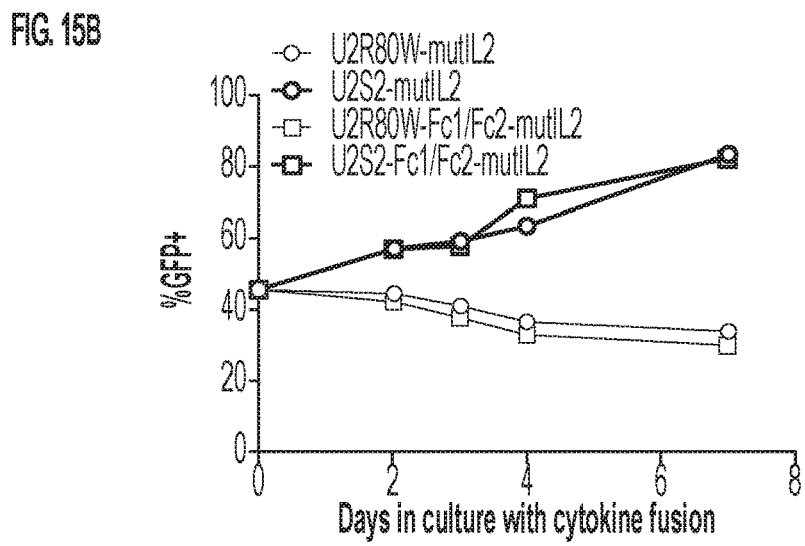
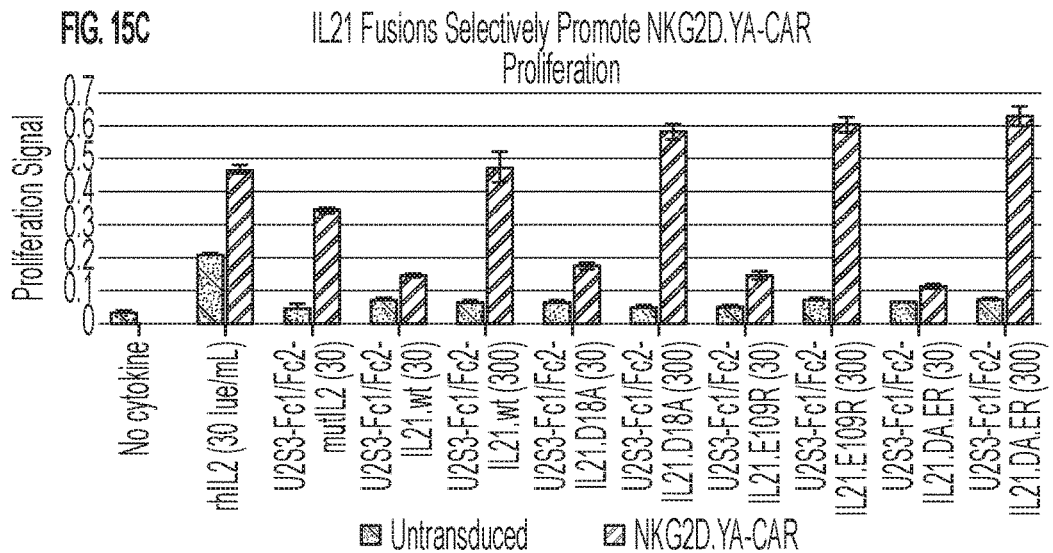

| eNKG2D variant | SEQ ID NO (ectodomain) | SEQ ID NO (Fc-fusion) | Y152 substitution | Y199 substitution | Protein aggregation (Akta SEC) |
|---|---|---|---|---|---|
| wild-type | 17 | 40 | | | Low |
| Y152A | 18 | 41 | A | | Low |
| Y199A | 19 | 42 | | A | High |
| Y152A/Y199A | 20 | 43 | A | A | High |
| 1 | 21 | 44 | | F | Low |
| 2 | 22 | 45 | S | | Low |
| 3 | 23 | 46 | T | | Low |
| 4 | 24 | 47 | V | | Low |
| 5 | 25 | 48 | A | F | Low |
| 6 | 26 | 49 | L | F | Intermediate |
| 7 | 27 | 50 | S | F | Low |
| 8 | 28 | 51 | T | F | Low |
| 9 | 29 | 52 | V | F | Intermediate |
| 10 | 30 | 53 | D | D | High |
| 11 | 31 | 54 | E | E | High |
| 12 | 32 | 55 | D | D | High |
| 13 | 33 | 56 | E | E | High |
| 14 | 34 | 57 | L | F | High |
| 15 | 35 | 58 | F | F | Low |

FIG. 18

| eNKG2D variant | Y152 substitution | Y199 substitution | MICwed MicAbody binding | MICwed MicAbody binding |
|---|---|---|---|---|
| wild-type | | | 100 | 100 |
| Y152A | A | | 50 | 100 |
| Y199A | | A | nt | nt |
| Y152A/Y199A | A | A | nt | nt |
| 1 | | F | 100 | 100 |
| 2 | S | | 50 | 100 |
| 3 | T | | 50 | 100 |
| 4 | V | | 50 | 100 |
| 5 | A | F | 0 | 50 |
| 6 | L | F | nt | nt |
| 7 | S | F | 0 | 50 |
| 8 | T | F | 0 | 50 |
| 9 | V | F | 0 | 50 |
| 10 | | D | nt | nt |
| 11 | | E | nt | nt |
| 12 | D | D | nt | nt |
| 13 | E | E | nt | nt |
| 14 | L | | nt | nt |
| 15 | F | F | nt | nt |

FIG. 19

|  |  | MicAbody | | |
|---|---|---|---|---|
|  | Fc-eNKG2D | ULBP2.wt | MICwed | MIC25 |
| wt | NKG2D.wt Y\|Y | 1.41 | 0.0067 | ~ 0.0039 |
| Y152 | eNKG2D A\|Y | 27.86 | 4.30 | 0.0057 |
| Y152 | eNKG2D2 S\|Y | 34.78 | 4.16 | 0.0056 |
| Y152 | eNKG2D3 T\|Y | 31.14 | 4.33 | 0.0056 |
| Y152 | eNKG2D4 V\|Y | 35.78 | 4.84 | ~ 0.0043 |
| Y152 | eNKG2D14 L\|Y | 87.63 | 9.39 | 0.010 |
| Y199 | eNKG2D1 Y\|F | 23.08 | 0.32 | 0.0048 |
| Y199 | eNKG2D10 Y\|D | nt | nt | nt |
| Y199 | eNKG2D11 Y\|E | nt | nt | nt |
| Y152\|Y199 | eNKG2D5 A\|F | nb | 280.5 | 0.79 |
| Y152\|Y199 | eNKG2D6 L\|F | nb | nb | 0.37 |
| Y152\|Y199 | eNKG2D7 S\|F | nb | 347.3 | 20.94 |
| Y152\|Y199 | eNKG2D8 T\|F | nb | 570.6 | 4.51 |
| Y152\|Y199 | eNKG2D9 V\|F | nb | 90.0 | 0.43 |
| Y152\|Y199 | eNKG2D15 F\|F | 57.05 | 31.3 | 0.046 |
| Y152\|Y199 | eNKG2D12 D\|D | nb | nb | nb |
| Y152\|Y199 | eNKG2D13 E\|E | nb | nb | nb |

FIG. 20

| Phage clone frequency (of the subset examined by spot ELISA) | ULBP2 residue | | | | | | | |
|---|---|---|---|---|---|---|---|---|
| | 8 C | 80 R | 154 M | 155 S | 156 F | 157 H | 158 Y | 159 F |
| 83 | S | W | T | T | F | W | Q | I |
| 9 | S | W | T | M | L | R | Q | W |
| 6 | S | W | T | L | L | W | G | W |
| 4 | S | W | T | I | L | W | Q | T |
| 4 | S | W | T | M | L | R | Q | F |
| 3 | S | W | T | L | L | W | Q | A |
| 3 | S | W | T | L | L | W | S | W |
| 2 | S | W | T | L | L | W | Q | W |
| 2 | S | W | T | M | F | W | S | W |
| 2 | S | W | T | M | L | W | K | W |
| 2 | S | W | T | S | L | W | S | W |
| 2 | S | W | T | T | L | W | Q | V |
| 2 | S | W | T | V | L | W | Q | A |
| 2 | S | W | T | V | L | W | S | A |
| 1 | S | W | T | E | L | W | R | T |
| 1 | S | W | T | G | L | W | H | A |
| 1 | S | W | T | H | L | W | G | V |
| 1 | S | W | T | H | L | W | K | F |
| 1 | S | W | T | I | L | W | S | T |
| 1 | S | W | T | L | F | S | W | Y |
| 1 | S | W | T | L | L | P | A | W |
| 1 | S | W | T | L | L | R | Q | F |
| 1 | S | W | T | L | L | W | A | A |
| 1 | S | W | T | L | L | W | H | A |
| 1 | S | W | T | L | M | S | W | W |
| 1 | S | W | T | L | M | W | Q | W |
| 1 | S | W | T | M | F | R | Q | W |
| 1 | S | W | T | M | F | R | Q | Y |
| 1 | S | W | T | M | F | W | Q | W |
| 1 | S | W | T | M | I | Y | S | W |
| 1 | S | W | T | M | L | A | H | W | to FIG. 21B

FIG. 21A

| Phage clone frequency (of the subset examined by spot ELISA) | ULBP2 residue | | | | | | | |
|---|---|---|---|---|---|---|---|---|
| | 8 | 80 | 154 | 155 | 156 | 157 | 158 | 159 |
| | C | R | M | S | F | H | Y | F |
| 1 | S | W | T | M | L | F | Q | W |
| 1 | S | W | T | M | L | K | Q | W |
| 1 | S | W | T | M | L | M | Q | W |
| 1 | S | W | T | M | L | P | Y | W |
| 1 | S | W | T | M | L | R | Q | S |
| 1 | S | W | T | M | L | R | Q | Y |
| 1 | S | W | T | M | L | T | Q | W |
| 1 | S | W | T | M | L | W | H | A |
| 1 | S | W | T | M | L | W | N | W |
| 1 | S | W | T | M | L | W | S | A |
| 1 | S | W | T | M | L | W | W | S |
| 1 | S | W | T | M | M | R | Q | W |
| 1 | S | W | T | N | I | W | Q | Y |
| 1 | S | W | T | N | L | W | N | V |
| 1 | S | W | T | N | L | W | Q | S |
| 1 | S | W | T | N | L | W | S | A |
| 1 | S | W | T | N | L | W | S | Y |
| 1 | S | W | T | N | M | W | G | W |
| 1 | S | W | T | S | L | C | W | Y |
| 1 | S | W | T | S | L | W | G | A |
| 1 | S | W | T | S | L | W | G | I |
| 1 | S | W | T | S | L | W | Q | S |
| 1 | S | W | T | S | L | W | Q | V |
| 1 | S | W | T | S | L | W | Q | Y |
| 1 | S | W | T | S | L | W | S | A |
| 1 | S | W | T | T | F | W | G | T |
| 1 | S | W | T | T | F | W | Q | M |
| 1 | S | W | T | T | L | W | P | S |
| 1 | S | W | T | T | L | W | S | S |
| 1 | S | W | T | T | M | W | Q | V |
| 1 | S | W | T | V | L | W | Q | M |

FIG. 21B

| ULBP2 variant | ULBP2 residue | | | | | | | | | ELISA EC50s - Rituximab-MicAbody (light-chain ULBP2 fusion) binding to NKG2D.wt or NKG2D.AF | | | |
|---|---|---|---|---|---|---|---|---|---|---|---|---|---|
| | 8 C | 80 R | 154 M | 155 S | 156 F | 157 H | 158 Y | 159 F | | wt EC50 nM | AF EC50 nM | wt/AF EC50 ratio | AF/wt EC50 ratio |
| A | S | W | T

| M154 | S155 | F156 | H157 | Y158 | F159 |
|------|------|------|------|------|------|
| T | M | L | E | L | W |
|   | K | M | T | V | I |
|   | W |   | S | I |   |
|   | L |   | Q | T |   |
|   | T |   | Y |   |   |
|   |   |   | R |   |   |

FIG. 23

| Name | Polypeptide A | Polypeptide B | Purification |
|---|---|---|---|
| mutIL2 | SEQ ID NO: 175 | | Ni-NTA |
| U2R80W-mutIL2 | SEQ ID NO: 177 | | Ni-NTA |
| U2S2-mutIL2 | SEQ ID NO: 179 | | Ni-NTA |
| U2R80W-Fc1/Fc2-mutIL2 | SEQ ID NO: 181 | SEQ ID NO: 183 | Protein A |
| U2S2-Fc1/Fc2-mutIL15 | SEQ ID NO: 187 | SEQ ID NO: 185 | Protein A |
| U2S2-Fc1/Fc2-mutIL2 | SEQ ID NO: 187 | SEQ ID NO: 183 | Protein A |
| U2S3-Fc1/Fc2-IL2.wt | SEQ ID NO: 189 | SEQ ID NO: 191 | Protein A |
| U2S3-Fc1/Fc2-mutIL2 | SEQ ID NO: 189 | SEQ ID NO: 183 | Protein A |
| U2S3-Fc1/Fc2-IL21.wt | SEQ ID NO: 189 | SEQ ID NO: 193 | Protein A |
| U2S3-Fc1/Fc2-IL21.D18A | SEQ ID NO: 189 | SEQ ID NO: 195 | Protein A |
| U2S3-Fc1/Fc2-IL21.E109R | SEQ ID NO: 189 | SEQ ID NO: 197 | Protein A |
| U2S3-Fc1/Fc2-IL21.D18A.E109R | SEQ ID NO: 189 | SEQ ID NO: 199 | Protein A |
| U2S3-Fc1/Fc2 | SEQ ID NO: 189 | SEQ ID NO: 201 | Protein A |

FIG. 24

NON-NATURAL NKG2D RECEPTORS THAT DO NOT DIRECTLY SIGNAL THE CELLS TO WHICH THEY ARE ATTACHED

BACKGROUND OF THE INVENTION

Incorporation by Reference of Material Submitted Electronically

A sequence Listing, which is a part of the present disclosure, is submitted concurrently with the specification as a text file. The name of the text file containing the Sequence Listing is "A251193SEQLISTELECTOFILE.txt." The Sequence Listing was created on Nov. 5, 2018, and is 440,429 bytes in size. The subject matter of the Sequence Listing is incorporated by reference herein in its entirety.

FIELD OF THE INVENTION

This application relates generally to a non-natural ectodomain of a non-natural NKG2D receptor attached to a mammalian cell wherein the receptor does not directly activate or directly signal the mammalian cell when bound by a non-natural NKG2D ligand modified to specifically bind the non-natural NKG2D receptor and to which heterologous molecules are attached to the modified α1-α2 domains of NKG2D ligand.

BACKGROUND INFORMATION

NKG2D is an activating receptor expressed as a type II homodimeric integral protein on the surface of Natural Killer (NK) cells and certain T cells and macrophages. When bound to one of its eight natural ligands expressed primarily on the surfaces of distressed cells, the NKG2D activates the NK cell to kill the stressed cell, or when on T cells, the ligand-occupied NKG2D co-stimulates an activated T-cell to carry out its effector function. The three-dimensional structures have been solved for the ectodomain of human natural NKG2D, several of its soluble natural ligands and, in some cases, the bound complex of soluble ligand and receptor ectodomain. The monomeric α1-α2 domains of NKG2D ligands bind specifically to the two ectodomains of the natural NKG2D homodimer.

SUMMARY OF THE INVENTION

The present disclosure relates to non-natural NKG2D receptors attached to mammalian cell surfaces wherein the non-natural receptors do not directly signal or directly activate the cell when the receptor is bound by cognate non-natural α1-α2 domains of NKG2D ligands modified to specifically bind the non-natural NKG2D receptors. The non-natural α1-α2 domains of NKG2D ligands may be attached to heterologous atoms or molecules including polypeptides, in some embodiments cytokines or modified cytokines, antibodies or fragments of antibodies. Direct activation of or direct signaling to the cell is not mediated by the attached non-natural NKG2D receptor and does not occur even when immunologic synapses have occurred.

BRIEF DESCRIPTION OF THE DRAWINGS

FIGS. 1A-1B: (FIG. 1A) Alignment of the natural NKG2D.wt ectodomain (SEQ ID NO: 17) along with the NKG2D.YA (SEQ ID NO: 18) and NKG2D.AF (SEQ ID NO: 25) non-natural variants. Indicated are the locations of Y152 and Y199 and highlighted in gray are the mutated residues present in the non-natural variants. (FIG. 1B) Alignment of the α1-α2 domain of natural/wild-type ULBP2 (SEQ ID NO: 4) and non-natural variants of ULBP2 including ULBP2.R80W (SEQ ID NO: 108). Highlighted in gray are the residues critical for binding of non-natural ULBP2 variants to the non-natural NKG2D.YA or NKG2D.AF receptors. Indicated are the locations of residue R80 as well as the M154-F159 region that was explored for orthoganal variants binding to NKG2D.YA (ULBP2.S3, SEQ ID NO.: 127) or NKG2D.AF (ULBP2.C, SEQ ID NO.: 111; ULBP2.R, SEQ ID NO.: 113; ULPB2.AA, SEQ ID NO.: 115; and ULBP2.AB, SEQ ID NO.: 117).

FIGS. 8A-8B: ULBP2.0 (SEQ ID NO: 111), ULBP2.R (SEQ ID NO: 113), ULBP2.AA (SEQ ID NO: 115), and ULBP2.AB (SEQ ID NO: 117) were examined for changes in peptide-MHCI immunogenicity relative to wild-type ULBP2 (SEQ ID NO: 4) using the NetMHC4.0 Server, querying against the HLA supertype representatives. For the input sequence, the variable region (residues 154-159 according to alignment in FIG. 1B) for each variant along with upstream and downstream nine residues (24 residues total) was entered and 9-mer peptide windows examined for predicted immunogenicity. Dark gray boxes correspond to peptides strongly predicted to bind the MHCI pocket (defined as having % rank<0.5) and therefore have a strong chance of being presented. Light gray boxes correspond to predicted weak binders (% rank<2). See Example 5 text for additional details.

FIGS. 9A-9I: ULBP2.0 (SEQ ID NO: 111), ULBP2.R (SEQ ID NO: 113), ULBP2.AA (SEQ ID NO: 115), and ULBP2.AB (SEQ ID NO: 117) were examined for changes in peptide-MHC class II immunogenicity relative to wild-type ULBP2 (SEQ ID NO: 4) using the NetM HCII 2.3 Server, querying against HLA-DR, HLA-DQ, HLA-DP. For the input sequence, the variable region (residues 154-159 according to alignment in FIG. 1B) for each variant along with upstream and downstream 15 residues (36 residues total) was entered and 15-mer peptide windows examined for predicted immunogenicity. Dark gray boxes correspond to peptides strongly predicted to bind the MHCII pocket and therefore likely to be presented and immunogenic. Light gray boxes correspond to predicted weak binders.

(FIG. 10A) ELISA curves. The reduction in 458 nm absorption for some assays at higher concentrations is an artifact that is often seen with high affinity engagers at higher concentrations due to precipitation of the TMB-Ultra ELISA development reagent. (FIG. 10B) EC50 values (reported in nM) as determined in GraphPad Prism based upon the curves in (A). nd=not determined due to the lack of relationship between increased concentration and binding.

FIGS. 11A-11C: In vitro cytolytic assays with CD8 effector cells that were either untransduced or transduced with NKG2D.wt, NKG2D.YA, or NKG2D.AF CAR constructs consisting of the CD8a hinge/transmembrane domain and intracellular 4-1BB and CD3zeta signaling domains. Target cells were pre-loaded with calcein and exposed to effector cells at increasing effector to target (E:T) ratios. Released calcein was quantified after five hours. (FIG. 11A) Cell lysis of HeLa cells, (FIG. 11B) lysis of HeLa cells transfected to over-express surface ULBP1, and (FIG. 11C) cytolysis of HeLa cells expressing non-natural ULBP2.R on their surface. Error bars correspond to standard deviation of technical replicates in the experiment.

(FIG. 12A) Ramos cells—which express CD20, the target of rituximab—were preloaded with calcein and exposed to NKG2D.AF- or NKG2D.YA-CAR cells at an E:T ratio of 20:1 along with increasing concentrations of either ULBP2.S3 or ULBP2.R rituximab-Micabody. The level of cytolysis was quantified after two hours of coincubation. (FIG. 12B) The mouse tumor line CT26 transfected to express human Her2 was used as a cytolysis target in parallel with Ramos cells. NKG2D.AF-CAR CD8 T cells were pre-armed with a saturating concentration (5 nM) of rituximab-ULBP2.R, trastuzumab-ULBP2.R, or an equimolar mixture of the two MicAbodies. Unbound MicAbody was removed by washing and CD8 cells added to target cells at two different E:T ratios. Cytolysis was measure after two hours.

FIGS. 13A-13D: Illustrations of potential MicAbody and MicAdaptor formats. (FIG. 13A) Various antibody Fc variants utilized in developing MicAbody and MicAdaptor reagents and include (a) wild-type human IgG1 Fc, (b) two mutations that render the Fc ADCC-deficient, and (c) electrostatic steering mutations in each Fc—Fc1 or Fc2—that allow for the generation of heterodimeric-Fc molecules which also contains the ADCC-deficiency mutations. (FIG. 13B) Example of how orthogonal ligands can be fused to the C-terminus of the (a) heavy- or (b) light-chain to generate MicAbody reagents. (FIG. 13C) MicAdaptor examples with direct orthogonal ligand fusion without antibody components. (FIG. 13D) Illustration of the variety of MicAdaptor molecules that can be generated in the context of a human IgG1 Fc for enhanced serum stability and may (a, b, c; denoted as "Fc1/Fc2" in text and legends) or may not (d, e) include the heterodimeric-Fc mutations depending upon the valency of the desired molecule for either the heterologous cargo or orthogonal ligand. This may also include utilizing the full antibody structure depending upon desired cargo, valency, and functionality (f, g) and may be either heavy- or light-chain fusions.

FIG. 14: Schematic of CAR constructs, silent CARs, and other CAR variants. SEQ ID NOs for each construct as indicated.

FIGS. 15A-15C: Selective delivery of cytokine fusions to NKG2D.YA-CAR expressing CD8 T cells. (FIG. 15A) CD8 cell expressing either the NKG2D.wt-CAR (SEQ ID NO: 151) or NKG2D.YA-CAR SEQ ID NO: 153) were exposed to 30 or 300 IUe/mL of recombinant human IL2 (rhIL2) or IL15 (rhIL15), or variations of mutant-IL2/-IL15 orthogonal ligand direct fusions or fusions in the context of a heterodimeric Fc (Fc1/Fc2). After three days proliferation was quantified by WST cell proliferation reagent. Data here are shown normalized to the no cytokine control. (FIG. 15B) Human T-cells transduced with a vector encoding NKG2D.YA-CAR were exposed to various ligand-cytokine fusion molecules for seven days and the percentage of GFP+ CAR− cells in the culture tracked over time. (FIG. 15C) Orthogonal ligand enhances delivery of IL21 and mutant-IL21 reagents to NKG2D.YA-CAR cells and promotes their expansion over untransduced cells over three days of culture as determined by WST assay. IUe/mL of cytokine or cytokine-MicAdaptor indicated in parentheses in the abscissa legend. See FIG. 24 for MicAdaptor SEQ ID NOs.

(FIG. 16A) NKG2D.YA ectodomain alone (SEQ ID NO: 157) was incapable of directing killing of Ramos cells with the rituximab-ULBP2.S3 MicAbody (SEQ ID NOs: 98 and 129). (FIG. 16B) WST proliferation assay after three days of exposure to various cytokine reagents. (FIG. 16C) WST proliferation assay demonstrated that engagement of NKG2D.YA-CAR with orthogonal ligand but in the absence of a fused cytokine or cytokine mutant was insufficient for driving cell expansion. See FIG. 24 for MicAdaptor SEQ ID NOs. IUE/mL amounts of cytokines and cytokine-MicAdaptors indicated in parentheses in abscissa legends.

(FIG. 17A) WST proliferation assay of various costimulatory domain mutants (SEQ ID NOs: 161, 163, and 165) after incubation with the designated cytokine or cytokine-MicAdaptor for three days. (FIG. 17B) Same costimulatory domain CAR mutants examined for their ability to effectively lyse calcein-loaded Ramos target cells in the presence of rituximab-ULBP2.S3 MicAbody (SEQ ID NOs: 98 and 129). (FIG. 17C) Co-expression of the NKG2D.YA ectodomain (NKG2D.YA-ecd) with a complete CD19scFv-CAR is sufficient for promoting proliferation as assessed by WST assay after three days incubation with cytokine reagents. See FIG. 24 for MicAdaptor SEQ ID NOs.

FIG. 18: Summary of candidate, non-natural Fc-eNKG2D variant mutations and protein aggregation properties determined by Size-Exclusion Chromatography (SEC).

FIG. 19: Percent saturation (Rmax) of eNKG2D variants normalized to wild-type NKG2D binding by either MICwed-MicAbody or to MIC25-MicAbody. Wild-type Fc-NKG2D and each Fc-eNKG2D receptor were captured on AHC biosensors then exposed to trastuzumab-specific MicAbodies at 20 nM. Dissociation kinetics were monitored and the Rmax values of the Fc-eNKG2D fusions ranked. Those samples not tested (nt) were due to either severe aggregation or inadequate amount of material expressed or recovered after SEC fractionation.

FIG. 20: EC50 values (nM) for Fc-eNKG2D ELISAs shown in FIG. 3. nt=not tested; nb=no binding or very low binding even at 300 nM so EC50 value not calculated.

FIGS. 21A-21B: Subset of combinatorial mutations within ULBP2 that resulted in phage clones with selective binding to NKG2D.AF versus natural NKG2D.wt as verified by spot ELISA. Mutants were ranked by frequency of appearance among the selected phages.

FIG. 22: Specificity of NKG2D.AF-selected ULBP2 variants in rituximab-MicAbody format retained their binding to NKG2D.AF by quantitative ELISA. The specific amino acid modifications of each ULBP2 variant are shown as are the ratios of their binding to Fc-NKG2D.wt fusion versus Fc-NKG2D.AF fusion. The amino acid residue locations of ULBP2 are those of FIG. 1B.

FIG. 23: Selected mutations at the indicated amino acid locations of ULBP2.R80W (FIG. 1B; SEQ ID NO: 108) that resulted in Y152A-specific phage clones.

FIG. 24: MicAdaptor SEQ ID NOs and Purification Method from Transient Transfections.

DETAILED DESCRIPTION OF THE INVENTION

Natural killer (NK) cells and certain (CD8+ αβ and γδ) T cells of the immune system have important roles in humans and other mammals as first-line, innate defense against neoplastic and infected cells (Cerwenka, A., and L. L. Lanier. 2001. NK cells, viruses and cancer. Nat. Rev. Immunol. 1:41-49). NK cells and certain T cells exhibit on their surfaces NKG2D, a prominent, homodimeric, surface immunoreceptor responsible for recognizing a target cell and activating the innate defense against the pathologic cell (Lanier, L L, 1998. NK cell receptors. Ann. Rev. Immunol. 16: 359-393; Houchins J P et al. 1991. DNA sequence analysis of NKG2, a family of related cDNA clones encoding type II integral membrane proteins on human NK cells. J. Exp. Med. 173: 1017-1020; Bauer, S et al., 1999. Activation of NK cells and T cells by NKG2D, a receptor for stress-inducible MICA. *Science* 285: 727-730). The human NKG2D molecule possesses a C-type lectin-like extracellular (ecto-)domain that binds to its eight distinct cognate ligands, the most studied ligands being the 84% sequence identical or homologous, monomeric MICA and MICB, polymorphic analogs of the Major Histocompatibility Complex (MHC) Class I chain-related glycoproteins (MIC) (Weis et al. 1998. The C-type lectin superfamily of the immune system. *Immunol. Rev.* 163: 19-34; Bahram et al. 1994. A second lineage of mammalian MHC class I genes. PNAS 91:6259-6263; Bahram et al. 1996a. Nucleotide sequence of the human MHC class I MICA gene. *Immunogenetics* 44: 80-81; Bahram and Spies T A. 1996. Nucleotide sequence of human MHC class I MICB cDNA. *Immunogenetics* 43: 230-233). Non-pathologic expression of MICA and MICB is restricted to some intestinal epithelium, keratinocytes, endothelial cells and monocytes, but aberrant surface expression of these MIC proteins occurs in response to many types of cellular stress such as proliferation, oxidation and heat shock and marks the cell as pathologic (Groh et al. 1996. Cell stress-regulated human MHC class I gene expressed in GI epithelium. PNAS 93: 12445-12450; Groh et al. 1998. Recognition of stress-induced MHC molecules by intestinal γδ T cells. *Science* 279: 1737-1740; Zwirner et al. 1999. Differential expression of MICA by endothelial cells, fibroblasts, keratinocytes and monocytes. Human Immunol. 60: 323-330). Pathologic expression of MIC proteins also seems involved in some autoimmune diseases (Ravetch, JV and Lanier L L. 2000. Immune Inhibitory Receptors. *Science* 290: 84-89; Burgess, S J. 2008. Immunol. Res. 40: 18-34). The differential regulation of NKG2D ligands, such as the polymorphic MICA and MICB, is important to provide the immunity system with a means to identify and respond to a broad range of emergency cues while still protecting healthy cells from unwanted attack (Stephens H A, (2001) MICA and MICB genes: can the enigma of their polymorphism be resolved? *Trends Immunol.* 22: 378-85; Spies, T. 2008. Regulation of NKG2D ligands: a purposeful but delicate affair. *Nature Immunol.* 9: 1013-1015).

Viral infection is a common inducer of MIC protein expression and identifies the viral-infected cell for NK or T cell attack (Groh et al. 1998; Groh et al. 2001. Co-stimulation of CD8+ αβT cells by NKG2D via engagement by MIC induced on virus-infected cells. *Nat. Immunol.* 2: 255-260; Cerwenka, A., and L. L. Lanier. 2001). In fact, to avoid such an attack on its host cell, cytomegalovirus and other viruses have evolved mechanisms that prevent the expression of MIC proteins on the surface of the cell they infect in order to escape targeting by the innate immunity system (Lodoen, M., K. Ogasawara, J. A. Hamerman, H. Arase, J. P. Houchins, E. S. Mocarski, and L. L. Lanier. 2003. NKG2D-mediated NK cell protection against cytomegalovirus is impaired by gp40 modulation of RAE-1 molecules. *J. Exp. Med.* 197:1245-1253; Stern-Ginossar et al., (2007) Host immune system gene targeting by viral miRNA. *Science* 317: 376-381; Stern-Ginossar et al., (2008) Human microRNAs regulate stress-induced immune responses mediated by the receptor NKG2D. *Nature Immunology* 9: 1065-73; Slavuljica, I A Busche, M Babic, M Mitrovic, I Gašparovic, Đ Cekinovic, E Markova Car, EP Pugel, A Cikovic, VILisnic, WJ Britt, U Koszinowski, M Messerle, A Krmpotic and S Jonjic. 2010. Recombinant mouse cytomegalovirus expressing a ligand for the NKG2D receptor is attenuated and has improved vaccine properties. *J. Clin. Invest.* 120: 4532-4545).

In spite of their stress, many malignant cells, such as those of lung cancer and glioblastoma brain cancer, also avoid the expression of MIC proteins and as a result may be particularly aggressive as they too escape the innate immune system (Busche, A et al. 2006, NK cell mediated rejection of experimental human lung cancer by genetic over expression of MHC class I chain-related gene A. *Human Gene Therapy* 17: 135-146; Doubrovina, E S, MM Doubrovin, E Vider, RB Sisson, RJ O'Reilly, B Dupont, and YM Vyas, 2003. Evasion from NK Cell Immunity by MHC Class I Chain-Related Molecules Expressing Colon Adenocarcinoma (2003) J. Immunology 6891-99; Friese, M. et al. 2003. MICA/NKG2D-mediated immunogene therapy of experimental gliomas. Cancer Research 63: 8996-9006; Fuertes, MB, MV Girart, LL Molinero, CI Domaica, LE Rossi, MM Barrio, J Mordoh, GA Rabinovich and NW Zwirner. (2008) Intracellular Retention of the NKG2D Ligand MHC Class I Chain-Related Gene A in Human Melanomas Confers Immune Privilege and Prevents NK Cell-Mediated Cytotoxicity. *J. Immunology,* 180: 4606-4614).

Figure 2:
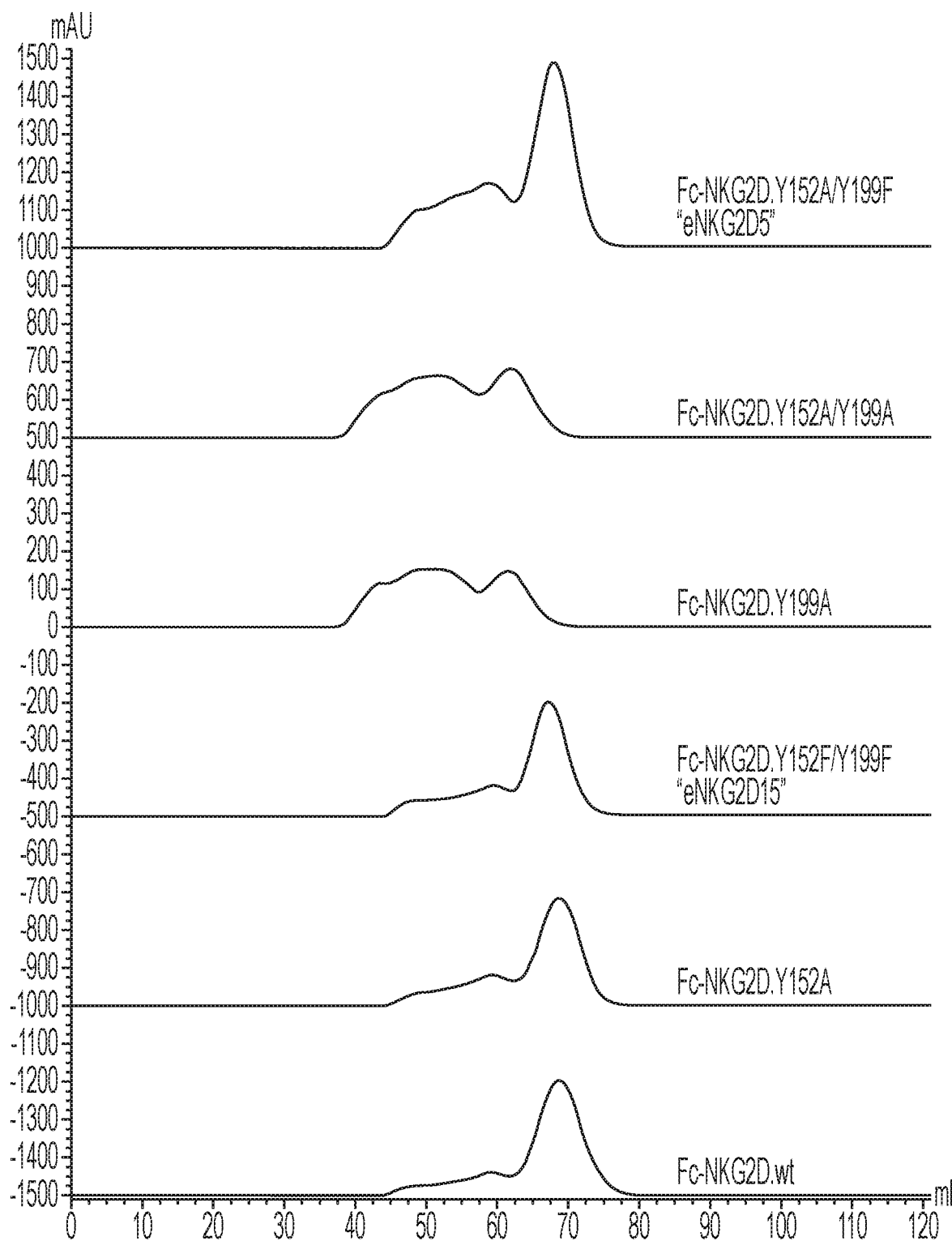
FIG. 2: Size-exclusion chromatography comparison of non-natural Fc-NKG2D fusion proteins analyzed on an Akta HiLoad 16/600 Superdex 200 column. Migration of correctly assembled material was exemplified by a discrete, symmetrical peak that eluted at higher volumes while aggregated material eluted sooner at lower volumes. The site and nature of the modifications are indicated by the amino acid numbers Y152, Y199, or both (SEQ ID NOs: 48, 43, 42, 58, 41, and 40 starting from the top of the figure).

The high resolution structure of human MICA bound to NKG2D has been solved and demonstrates that the α3 domain of MICA has no direct interaction with the NKG2D (Li et al. 2001. Complex structure of the activating immunoreceptor NKG2D and its MHC class I-like ligand MICA. *Nature Immunol.* 2: 443-451; Protein Data Bank accession code 1HYR). The α3 domain of MICA, like that of MICB, is connected to the α1-α2 platform domain by a short, flexible linker peptide, and itself is positioned naturally as "spacer" between the platform and the surface of the MIC expressing cell. The three-dimensional structures of the human MICA and MICB a3 domains are nearly identical (root-mean square distance <1 Å on 94 C-αα's) and functionally interchangeable (Holmes et al. 2001. Structural Studies of Allelic Diversity of the MHC Class I Homolog MICB, a Stress-Inducible Ligand for the Activating Immunoreceptor NKG2D. *J Immunol.* 169: 1395-1400).

T cells, NK-cells, and macrophages can be modified using gene transfer technologies to directly and stably express on their surface binding domains of an antibody that confer novel antigen specificities (Saar Gill & Carl H. June. Going viral: Chimeric Antigen Receptor (CAR) T cell therapy for hematological malignancies. Immunological Reviews 2015. Vol. 263: 68-89; Wolfgang Glienke, Ruth Esser, Christoph Priesner, Julia D. Suerth, Axel Schambach, Winfried S. Wels, Manuel Grez, Stephan Kloess, Lubomir Arseniev and Ulrike Koehl. 2015. Advantages and applications of CAR-expressing natural killer cells. *Front. Pharmacol.* doi: 10.3389/fphar.2015.00021). CAR-T cells are applications of this approach that combines an antigen recognition domain of a specific antibody along with a fused intracellular domain of the CD3-zeta chain. The CD3-zeta chain is the primary transmitter of signals from the ectodomain of endogenous T cell Receptors (TCRs) to the intracellular space. CARs constructed with the CD3-zeta chain and co-stimulatory molecules such as CD27, CD28, ICOS, 4-1BB, or OX40 trigger CAR-T cell activation upon binding the targeted antigen in a manner similar to an endogenous T cell receptor but independent of the major histocompatibility complex (MHC).

Certain non-natural α1-α2 domains of NKG2D ligands modified to bind the natural human NKG2D receptor with higher affinities than do natural α1-α2 domains have been described (Candice S. E. Lengyel, Lindsey J. Willis, Patrick Mann, David Baker, Tanja Kortemme, Roland K. Strong and Benjamin J. McFarland. Mutations Designed to Destabilize the Receptor-Bound Conformation Increase MICA-NKG2D Association Rate and Affinity. *Journal of Biological Chemistry* Vol. 282, no. 42, pp. 30658-30666, 2007; Samuel H. Henager, Melissa A. Hale, Nicholas J. Maurice, Erin C. Dunnington, Carter J. Swanson, Megan J. Peterson, Joseph J. Ban, David J. Culpepper, Luke D. Davies, Lisa K. Sanders, and Benjamin J. McFarland. Combining different design strategies for rational affinity maturation of the MICA-NKG2D interface. *Protein Science* 2012 VOL 21:1396-1402. Herein we describe the attachment of non-natural NKG2D receptors to the surface of mammalian cells in a format that retains the specific binding of modified non-natural NKG2D ligands with attached heterologous molecules, but the non-natural receptors avoid the direct or cis activation of or intracellular signaling to the mammalian cell even when the cell forms an immunologic synapse with a cell or other surface targeted by the heterologous molecule.

The non-natural NKG2D receptors themselves have been mutated at one or two specific sites, each of which results in compromised or loss of binding to all natural α1-α2 domains of NKG2D ligands (David J. Culpepper, Michael K. Maddox, Andrew B. Caldwell, and Benjamin J. McFarland. Systematic mutation and thermodynamic analysis of central tyrosine pairs in polyspecific NKG2D receptor interactions. Mol Immunol. 2011 January; 48(4): 516-523; U.S. PTO application Ser. No. 14/562,534; USPTO provisional application 62/088,456)). The instant invention creates CARs that when attached to a mammalian cell surface provide a silenced receptor that can serve as a surrogate high affinity receptor for the attachment to the cell surface of heterologous atoms or molecules Accordingly, via attached non-natural ligands specific for the non-natural modified NKG2D receptor, heterologous molecules comprising a defective cytokine, for example, can be delivered specifically to the silent receptor on the surface of the mammalian cell but not to cells lacking the cognate silent receptor. Once bound to the cell bearing the silent receptor, the defective heterologous molecule may bind to its respective receptor subunits on the cell surface to which binding has been retained and thereby directly signal the cell as if it were stimulated by the wildtype ligand.

Of course, a CAR comprised of an inert non-natural NKG2D, CD3-zeta and costimulatory domain such as CD28, 4-1BB, ICOS, or OX40 on a mammalian cell is capable of directly stimulating and activating the CAR-cell upon forming an immunologic synapse. The activation of such a second or third generation CAR-T cell is dependent upon the function of its CD3-zeta domain and that of at least one costimulatory domain, e.g. 4-1BB or CD28. However, such a CAR can, as a silent CAR, serve as a surrogate high affinity receptor for the binding of cognate non-natural ligand-attached heterologous molecules that have defective binding to their respective natural receptor or receptor subunit(s). This high affinity binding enables the heterologous molecule attached to the non-natural ligand to transmit signals to the cell via their respective other receptor subunits for which binding has been retained.

Importantly, when the CD3-zeta domain of such a direct activation-competent CAR is selectively inactivated, it can still act as a silent CAR and enable the cognate non-natural ligand-attached heterologous molecules that have defective binding to their respective natural receptor or receptor subunit(s) to transmit signals to the cell via their respective other receptor subunits. When the CAR costimulatory domain such as 4-1BB is inactivated and an active CD3-zeta domain is retained, the CAR cannot serve as a silent receptor. That is, although CD3-zeta is not required, a functional costimulatory domain is required to enable a heterologous molecule such as a defective cytokine attached to a cognate non-natural ligand bound to the receptor to mediate its respective signal to the CAR cell.

The instant invention revealed the unexpected need for a costimulatory domain but not CD3-zeta to enable the heterologous defective cytokine attached to a cognate non-natural ligand to mediate its respective signal to the CAR cell. Furthermore, the invention discloses that the costimulatory domain can act in cis or trans to the silent receptor to which is attached the cognate ligand fused to the defective heterologous defective molecule.

When a heterologous molecule such as an antibody or antibody fragment that targets a specific molecule is attached to a cognate non-natural NKG2D ligand which in turn attaches to the silent receptor, the silent receptor-bearing mammalian cell will home to the surface to which the targeting heterologous molecule directs it. Even when a "synapse" is effected between the silent receptor-bearing cell and the targeted cell surface, the former will not be activated by the silent receptor.

Because there are many copies of the non-natural NKG2D-based silent receptors of the instant invention on the cell surface, the homing and/or the selective activation by heterologous molecules can be multiplexed or changed sequentially during manufacturing processes or treatment protocols.

A cell bearing a silent receptor CAR may also express another receptor(s) or CAR orthogonal to the silent CAR and act independently of the silent CAR to specifically and directly activate or otherwise signal that same cell when appropriately stimulated. The other or "second" orthogonal CAR may be a traditional single chain-hi (scFv)-CAR or a second orthogonal, non-natural modified NKG2D-based CAR with its own cognate non-natural α1-α2 ligand(s). (AF provisional reference). The ability to create effector cells of the immunity system with more than one orthogonal non-natural CAR, silent or active, and multiple cognate non-natural ligands with attached heterologous molecules or atoms, greatly expands the utility, flexibility, and control of Adoptive Cell Therapy (ACT).

In the process of characterizing the silent CAR on a cell and its dependency on a cis or trans acting costimulatory domain, such as 4-1BB, it was observed that compared to an unmodified human T-cell, a human T-cell expressing a silent CAR with a costimulatory domain exhibited a significantly enhanced response to natural IL-2 or to a cognate non-natural ligand fused to either a natural or to a mutant IL-2 with low affinity to its receptor α-subunit. This observation has important utility in the ex vivo or in vivo preferential expansion of cells expressing a CAR comprised of a costimulatory domain with or without a CD3-zeta domain.

As used herein, a "soluble MIC protein", "soluble MICA" and "soluble MICB" refer to a MIC protein containing the α1-α2 domains with or without α3 domain of the MIC protein but without the transmembrane or intracellular domains. The NKG2D ligands, ULBP1-6, do not naturally possess an α3 domain (Cerwenka A, Lanier L L. 2004. NKG2D ligands: unconventional MHC class I-like molecules exploited by viruses and cancer. Tissue Antigens 61 (5): 335-43. doi:10.1034/j.1399-0039.2003.00070.x. PMID: 12753652). An "α1-α2 domain" of an NKG2D ligand refers to the protein domain of the ligand that binds an NKG2D receptor.

In some embodiments, the α1-α2 domains of the non-natural NKG2D ligand proteins of the invention are at least 80% identical or homologous to the native or natural α1-α2 domain of an NKG2D ligand (SEQ ID NOs: 1-9 for MICA, MICB, ULBP1, ULBP2, ULBP3, ULBP4, ULBP5, ULBP6, and OMCP, respectively). In other embodiments, the modified α1-α2 domain is 85% identical to a native or natural α1-α2 domain of an NKG2D ligand. In yet other embodiments, the modified α1-α2 domain is 90% identical to a native or natural α1-α2 domain of a natural NKG2D ligand protein and binds non-natural NKG2D.

Preferably the modified or non-natural α1-α2 domains of the non-natural MIC proteins of the invention are at least 80% identical or homologous to a native or natural α1-α2 domain of one of the 8 human NKG2D ligand proteins (SEQ ID NOs: 1-8) and bind the non-natural NKG2D ectodomain. In some embodiments, the non-natural α1-α2 domain is 85% identical to a native or natural α1-α2 domain of an NKG2D ligand protein and binds the non-natural NKG2D. In other embodiments, the non-natural α1-α2 platform domain is 90%, 95%, 96%, 97%, 98%, or 99% identical to a native or natural α1-α2 platform of a human natural α1-α2 domain protein and binds the non-natural NKG2D.

In some embodiments, a heterologous molecular tag may be fused to the N-terminus or C-terminus of a non-natural α1-α2 domain of a soluble MIC protein or to that of an attached heterologous peptide or protein to aid in the purification of the soluble ligand. Tag sequences include peptides such as a poly-histidine, myc-peptide, a FLAG tag, streptavidin-like tag, or a small molecule such as biotin. Such tags may be removed after isolation of the MIC molecule by methods known to one skilled in the art.

Specific mutations in α1-α2 domains of NKG2D ligands can be made to create non-natural α1-α2 domains that bind non-natural NKG2D receptors, themselves engineered so as to have reduced affinity for natural NKG2D ligands. This can be done, for example, through genetic engineering. A non-natural NKG2D receptor so modified can be used to create on the surface of NK-cells, T cells, macrophages or other cells of the immune system an NKG2D-based CAR that can bind to molecules comprised of the non-natural α1-α2 domains. These non-natural NKG2D receptors and their cognate non-natural NKG2D ligands will provide important safety, efficacy, and manufacturing advantages for treating cancer and viral infections as compared to the current CAR-T cells and CAR-NK cells, as described below. When the intracellular signaling of non-natural NKG2D receptors on the surface of mammalian cells has been silenced as in the instant invention, these invented CARs can act as surrogate high affinity receptors for otherwise defective heterologous molecules such as cytokines, chemokines, lymphokines, cytotoxins, and atoms fused or conjugated to the orthogonal NKG2D ligands. This provides delivery of the heterologous molecules directly and specifically to the silent receptor-bearing cell without the silent-receptor per se directly activating its host cell. Furthermore, heterologous molecules that bind specific targets and thereby cells or other surfaces bearing such targets can provide specific homing functions to the silent receptor-bearing cell without its unintended activation or stimulation.

CAR-T or CAR-NK cells comprised of ectodomains of non-natural NKG2D receptors that do not or only poorly bind natural NKG2D ligands will not be subject to activation by any natural ligands and thus will not be toxigenic as are cells expressing a CAR based on a natural NKG2D receptor. Furthermore, ectodomains of non-natural NKG2D receptors on cells will not be subject to down-regulation by natural NKG2D ligands in a soluble format or on Myeloid Derived Suppressor Cells (MDSC) (Deng W, Gowen B G, Zhang L, Wang L, Lau S, Iannello A, Xu J, Rovis T L, Xiong N, Raulet D H, 2015. Antitumor immunity. A shed NKG2D ligand that promotes natural killer cell activation and tumor rejection. *Science.* 2015 Apr. 3; 348(6230):136-9. doi: 10.1126/science.1258867. Epub 2015 Mar. 5). However, when such CAR cells bearing ectodomains of non-natural NKG2D receptors are engaged by bispecific molecules with the cognate non-natural α1-α2 domains of the instant invention and its heterologous targeting motif which has found and bound its intended target, the CAR will be activated and the CAR-cell's effector functions expressed.

Because the CAR-T or CAR-NK cells comprised of non-natural NKG2D receptor ectodomains are not activated except in the presence of an engaged bispecific molecule comprised of a cognate non-natural α1-α2 domain, their activation can be controlled by the administered bispecific molecules, which as biopharmaceuticals will exhibit pharmacokinetics and pharmacodynamics well known in the field. In the event that an adverse event develops, the physician can simply modify the dosing regimen of the administered bispecific molecule rather than having to deploy an induced suicide mechanism to destroy the infused CAR cells as currently done (Monica Casucci and Attilio Bondanza. Suicide Gene Therapy to Increase the Safety of Chimeric Antigen Receptor-Redirected T Lymphocytes. *J Cancer.* 2011; 2: 378-382). Furthermore, such bispecific molecules with different specific targeting motifs can be administered simultaneously or sequentially to help address tumor resistance and escape as a results of target antigen loss without having to create, expand and infuse multiple different autologous CAR cells (Gill & June, 2015). Since all CAR constructions can be identical for all CAR cells and the targeting specificity determined simply by the targeting motif of the administered bispecific molecule of the instant invention, manufacturing processes will be simplified and less expensive.

Examples of parent or recipient proteins or polypeptides that are candidates for attachment to non-natural α1-α2 domains of NKG2D ligands include but are not limited to antibodies, proteins comprised of Ig folds or Ig domains, including modified Fc domains that recruit natural molecules or fail to recruit or bind natural molecules, globulins, albumens, fibronectins and fibronectin domains, integrins, fluorescent proteins, enzymes, outer membrane proteins, receptor proteins, T cell receptors, chimeric antigen receptors, viral antigens, virus capsids, viral ligands for cell receptors, hormones, cytokines and modified cytokines such as interleukins, knottins, cyclic peptides or polypeptides, major histocompatibility (MHC) family proteins, MIC proteins, lectins, and ligands for lectins. It is also possible to attach non-protein molecules such a polysaccharides, dendrimers, polyglycols, peptidoglycans, antibiotics, and polyketides to the modified α1-α2 domains of NKG2D ligands.

Thus, the instant invention expands the diversity and practicality of this remarkable, very promising immunologic approach to managing cancer with CAR-T cells, CAR-NK cells, and CAR-macrophage-like cells while overcoming many of these current, recognized difficulties.

As used herein "peptide", "polypeptide", and "protein" are used interchangeably; and a "heterologous molecule", "heterologous peptide", "heterologous sequence" or "heterologous atom" is a molecule, peptide, nucleic acid or amino acid sequence, or atom, respectively, that is not naturally or normally found in physical conjunction with the subject molecule. As used herein, "non-natural" and "modified" are used interchangeably. As used herein, "natural", "native", and "wild-type" are used interchangeably and "NKG2D" and "NKG2D receptor" are used interchangeably. The term "antibody" herein is used in the broadest sense and specifically covers monoclonal antibodies, multispecific antibodies (e.g. bispecific antibodies), and antibody fragments, so long as they exhibit the desired biological activity. "Antibody fragments" comprise a portion of an antibody, preferably comprising the antigen binding region thereof. Examples of antibody fragments include Fab, Fab', F(ab')$_2$, Fv fragments and insertible Fv's; diabodies; linear antibodies; single-chain antibody molecules; and multi-specific antibodies formed from antibody fragment(s).

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein are hereby incorporated by reference in their entireties, whether previously specifically incorporated or not. As used herein, the terms "a", "an", and "any" are each intended to include both the singular and plural forms.

Having now fully described the invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and may be applied to the essential features hereinbefore set forth.

EXAMPLES

Modified NKG2D Receptor Ectodomain and Modified α1-α2 Domains of NKG2D Ligands

Example 1. Modification of Tyrosine 152 to Alanine (Y152A) and Tyrosine 199 to Phenylalanine (Y199F) of the Human NKG2D Receptor to Create an Inert NKG2D Ectodomain It had been demonstrated by others that mutations at tyrosine 152 or at tyrosine 199 in human NKG2D, the equivalent of positions 73 and 120 of the NKG2D ectodomain (FIG. 1A, SEQ ID NO.:17) can greatly reduce binding to the natural ligand, MICA (David J. Culpepper, Michael K. Maddox, Andrew B. Caldwell, and Benjamin J. McFarland. Systematic mutation and thermodynamic analysis of central tyrosine pairs in polyspecific NKG2D receptor interactions. Mol Immunol. 2011 January; 48(4): 516-523). We reasoned that while mutation of either tyrosine residue greatly affected the ability of NKG2D to bind to its natural ligands, simultaneous mutation at both tyrosine 152 (Y152) and tyrosine 199 (Y199) would virtually eliminate the receptor's ability to engage with all native ligands. We therefore sought to explore individual and combinatorial Y152 and Y199 substitutions and characterize them with regard to their biochemical behavior with the objective of identifying both single and double-mutant variants incapable of engaging any natural ligands. Those variants that also expressed and assembled well were of particular interest as these signified inert ligands that could be more easily produced for analysis.

Natural NKG2D (wild-type) ectodomain (NKG2D.wt, SEQ ID NO: 17) and candidate non-natural NKG2D variant ectodomains (SEQ ID NOs: 18-35)—also termed "engineered NKG2D" or "eNKG2D" were cloned as fusions to the C-terminus of human IgG1 Fc (without Fab domains), via a short factor Xa recognizable Ile-Glu-Gly-Arg linker (SEQ ID NO: 38) and are interchangeably referred to as Fc-NKG2D.wt or NKG2D.wt and Fc-eNKG2D or eNKG2D (SEQ ID NOs: 40-58). gBlocks® DNA Fragments (Integrated DNA Technologies, San Diego, CA), corresponding to the MHCI signal sequence (SEQ ID NOs: 36 and 37), human IgG1 Fc with linker (SEQ ID NO: 39), and NKG2D ectodomain variants (SEQ ID NOs: 59-77) were synthesized and inserted into pD2610-V12 (ATUM, Newark, CA). DNA constructs exploring substitutions at Y152, Y199, or a combination of Y152/Y199 mutations (FIG. 18) were expressed transiently in Expi293™ cells (ThermoFisher Scientific, Waltham, MA) and secreted protein purified by Protein A affinity chromatography (cat. no. 20334, Pierce Biotechnology, Rockford, IL). Eluted material was characterized by size-exclusion chromatography (SEC) on Akta Pur Superdex columns and correctly assembled, size-appropriate material was fractionated and isolated from aggregate peaks prior to inclusion in assays.

Figure 3:
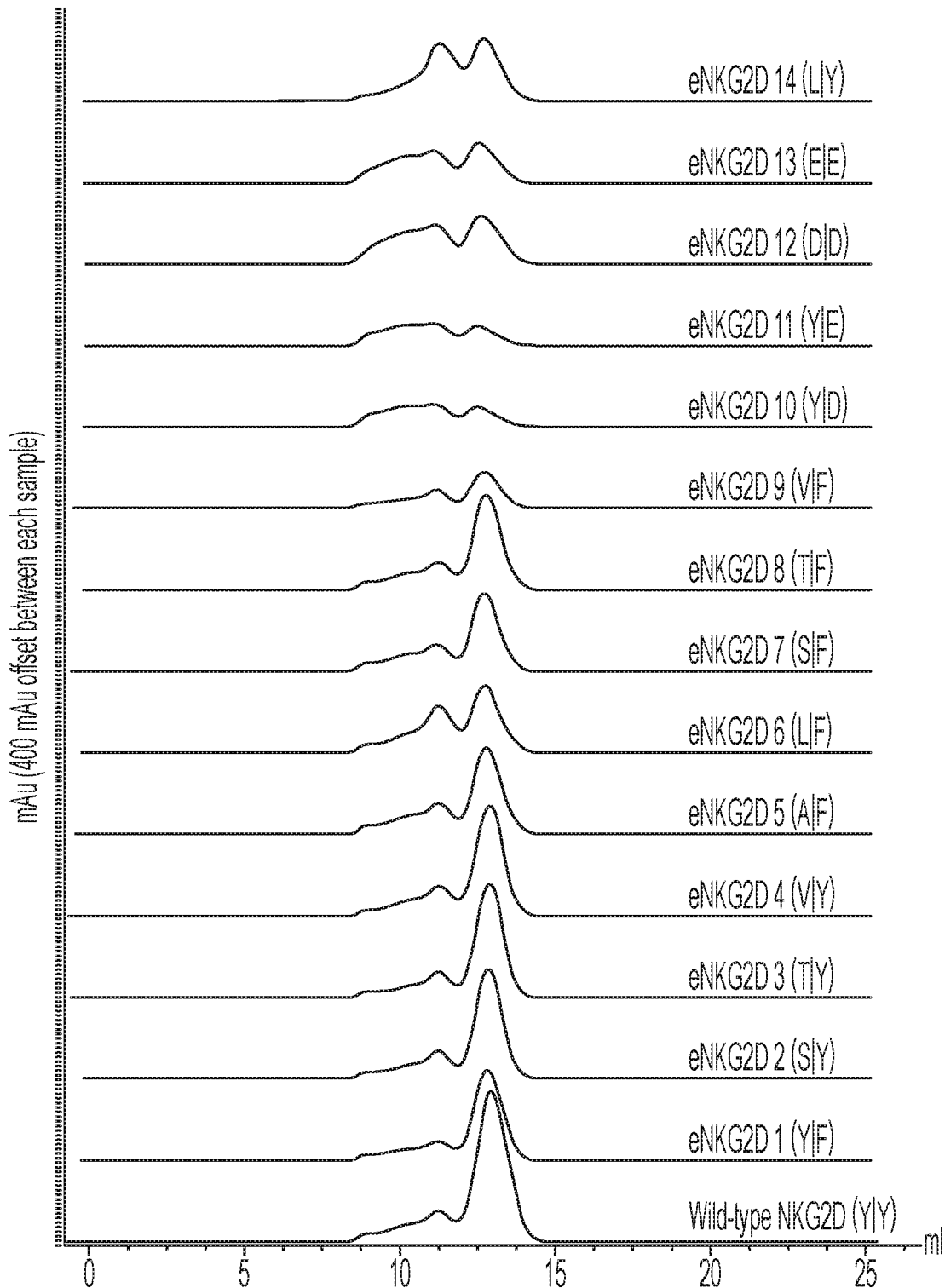
FIG. 3: Size-exclusion chromatography profiles of non-natural Fc-eNKG2D variants with one or two amino acid changes were analyzed on an Akta Superdex 200 Increase 10/300 GL column. Migration of correctly assembled material is exemplified by a discrete, symmetrical peak eluting at higher volumes while aggregated material—characterized by a low amplitude broad peak or series of peaks—eluted at lower volumes. The letters in parentheses represent the amino acids at positions 152 and 199 (SEQ ID NOs: 57, 56, 55, 54, 53, 52, 51, 50, 49, 48, 47, 46, 45, 44, and 40 in order from the top), respectively.

SEC characterization of purified NKG2D.Y199A-Fc fusion revealed a composition of predominantly aggregated material (FIG. 2). In comparison, both the natural Fc-NKG2D fusion and Fc-NKG2D.Y152A fusion material were distinguished by a discrete, non-aggregated peak that was readily differentiated from more rapidly migrating aggregate. The effect of the Y199A mutation on aggregation was also apparent in the Y152A/Y199A double-mutant Fc-NKG2D fusion variant, indicating that it had an overriding influence on protein misfolding (FIG. 2). This aspect of including Y199A with any combination of Y152 mutations in NKG2D variants therefore presented a challenge for the production of material necessary for subsequent engineering efforts and raised a concern about assembly and presentation on a cell surface. As a consequence, an effort was made to explore other substitutions at Y152 and Y199 that could be combined to yield a more robust molecule. eNKG2D combinatorial Y152 and Y199 mutant candidates were examined as Fc fusions and detailed in (FIG. 18). In addition, all purified and expressed Fc-eNKG2D fusion candidates were profiled by SEC and their chromatograms revealed varying levels of aggregate formation (FIGS. 2 and 3, FIG. 18). Of the single amino acid substitutions explored at residue 152 alanine, serine, threonine, and valine all did not impact assembly of the Fc-NKG2D molecule although Y152-leucine (Y152L) resulted in highly aggregated material. Similar to alanine, neither glutamate nor aspartate were tolerated at position 199, although phenylalanine only modestly increased aggregate formation. Of the combinations of mutations that were explored, Y152A/Y199F, Y152S/Y199F, Y152T/Y199F, and Y152F/Y199F did not negatively impact the desired dimer formation, whereas other combinations resulted in increased aggregation (FIG. 18, FIGS. 2 and 3).

Example 2: Generation of Antibody-Based Bispecific Molecules, "MicAbodies", with Non-Natural NKG2D Ligand Variants To generate non-natural MicA variants fused to human IgG1, the DNA polynucleotides encoding the α1-α2 domains of, for example, MICwed (SEQ ID NO: 79) and MIC25 (SEQ ID NO: 81), were PCR amplified using primers that also introduced the polynucleotide encoding either an APTSSSGGGGS linker for fusion to C-terminal kappa light chain (SEQ ID NO: 84) or for a GGGS linker for fusion to C-terminal heavy chain of human IgG1 (SEQ ID NO: 82). Furthermore, two mutations were introduced into the CH2 domain of the heavy chain—D265A/N297A (Kabat numbering; FIGS. 13A and 13B)—that reduce binding to all FcγR receptors thus eliminating antibody-dependent cell cytotoxicity (ADCC) function (Shields et al., 2001 *JBC*, 276:6591-6604). The polynucleotide encoding the α1-α2 domain of wild-type ULBP2 (ULBP2.wt) without its GPI-linkage (SEQ ID NO: 12) was similarly cloned and fused to the DNA polynucleotides encoding the linkers and the IgG1 heavy chain or light chain. These bispecific antibodies—termed "MicAbody™" in the singular, "MicAbodies" in the plural—are bivalent for the fused α1-α2 domain. Examples of antibodies used to generate MicAbodies for the purposes of exploring eNKG2D engineering include but were not limited to trastuzumab (SEQ ID NOs: 94 and 96) and rituximab (SEQ ID NOs: 98 and 100) and subsequently termed "trastuzumab-MicAbody" (e.g. SEQ ID NOs: 102 and 104) and "rituximab-MicAbody" (e.g. SEQ ID NO: 106), respectively. The fusion constructs were inserted individually into pD2610-V12 (ATUM, Newark, CA) via Gibson cloning (New England Biolabs Inc., Ipswich, MA). For a given antibody recognizing a specific antigen, the plasmid encoding the heavy chain and the plasmid encoding the light chain fused to either natural or non-natural NKG2D ligand were co-transfected for transient expression in Expi293™ cells (ThermoFisher Scientific, Waltham, MA). Alternatively, the plasmid encoding the heavy chain fused to either natural or non-natural NKG2D ligand and the plasmid for light chain were co-transfected. Secreted bispecific antibodies were purified by Protein A affinity chromatography (cat. no. 20334, Pierce Biotechnology, Rockford, IL), eluted material was characterized by size-exclusion chromatography (SEC) on Akta Pur Superdex columns, and fractionation performed as needed. In addition, SDS-PAGE analysis was performed on purified samples to verify the expected molecular weights of the fused heavy chain and fused light chain species.

Example 3: Identifying Modified NK2GD Variants Incapable of Binding to Either Natural NKG2D-Binding Ligands or to Non-Natural Ligands that have Enhanced Binding to Wild-Type NKG2D The binding affinities of α1-α2 variants to the extracellular domains of natural (wild-type) NKG2D and non-natural eNKG2D proteins were analyzed using a plate-based ELISA method. Each of the SEC fractionated natural Fc-NKG2D and non-natural Fc-eNKG2D fusions were coated overnight at 4° C. onto separate wells of Nunc Maxisorp 96 well plates (Thermo Fisher Scientific, Waltham, MA) using a coating concentration of 1 μg/mL in phosphate-buffered saline (PBS). The plates were washed three times in PBS/0.05% Tween-20 (PBS-T) at 20-22° C., and blocked with 0.5% bovine serum albumin in PBS (PBS-B) for 2 hours at 20-22° C. MicAbodies were titrated against the plate-bound natural or non-natural Fc-NKG2D fusions for 60 minutes at 20-22° C. in PBS/0.5% bovine serum albumin (BSA)/0.05% Tween-20 (PBS-BT), washed 3 times with PBS-T at 20-22° C., and the bound bispecific proteins detected using an HRP-conjugated anti-human kappa in PBS-BT (Abcam, Cambridge MA) and developed with 1-Step™ Ultra TMB ELISA Substrate Solution (Thermo Fisher Scientific, Waltham, MA). The binding of the ULBP2.wt rituximab-MicAbody (SEQ ID NOs: 98 and 106) discriminated between wild-type NKG2D and eNKG2D variants with reduced binding to the latter, and ligand variants—MICwed (SEQ ID NOs: 96 and 102) and MIC25 (SEQ ID NOs: 96 and 104)—were more stringent at identifying eNKG2D variants with abolished ligand binding. The binding behaviors for each eNKG2D variant against all three bispecific ligands revealed the combinations of NKG2D modifications that led to the greatest reduction in binding of wild-type and variant ligands and enabled the selection of lead inert NKG2D variants.

Additional biophysical analysis of eNKG2D variant binding to ligands was also performed with Bio-Layer Interferometry (BLI) using the Fortaio Octet system (all Fortaio LLC, Fremont, CA). For these experiments human NKG2D ligands MICA-Fc, MICB-Fc, ULBP1-Fc, ULBP2-Fc, ULBP3-Fc, and ULBP4-Fc were purchased from R&D Systems, Inc. (Minneapolis, MN). Ligands in the MicAbody format were captured on anti-human IgG Fc capture (AHC) biosensor tips. After a baselines were established, tips were exposed to a titration series of Fc-eNKG2D fusion proteins ranging from 300 nM to 0.41 nM and association/dissociation kinetics monitored with all steps performed in PBS-BT. Subsequently, Fc-eNKG2D fusion proteins were captured onto AHC tips and MicAbodies were titrated to characterize binding kinetics.

To determine the maximum response as defined by binding of natural NKG2D to either MICwed or MIC25, natural Fc-NKG2D fusions were captured onto AHC biosensors and 20 nM trastuzumab-MICwed or 20 nM trastuzumab-MIC25 MicAbodies were incubated for two minutes and then dissociation kinetics observed for 30 seconds. Binding analysis under the same conditions was then performed with Fc-eNKG2D fusion receptors as the capture agent, and the level of binding for each eNKG2D ranked as a percentage of the maximal binding response established by Fc-NKG2D.wt (FIG. 19). For MICwed, the responses of all single mutant Fc-eNKG2D variants, except for Y199F, were diminished to 50%. Y199F maintained 100% binding response. However, all double-mutant Fc-eNKG2D variants had completely abolished binding to MICwed. For MIC25, all single mutant Fc-eNKG2D variants and Y152V/Y199F maintained 100% binding response relative to wild-type Fc-NKG2D binding. However, binding was reduced to 50% with several of the double-mutant Fc-eNKG2D variants including Y152A/Y199F, Y152S/Y199F, and Y152T/Y199F.

Figure 4:
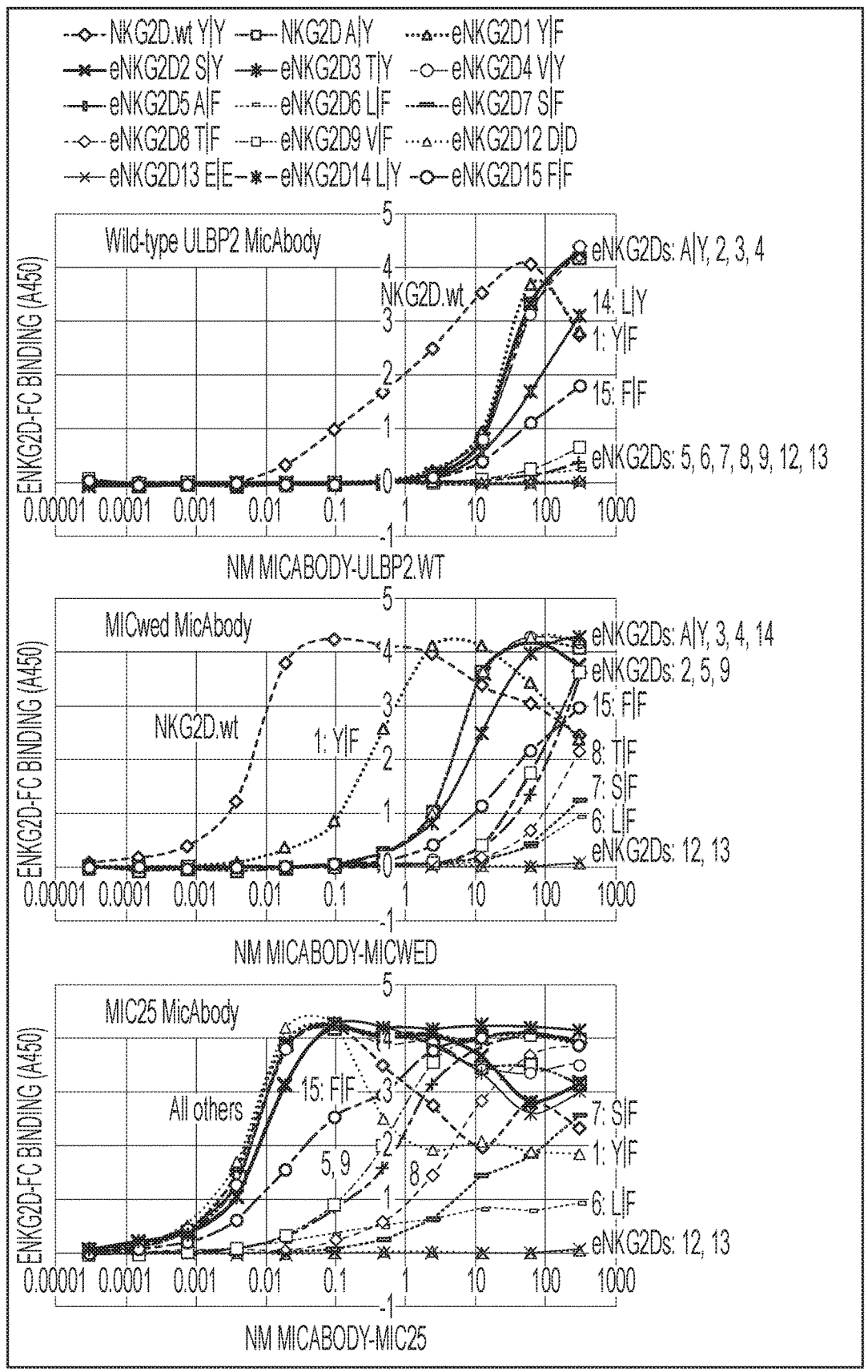
FIG. 4: ELISA binding of ULBP2 wild-type, MICwed- and MIC25-rituximab MicAbodies to Fc-eNKG2D candidates. Key is indicated at the top of the figure, but since many of the curves overlapped, individual curves were also labeled in each graph.
Figure 5:
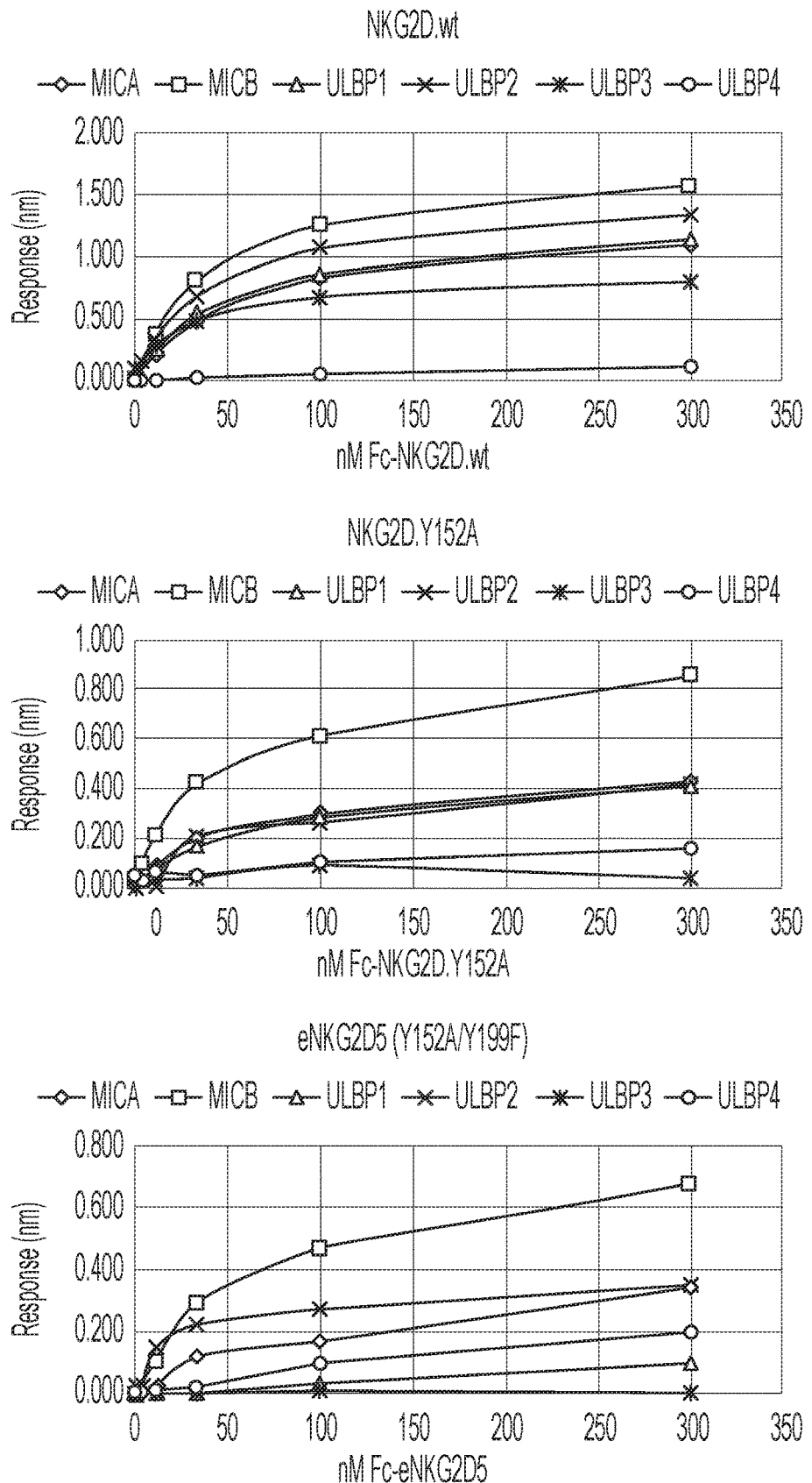
FIG. 5: Binding of eNKG2D variants to wild-type ligands. Wild-type ligands (all in Fc-fusion format) were captured onto Octet AHC biosensors, and each natural NKG2D, NKG2D.Y152A, or eNKG2D5 (Y152A/Y199F) as an Fc-fusion was titrated from 300 nM to 0.41 nM. Maximal binding responses were quantified by Octet. (Note the different ordinates for each graph).

ELISA assays with Fc-eNKG2D fusions as capture agents were performed with ULBP2.wt, MICwed, MIC25 MicAbodies titrated starting at 300 nM (FIG. 4). $EC_{50}$ values were calculated when possible using GraphPad Prism (FIG. 20). Natural NKG2D bound to ULBP2, MICwed, and MIC25-based MicAbodies with affinities calculated as Kds values of 1.4, 0.007, and 0.005 nM, respectively. While affinity was diminished for ULBP2 and MICwed MicAbodies with all single mutant eNKG2D candidates, binding of MIC25 to eNKG2D candidates was retained. However, all double-mutant eNKG2D candidates had eliminated or significantly reduced binding to all three ligands—ULBP2, MICwed, and MIC25—in Micabody formats.

eNKG2D variants eNKG2D5 (Y152A/Y199F), eNKG2D7 (Y152S/Y199F), eNKG2D8 (Y152T/Y199F), and eNKG2D9 (Y152V/Y199F) had reduced or abolished binding to ULBP2, MICwed, and MIC25-based MicAbodies by both Octet analysis and ELISA (FIGS. 19 and 20). Furthermore, eNKG2Ds 5, 7, and 8 had the least amount of aggregation, suggestive of more robust protein assembly upon 293T expression (FIG. 18). eNKG2D5 (SEQ ID NO: 48) was examined more closely for binding to wild-type ligands as MicAbodies captured on Octet AHC tips. Single mutant Fc-NKG2D.Y152A (SEQ ID NO: 41) had reduced binding to all natural ligands relative to natural (SEQ ID NO: 40) NKG2D (FIG. 5). The response curve for binding of eNKG2D5 (Y152A/Y199F) was reduced even further relative to Y152A eNKG2D. eNKG2D5 (Y152A/Y199F, henceforth referred to as "AF" or "NKG2D.AF") was chosen as the lead NKG2D variant for which to engineer cognate selective, orthogonal, non-natural ligands.

Example 4: Constructing Orthogonal Non-Natural α1-α2 Domains with Selective Binding to Non-Natural NKG2D.AF Ectodomain We employed phage display to engineer orthogonal non-natural α1-α2 domains that exhibit selective binding to the NKG2D.AF (SEQ ID NO: 48) receptor. As a starting point, the non-natural ULBP2.R80W α1-α2 domain (FIG. 1B; SEQ ID NO: 108) with high affinity for natural, wild-type NKG2D (NKG2D.wt) ectodomain was selected as the parent domain for further mutagenesis and screening by phage display. Synthetic DNA libraries were generated for the α1-α2 domain of ULBP2.R80W (SEQ ID NO: 108) which additionally has a C8S mutation to eliminate the potential for disulfide linkages. Codons of amino acid residues of the ligand that in the bound state are positioned in close proximity to the Y152 and Y199 positions on the natural NKG2D receptor were replaced with NNK codons; the libraries consisted of NNK codons at positions 154-159 (FIG. 1B; SEQ ID NO: 110). Libraries were cloned as fusions to the pIII minor coat protein of M13 phage, and phage particles displaying the mutagenized α1-α2 domain variants were produced in SS320 *E. coli* cells according to standard methodologies (Andris-Widhopf, J., Steinberger, P., Fuller, R., Rader, C., and Barbas, C. F., 3rd. (2011). These α1-α2 phage display libraries were sorted for high binding affinity to the non-natural NKG2D.AF receptor by selectively capturing phage clones bound to biotinylated Fc-NKG2D.AF protein in the presence of non-biotinylated natural Fc-NKG2D.wt competitor protein. Selective clones were enriched by cycling through multiple rounds of competitive selection with increasing concentrations of the non-biotinylated natural Fc-NKG2D.

After four rounds of selection, phage clones were individually arrayed in 96-well format, spot ELISAs were performed to verify preferred differential binding to plate-bound non-natural NKG2D.AF versus NKG2D.wt. Bound phages were detected with biotinylated M13 phage coat protein monoclonal antibody E1 (ThermoFisher Scientific, Waltham, MA), streptavidin-HRP detection (R&D Systems, Minneapolis, MN), and 1-Step Ultra TMB ELISA development (ThermoFisher Scientific, Waltham, MA). The spot ELISA signal for each clone was expressed as a ratio of phage binding NKG2D.AF to phage binding NKG2D.wt. Those phages with a ratio greater than or equal to 14 were sequenced to identify the specific mutations within the NNK mutagenized regions. FIGS. 21A-21B show the selected amino acid residues for each α1-α2 phage variant that selectively bound NKG2D.AF. In instances where multiple clones representing the same sequence were identified, the ratio of ELISA signals was plotted, and consistency of phage clones was verified by the clustering of data points (data not shown).

Figure 6:
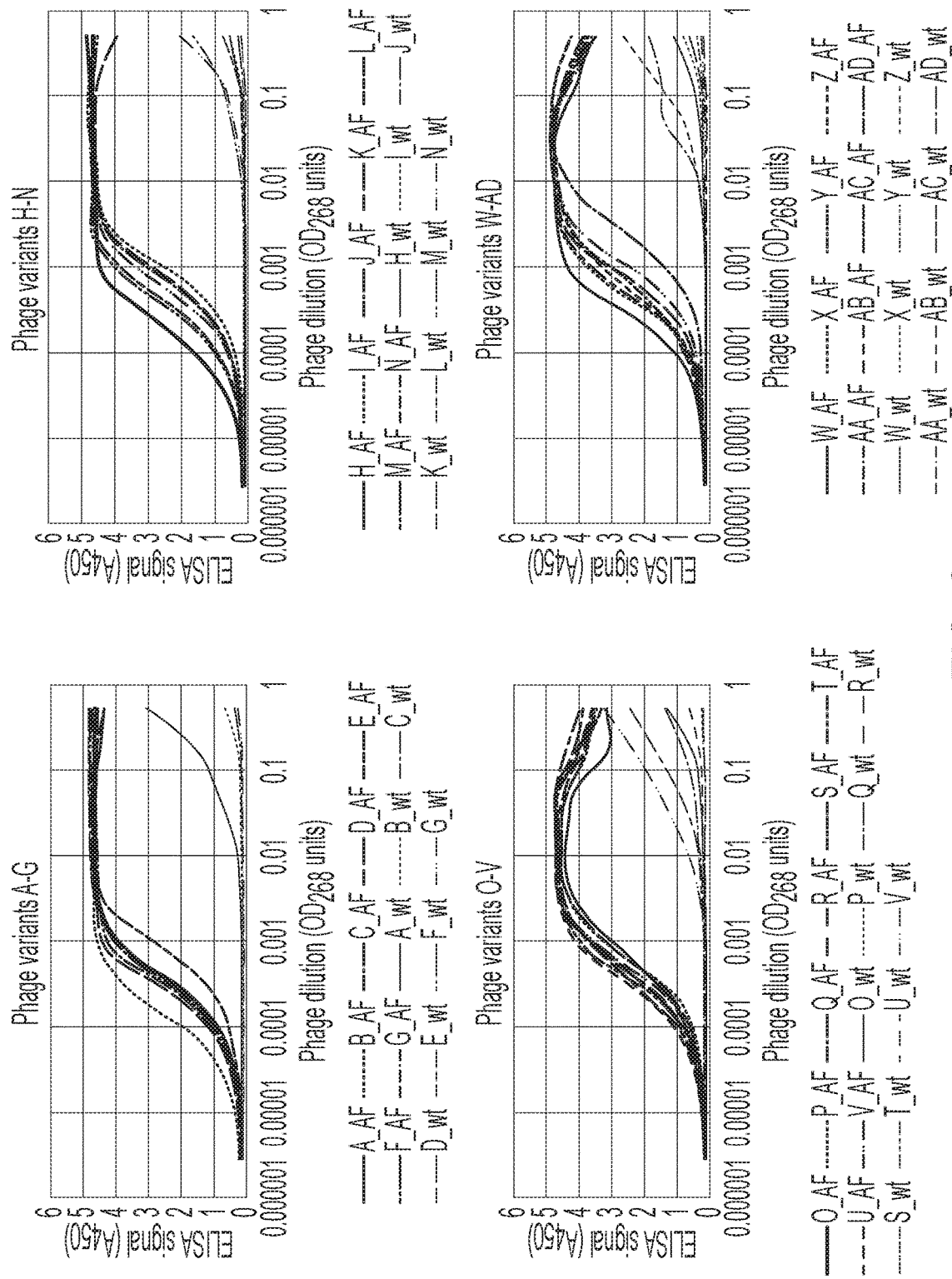
FIG. 6: Titration ELISA of individual phage variants to confirm selective binding to Fc-NKG2D.AF and reduced or eliminated binding to Fc-NKG2D.wt. Mutations are detailed in FIG. 22.

Thirty of the variants identified in ELISAs were expanded in individual monocultures to generate high titer microbatches of phage. Purified phage concentrations were normalized to an $OD_{268}=0.5$ then subject to 1:3 dilution series against plate-bound Fc-NKG2D.AF or Fc-NKG2D.wt with phage detection and ELISA development performed as described above. All thirty variants assayed in this manner consistently demonstrated selective binding to NKG2D.AF with little to no binding to NKG2D.wt (FIG. 6) even at the highest concentrations of phage assayed. The selected phages also exhibited a shift of two or more logs of phage concentration to achieve half-maximal binding between NKG2D.AF and NKG2D.wt.

To confirm that the NKG2D.AF-selective α1-α2 domain variants retained specific binding properties in the context of antibody fusions, 21 variants (FIG. 22; e.g. SEQ ID NOs: 111-118) were cloned as C-terminal fusions with an APTSSSGGGGS linker to the light chain of the rituximab antibody (SEQ ID NOs: 119-126). The resulting fusions were cloned into the mammalian expression vector pD2610-V12 (ATUM, Newark, CA) via Gibson cloning (New England Biolabs Inc., Ipswich, MA) and co-expressed with the heavy chain of the parent antibody (SEQ ID NO: 99) as paired full IgG antibodies. Transient expressions were carried out in Expi293™ cells (ThermoFisher Scientific, Waltham, MA) according to the manufacturer's protocol, and purified using standard protein-A affinity chromatography (cat. no. 20334, Pierce Biotechnology, Rockford, IL). ELISAs measuring the binding of each variant ULBP2 α1-α2 antibody fusions to non-natural Fc-NKG2D.AF and to natural Fc-NKG2D.wt demonstrated their significantly greater binding affinity toward NKG2D.AF relative to the natural NKG2D.wt (FIG. 22). Collectively, these data demonstrated the invention of non-natural, orthogonal α1-α2 domains that possessed high affinity binding to the non-natural NKG2D.AF receptor and significantly reduced binding affinity to the natural NKG2D receptor. Furthermore, fusions of these orthogonal α1-α2 domains to antibody polypeptides retained their selective binding properties and were used, for example, in the context of chimeric antigen receptor (CAR) T cells, to redirect non-natural NKG2D.AF receptors toward specific antigens.

Example 5: Identifying Non-Natural NKG2D Ligands that can Discriminate Between Non-Natural NKG2D Receptor Variants by Selectively Binding One or the Other Phage display to engineer orthogonal non-natural α1-α2 domains with selective binding to NKG2D.Y152A (henceforth referred to as NKG2D.YA) receptor was performed with non-natural ULBP2.R80W α1-α2 domain (SEQ ID NO: 108) as the starting point as described above. The α1-α2 phage display libraries were panned for high binding affinity to the non-natural Fc-NKG2D.YA receptor by selectively capturing phage clones bound to biotinylated Fc-NKG2D.YA (SEQ ID NO: 41) protein in the presence of non-biotinylated natural Fc-NKG2D.wt (SEQ ID NO: 40) competitor protein. Additional phage clone validation work resulted in the identification of variants with preferential binding to Fc-NKG2D.YA versus Fc-NKG2D.wt (FIG. 23). ULBP2.S3 (SEQ ID NO: 127), for example, consistently demonstrated selective binding by ELISA and Octet analysis (both in monomeric His-tagged and bispecific antibody fused format) to non-natural NKG2D.YA relative to natural NKG2D.wt. This represented a distinct form of the invention of non-natural orthogonal α1-α2 domains possessing high affinity binding to non-natural NKG2D receptors (in this case NKG2D.YA as opposed to NKG2D.AF as in Example 4). Furthermore, fusions of orthogonal α1-α2 domains to antibody polypeptides retained their selective binding properties and were used to selectively redirect non-natural NKG2D receptors towards specific molecules determined by fused heterologous peptides such as antibodies.

Figure 7:
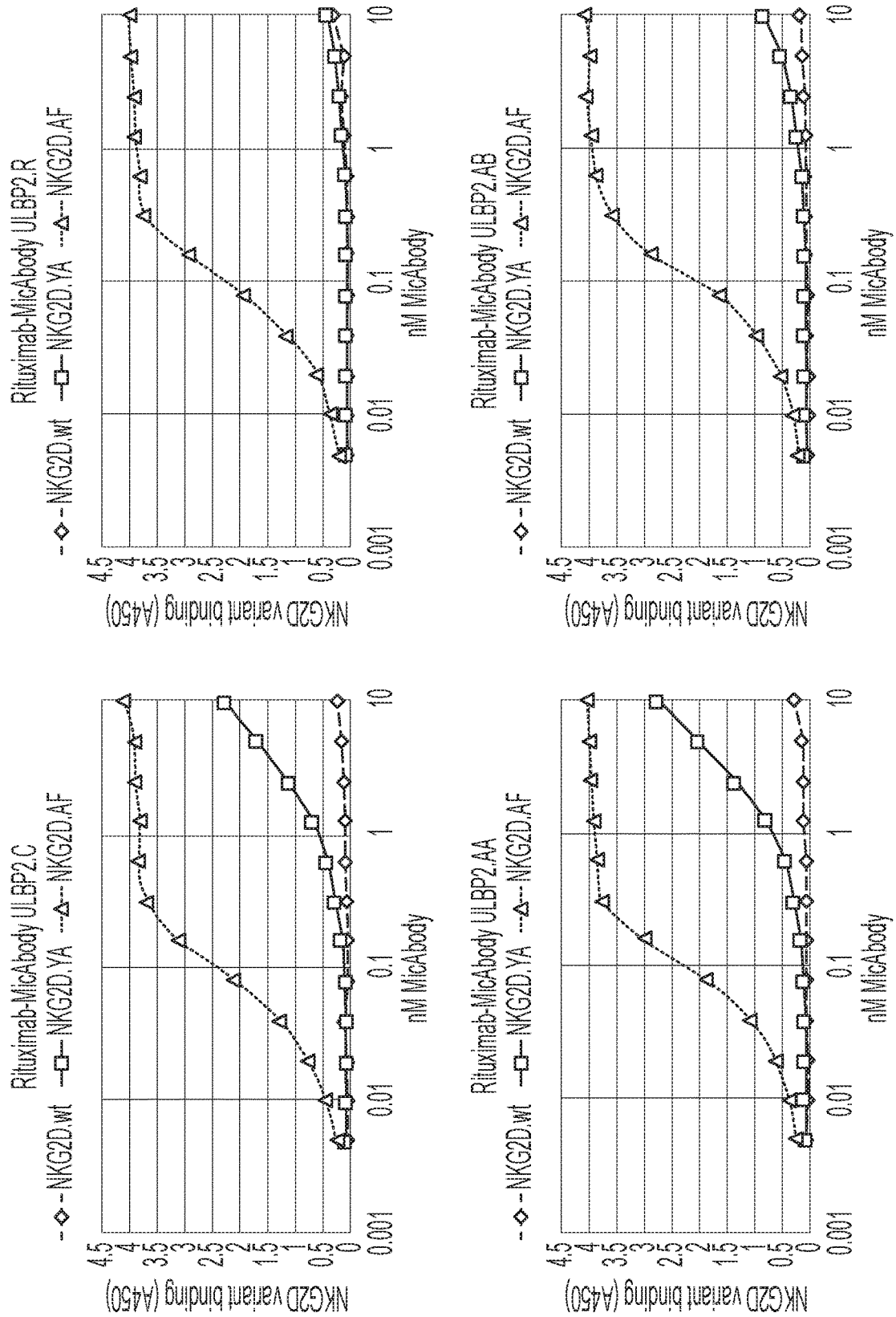
FIG. 7: ELISA data of four non-natural α1-α2 ULBP2 variant MicAbodies binding to NKG2D.wt, NKG2D.YA, and NKG2D.AF. The Fc-NKG2D variants were used as capture agents. MicAbodies were titrated in and detected with HRP-conjugated anti-human kappa.
Figure 9E:
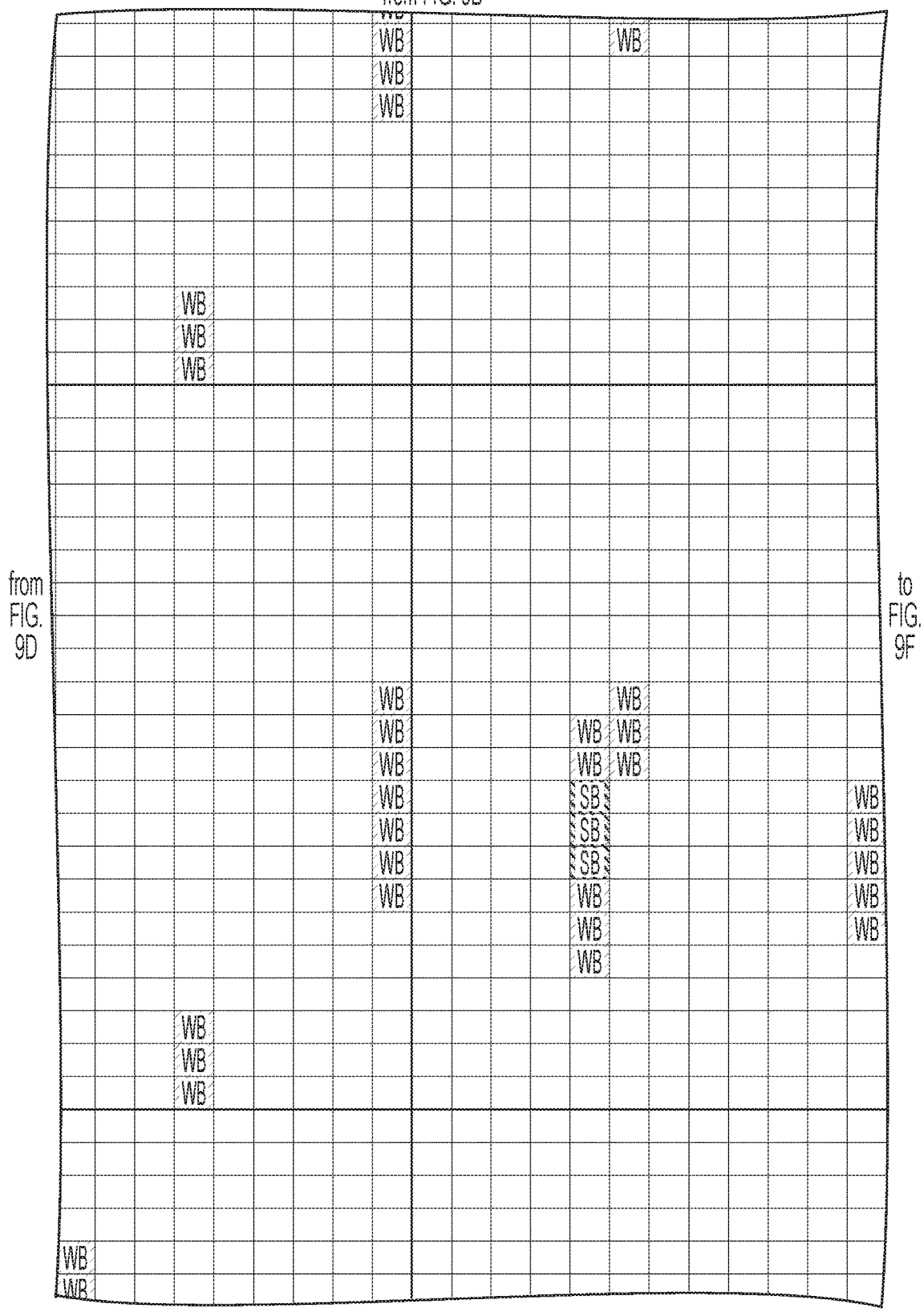
Figure 9F:
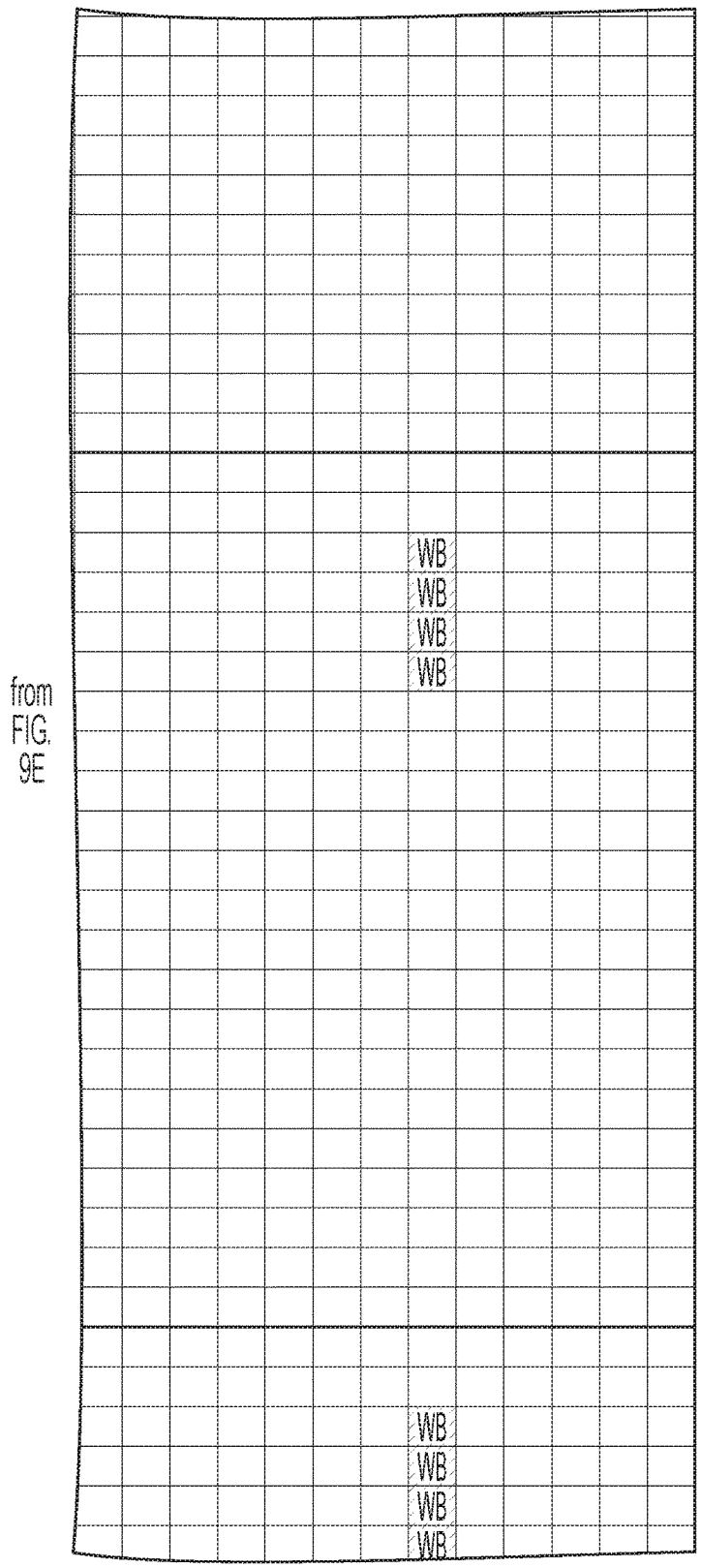
Figure 9G:
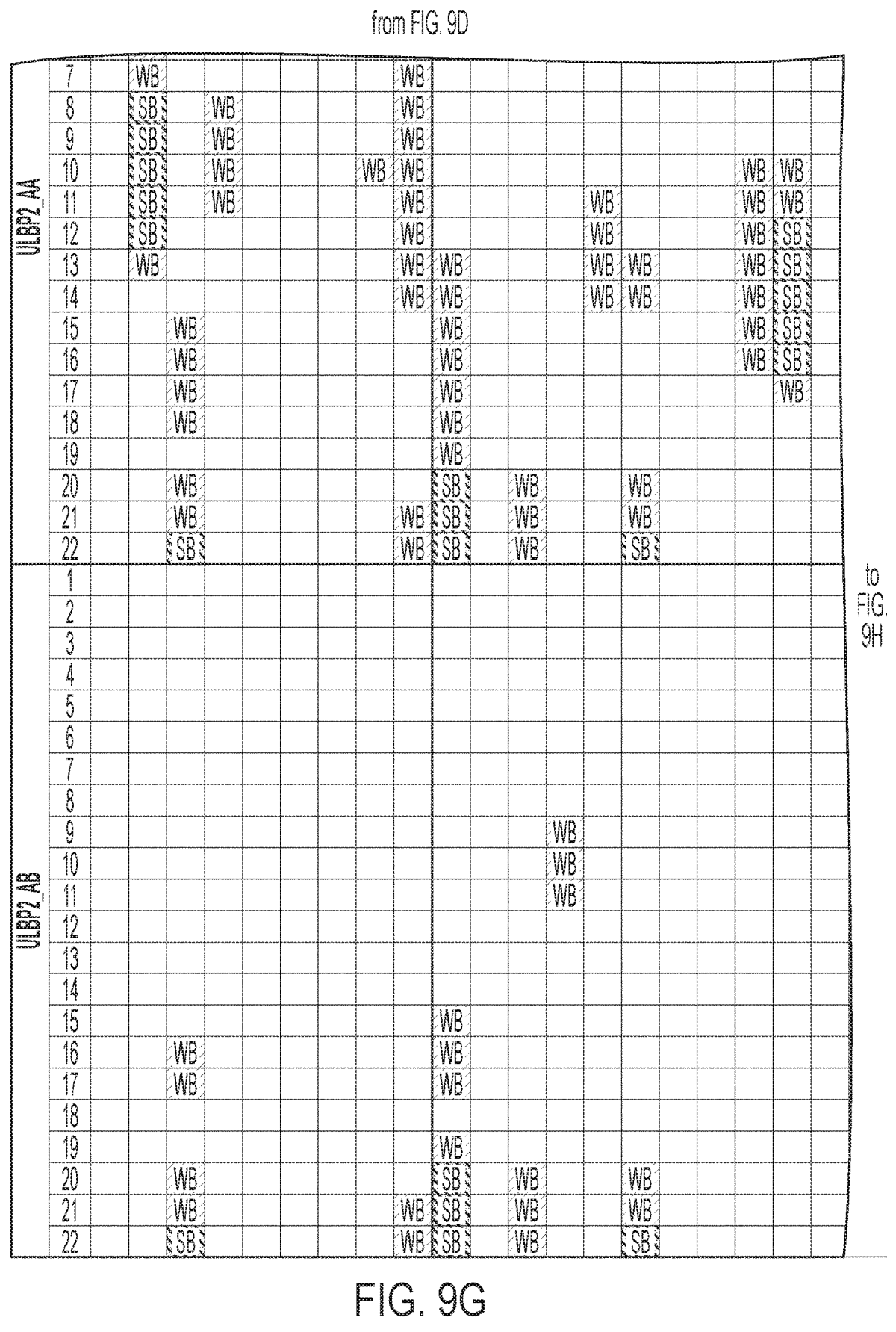
Figure 9H:
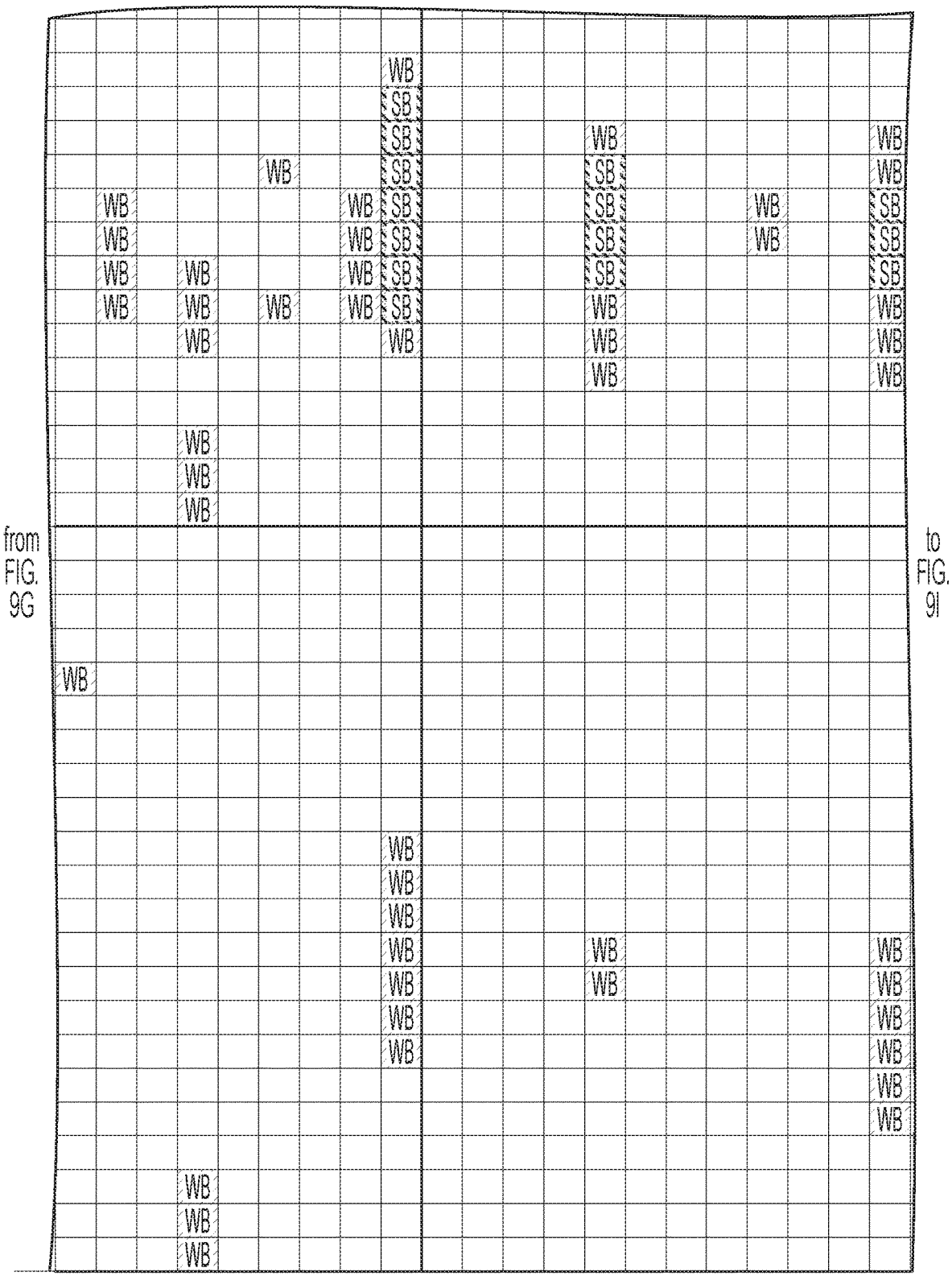
Figure 9I:
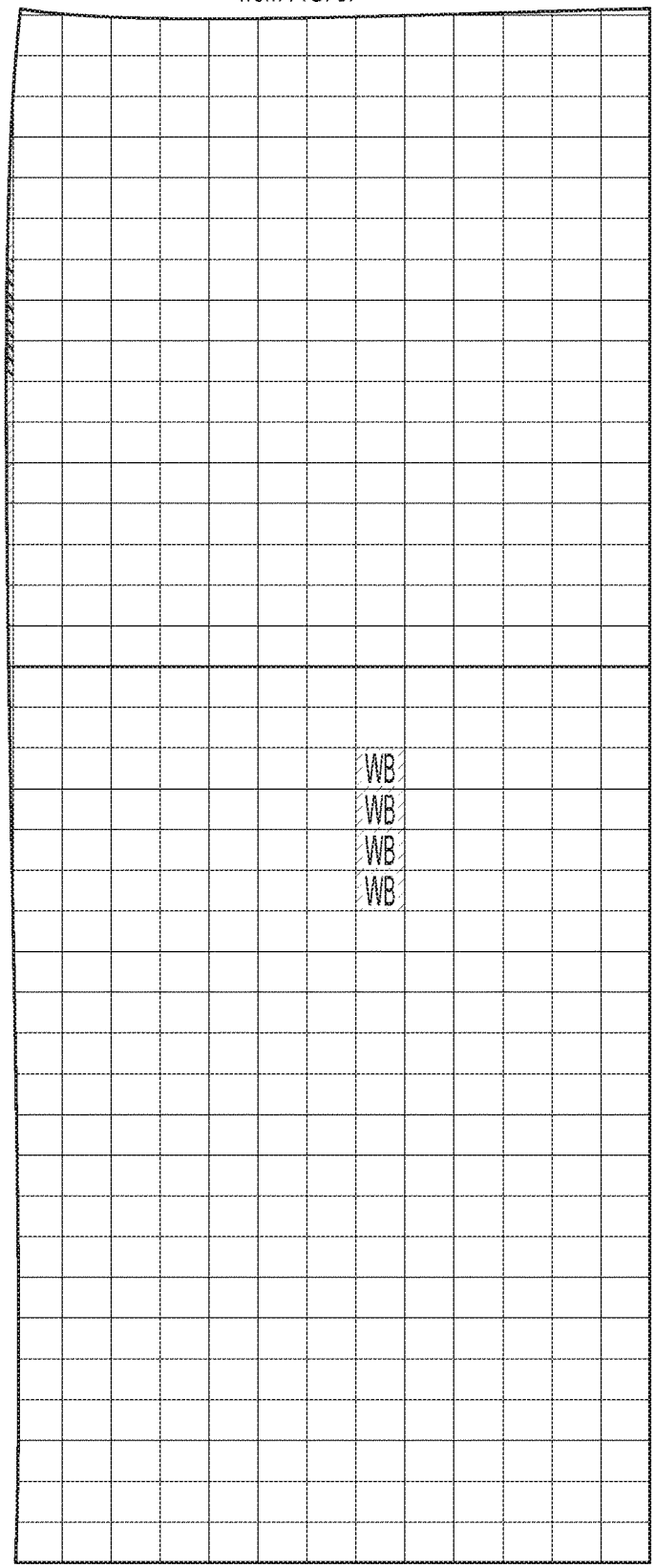
Figures 10A, 10B:
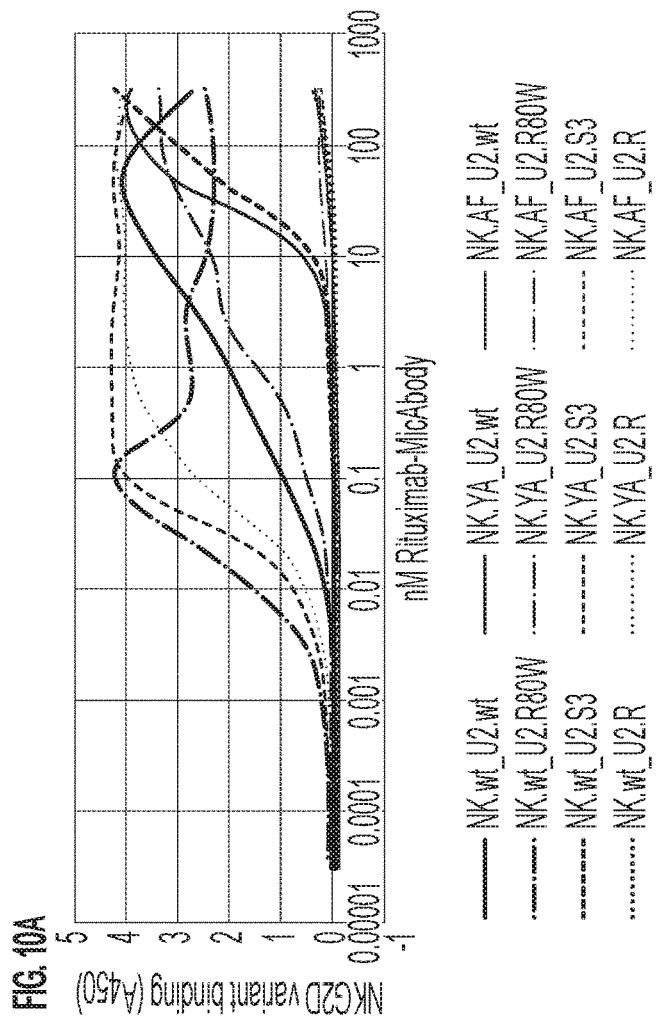
FIGS. 10A-10B: ELISA-measured binding of rituximab-MicAbodies comprised of ULBP2.wt (wild-type), ULBP2.R80W (which has enhanced affinity for wild-type NKG2D), ULPB2.S3 (NKG2D.YA-selected orthogonal variant), or ULBP2.R (NKG2D.AF-selected orthogonal variant) to natural NKG2D.wt, to NKG2D.YA, and to NKG2D.AF.

In order to determine whether a non-natural α1-α2 domain with selective binding to NKG2D.YA (ULBP2.S3, SEQ ID NO: 127) and the non-natural α1-α2 domains with selective binding to NKG2D.AF could discriminate between these two non-natural receptor variants, titration ELISAs were performed. All 21 of the selected α1-α2 variants that bound NKG2D.AF were directly compared for binding to NKG2D.AF versus NKG2D.YA. Of these, four demonstrated the properties of inability to bind NKG2D.wt, strong affinity for NKG2D.AF, and greatly reduced (15-20 fold) or eliminated binding to NKG2D.YA relative to NKG2D.AF (FIG. 7). These four non-natural ULBP2 α1-α2 variants—ULBP2.C, ULBP2.R, ULBP2.AA, and ULBP2.AB (SEQ ID NOs: 111, 113, 115, and 117)—were also examined for alterations in predicted immunogenicity profile relative to the wild-type ULBP2 peptide sequence (SEQ ID NO: 4) using the NetMHC4.0 Server (for peptide-MHC class I binding querying against all the HLA supertype representatives with 9-mer peptide analysis; www.cbs.dtu.dk/services/NetMHC/) and NetM HCII 2.3 Server (for peptide-MHC class II binding querying against HLA-DR, HLA-DQ, HLA-DP haplotypes with 15-mer peptide analysis; www.cbs.dtu.dk/services/NetMHCII/), both algorithms which were developed by the Technical University of Denmark (www.bioinformatics.dtu.dk/; Andreatta M and Nielsen M, Gapped sequence alignment using artificial neural networks: application to the MHC class I system, 2016 Bioinformatics, 32:511, PMID: 26515819; Jensen K K, Andreatta M, Marcatili P, Buus S, Greenbaum J A, Yan Z, Sette A, Peters B, and Nielsen M, Improved methods for predicting peptide binding affinity to MHC class I molecules, 2018 Immunology, PMID: 29315598). The mutations incorporated into ULBP2.C, ULBP2.R, and ULBP2.AB did not increase predicted immunogenicity while that of ULPB2.AA was increased slightly for a few haplotypes (FIGS. 8 and 9). As a consequence of the specificity of ULBP2.R for NKG2D.AF and its lack of predictable immunogenicity, ULBP2.R was selected for further ELISA analysis to directly compare its binding behavior with ULBP2.S3 (the NKG2D.YA-selected, non-natural, orthogonal ligand), ULBP2.R80W (non-natural ligand with enhanced affinity for wild-type NKG2D), and wild-type ULBP2 (ULBP2.wt). Binding of the four rituximab-MicAbody reagents (SEQ ID NOs: 98 and 121, 98 and 129, 131 and 100, and 98 and 106 as heavy chain and light chain for ULBP2.R, ULBP2.S3, ULBP2.R80W, and ULBP2.wt, respectively) was assayed against wild-type NKG2D (NKG2D.wt) and the two inert, non-natural variants NKG2D.YA and NKG2D.AF (FIGS. 10A-106). The data demonstrated that NKG2D.YA-selected variant ULBP2.S3 as a MicAbody bound with high affinity to NKG2D.YA but did not engage NKG2D.AF or natural NKG2D. Furthermore, the NKG2D.AF-selected variant ULBP2.R in MicAbody format bound with high affinity to NKG2D.AF but did not engage NKG2D.YA or natural NKG2D. These results demonstrated the tremendous potential of exploring the NKG2D-MIC ligand axis and for developing unique pairs of novel, selective non-natural NKG2D receptors and their respective, cognate non-natural MIC ligand binding partners.

Example 6: The Targeting and Killing Activity of CAR-T Cells Expressing the Non-Natural NKG2D.AF Ectodomain are Controlled by Orthogonal α1-α2 Domains Fused to Heterologous Targeting Polypeptides Means to selectively control CAR-T cell therapies are highly sought after to mitigate toxicity and improve efficacy against tumors (Gill and June, op cit). Previous attempts have been made to develop CARs using the ectodomain of CD16 which can then be engaged through the Fc domain of therapeutic monoclonal antibodies, allowing for antibody-based control of CAR-T targeting (Chang et al., op cit). However, CD16-based CAR-T cells can recognize nearly all endogenous antibody molecules in blood and tissues, and the therapeutic antibodies used to control these cells will encounter competition from endogenous CD16 receptors on NK cells, PMN's, monocytes and macrophages. Both of these features contribute problems of off-tumor toxicity and poor pharmacokinetics, respectively.

Natural NKG2D ligands are present on certain healthy tissues and many stressed tissues, creating an extreme risk for toxicity using current NKG2D CAR approaches (Van-Seggelen et al. 2015). The Y152A non-natural NKG2D receptor specifically bound to non-natural α1-α2 domain NKG2D ligands constituting an example of a means by which the activity of a non-natural NKG2D CAR could be selectively controlled using bispecific proteins comprised of the invented non-natural α1-α2 domain of NKG2D ligands.

We engineered CAR-T cells with a Receptor comprised of a modified Y152A/Y199F ("AF") ectodomain of NKG2D which lacks binding to all natural NKG2D ligands or previously described non-natural α1-α2 domains orthogonal and cognate to Y152A modified NKG2D (NKG2D.YA). The invented cognate non-natural α1-α2 domains bound with high affinity to the non-natural NKG2D.AF ectodomain and avoided binding to natural NKG2D ectodomains and to the NKG2D.YA ectodomain. Thus, engineered α1-α2 domains that exhibited strong selectivity for non-natural NKG2D.AF ectodomain over natural NKG2D and non-natural NKG2D.YA represent an ideal system for selective control of non-natural NKG2D CAR receptors, or any receptor or protein fused to non-natural NKG2D ectodomains that can be selectively engaged by the non-natural α1-α2 domains of the instant invention. The instant invention further enables single cells expressing two distinct CARs—one comprised of NKG2D.YA and the other of NKG2D.AF—each signaling with distinctly different intracellular domains. These distinct CARs would possess independent, dual controls of the cell's activities by extracellular exposure to the respective, cognate orthogonal MicAbody or another non-antibody fusion polypeptide.

To demonstrate selective control of CAR-T cells constructed with a chimeric receptor deploying the non-natural NKG2D.AF ectodomain, we constructed CARs with either the natural NKG2D.wt (SEQ ID NO: 135), non-natural NKG2D.YA (SEQ ID NO: 137), or the non-natural NKG2D.AF (SEQ ID NO: 139) ectodomains based on previous work using 4-1BB/CD3-zeta CAR constructs (Campana U.S. Pat. No. 8,399,645) fusing the respective NKG2D ectodomains to the CD8 hinge region of CARs (SEQ ID NOs: 151, 153, 155). These constructs (SEQ ID NOs: 152, 154, 156) were cloned into a lentiviral vector and expressed in primary human CD8-positive T cells using lentiviral transduction. HeLa cells have constitutively upregulated levels of MIC ligands on their surface including MICA, MICB, ULBP3, and ULBP2/5/6 (the antibody used to ascertain this cannot distinguish between these three ULBPs; Human ULBP-2/5/6 Antibody, R&D Systems, Minneapolis, MN). HeLa cells were transfected to over-express either natural ULBP1 or the NKG2D.AF-selected variant ULBP2.R on their surface, and these cells were used as a target for in vitro killing assays. HeLa target cells were pre-loaded with calcein and exposed to NKG2D.wt-CAR, NKG2D.YA-CAR, or NKG2D.AF-CAR CD8 cells at increasing effector to target (E:T) ratios for five hours, after which the amount of calcein released into the supernatant was quantified and normalized to the total calcein released upon detergent treatment (FIGS. 11A-11C). Due to the elevated levels of MIC ligands naturally expressed on the surface of HeLa cells, the CD8 cells expressing natural NKG2D (NKG2D.wt) as the CAR engaged the HeLa cells via this over-expressed natural ligand and effected cytolysis. However, both the NKG2D.YA- and NKG2D.AF-CAR transduced CD8 cells demonstrated very little lysis of natural HeLa cells even at high E:T ratios, a level of activity that is on par with untransduced CD8 T cells. When ULBP1 is overexpressed on the surface of HeLa cells, only the NKG2D.wt-CAR CD8 T cells significantly lysed them. There is some additional killing at high E:T ratio with NKG2D.YA-CAR cells, but this is non-existent with NKG2D.AF-CAR cells showing that the double mutation Y152A/Y199F renders NKG2D even more inert than the single Y152A mutation. In HeLa cells over-expressing the NKG2D.AF-selective non-natural ULBP2.R, NKG2D.wt-CAR cells direct lysis (due to recognition of endogenous MIC ligands) while NKG2D.AF-CAR cells directed significant levels of lysis consistent with engagement of the receptor and its selective ligand.

Figure 12A:
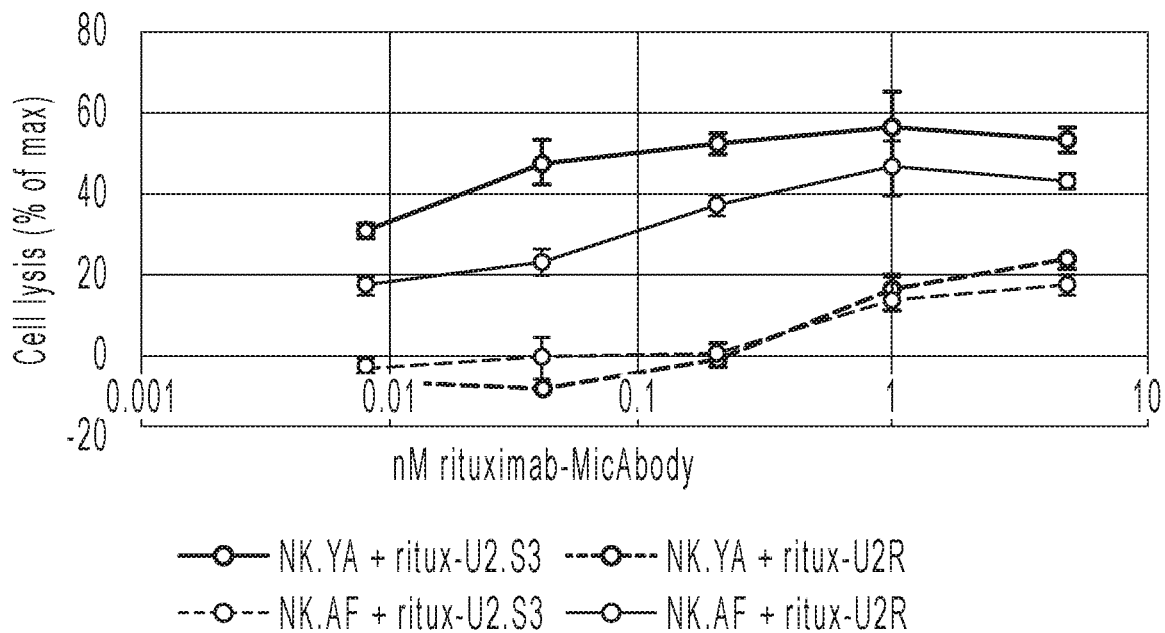
FIGS. 12A-12B: MicAbody directed cytolysis of tumor lines by NKG2D-CAR CD8 T cells.
Figure 12B:
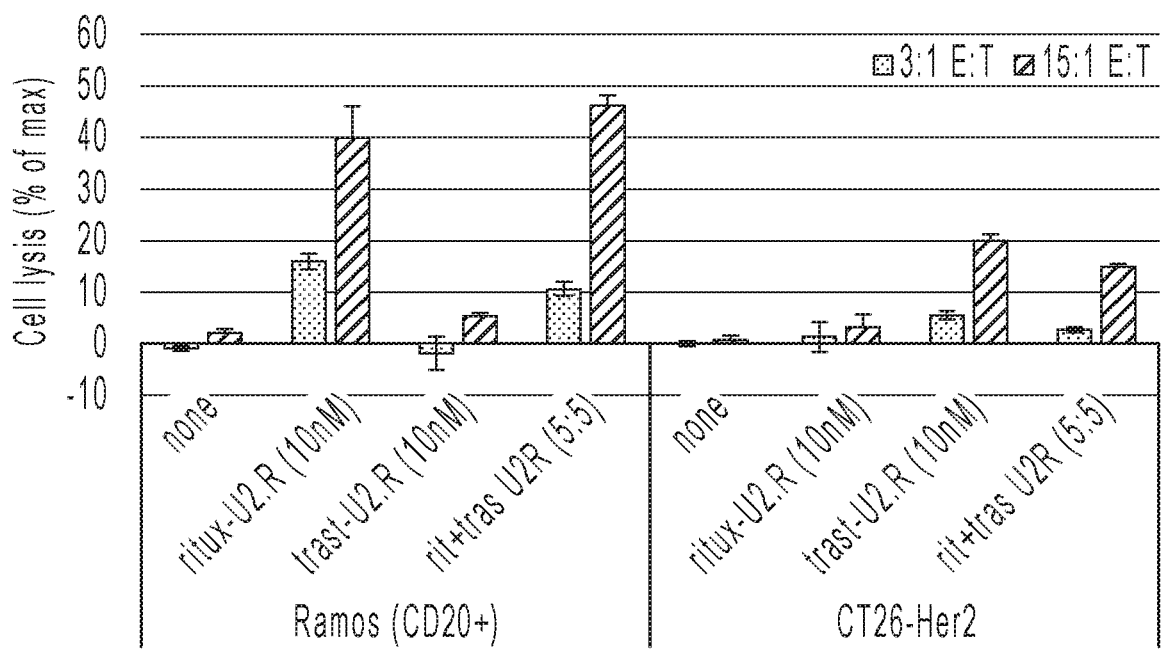

In order to demonstrate that lysis of either NKG2D.YA- or NKG2D.AF-CAR cells could only be directed by the appropriate, cognate targeting MicAbody, Ramos cells were used as a target for cytolysis in combination with rituximab-based MicAbodies linked to either non-natural ULBP2.S3 or ULBP2.R orthogonal ligands. As demonstrated in FIG. 12A, the rituximab-ULBP2.S3 MicAbody could direct the cell killing activity of NKG2D.YA-CAR CD8 cells but not NKG2D.AF-CAR cells, while the rituximab-ULBP2.R MicAbody could direct the activity of NKG2D.AF-CAR but not NKG2D.YA-CAR cells. This further demonstrates the selectivity of the two non-natural ULBP2 variants for their cognate non-natural NKG2D variants for which they were engineered as preferred partners. In order to demonstrate the specificity of the antibody portion of the MicAbody, in vitro killing assays were performed with NKG2D.AF-CAR CD8 T-cells that were pre-armed by incubation with either rituximab-ULBP2.R, trastuzumab-ULPB2.R (SEQ ID NOs: 95 and 133, heavy and light chain, respectively), or an equimolar combination of the two at a saturating total concentration of MicAbody. After unbound MicAbody was removed by washing, the CD8 cells were applied to either Ramos cells (expressing CD20, the target of rituximab) or to CT26-Her2 (a mouse cell line transfected to express human Her2) that had been pre-loaded with calcein. After a two hour incubation at two different E:T ratios, the amount of calcein released was quantified. As shown in FIG. 12B, when cells were pre-armed with rituximab-MicAbody, only Ramos cells were lysed while trastuzumab-MicAbody directed cytolytic activity only against CT26-Her2 cells. However, when NKG2D.AF-CAR CD8 cells were simultaneously pre-armed with both rituximab- and trastuzumab-ULBP2.R MicAbodies, both target cells lines were lysed demonstrating that these CAR cells—by virtue of the selective, privileged partnering that has been engineered between receptor and ligand—were readily multiplexed and thereby directed to engage different tumor targets simultaneously.

Figure 16A:
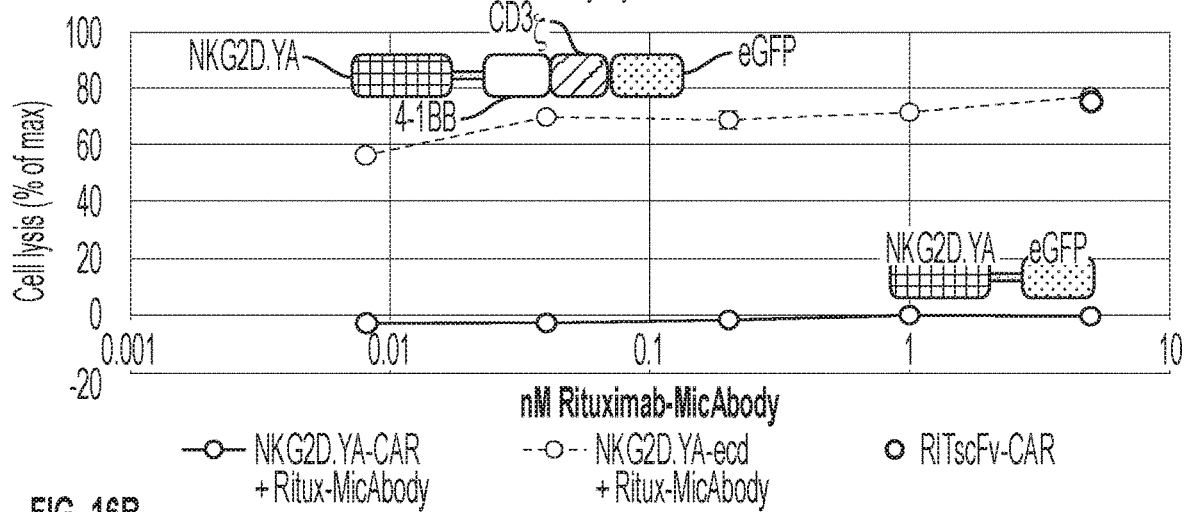
FIGS. 16A-16C: Data exploring sufficiency of the NKG2D.YA ectodomain alone in promoting orthogonal ligand-cytokine-fusion delivery to cells.
Figure 16B:
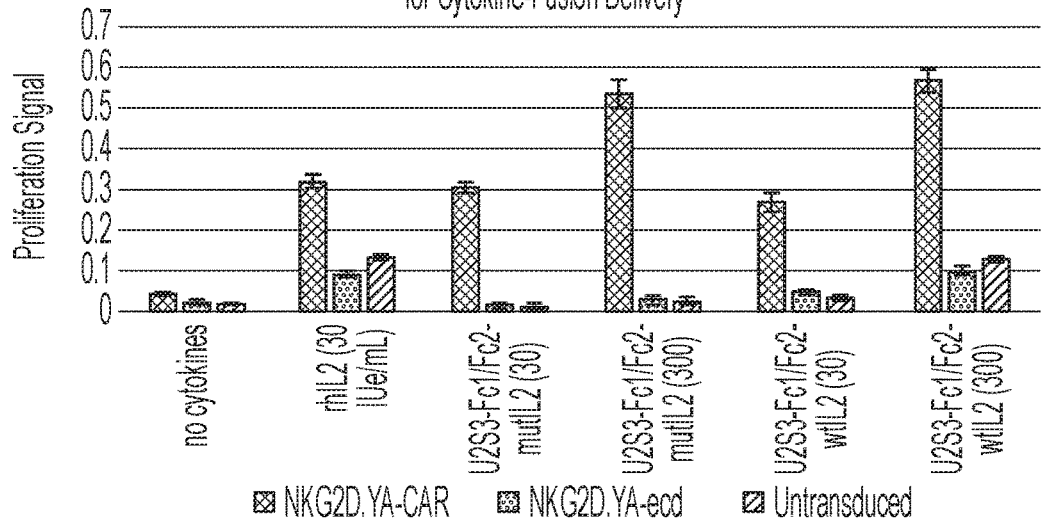
Figure 16C:
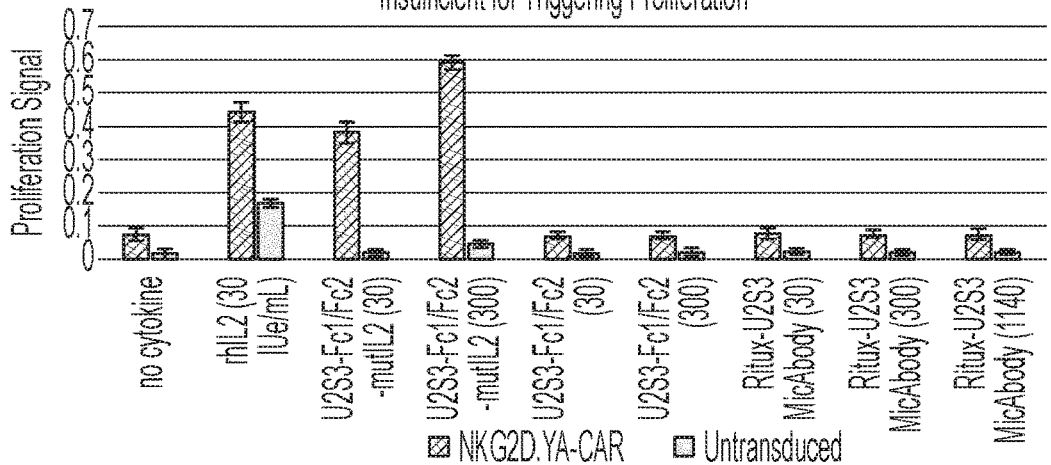

Example 7: Orthogonal α1-α2 Domains as a Means of Selectively Delivering Cytokines to Non-Natural Engineered NKG2D-Expressing T Cells Bispecific MicAbodies (FIG. 13B) utilizing the antigen targeting Fv domains of antibodies and the privileged interaction between orthogonal α1-α2 domains and engineered non-natural NKG2D.YA or NKG2D.AF (SEQ ID NOs: 137 and 139, respectively) can effectively direct the cytolytic capabilities of NKG2D.YA- or NKG2D.AF-CAR bearing T cells (SEQ ID NOs: 153 and 155, respectively) to eliminate antigen-expressing target cells. Additionally, the highly selective interaction between cognate orthogonal ligands and non-natural, modified (also called "engineered") NKG2D (eNKG2D) can be utilized to selectively deliver molecules to eNKG2D-ectodomain (eNKG2D-ecd)-bearing cells. If the heterologous atom or molecule (payload/cargo) to which the orthogonal ligand is fused is inherently bioactive with potentially undesirable functions when delivered to a non-eNKG2D expressing cell, mutations in the bioactive molecule can be explored that reduce interactions with native receptors or targets. When fused with an orthogonal ligand, the final molecule would therefore be effectively inert for all biological function except when cells bearing cognate eNKG2D receptor are present. Only when the high affinity interaction between orthogonal ligand and eNKG2D receptor occurs is interaction between the affinity-reduced mutant of the bioactive molecule and its natural target or receptor encouraged and residual function of the bioactive molecule enabled. All orthogonal ligand fusions to entities for the purpose of directing them to eNKG2D-expressing cells are collectively referred to as MicAdaptors and can, in principle, take the form of direct protein fusions as a single polypeptide between the payload and the orthogonal ligand at either the N- or C-terminus with or without a linker or tag (e.g. His tag) for assays or purification (FIG. 13C). Additionally, if enhanced serum stability is desired the antibody Fc domain may be included either as just the CH2-CH3 domains or in the format of a complete antibody, depending upon the desired number of unique payloads, the valency of either orthogonal ligand or heterologous cargo, and general experimentally determined architecture that promotes the greatest functionality of all components (FIG. 13D).

To determine whether cytokines can be selectively delivered to NKG2D.YA-CAR expressing cells (SEQ ID NO: 153), the cognate orthogonal ligand ULBP2.S3 (U2S3, SEQ ID NO: 127) was expressed fused to the N-terminus of Fc1 which has been altered to at two residues to express negatively charged aspartic acid residues at the interface of Fc homo-dimerization (SEQ ID NO: 189). A mutant form of human IL2 (mutIL2), containing two mutations R38A/F42K that significantly reduced the affinity of the cytokine to IL2R-alpha complex (K. M. Heaton, G. Ju, and E. A. Grimm, Human Interleukin 2 Analogues That Preferentially Bind the Intermediate-Affinity Interleukin 2 Receptor Lead to Reduced Secondary Cytokine Secretion: Implications for the Use of These Interleukin 2 Analogues in Cancer Immunotherapy, 1993 Cancer Res 53:2597, PMID: 8495422; K. Sauvé et al., Localization in Human Interleukin 2 of the Binding Site to the Alpha Chain (P55) of the Interleukin 2 Receptor, 1991 PNAS 88:4636, PMID: 2052547), was fused to the C-terminus of Fc2 which had been altered at two residues to express positively charged lysine residues at the interface of Fc homo-dimerization (SEQ ID NO: 183). Both were cloned independently into the mammalian expression vector pD2610-V12 (ATUM, Newark, CA), co-transfected into Expi293™ cells (ThermoFisher Scientific, Waltham, MA) according to the manufacturer's protocol, and purified using standard protein-A affinity chromatography (cat. no. 20334, Pierce Biotechnology, Rockford, IL). Purified material was fractionated by size-exclusion chromatography (SEC) on Akta Pur Superdex columns. The negatively charged residues on Fc1 and the positive charges on Fc2 provided an electrostatic steering effect (Kannan Gunasekaran et al., Enhancing Antibody Fc Heterodimer Formation through Electrostatic Steering Effects: Applications to Bispecific Molecules and Monovalent IgG, 2010 J Biol Chem 285:19637, PMID: 20400508) that promoted heterodimeric assembly of a molecule that was mono-valent for the orthogonal U2S3 ligand and mutIL2 (FIG. 13D, antibody (a)). Additionally, MicAdaptors comprised of other combinations of ULBP2 orthogonal ligands with cytokine fusions were explored—either as heterodimeric Fc1/Fc2 fusions or as a single polypeptide where both components were directly fused—and their DNAs similarly cloned, co-expressed, and purified as detailed in FIG. 24 and as described above. Recombinant human IL2 (rhIL2, Peprotech) and recombinant human IL15 (rhIL15, Peprotech) were included as controls in assays as needed.

CD8 human T cells were transduced to express either the NKG2D.wt-CAR construct (SEQ ID NO: 151) or the NKG2D.YA-CAR construct (SEQ ID NO: 153) and exposed to 30 lUe/mL of control cytokine or various MicAdaptors for three days and the level of cell proliferation quantified with the WST-1 Cell Proliferation Reagent (Millipore Sigma). Control rhIL2 promoted proliferation of both CAR-expressing cell while mutIL2 alone did not as would be expected from reduced ability to engage IL2R-alpha and therefore reduced ability to signal through IL2R-beta/gamma-C (FIG. 15A). When the MicAdaptor was comprised of the non-selective U2R80W ligand (U2R80W-mutIL2, SEQ ID NO: 177), which engaged with high affinity to both wild-type and the modified NKG2D.YA receptors, cells expressing either of the CARs responded by proliferating. However, when the mutIL2 was fused to an orthogonal ligand, such as ULBP2.S2 (SEQ ID NO: 179) that selectively engages only NKG2D.YA, the MicAdaptor, U2S2-mutIL2) that only engages with NKG2D.YA, only NKG2D.YA-CAR cells responded by proliferating. Similar results were obtained when the cytokine fused to U2S2 was a mutant version of IL15 with a V49D mutation (Bernard, J. et al., Identification of an Interleukin-15a Receptor-binding Site on Human Interleukin-15, 2004 Journal of Biological Chemistry, 279: 24313, PMID: 15039446) that reduced engagement with IL15R-alpha (FIG. 15A). When NKG2D.YA-CAR-T cells were co-cultured for seven days with these reagents, the % GFP+(indicative of the percentage of CAR-expressing cells present as compared to the untransduced, GFP-negative cells) increased but only when the orthogonal ULBP2.S2 ligand (U2S2-mutIL2 or U252-Fc1/Fc2-mutIL2, FIG. 24 for SEQ ID NOs) was present and not with the non-selective U2R80W variant (which bound natural wild-type NKG2D receptor constitutively present on human CD8 cells) (FIG. 15B). IL21 was also explored as either a wild-type fusion (IL21.wt), with single mutations that affected IL21R-alpha binding (D18A or E109R), or a version with both mutations included (D18A/E109R) (Kang, L. et al., Rational Design of Interleukin-21 Antagonist through Selective Elimination of the γC Binding Epitope, 2010 Journal of Biological Chemistry, 285:12223, PMID: 20167599). In a comparison between untransduced CD8 cells or NKG2D.YA-CAR-expressing cells, only NKG2D.YA-bearing cells responded to all versions of IL21 fusions (see FIG. 24 for SEQ ID NOs), including to the IL21.wt fusion (FIG. 15C). Interestingly, while both untransduced and NKG2D.YA-CAR cells expanded in response to rhIL2 as compared to the no cytokine control, the amount of proliferation was higher with NKG2D.YA-CAR cells. The proliferative response of NKG2D.YA-CAR expressing cells was independent of a generalized binding or engagement of the NKG2D.YA domain since a U253-Fc1/Fc2 (heterodimeric Fc molecule with a single U2S3 domain and no attached cytokines or cytokine mutants) and the ritixumab-MicAbody (bivalent for the U2S3 domain but lacking any cytokine component, FIG. 13B, MicAbody (b)) did not induce proliferation over the course of three days of culture, even at lUe/mL concentrations much higher than with the rhIL2 control (FIG. 16C).

Example 8: Presence of Intracellular Costimulatory Domains, Either in Cis or Trans, Promotes the Responsiveness of Non-Natural, Modified NKG2D-Bearing Cells to Cytokines and Cytokine MicAdaptors Upon demonstration that the modified NKG2D.YA domain, in the context of a chimeric antigen receptor construct, did in fact serve as a highly selective docking site for delivery of heterologous cargo attached to an orthogonal ligand, we sought to determine if the NKG2D.YA receptor was not only necessary but also sufficient for targeted delivery of cytokines that could then act on the receiving cell. The NKG2D.YA extracellular domain (NKG2D.YA-ecd) was expressed as a transmembrane domain stripped of all intracellular components with the exception of the retention of an intracellular eGFP tag (FIG. 14, SEQ ID NO: 157). CD8 cells were transduced to express this "silent CAR" and demonstrated to be unable to direct killing of Ramos target cells in the presence of a rituximab-ULBP2.S3 MicAbody (SEQ ID NOs: 98 and 129) as would be expected without costimulatory domains (FIG. 16A). Importantly, cells expressing this completely inert or silent CAR did not proliferate when exposed to U253-Fc1/Fc2-mutIL2 (SEQ ID NOs: 189 and 193), but responded at a level comparable to untransduced cells (FIG. 16B). This observation—in addition to (a) the consistent observation of greater levels of NKG2D.YA-CAR proliferation with rhIL2 compared to untransduced cells (FIGS. 15C, 16B, 16C) and (b) the observation that only NKG2D.YA-CAR cells responded to all forms of IL21-MicAdaptor including IL21.wt—led us to speculate that the intracellular domains present in the NKG2D.YA-CAR construct enhanced responsiveness to these cytokines and cytokine MicAdaptors.

Figure 17A:
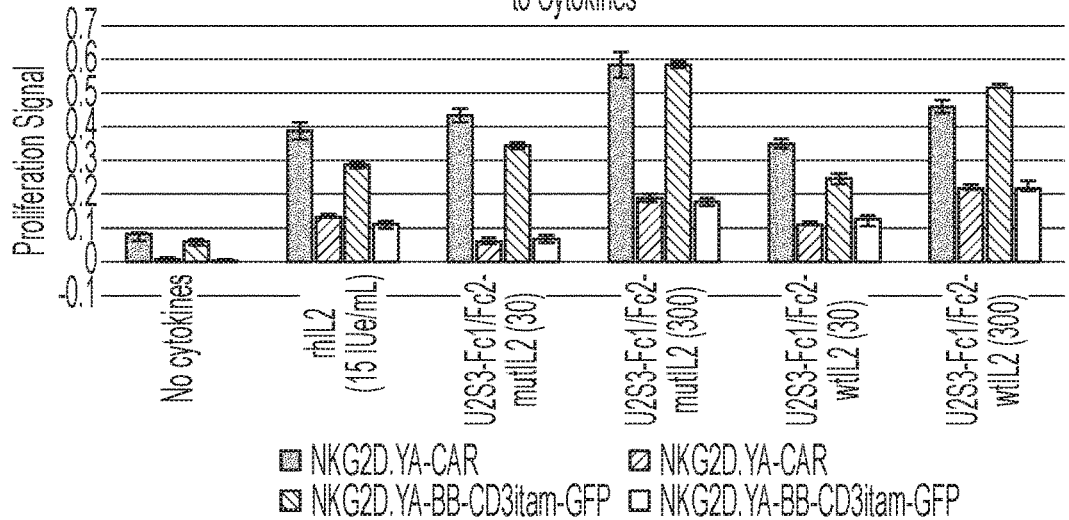
FIGS. 17A-17C.
Figure 17B:
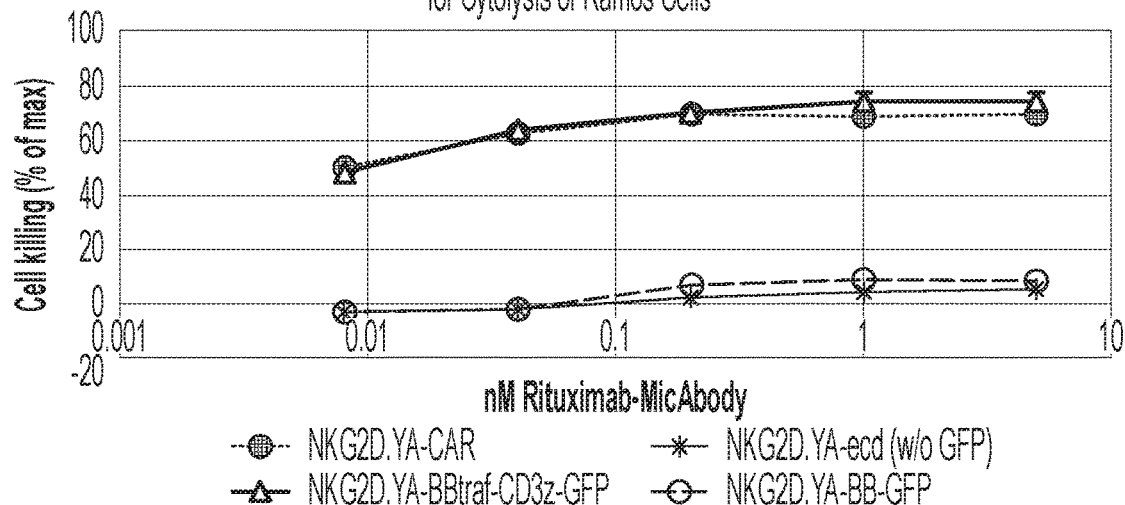

To examine this, a series of CAR constructs were generated where the signaling motifs of the intracellular domains of the CAR were mutated—either the two TRAF2 consensus-binding sites of 4-1BB (SEQ ID NO: 161), the three pairs of ITAM motifs in CD3-zeta (SEQ ID NO: 163), or combined 4-1BB/CD3-zeta mutants (SEQ ID NO: 165). These constructs (FIG. 14) were transduced into CD8 cells, co-incubated with the indicated cytokine reagents and proliferation quantified after three days (FIG. 17A). NKG2D.YA-BB-CD3$_{\Delta ITAM}$-GFP (SEQ ID NO: 163) retained a proliferative response on par with NKG2D.YA-CAR under all conditions tested, thereby demonstrated that the CD3-zeta domain (SEQ ID NO: 145) is dispensable for responsiveness to both cytokines and cytokine-MicAdaptors in the context of a CAR. However, NKG2D.YA-BB$_{\Delta TRAF2}$-CD3zeta-GFP receptor-expressing cells (SEQ ID NO: 161) had significantly reduced responsiveness to all cytokines and cytokine-MicAdaptors as did the NKG2D.YA-BB$_{\Delta TRAF2}$-CD3$_{\Delta ITAM}$-GFP (SEQ ID NO: 165) receptor bearing mutations in both intracellular domains. This indicated that the costimulatory 4-1BB (SEQ ID NO: 143) played a role in responsiveness of NKG2D.YA-CAR cells to both cytokines and cytokine-MicAdaptors and that a silent CAR expressed on a cell surface needed to also have the an intracellular costimulatory domain present to promote cytokine-MicAdaptor responsiveness. The inability of an NKG2D.YA-BB silent CAR (SEQ ID NO: 169, FIG. 14) to direct MicAbody-mediated cell killing (FIG. 17B) demonstrated that this CAR architecture that lacked CD3-zeta was suitable as the silent docking site for MicAdaptors and enabled cytokine-MicAdaptors signaling but did not function to mediate cytolysis of a MicAbody targeted cell.

Figure 17C:
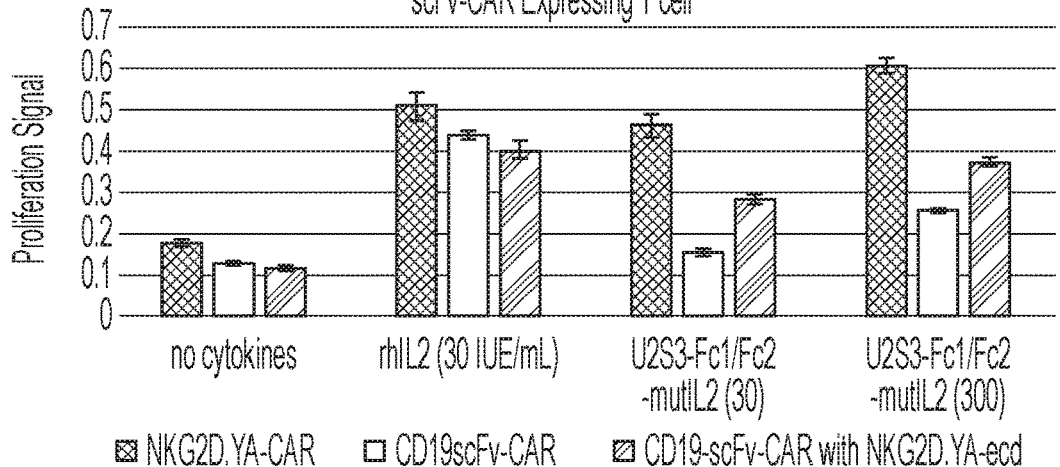

To further explore how the 4-1BB domain contributes to cytokine and cytokine-MicAdaptor responsiveness, a construct was generated where a CD19scFv-CAR (based on FMC63 Fv's), containing the full complement of functional 4-1BB and CD3-zeta domains (SEQ ID NO: 173). The CD19scFv-CAR was co-expressed with the NKG2D.YA-ecd (FIG. 14). Both components were expressed as a single polypeptide with a T2A self-cleaving peptide motif separating the upstream CD19scFv-CAR construct from the downstream NKG2D.YA-ecd which possessed an independent GMCSFR alpha chain signal sequence, CD8a hinge, and CD8a transmembrane domain. This construct was transduced into CD8 T-cells, and the co-expression of the CD19scFv-CAR and the NKG2D.YA-ecd on the surface was verified by flow cytometry examining GFP signal and phycoerythrin-conjugated MicAbody staining, respectively. These cells were incubated for three days with cytokines and cytokine-MicAdaptors and proliferation quantified by WST assay. The NKG2D.YA-CAR responded to both rhIL2 and U253-Fc1/Fc2-mutIL2 as expected although control cells harboring only the CD19scFv-CAR (SEQ ID NO: 171) expanded with rhIL2 and to a lesser degree to the highest concentration (300 IUe/mL) of U253-Fc1/Fc2-mutIL2 (FIG. 17C). Coexpression of the NKG2D.YA-ecd on CD19scFv-CAR expressing cells (SEQ ID NO: 173) exhibited greater proliferative response to the U253-Fc1/Fc2-mutIL2 cytokine-MicAdaptor than cells expressing only CD19scFv-CAR (SEQ ID NO: 171). In this context, the 4-1BB domain was constitutively provided in trans to NKG2D.YA-ecd. These data demonstrated that responsiveness of NKG2D.YA-ecd expressing cells to cytokines and cytokine-MicAdaptors was promoted by the 4-1BB domain either in cis or trans and that the NKG2D.YA-ecd domain can be coexpressed with a costimulatory 4-1BB-containing CAR cell to provide added versatile functionality to engineered cells of adoptive cell therapy strategies. This functionality is not only limited to engagement of surface receptors upon ligand/silent CAR engagement, but could be extended to intracellular delivery by incorporating cytoplasmic sequence motifs (K. N. Pandey, Functional roles of short sequence motifs in the endocytosis of membrane receptors, 2009 Front Biosci, 14:5339, PMID: 19482617) that promote the turnover of non-natural NKG2D variants such that any bound MicAdaptor would be co-internalized and the heterologous cargo delivered intracellularly.

What is claimed is:

1. A non-natural, modified NKG2D receptor comprising a human NKG2D ectodomain that comprises a substitution at position 152 selected from alanine, serine, threonine or valine and/or a substitution at residue 199 which is phenylalanine, wherein the receptor is attached to a mammalian cell, and wherein the receptor binds to non-natural, modified α1-α2 domains of NKG2D ligands but not to natural ligands of NKG2D, and wherein the modified NKG2D receptor does not comprise an active CD3-zeta intracellular signaling domain and does not activate intracellular signaling in the mammalian cell upon formation of an immunological synapse.

2. The non-natural, modified NKG2D receptor of claim 1, wherein the modified NKG2D receptor further comprises a costimulatory domain.

3. The non-natural, modified NKG2D receptor of claim 2, wherein the costimulatory domain is a 4-1 BB costimulatory domain.

4. The non-natural, modified NKG2D receptor of claim 1 wherein the human NKG2D ectodomain comprises the amino acid sequence of any one of SEQ ID NOs: 18-25 and 27-29.

* * * * *

SEQUENCE LISTING

<160> NUMBER OF SEQ ID NOS: 202

<210> SEQ ID NO 1
<211> LENGTH: 183
<212> TYPE: PRT
<213> ORGANISM: Artificial sequence
<220> FEATURE:
<223> OTHER INFORMATION: Synthetic peptide MICA alpha1-alpha2 domain

<400> SEQUENCE: 1

```
Ala Ala Glu Pro His Ser Leu Arg Tyr Asn Leu Thr Val Leu Ser Trp
1               5                   10                  15

Asp Gly Ser Val Gln Ser Gly Phe Leu Thr Glu Val His Leu Asp Gly
                20                  25                  30

Gln Pro Phe Leu Arg Cys Asp Arg Gln Lys Cys Arg Ala Lys Pro Gln
            35                  40                  45

Gly Gln Trp Ala Glu Asp Val Leu Gly Asn Lys Thr Trp Asp Arg Glu
        50                  55                  60

Thr Arg Asp Leu Thr Gly Asn Gly Lys Asp Leu Arg Met Thr Leu Ala
65                  70                  75                  80

His Ile Lys Asp Gln Lys Glu Gly Leu His Ser Leu Gln Glu Ile Arg
                85                  90                  95

Val Cys Glu Ile His Glu Asp Asn Ser Thr Arg Ser Ser Gln His Phe
            100                 105                 110

Tyr Tyr Asp Gly Glu Leu Phe Leu Ser Gln Asn Leu Glu Thr Lys Glu
        115                 120                 125

Trp Thr Met Pro Gln Ser Ser Arg Ala Gln Thr Leu Ala Met Asn Val
130                 135                 140

Arg Asn Phe Leu Lys Glu Asp Ala Met Lys Thr Lys Thr His Tyr His
145                 150                 155                 160

Ala Met His Ala Asp Cys Leu Gln Glu Leu Arg Arg Tyr Leu Lys Ser
                165                 170                 175

Gly Val Val Leu Arg Arg Thr
            180
```

<210> SEQ ID NO 2
<211> LENGTH: 182
<212> TYPE: PRT
<213> ORGANISM: Artificial sequence
<220> FEATURE:
<223> OTHER INFORMATION: Synthetic peptide MICB alpha1-alpha2 domain

<400> SEQUENCE: 2

```
Ala Glu Pro His Ser Leu Arg Tyr Asn Leu Met Val Leu Ser Gln Asp
1               5                   10                  15

Glu Ser Val Gln Ser Gly Phe Leu Ala Glu Gly His Leu Asp Gly Gln
                20                  25                  30

Pro Phe Leu Arg Tyr Asp Arg Gln Lys Arg Arg Ala Lys Pro Gln Gly
            35                  40                  45

Gln Trp Ala Glu Asp Val Leu Gly Ala Lys Thr Trp Asp Thr Glu Thr
        50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95

Cys Glu Ile His Glu Asp Ser Ser Thr Arg Gly Ser Arg His Phe Tyr
            100                 105                 110
```

```
Tyr Asp Gly Glu Leu Phe Leu Ser Gln Asn Leu Glu Thr Gln Glu Ser
            115                 120                 125

Thr Val Pro Gln Ser Ser Arg Ala Gln Thr Leu Ala Met Asn Val Thr
        130                 135                 140

Asn Phe Trp Lys Glu Asp Ala Met Lys Thr Lys Thr His Tyr Arg Ala
145                 150                 155                 160

Met Gln Ala Asp Cys Leu Gln Lys Leu Gln Arg Tyr Leu Lys Ser Gly
                165                 170                 175

Val Ala Ile Arg Arg Thr
            180

<210> SEQ ID NO 3
<211> LENGTH: 187
<212> TYPE: PRT
<213> ORGANISM: Artificial sequence
<220> FEATURE:
<223> OTHER INFORMATION: Synthetic peptide ULBP1 alpha1-alpha2 domain

<400> SEQUENCE: 3

Ala Ala Glu Pro His Cys Leu Cys Tyr Asp Phe Ile Ile Thr Pro Lys
1               5                   10                  15

Ser Arg Pro Glu Pro Gln Trp Cys Glu Val Gln Gly Leu Val Asp Glu
            20                  25                  30

Arg Pro Phe Leu His Tyr Asp Cys Val Asn His Lys Ala Lys Ala Phe
        35                  40                  45

Ala Ser Leu Gly Lys Lys Val Asn Val Thr Lys Thr Trp Glu Glu Gln
    50                  55                  60

Thr Glu Thr Leu Arg Asp Val Val Asp Phe Leu Lys Gly Gln Leu Leu
65                  70                  75                  80

Asp Ile Gln Val Glu Asn Leu Ile Pro Ile Glu Pro Leu Thr Leu Gln
                85                  90                  95

Ala Arg Met Ser Cys Glu His Glu Ala His Gly His Gly Arg Gly Ser
            100                 105                 110

Trp Gln Phe Leu Phe Asn Gly Gln Lys Phe Leu Leu Phe Asp Ser Asn
        115                 120                 125

Asn Arg Lys Trp Thr Ala Leu His Pro Gly Ala Lys Lys Met Thr Glu
    130                 135                 140

Lys Trp Glu Lys Asn Arg Asp Val Thr Met Phe Phe Gln Lys Ile Ser
145                 150                 155                 160

Leu Gly Asp Cys Lys Met Trp Leu Glu Glu Phe Leu Met Tyr Trp Glu
                165                 170                 175

Gln Met Leu Asp Pro Thr Lys Pro Pro Met Val
            180                 185

<210> SEQ ID NO 4
<211> LENGTH: 189
<212> TYPE: PRT
<213> ORGANISM: Artificial sequence
<220> FEATURE:
<223> OTHER INFORMATION: Synthetic peptide ULBP2 alpha1-alpha2 domain

<400> SEQUENCE: 4

Ala Ala Glu Pro His Ser Leu Cys Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
        35                  40                  45
```

```
Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Arg
 65                  70                  75                  80

Asp Ile Gln Leu Glu Asn Tyr Thr Pro Lys Glu Pro Leu Thr Leu Gln
                 85                  90                  95

Ala Arg Met Ser Cys Glu Gln Lys Ala Glu Gly His Ser Ser Gly Ser
                100                 105                 110

Trp Gln Phe Ser Phe Asp Gly Gln Ile Phe Leu Leu Phe Asp Ser Glu
            115                 120                 125

Lys Arg Met Trp Thr Thr Val His Pro Gly Ala Arg Lys Met Lys Glu
            130                 135                 140

Lys Trp Glu Asn Asp Lys Val Val Ala Met Ser Phe His Tyr Phe Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro Pro Met Val
            180                 185
```

<210> SEQ ID NO 5
<211> LENGTH: 187
<212> TYPE: PRT
<213> ORGANISM: Artificial sequence
<220> FEATURE:
<223> OTHER INFORMATION: Synthetic peptide ULBP3 alpha1-alpha2 domain

<400> SEQUENCE: 5

```
Ala Ala Glu Pro His Ser Leu Trp Tyr Asn Phe Thr Ile Ile His Leu
 1               5                  10                  15

Pro Arg His Gly Gln Gln Trp Cys Glu Val Gln Ser Gln Val Asp Gln
                20                  25                  30

Lys Asn Phe Leu Ser Tyr Asp Cys Gly Ser Asp Lys Val Leu Ser Met
            35                  40                  45

Gly His Leu Glu Glu Gln Leu Tyr Ala Thr Asp Ala Trp Gly Lys Gln
        50                  55                  60

Leu Glu Met Leu Arg Glu Val Gly Gln Arg Leu Arg Leu Glu Leu Ala
 65                  70                  75                  80

Asp Thr Glu Leu Glu Asp Phe Thr Pro Ser Gly Pro Leu Thr Leu Gln
                 85                  90                  95

Val Arg Met Ser Cys Glu Cys Glu Ala Asp Gly Tyr Ile Arg Gly Ser
                100                 105                 110

Trp Gln Phe Ser Phe Asp Gly Arg Lys Phe Leu Leu Phe Asp Ser Asn
            115                 120                 125

Asn Arg Lys Trp Thr Val Val His Ala Gly Ala Arg Arg Met Lys Glu
            130                 135                 140

Lys Trp Glu Lys Asp Ser Gly Leu Thr Thr Phe Phe Lys Met Val Ser
145                 150                 155                 160

Met Arg Asp Cys Lys Ser Trp Leu Arg Asp Phe Leu Met His Arg Lys
                165                 170                 175

Lys Arg Leu Glu Pro Thr Ala Pro Pro Met Val
            180                 185
```

<210> SEQ ID NO 6
<211> LENGTH: 187
<212> TYPE: PRT
<213> ORGANISM: Artificial sequence

```
<220> FEATURE:
<223> OTHER INFORMATION: Synthetic peptide ULBP4 alpha1-alpha2 domain

<400> SEQUENCE: 6

Ala Ala Glu Pro His Ser Leu Cys Phe Asn Phe Thr Ile Lys Ser Leu
1               5                   10                  15

Ser Arg Pro Gly Gln Pro Trp Cys Glu Ala Gln Val Phe Leu Asn Lys
            20                  25                  30

Asn Leu Phe Leu Gln Tyr Asn Ser Asp Asn Asn Met Val Lys Pro Leu
        35                  40                  45

Gly Leu Leu Gly Lys Lys Val Tyr Ala Thr Ser Thr Trp Gly Glu Leu
    50                  55                  60

Thr Gln Thr Leu Gly Glu Val Gly Arg Asp Leu Arg Met Leu Leu Cys
65                  70                  75                  80

Asp Ile Lys Pro Gln Ile Lys Thr Ser Asp Pro Ser Thr Leu Gln Val
                85                  90                  95

Glu Met Phe Cys Gln Arg Glu Ala Glu Arg Cys Thr Gly Ala Ser Trp
            100                 105                 110

Gln Phe Ala Thr Asn Gly Glu Lys Ser Leu Leu Phe Asp Ala Met Asn
        115                 120                 125

Met Thr Trp Thr Val Ile Asn His Glu Ala Ser Lys Ile Lys Glu Thr
    130                 135                 140

Trp Lys Lys Asp Arg Gly Leu Glu Lys Tyr Phe Arg Lys Leu Ser Lys
145                 150                 155                 160

Gly Asp Cys Asp His Trp Leu Arg Glu Phe Leu Gly His Trp Glu Ala
                165                 170                 175

Met Pro Glu Pro Thr Val Ser Pro Pro Met Val
            180                 185

<210> SEQ ID NO 7
<211> LENGTH: 198
<212> TYPE: PRT
<213> ORGANISM: Artificial sequence
<220> FEATURE:
<223> OTHER INFORMATION: Synthetic peptide ULBP5 alpha1-alpha2 domain

<400> SEQUENCE: 7

Gly Leu Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Ser Lys Thr Val Thr Pro
        35                  40                  45

Val Ser Pro Leu Gly Lys Lys Leu Asn Val Thr Thr Ala Trp Lys Ala
    50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Ile Pro Lys Glu Pro Leu Thr Leu
                85                  90                  95

Gln Ala Arg Met Ser Cys Glu Gln Lys Ala Glu Gly His Gly Ser Gly
            100                 105                 110

Ser Trp Gln Leu Ser Phe Asp Gly Gln Ile Phe Leu Leu Phe Asp Ser
        115                 120                 125

Glu Asn Arg Met Trp Thr Thr Val His Pro Gly Ala Arg Lys Met Lys
    130                 135                 140

Glu Lys Trp Glu Asn Asp Lys Asp Met Thr Met Ser Phe His Tyr Ile
```

```
                145                 150                 155                 160
Ser Met Gly Asp Cys Thr Gly Trp Leu Glu Asp Phe Leu Met Gly Met
                    165                 170                 175

Asp Ser Thr Leu Glu Pro Ser Ala Gly Ala Pro Pro Thr Met Ser Ser
                    180                 185                 190

Gly Thr Ala Gln Pro Arg
            195

<210> SEQ ID NO 8
<211> LENGTH: 189
<212> TYPE: PRT
<213> ORGANISM: Artificial sequence
<220> FEATURE:
<223> OTHER INFORMATION: Synthetic peptide ULBP6 alpha1-alpha2 domain

<400> SEQUENCE: 8

Ala Ala Glu Pro His Ser Leu Cys Tyr Asp Ile Thr Val Ile Pro Lys
1               5                   10                  15

Phe Arg Pro Gly Pro Arg Trp Cys Ala Val Gln Gly Gln Val Asp Glu
                20                  25                  30

Lys Thr Phe Leu His Tyr Asp Cys Gly Asn Lys Thr Val Thr Pro Val
            35                  40                  45

Ser Pro Leu Gly Lys Lys Leu Asn Val Thr Thr Ala Trp Lys Ala Gln
        50                  55                  60

Asn Pro Val Leu Arg Glu Val Val Asp Ile Leu Thr Glu Gln Leu Leu
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
                100                 105                 110

Trp Gln Phe Ser Ile Asp Gly Gln Thr Phe Leu Leu Phe Asp Ser Glu
            115                 120                 125

Lys Arg Met Trp Thr Thr Val His Pro Gly Ala Arg Lys Met Lys Glu
        130                 135                 140

Lys Trp Glu Asn Asp Lys Asp Val Ala Met Ser Phe His Tyr Ile Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro Pro Met Val
            180                 185

<210> SEQ ID NO 9
<211> LENGTH: 161
<212> TYPE: PRT
<213> ORGANISM: Artificial sequence
<220> FEATURE:
<223> OTHER INFORMATION: Synthetic peptide OMCP alpha1-alpha2 domain

<400> SEQUENCE: 9

Ala Ala Ala Glu Pro His Lys Leu Ala Phe Asn Phe Asn Leu Glu Ile
1               5                   10                  15

Asn Gly Ser Asp Thr His Ser Thr Val Asp Val Tyr Leu Asp Asp Ser
                20                  25                  30

Gln Ile Ile Thr Phe Asp Gly Lys Asp Ile Arg Pro Thr Ile Pro Phe
            35                  40                  45

Met Ile Gly Asp Glu Ile Phe Leu Pro Phe Tyr Lys Asn Val Phe Ser
        50                  55                  60
```

-continued

```
Glu Phe Phe Ser Leu Phe Arg Arg Val Pro Thr Ser Thr Pro Tyr Glu
 65                  70                  75                  80

Asp Leu Thr Tyr Phe Tyr Glu Cys Asp Tyr Asp Asn Lys Ser Thr
                 85                  90                  95

Phe Asp Gln Phe Tyr Leu Tyr Asn Gly Glu Glu Tyr Thr Val Lys Thr
            100                 105                 110

Gln Glu Ala Thr Asn Lys Asn Met Trp Leu Thr Ser Glu Phe Arg
        115                 120                 125

Leu Lys Lys Trp Phe Asp Gly Glu Asp Cys Ile Met His Leu Arg Ser
    130                 135                 140

Leu Val Arg Lys Met Glu Asp Ser Lys Arg Arg Thr Val Pro Pro Met
145                 150                 155                 160

Val
```

<210> SEQ ID NO 10
<211> LENGTH: 543
<212> TYPE: DNA
<213> ORGANISM: Artificial sequence
<220> FEATURE:
<223> OTHER INFORMATION: Synthetic polynucleotide, encoding MICA alpha1-
      alpha2 domain

<400> SEQUENCE: 10

```
gagccccaca gtcttcgtta taacctcacg gtgctgtcct gggatggatc tgtgcagtca    60
gggtttctca ctgaggtaca tctggatggt cagcccttcc tgcgctgtga caggcagaaa   120
tgcagggcaa agccccaggg acagtgggca gaagatgtcc tgggaaataa gacatgggac   180
agagagacca gagacttgac agggaacgga aaggacctca ggatgaccct ggctcatatc   240
aaggaccaga agaaggcttg cattccctc caggagatta gggtctgtga atccatgaa    300
gacaacagca ccaggagctc ccagcatttc tactacgatg gggagctctt cctctcccaa   360
aacctggaga ctaaggaatg gacaatgccc cagtcctcca gagctcagac cttggccatg   420
aacgtcagga atttcttgaa ggaagatgcc atgaagacca gacacactta tcacgctatg   480
catgcagact gcctgcagga actacggcga tatctaaaat ccggcgtagt cctgaggaga   540
aca                                                                 543
```

<210> SEQ ID NO 11
<211> LENGTH: 561
<212> TYPE: DNA
<213> ORGANISM: Artificial sequence
<220> FEATURE:
<223> OTHER INFORMATION: Synthetic polynucleotide, encoding ULBP1
      alpha1-alpha2 domain

<400> SEQUENCE: 11

```
gctgctgagc cccactgtct ctgctacgac tttattataa ctcctaagtc aagaccagag    60
cctcagtggt gcgaagtaca aggtttggtt gacgaaaggc ctttccttca ctacgattgt   120
gtgaaccata aggcaaaggc tttcgccagc ctgggtaaga aggtaaacgt tactaagacg   180
tgggaggagc agacggaaac cctccgtgat gtggttgact tcttaaggg tcagctcctc   240
gatatccaag tggagaattt aatccctatc gaaccgctca ctctgcaggc cagaatgtca   300
tgcgaacatg aagcacacgg tcatggaaga ggtagttggc aatttttatt taacggtcaa   360
aaattcctgc tgttcgactc aaacaaccgc aaatggactg cgctgcaccc tggagctaag   420
aagatgactg aaaaatggga agaaacagac gttacca tgttcttcca gaagatttcc   480
ctgggagatt gtaagatgtg gttagaggag ttcttaatgt actgggaaca gatgctggac   540
```

```
cccacaaaac cccccatggt g                                              561
```

<210> SEQ ID NO 12
<211> LENGTH: 567
<212> TYPE: DNA
<213> ORGANISM: Artificial sequence
<220> FEATURE:
<223> OTHER INFORMATION: Synthetic polynucleotide, encoding ULBP2
      alpha1-alpha2 domain

<400> SEQUENCE: 12

```
gctgctgagc cccatagtct gtgttacgac atcacagtta ttcccaagtt caggcccgga    60
ccgcgctggt gtgccgtgca aggacaagtc gacgaaaaaa cctttcttca ttacgattgc   120
ggaaataaga ctgtaacgcc agtctctcct ttaggtaaga agttaaacgt cactacgggcg  180
tggaaggcac aaaaccccgt cctgcgcgag gtcgtcgaca tcctgactga acaattgcgc   240
gacatccagc tcgagaatta cactccaaag gagcctctta ccctgcaggc tagaatgtct   300
tgcgagcaaa aggcagaggg ccactcctcc ggcagctggc agttcagttt cgacggacaa   360
atctttctgt tattcgattc agagaagaga atgtggacta cagttcaccc cggtgcccgt   420
aaaatgaagg agaagtggga aaacgacaaa gtggtggcga tgtcattcca ctatttctcg   480
atgggagact gcatcggttg gctggaagat ttcctcatgg gtatggactc cactttggag   540
ccatcggctg gtgccccccc catggtg                                       567
```

<210> SEQ ID NO 13
<211> LENGTH: 561
<212> TYPE: DNA
<213> ORGANISM: Artificial sequence
<220> FEATURE:
<223> OTHER INFORMATION: Synthetic polynucleotide, encoding ULBP3
      alpha1-alpha2 domain

<400> SEQUENCE: 13

```
gctgctgagc cccacagctt gtggtacaac ttcaccatta tccacttgcc gagacatggc    60
cagcagtggt gcgaagtgca atcgcaagtc gaccaaaaaa acttcttatc atacgactgc   120
ggcagcgata aggtcttatc tatgggtcat ttggaggaac agctctacgc gaccgacgcc   180
tggggtaaac agctcgagat gctccgtgag gttggacaga ggctgagact ggaactggct   240
gacactgagc tggaagattt cacacctagt ggtccactca cattgcaagt acgcatgagc   300
tgcgagtgtg aggccgatgg atacattagg ggcagctggc agtttagctt cgacggaagg   360
aaattcctgc tcttcgacag taacaatagg aagtggactg ttgtgcatgc tggtgcgcgc   420
agaatgaagg aaaagtggga gaaagatagc ggcctgacga ccttcttcaa gatggtgtct   480
atgcgtgact gtaagagctg gctcagagat ttcctcatgc atcgcaagaa gaggttagaa   540
cctaccgctc cccccatggt g                                             561
```

<210> SEQ ID NO 14
<211> LENGTH: 561
<212> TYPE: DNA
<213> ORGANISM: Artificial sequence
<220> FEATURE:
<223> OTHER INFORMATION: Synthetic polynucleotide, encoding ULBP4
      alpha1-alpha2 domain

<400> SEQUENCE: 14

```
gctgctgagc cccactctct ttgcttcaac ttcaccatta aatccctgag caggcctggt    60
cagccgtggt gtgaggcgca ggtctttctt aacaagaatc tcttcctcca atacaactct   120
```

```
gataacaaca tggtaaagcc actgggtctc ctgggtaaaa aagtctatgc tacgagcact    180
tggggagaac tcacccagac tcttggcgag gtaggaagag acctgcgcat gctcctctgc    240
gatataaagc cccaaattaa gaccagtgat ccgtccactt tacaagtcga atgttctgc     300 caaagggagg ctgaacgctg caccggagcc tcttggcagt tcgcgaccaa tggcgaaaag    360
tccctcttgt tcgatgccat gaatatgacc tggaccgtga tcaatcatga ggcctctaag    420
atcaaggaga cgtggaaaaa ggaccgcggc cttgaaaagt actttaggaa gttgtctaaa    480
ggagactgcg accattggtt acgcgagttc ctcggccatt gggaagcgat gcccgagcca    540
acggttagcc cccccatggt g                                              561
```

```
<210> SEQ ID NO 15
<211> LENGTH: 567
<212> TYPE: DNA
<213> ORGANISM: Artificial sequence
<220> FEATURE:
<223> OTHER INFORMATION: Synthetic polynucleotide, encoding ULBP6
      alpha1-alpha2 domain

<400> SEQUENCE: 15
```

```
gctgctgagc cccactcctt atgctatgat atcaccgtga ttccaaagtt ccgaccagga     60
ccccgatggt gcgccgtaca gggacaggtc gacgaaaaga cttttttaca ttacgactgc    120
ggtaacaaga cagtcacacc ggtaagtcct ttggaaaaaa agtaaacgt aaccactgct     180 tggaaggccc agaaccccgt ccttcgagaa gtagtggata ttttgactga acagctgctt    240
gacatccagc tggaaaacta cacacccaaa gagcccctga ctcttcaagc gcgtatgtcg    300
tgtgagcaaa aggccgaagg acacagctcc ggatcctggc agttcagtat cgacggtcag    360
accttcctcc tcttcgattc agaaaagcgc atgtggacta ctgtgcaccc cggcgctcgt    420
aagatgaagg aaaagtggga gaatgataag gacgttgcca tgagttttca ttacattagt    480
atgggagatt gcatcggttg gctggaagac ttcctgatgg gtatggatag tacccttgaa    540
cctagtgccg gagctccccc catggtg                                        567
```

```
<210> SEQ ID NO 16
<211> LENGTH: 483
<212> TYPE: DNA
<213> ORGANISM: Artificial sequence
<220> FEATURE:
<223> OTHER INFORMATION: Synthetic polynucleotide, encoding OMCP alpha1-
      alpha2 domain

<400> SEQUENCE: 16
```

```
gctgctgctg agccccacaa gcttgcgttc aacttcaatc tggaaataaa cggttcagat     60
acccattcaa ccgtggacgt ttatttagac gattcgcaga taatcacctt tgacggcaag    120
gacatccgcc caactatccc gttcatgata ggtgacgaaa tcttccttcc tttttataag    180
aatgtgttct ctgagttctt cagtttgttc cgccgcgtcc ctacctcaac cccctacgaa    240
gacttgactt atttctatga atgcgactac accgacaaca atctacatt cgatcaattc     300 tacctgtaca cggtgaaga gtacaccgtg aagactcaag aggctactaa caagaacatg    360
tggctgacca cttccgagtt cagactgaag aagtggttcg acggcgagga ctgtatcatg    420
caccttagaa gtttagtgag gaaaatggaa gatagcaaga aagaacagt gccccccatg     480 gtg                                                                  483
```

```
<210> SEQ ID NO 17
```

```
<211> LENGTH: 139
<212> TYPE: PRT
<213> ORGANISM: Artificial sequence
<220> FEATURE:
<223> OTHER INFORMATION: Synthetic peptide natural NKG2D ectodomain

<400> SEQUENCE: 17

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135

<210> SEQ ID NO 18
<211> LENGTH: 139
<212> TYPE: PRT
<213> ORGANISM: Artificial sequence
<220> FEATURE:
<223> OTHER INFORMATION: Synthetic peptide non-natural NKG2D Y152A
      ectodomain

<400> SEQUENCE: 18

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Ala His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135

<210> SEQ ID NO 19
<211> LENGTH: 139
<212> TYPE: PRT
<213> ORGANISM: Artificial sequence
<220> FEATURE:
```

<223> OTHER INFORMATION: Synthetic peptide non-natural NKG2D Y199A
    ectodomain

<400> SEQUENCE: 19

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Ala Ile Glu Asn Cys Ser Thr
        115                 120                 125

Pro Asn Thr Tyr Ile Cys Met Gln Arg Thr Val
    130                 135

<210> SEQ ID NO 20
<211> LENGTH: 139
<212> TYPE: PRT
<213> ORGANISM: Artificial sequence
<220> FEATURE:
<223> OTHER INFORMATION: Synthetic peptide non-natural NKG2D Y152A/Y199A
    ectodomain

<400> SEQUENCE: 20

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Ala His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Ala Ile Glu Asn Cys Ser Thr
        115                 120                 125

Pro Asn Thr Tyr Ile Cys Met Gln Arg Thr Val
    130                 135

<210> SEQ ID NO 21
<211> LENGTH: 139
<212> TYPE: PRT
<213> ORGANISM: Artificial sequence
<220> FEATURE:
<223> OTHER INFORMATION: Synthetic peptide non-natural NKG2D Y199F
    eNKG2D1 ectodomain

```
<400> SEQUENCE: 21

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
    130                 135

<210> SEQ ID NO 22
<211> LENGTH: 139
<212> TYPE: PRT
<213> ORGANISM: Artificial sequence
<220> FEATURE:
<223> OTHER INFORMATION: Synthetic peptide non-natural NKG2D Y152S
      eNKG2D2 ectodomain

<400> SEQUENCE: 22

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Ser His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135

<210> SEQ ID NO 23
<211> LENGTH: 139
<212> TYPE: PRT
<213> ORGANISM: Artificial sequence
<220> FEATURE:
<223> OTHER INFORMATION: Synthetic peptide non-natural NKG2D Y152T
      eNKG2D3 ectodomain

<400> SEQUENCE: 23

Phe Leu Asn Ser Leu Phe Asn Gln Glu Val Gln Ile Pro Leu Thr Glu
```

```
                1               5                  10                 15
Ser Tyr Cys Gly Pro Cys Pro Lys Asn Trp Ile Cys Tyr Lys Asn Asn
                20                 25                 30

Cys Tyr Gln Phe Phe Asp Glu Ser Lys Asn Trp Tyr Glu Ser Gln Ala
                35                 40                 45

Ser Cys Met Ser Gln Asn Ala Ser Leu Leu Lys Val Tyr Ser Lys Glu
                50                 55                 60

Asp Gln Asp Leu Leu Lys Leu Val Lys Ser Thr His Trp Met Gly Leu
 65                 70                 75                 80

Val His Ile Pro Thr Asn Gly Ser Trp Gln Trp Glu Asp Gly Ser Ile
                85                 90                 95

Leu Ser Pro Asn Leu Leu Thr Ile Ile Glu Met Gln Lys Gly Asp Cys
                100                105                110

Ala Leu Tyr Ala Ser Ser Phe Lys Gly Tyr Ile Glu Asn Cys Ser Thr
                115                120                125

Pro Asn Thr Tyr Ile Cys Met Gln Arg Thr Val
                130                135

<210> SEQ ID NO 24
<211> LENGTH: 139
<212> TYPE: PRT
<213> ORGANISM: Artificial sequence
<220> FEATURE:
<223> OTHER INFORMATION: Synthetic peptide non-natural NKG2D Y152V
      eNKG2D4 ectodomain

<400> SEQUENCE: 24

Phe Leu Asn Ser Leu Phe Asn Gln Glu Val Gln Ile Pro Leu Thr Glu
 1               5                  10                 15

Ser Tyr Cys Gly Pro Cys Pro Lys Asn Trp Ile Cys Tyr Lys Asn Asn
                20                 25                 30

Cys Tyr Gln Phe Phe Asp Glu Ser Lys Asn Trp Tyr Glu Ser Gln Ala
                35                 40                 45

Ser Cys Met Ser Gln Asn Ala Ser Leu Leu Lys Val Tyr Ser Lys Glu
                50                 55                 60

Asp Gln Asp Leu Leu Lys Leu Val Lys Ser Val His Trp Met Gly Leu
 65                 70                 75                 80

Val His Ile Pro Thr Asn Gly Ser Trp Gln Trp Glu Asp Gly Ser Ile
                85                 90                 95

Leu Ser Pro Asn Leu Leu Thr Ile Ile Glu Met Gln Lys Gly Asp Cys
                100                105                110

Ala Leu Tyr Ala Ser Ser Phe Lys Gly Tyr Ile Glu Asn Cys Ser Thr
                115                120                125

Pro Asn Thr Tyr Ile Cys Met Gln Arg Thr Val
                130                135

<210> SEQ ID NO 25
<211> LENGTH: 139
<212> TYPE: PRT
<213> ORGANISM: Artificial sequence
<220> FEATURE:
<223> OTHER INFORMATION: Synthetic peptide non-natural NKG2D Y152A/Y199F
      eNKG2D5 ectodomain

<400> SEQUENCE: 25

Phe Leu Asn Ser Leu Phe Asn Gln Glu Val Gln Ile Pro Leu Thr Glu
 1               5                  10                 15

Ser Tyr Cys Gly Pro Cys Pro Lys Asn Trp Ile Cys Tyr Lys Asn Asn
```

```
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Ala His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
        130                 135
```

<210> SEQ ID NO 26
<211> LENGTH: 139
<212> TYPE: PRT
<213> ORGANISM: Artificial sequence
<220> FEATURE:
<223> OTHER INFORMATION: Synthetic peptide non-natural NKG2D Y152L/Y199F
      eNKG2D6 ectodomain

<400> SEQUENCE: 26

```
Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Leu His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
        130                 135
```

<210> SEQ ID NO 27
<211> LENGTH: 139
<212> TYPE: PRT
<213> ORGANISM: Artificial sequence
<220> FEATURE:
<223> OTHER INFORMATION: Synthetic peptide non-natural NKG2D Y152S/Y199F
      eNKG2D7 ectodomain

<400> SEQUENCE: 27

```
Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
```

-continued

```
                        35                  40                  45

Ser Cys Met Ser Gln Asn Ala Ser Leu Leu Lys Val Tyr Ser Lys Glu
 50                  55                  60

Asp Gln Asp Leu Leu Lys Leu Val Lys Ser Ser His Trp Met Gly Leu
 65                  70                  75                  80

Val His Ile Pro Thr Asn Gly Ser Trp Gln Trp Glu Asp Gly Ser Ile
                     85                  90                  95

Leu Ser Pro Asn Leu Leu Thr Ile Ile Glu Met Gln Lys Gly Asp Cys
                    100                 105                 110

Ala Leu Tyr Ala Ser Ser Phe Lys Gly Phe Ile Glu Asn Cys Ser Thr
                    115                 120                 125

Pro Asn Thr Tyr Ile Cys Met Gln Arg Thr Val
                    130                 135

<210> SEQ ID NO 28
<211> LENGTH: 139
<212> TYPE: PRT
<213> ORGANISM: Artificial sequence
<220> FEATURE:
<223> OTHER INFORMATION: Synthetic peptide non-natural NKG2D Y152T/Y199F
      eNKG2D8 ectodomain

<400> SEQUENCE: 28

Phe Leu Asn Ser Leu Phe Asn Gln Glu Val Gln Ile Pro Leu Thr Glu
 1               5                  10                  15

Ser Tyr Cys Gly Pro Cys Pro Lys Asn Trp Ile Cys Tyr Lys Asn Asn
                    20                  25                  30

Cys Tyr Gln Phe Phe Asp Glu Ser Lys Asn Trp Tyr Glu Ser Gln Ala
                    35                  40                  45

Ser Cys Met Ser Gln Asn Ala Ser Leu Leu Lys Val Tyr Ser Lys Glu
 50                  55                  60

Asp Gln Asp Leu Leu Lys Leu Val Lys Ser Thr His Trp Met Gly Leu
 65                  70                  75                  80

Val His Ile Pro Thr Asn Gly Ser Trp Gln Trp Glu Asp Gly Ser Ile
                     85                  90                  95

Leu Ser Pro Asn Leu Leu Thr Ile Ile Glu Met Gln Lys Gly Asp Cys
                    100                 105                 110

Ala Leu Tyr Ala Ser Ser Phe Lys Gly Phe Ile Glu Asn Cys Ser Thr
                    115                 120                 125

Pro Asn Thr Tyr Ile Cys Met Gln Arg Thr Val
                    130                 135

<210> SEQ ID NO 29
<211> LENGTH: 139
<212> TYPE: PRT
<213> ORGANISM: Artificial sequence
<220> FEATURE:
<223> OTHER INFORMATION: Synthetic peptide non-natural NKG2D Y152V/Y199F
      eNKG2D9 ectodomain

<400> SEQUENCE: 29

Phe Leu Asn Ser Leu Phe Asn Gln Glu Val Gln Ile Pro Leu Thr Glu
 1               5                  10                  15

Ser Tyr Cys Gly Pro Cys Pro Lys Asn Trp Ile Cys Tyr Lys Asn Asn
                    20                  25                  30

Cys Tyr Gln Phe Phe Asp Glu Ser Lys Asn Trp Tyr Glu Ser Gln Ala
                    35                  40                  45

Ser Cys Met Ser Gln Asn Ala Ser Leu Leu Lys Val Tyr Ser Lys Glu
```

```
                50                  55                  60
Asp Gln Asp Leu Leu Lys Leu Val Lys Ser Val His Trp Met Gly Leu
 65                  70                  75                  80

Val His Ile Pro Thr Asn Gly Ser Trp Gln Trp Glu Asp Gly Ser Ile
                 85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Phe Ile Glu Asn Cys Ser Thr
                115                 120                 125

Pro Asn Thr Tyr Ile Cys Met Gln Arg Thr Val
                130                 135

<210> SEQ ID NO 30
<211> LENGTH: 139
<212> TYPE: PRT
<213> ORGANISM: Artificial sequence
<220> FEATURE:
<223> OTHER INFORMATION: Synthetic peptide non-natural NKG2D Y199D
      eNKG2D10 ectodomain

<400> SEQUENCE: 30

Phe Leu Asn Ser Leu Phe Asn Gln Glu Val Gln Ile Pro Leu Thr Glu
  1               5                  10                  15

Ser Tyr Cys Gly Pro Cys Pro Lys Asn Trp Ile Cys Tyr Lys Asn Asn
                 20                  25                  30

Cys Tyr Gln Phe Phe Asp Glu Ser Lys Asn Trp Tyr Glu Ser Gln Ala
                 35                  40                  45

Ser Cys Met Ser Gln Asn Ala Ser Leu Leu Lys Val Tyr Ser Lys Glu
                 50                  55                  60

Asp Gln Asp Leu Leu Lys Leu Val Lys Ser Tyr His Trp Met Gly Leu
 65                  70                  75                  80

Val His Ile Pro Thr Asn Gly Ser Trp Gln Trp Glu Asp Gly Ser Ile
                 85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Asp Ile Glu Asn Cys Ser Thr
                115                 120                 125

Pro Asn Thr Tyr Ile Cys Met Gln Arg Thr Val
                130                 135

<210> SEQ ID NO 31
<211> LENGTH: 139
<212> TYPE: PRT
<213> ORGANISM: Artificial sequence
<220> FEATURE:
<223> OTHER INFORMATION: Synthetic peptide non-natural NKG2D Y199E
      eNKG2D11 ectodomain

<400> SEQUENCE: 31

Phe Leu Asn Ser Leu Phe Asn Gln Glu Val Gln Ile Pro Leu Thr Glu
  1               5                  10                  15

Ser Tyr Cys Gly Pro Cys Pro Lys Asn Trp Ile Cys Tyr Lys Asn Asn
                 20                  25                  30

Cys Tyr Gln Phe Phe Asp Glu Ser Lys Asn Trp Tyr Glu Ser Gln Ala
                 35                  40                  45

Ser Cys Met Ser Gln Asn Ala Ser Leu Leu Lys Val Tyr Ser Lys Glu
                 50                  55                  60

Asp Gln Asp Leu Leu Lys Leu Val Lys Ser Tyr His Trp Met Gly Leu
```

```
                65                  70                  75                  80
Val His Ile Pro Thr Asn Gly Ser Trp Gln Trp Glu Asp Gly Ser Ile
                    85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Glu Ile Glu Asn Cys Ser Thr
            115                 120                 125

Pro Asn Thr Tyr Ile Cys Met Gln Arg Thr Val
        130                 135

<210> SEQ ID NO 32
<211> LENGTH: 139
<212> TYPE: PRT
<213> ORGANISM: Artificial sequence
<220> FEATURE:
<223> OTHER INFORMATION: Synthetic peptide non-natural NKG2D Y152D/Y199D
      eNKG2D12 ectodomain

<400> SEQUENCE: 32

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser His Trp Met Gly Leu
65                  70                  75                  80

Val His Ile Pro Thr Asn Gly Ser Trp Gln Trp Glu Asp Gly Ser Ile
                    85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Asp Ile Glu Asn Cys Ser Thr
            115                 120                 125

Pro Asn Thr Tyr Ile Cys Met Gln Arg Thr Val
        130                 135

<210> SEQ ID NO 33
<211> LENGTH: 139
<212> TYPE: PRT
<213> ORGANISM: Artificial sequence
<220> FEATURE:
<223> OTHER INFORMATION: Synthetic peptide non-natural NKG2D Y152E/Y199E
      eNKG2D13 ectodomain

<400> SEQUENCE: 33

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Glu His Trp Met Gly Leu
65                  70                  75                  80

Val His Ile Pro Thr Asn Gly Ser Trp Gln Trp Glu Asp Gly Ser Ile
```

```
                85                  90                  95
Leu Ser Pro Asn Leu Leu Thr Ile Ile Glu Met Gln Lys Gly Asp Cys
            100                 105                 110

Ala Leu Tyr Ala Ser Ser Phe Lys Gly Glu Ile Glu Asn Cys Ser Thr
            115                 120                 125

Pro Asn Thr Tyr Ile Cys Met Gln Arg Thr Val
            130                 135

<210> SEQ ID NO 34
<211> LENGTH: 139
<212> TYPE: PRT
<213> ORGANISM: Artificial sequence
<220> FEATURE:
<223> OTHER INFORMATION: Synthetic peptide non-natural NKG2D Y152L
      eNKG2D14 ectodomain

<400> SEQUENCE: 34

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
            35                  40                  45

Ser Cys Met Ser Gln Asn Ala Ser Leu Leu Lys Val Tyr Ser Lys Glu
        50                  55                  60

Asp Gln Asp Leu Leu Lys Leu Val Lys Ser Leu His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
            115                 120                 125

Pro Asn Thr Tyr Ile Cys Met Gln Arg Thr Val
            130                 135

<210> SEQ ID NO 35
<211> LENGTH: 139
<212> TYPE: PRT
<213> ORGANISM: Artificial sequence
<220> FEATURE:
<223> OTHER INFORMATION: Synthetic peptide non-natural NKG2D Y152F/Y199F
      eNKG2D15 ectodomain

<400> SEQUENCE: 35

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
            35                  40                  45

Ser Cys Met Ser Gln Asn Ala Ser Leu Leu Lys Val Tyr Ser Lys Glu
        50                  55                  60

Asp Gln Asp Leu Leu Lys Leu Val Lys Ser Phe His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
```

```
                  100                 105                 110
Ala Leu Tyr Ala Ser Ser Phe Lys Gly Phe Ile Glu Asn Cys Ser Thr
            115                 120                 125

Pro Asn Thr Tyr Ile Cys Met Gln Arg Thr Val
        130                 135

<210> SEQ ID NO 36
<211> LENGTH: 23
<212> TYPE: PRT
<213> ORGANISM: Artificial sequence
<220> FEATURE:
<223> OTHER INFORMATION: Synthetic peptide MHCI signal sequence

<400> SEQUENCE: 36

Met Gly Leu Gly Pro Val Phe Leu Leu Leu Ala Gly Ile Phe Pro Phe
1               5                   10                  15

Ala Pro Pro Gly Ala Ala Ala
            20

<210> SEQ ID NO 37
<211> LENGTH: 69
<212> TYPE: DNA
<213> ORGANISM: Artificial sequence
<220> FEATURE:
<223> OTHER INFORMATION: Synthetic polynucleotide, encoding MHCI signal
      sequence

<400> SEQUENCE: 37
atgggccttg cccagtgtt tctgctgttg gcaggcattt ccctttttgc tccgcccggc       60
gccgcagcc                                                             69

<210> SEQ ID NO 38
<211> LENGTH: 237
<212> TYPE: PRT
<213> ORGANISM: Artificial sequence
<220> FEATURE:
<223> OTHER INFORMATION: Synthetic peptide human IgG1 Fc with IEGR
      linker

<400> SEQUENCE: 38

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160
```

```
Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
        210                 215                 220

Lys Ser Leu Ser Leu Ser Pro Gly Lys Ile Glu Gly Arg
225                 230                 235

<210> SEQ ID NO 39
<211> LENGTH: 711
<212> TYPE: DNA
<213> ORGANISM: Artificial sequence
<220> FEATURE:
<223> OTHER INFORMATION: Synthetic polynucleotide, encoding human IgG1
      Fc with IEGR linker

<400> SEQUENCE: 39
atggacccga aaagctgcga caagactcac acttgtccgc cgtgccccgc ccccgaactg     60
ctgggtggcc cctccgtgtt cctgttcccg cctaagccta aggacaccct tatgatcagc    120 cgcaccctg aagtgacctg tgtcgtcgtg gatgtgtcac acgaggaccc ggaggtcaag    180
ttcaattggt acgtggacgg cgtggaagtg cataacgcaa agaccaagcc tcgggaggaa    240
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg c              711

<210> SEQ ID NO 40
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D fusion

<400> SEQUENCE: 40

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95
```

```
Gln Asp Trp Leu Asn Gly Lys Glu Tyr Lys Cys Lys Val Ser Asn Lys
             100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Tyr Ile Glu Asn Cys Ser Thr Pro Asn Thr
        355                 360                 365

Tyr Ile Cys Met Gln Arg Thr Val
    370                 375

<210> SEQ ID NO 41
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152A
      fusion

<400> SEQUENCE: 41

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80
```

```
Gln Tyr Asn Ser Thr Tyr Arg Val Val Ser Val Leu Thr Val Leu His
                85                  90                  95
Gln Asp Trp Leu Asn Gly Lys Glu Tyr Lys Cys Lys Val Ser Asn Lys
            100                 105                 110
Ala Leu Pro Ala Pro Ile Glu Lys Thr Ile Ser Lys Ala Lys Gly Gln
        115                 120                 125
Pro Arg Glu Pro Gln Val Tyr Thr Leu Pro Pro Ser Arg Asp Glu Leu
    130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
            180                 185                 190
Tyr Ser Lys Leu Thr Val Asp Lys Ser Arg Trp Gln Gln Gly Asn Val
        195                 200                 205
Phe Ser Cys Ser Val Met His Glu Ala Leu His Asn His Tyr Thr Gln
    210                 215                 220
Lys Ser Leu Ser Leu Ser Pro Gly Lys Ile Glu Gly Arg Phe Leu Asn
225                 230                 235                 240
Ser Leu Phe Asn Gln Glu Val Gln Ile Pro Leu Thr Glu Ser Tyr Cys
                245                 250                 255
Gly Pro Cys Pro Lys Asn Trp Ile Cys Tyr Lys Asn Asn Cys Tyr Gln
            260                 265                 270
Phe Phe Asp Glu Ser Lys Asn Trp Tyr Glu Ser Gln Ala Ser Cys Met
        275                 280                 285
Ser Gln Asn Ala Ser Leu Leu Lys Val Tyr Ser Lys Glu Asp Gln Asp
    290                 295                 300
Leu Leu Lys Leu Val Lys Ser Ala His Trp Met Gly Leu Val His Ile
305                 310                 315                 320
Pro Thr Asn Gly Ser Trp Gln Trp Glu Asp Gly Ser Ile Leu Ser Pro
                325                 330                 335
Asn Leu Leu Thr Ile Ile Glu Met Gln Lys Gly Asp Cys Ala Leu Tyr
            340                 345                 350
Ala Ser Ser Phe Lys Gly Tyr Ile Glu Asn Cys Ser Thr Pro Asn Thr
        355                 360                 365
Tyr Ile Cys Met Gln Arg Thr Val
    370                 375

<210> SEQ ID NO 42
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199A
      ectodomain

<400> SEQUENCE: 42

Met Asp Pro Lys Ser Cys Asp Lys Thr His Thr Cys Pro Pro Cys Pro
1               5                   10                  15
Ala Pro Glu Leu Leu Gly Gly Pro Ser Val Phe Leu Phe Pro Pro Lys
                20                  25                  30
Pro Lys Asp Thr Leu Met Ile Ser Arg Thr Pro Glu Val Thr Cys Val
            35                  40                  45
Val Val Asp Val Ser His Glu Asp Pro Glu Val Lys Phe Asn Trp Tyr
```

```
                    50                  55                  60
Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                     85                  90                  95

Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Ala Ile Glu Asn Cys Ser Thr Pro Asn Thr
        355                 360                 365

Tyr Ile Cys Met Gln Arg Thr Val
370                 375

<210> SEQ ID NO 43
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152A/Y199A ectodomain

<400> SEQUENCE: 43

Met Asp Pro Lys Ser Cys Asp Lys Thr His Thr Cys Pro Pro Cys Pro
 1               5                  10                  15

Ala Pro Glu Leu Leu Gly Gly Pro Ser Val Phe Leu Phe Pro Pro Lys
            20                  25                  30
```

```
Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Ala His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Ala Ile Glu Asn Cys Ser Thr Pro Asn Thr
        355                 360                 365

Tyr Ile Cys Met Gln Arg Thr Val
    370                 375

<210> SEQ ID NO 44
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199F
      eNKG2D1 fusion

<400> SEQUENCE: 44

Met Asp Pro Lys Ser Cys Asp Lys Thr His Thr Cys Pro Pro Cys Pro
1               5                   10                  15
```

Ala Pro Glu Leu Leu Gly Gly Pro Ser Val Phe Leu Phe Pro Pro Lys
          20                  25                  30

Pro Lys Asp Thr Leu Met Ile Ser Arg Thr Pro Glu Val Thr Cys Val
          35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
         100                 105                 110

Ala Leu Pro Ala Pro Ile Glu Lys Thr Ile Ser Lys Ala Lys Gly Gln
         115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
         180                 185                 190

Tyr Ser Lys Leu Thr Val Asp Lys Ser Arg Trp Gln Gln Gly Asn Val
         195                 200                 205

Phe Ser Cys Ser Val Met His Glu Ala Leu His Asn His Tyr Thr Gln
         210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
         260                 265                 270

Phe Phe Asp Glu Ser Lys Asn Trp Tyr Glu Ser Gln Ala Ser Cys Met
         275                 280                 285

Ser Gln Asn Ala Ser Leu Leu Lys Val Tyr Ser Lys Glu Asp Gln Asp
290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
         340                 345                 350

Ala Ser Ser Phe Lys Gly Phe Ile Glu Asn Cys Ser Thr Pro Asn Thr
         355                 360                 365

Tyr Ile Cys Met Gln Arg Thr Val
370                 375

<210> SEQ ID NO 45
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152S
      eNKG2D2 fusion

```
<400> SEQUENCE: 45

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 46
<211> LENGTH: 376
<212> TYPE: PRT
<213> ORGANISM: Artificial sequence
```

<220> FEATURE:
<223> OTHER INFORMATION: Synthetic peptide human IgG1 Fc-NKG2D Y152T eNKG2D3 fusion

<400> SEQUENCE: 46

```
Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Thr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Tyr Ile Glu Asn Cys Ser Thr Pro Asn Thr
        355                 360                 365

Tyr Ile Cys Met Gln Arg Thr Val
370                 375
```

<210> SEQ ID NO 47
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152V eNKG2D4 fusion

<400> SEQUENCE: 47

```
Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Val His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Tyr Ile Glu Asn Cys Ser Thr Pro Asn Thr
        355                 360                 365
```

```
Tyr Ile Cys Met Gln Arg Thr Val
    370                 375
```

<210> SEQ ID NO 48
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152A/Y199F eNKG2D5 fusion

<400> SEQUENCE: 48

```
Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Ala His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350
```

```
Ala Ser Ser Phe Lys Gly Phe Ile Glu Asn Cys Ser Thr Pro Asn Thr
        355                 360                 365

Tyr Ile Cys Met Gln Arg Thr Val
370                 375

<210> SEQ ID NO 49
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152L/Y199F eNKG2D6 fusion

<400> SEQUENCE: 49

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Leu His Trp Met Gly Leu Val His Ile
305                 310                 315                 320

Pro Thr Asn Gly Ser Trp Gln Trp Glu Asp Gly Ser Ile Leu Ser Pro
```

-continued

```
                325                 330                 335
Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
            355                 360                 365

Tyr Ile Cys Met Gln Arg Thr Val
            370                 375

<210> SEQ ID NO 50
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152S/Y199F eNKG2D7 fusion

<400> SEQUENCE: 50

Met Asp Pro Lys Ser Cys Asp Lys Thr His Thr Cys Pro Pro Cys Pro
1               5                  10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300
```

```
Leu Leu Lys Leu Val Lys Ser Ser His Trp Met Gly Leu Val His Ile
305                 310                 315                 320

Pro Thr Asn Gly Ser Trp Gln Trp Glu Asp Gly Ser Ile Leu Ser Pro
            325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
            355                 360                 365

Tyr Ile Cys Met Gln Arg Thr Val
370                 375

<210> SEQ ID NO 51
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152T/Y199F eNKG2D8 fusion

<400> SEQUENCE: 51

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285
```

```
Ser Gln Asn Ala Ser Leu Leu Lys Val Tyr Ser Lys Glu Asp Gln Asp
            290                 295                 300

Leu Leu Lys Leu Val Lys Ser Thr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 52
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152V/Y199F eNKG2D9 fusion

<400> SEQUENCE: 52

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
```

```
                260                 265                 270
Phe Phe Asp Glu Ser Lys Asn Trp Tyr Glu Ser Gln Ala Ser Cys Met
            275                 280                 285
Ser Gln Asn Ala Ser Leu Leu Lys Val Tyr Ser Lys Glu Asp Gln Asp
            290                 295                 300
Leu Leu Lys Leu Val Lys Ser Val His Trp Met Gly Leu Val His Ile
305                 310                 315                 320
Pro Thr Asn Gly Ser Trp Gln Trp Glu Asp Gly Ser Ile Leu Ser Pro
                325                 330                 335
Asn Leu Leu Thr Ile Ile Glu Met Gln Lys Gly Asp Cys Ala Leu Tyr
                340                 345                 350
Ala Ser Ser Phe Lys Gly Phe Ile Glu Asn Cys Ser Thr Pro Asn Thr
            355                 360                 365
Tyr Ile Cys Met Gln Arg Thr Val
            370                 375

<210> SEQ ID NO 53
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199D
      eNKG2D10 fusion

<400> SEQUENCE: 53

Met Asp Pro Lys Ser Cys Asp Lys Thr His Thr Cys Pro Pro Cys Pro
1               5                   10                  15
Ala Pro Glu Leu Leu Gly Gly Pro Ser Val Phe Leu Phe Pro Pro Lys
                20                  25                  30
Pro Lys Asp Thr Leu Met Ile Ser Arg Thr Pro Glu Val Thr Cys Val
            35                  40                  45
Val Val Asp Val Ser His Glu Asp Pro Glu Val Lys Phe Asn Trp Tyr
50                  55                  60
Val Asp Gly Val Glu Val His Asn Ala Lys Thr Lys Pro Arg Glu Glu
65                  70                  75                  80
Gln Tyr Asn Ser Thr Tyr Arg Val Val Ser Val Leu Thr Val Leu His
                85                  90                  95
Gln Asp Trp Leu Asn Gly Lys Glu Tyr Lys Cys Lys Val Ser Asn Lys
            100                 105                 110
Ala Leu Pro Ala Pro Ile Glu Lys Thr Ile Ser Lys Ala Lys Gly Gln
        115                 120                 125
Pro Arg Glu Pro Gln Val Tyr Thr Leu Pro Pro Ser Arg Asp Glu Leu
    130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
            180                 185                 190
Tyr Ser Lys Leu Thr Val Asp Lys Ser Arg Trp Gln Gln Gly Asn Val
        195                 200                 205
Phe Ser Cys Ser Val Met His Glu Ala Leu His Asn His Tyr Thr Gln
    210                 215                 220
Lys Ser Leu Ser Leu Ser Pro Gly Lys Ile Glu Gly Arg Phe Leu Asn
225                 230                 235                 240
```

```
Ser Leu Phe Asn Gln Glu Val Gln Ile Pro Leu Thr Glu Ser Tyr Cys
            245                 250                 255

Gly Pro Cys Pro Lys Asn Trp Ile Cys Tyr Lys Asn Asn Cys Tyr Gln
        260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
        290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Asp Ile Glu Asn Cys Ser Thr Pro Asn Thr
        355                 360                 365

Tyr Ile Cys Met Gln Arg Thr Val
        370                 375

<210> SEQ ID NO 54
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199E
      eNKG2D11 fusion

<400> SEQUENCE: 54

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220
```

```
Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
                340                 345                 350

Ala Ser Ser Phe Lys Gly Glu Ile Glu Asn Cys Ser Thr Pro Asn Thr
            355                 360                 365

Tyr Ile Cys Met Gln Arg Thr Val
        370                 375

<210> SEQ ID NO 55
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152D/Y199D eNKG2D12 fusion

<400> SEQUENCE: 55

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
```

```
                195                 200                 205
Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
                260                 265                 270

Phe Phe Asp Glu Ser Lys Asn Trp Tyr Glu Ser Gln Ala Ser Cys Met
                275                 280                 285

Ser Gln Asn Ala Ser Leu Leu Lys Val Tyr Ser Lys Glu Asp Gln Asp
                290                 295                 300

Leu Leu Lys Leu Val Lys Ser Asp His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
                340                 345                 350

Ala Ser Ser Phe Lys Gly Asp Ile Glu Asn Cys Ser Thr Pro Asn Thr
                355                 360                 365

Tyr Ile Cys Met Gln Arg Thr Val
                370                 375

<210> SEQ ID NO 56
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152E/Y199E eNKG2D13 fusion

<400> SEQUENCE: 56

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
        50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175
```

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Glu His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Glu Ile Glu Asn Cys Ser Thr Pro Asn Thr
        355                 360                 365

Tyr Ile Cys Met Gln Arg Thr Val
    370                 375

<210> SEQ ID NO 57
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152L
      eNKG2D14 fusion

<400> SEQUENCE: 57

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

```
Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
                260                 265                 270

Phe Phe Asp Glu Ser Lys Asn Trp Tyr Glu Ser Gln Ala Ser Cys Met
            275                 280                 285

Ser Gln Asn Ala Ser Leu Leu Lys Val Tyr Ser Lys Glu Asp Gln Asp
    290                 295                 300

Leu Leu Lys Leu Val Lys Ser Leu His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
                340                 345                 350

Ala Ser Ser Phe Lys Gly Tyr Ile Glu Asn Cys Ser Thr Pro Asn Thr
            355                 360                 365

Tyr Ile Cys Met Gln Arg Thr Val
        370                 375

<210> SEQ ID NO 58
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152F/Y199F eNKG2D15 fusion

<400> SEQUENCE: 58

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
```

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Phe His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 59
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D fusion

<400> SEQUENCE: 59
atggacccga aaagctgcga caagactcac acttgtccgc cgtgccccgc ccccgaactg      60
ctgggtggcc cctccgtgtt cctgttcccg cctaagccta aggacaccct tatgatcagc     120 cgcaccccctg aagtgacctg tgtcgtcgtg gatgtgtcac acgaggaccc ggaggtcaag    180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660

```
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcatatcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggctatata   1080
gaaaactgtt caactccaaa tacatacatc tgcatgcaaa ggactgtg               1128
```

<210> SEQ ID NO 60
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152A fusion

<400> SEQUENCE: 60

```
atggacccga aaagctgcga caagactcac acttgtccgc cgtgccccgc ccccgaactg     60
ctgggtggcc cctccgtgtt cctgttcccg cctaagccta aggacaccct tatgatcagc    120
cgcacccctg aagtgacctg tgtcgtcgtg gatgtgtcac acgaggaccc ggaggtcaag    180
ttcaattggt acgtggacgg cgtggaagtg cataacgcaa agaccaagcc tcgggaggaa    240
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcagctcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggctatata   1080
gaaaactgtt caactccaaa tacatacatc tgcatgcaaa ggactgtg               1128
```

<210> SEQ ID NO 61
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y199A ectodomain

<400> SEQUENCE: 61

```
atggacccga aaagctgcga caagactcac acttgtccgc cgtgccccgc ccccgaactg     60
```

```
ctgggtggcc cctccgtgtt cctgttcccg cctaagccta aggacaccct tatgatcagc      120
cgcacccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa      240
cagtacaact cgacctaccg cgtggtgtca gtcctgactg tgctgcacca ggactggctg      300
aacgggaagg agtacaagtg caaagtgtcg aacaaggccc tgccggctcc aattgaaaag      360
accatcagca aggccaaggg ccagccaagg gaaccacagg tgtacaccct ccctccttcc      420
cgggacgagc tgaccaaaaa ccaagtgtcc ctgacttgcc ttgtgaaggg gttctaccct      480
tctgacattg ccgtcgaatg ggaatcgaac ggacagcctg aaaacaacta taagactacc      540
ccgcccgtgc tggattccga cggaagcttc ttcctgtact ccaagctgac cgtggacaag      600
tcgagatggc agcagggaaa tgtgttcagc tgctccgtga tgcatgaggc gctgcacaac      660
cactacaccc agaagtcact gagcctctcc cccggaaaga tcgaaggacg cttcttaaac      720
tcattattca accaagaagt tcaaattccc ttgaccgaaa gttactgtgg cccatgtcct      780
aaaaactgga tatgttacaa aaataactgc taccaatttt tgatgagag taaaaactgg      840 tatgagagcc aggcttcttg tatgtctcaa aatgccagcc ttctgaaagt atacagcaaa      900
gaggaccagg atttacttaa actggtgaag tcataccatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggcgctata     1080
gaaaactgtt caactccaaa tacatacatc tgcatgcaaa ggactgtg                  1128
```

<210> SEQ ID NO 62
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152A/Y199A ectodomain

<400> SEQUENCE: 62

```
atggacccga aaagctgcga caagactcac acttgtccgc cgtgccccgc ccccgaactg       60
ctgggtggcc cctccgtgtt cctgttcccg cctaagccta aggacaccct tatgatcagc      120
cgcacccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa      240
cagtacaact cgacctaccg cgtggtgtca gtcctgactg tgctgcacca ggactggctg      300
aacgggaagg agtacaagtg caaagtgtcg aacaaggccc tgccggctcc aattgaaaag      360
accatcagca aggccaaggg ccagccaagg gaaccacagg tgtacaccct ccctccttcc      420
cgggacgagc tgaccaaaaa ccaagtgtcc ctgacttgcc ttgtgaaggg gttctaccct      480
tctgacattg ccgtcgaatg ggaatcgaac ggacagcctg aaaacaacta taagactacc      540
ccgcccgtgc tggattccga cggaagcttc ttcctgtact ccaagctgac cgtggacaag      600
tcgagatggc agcagggaaa tgtgttcagc tgctccgtga tgcatgaggc gctgcacaac      660
cactacaccc agaagtcact gagcctctcc cccggaaaga tcgaaggacg cttcttaaac      720
tcattattca accaagaagt tcaaattccc ttgaccgaaa gttactgtgg cccatgtcct      780
aaaaactgga tatgttacaa aaataactgc taccaatttt tgatgagag taaaaactgg      840 tatgagagcc aggcttcttg tatgtctcaa aatgccagcc ttctgaaagt atacagcaaa      900
gaggaccagg atttacttaa actggtgaag tcagctcatt ggatgggact agtacacatt      960
```

| | |
|---|---|
| ccaacaaatg gatcttggca gtgggaagat ggctccattc tctcacccaa cctactaaca | 1020 |
| ataattgaaa tgcagaaggg agactgtgca ctctatgcct cgagctttaa aggcgctata | 1080 |
| gaaaactgtt caactccaaa tacatacatc tgcatgcaaa ggactgtg | 1128 |

<210> SEQ ID NO 63
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y199F eNKG2D1 fusion

<400> SEQUENCE: 63

| | |
|---|---|
| atggacccga aaagctgcga caagactcac acttgtccgc cgtgccccgc ccccgaactg | 60 |
| ctgggtggcc cctccgtgtt cctgttcccg cctaagccta aggacaccct tatgatcagc | 120 |
| cgcacccctg aagtgacctg tgtcgtcgtg gatgtgtcac acgaggaccc ggaggtcaag | 180 |
| ttcaattggt acgtggacgg cgtggaagtg cataacgcaa agaccaagcc tcgggaggaa | 240 |
| cagtacaact cgacctaccg cgtggtgtca gtcctgactg tgctgcacca ggactggctg | 300 |
| aacgggaagg agtacaagtg caaagtgtcg aacaaggccc tgccggctcc aattgaaaag | 360 |
| accatcagca aggccaaggg ccagccaagg gaaccacagg tgtacaccct ccctccttcc | 420 |
| cgggacgagc tgaccaaaaa ccaagtgtcc ctgacttgcc ttgtgaaggg gttctaccct | 480 |
| tctgacattg ccgtcgaatg ggaatcgaac ggacagcctg aaaacaacta taagactacc | 540 |
| ccgcccgtgc tggattccga cggaagcttc ttcctgtact ccaagctgac cgtggacaag | 600 |
| tcgagatggc agcagggaaa tgtgttcagc tgctccgtga gcatgaggc gctgcacaac | 660 |
| cactacaccc agaagtcact gagcctctcc cccggaaaga tcgaaggacg cttcttaaac | 720 |
| tcattattca accaagaagt tcaaattccc ttgaccgaaa gttactgtgg cccatgtcct | 780 |
| aaaaactgga tatgttacaa aaataactgc taccaatttt ttgatgagag taaaaactgg | 840 |
| tatgagagcc aggcttcttg tatgtctcaa aatgccagcc ttctgaaagt atacagcaaa | 900 |
| gaggaccagg atttacttaa actggtgaag tcataccatt ggatgggact agtacacatt | 960 |
| ccaacaaatg gatcttggca gtgggaagat ggctccattc tctcacccaa cctactaaca | 1020 |
| ataattgaaa tgcagaaggg agactgtgca ctctatgcct cgagctttaa aggcttcata | 1080 |
| gaaaactgtt caactccaaa tacatacatc tgcatgcaaa ggactgtg | 1128 |

<210> SEQ ID NO 64
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152S eNKG2D2 fusion

<400> SEQUENCE: 64

| | |
|---|---|
| atggacccga aaagctgcga caagactcac acttgtccgc cgtgccccgc ccccgaactg | 60 |
| ctgggtggcc cctccgtgtt cctgttcccg cctaagccta aggacaccct tatgatcagc | 120 |
| cgcacccctg aagtgacctg tgtcgtcgtg gatgtgtcac acgaggaccc ggaggtcaag | 180 |
| ttcaattggt acgtggacgg cgtggaagtg cataacgcaa agaccaagcc tcgggaggaa | 240 |
| cagtacaact cgacctaccg cgtggtgtca gtcctgactg tgctgcacca ggactggctg | 300 |
| aacgggaagg agtacaagtg caaagtgtcg aacaaggccc tgccggctcc aattgaaaag | 360 |
| accatcagca aggccaaggg ccagccaagg gaaccacagg tgtacaccct ccctccttcc | 420 |

```
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcataccatt ggatgggact agtacacatt    960
ccaacaaatg gatcttggca gtgggaagat ggctccattc tctcacccaa cctactaaca    1020
ataattgaaa tgcagaaggg agactgtgca ctctatgcct cgagctttaa aggcttcata    1080
gaaaactgtt caactccaaa tacatacatc tgcatgcaaa ggactgtg                 1128
```

<210> SEQ ID NO 65
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152T eNKG2D3 fusion

<400> SEQUENCE: 65

```
atggacccga aaagctgcga caagactcac acttgtccgc cgtgccccgc ccccgaactg    60
ctgggtggcc cctccgtgtt cctgttcccg cctaagccta aggacaccct tatgatcagc    120
cgcacccctg aagtgacctg tgtcgtcgtg gatgtgtcac acgaggaccc ggaggtcaag    180
ttcaattggt acgtggacgg cgtggaagtg cataacgcaa agaccaagcc tcgggaggaa    240
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcaactcatt ggatgggact agtacacatt    960
ccaacaaatg gatcttggca gtgggaagat ggctccattc tctcacccaa cctactaaca    1020
ataattgaaa tgcagaaggg agactgtgca ctctatgcct cgagctttaa aggctatata    1080
gaaaactgtt caactccaaa tacatacatc tgcatgcaaa ggactgtg                 1128
```

<210> SEQ ID NO 66
<211> LENGTH: 1128
<212> TYPE: DNA
<213> ORGANISM: Artificial sequence -continued

```
<220> FEATURE:
<223> OTHER INFORMATION: Synthetic polynucleotide, encoding human IgG1
      Fc-NKG2D Y152V eNKG2D4 fusion

<400> SEQUENCE: 66
atggacccga aaagctgcga caagactcac acttgtccgc cgtgccccgc ccccgaactg      60
ctgggtggcc cctccgtgtt cctgttcccg cctaagccta aggacaccct tatgatcagc    120
cgcaccctg aagtgacctg tgtcgtcgtg gatgtgtcac acgaggaccc ggaggtcaag     180
ttcaattggt acgtggacgg cgtggaagtg cataacgcaa agaccaagcc tcgggaggaa    240
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc ccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcagtgcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggctatata   1080
gaaaactgtt caactccaaa tacatacatc tgcatgcaaa ggactgtg               1128

<210> SEQ ID NO 67
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152A/Y199F eNKG2D5 fusion

<400> SEQUENCE: 67
atggacccga aaagctgcga caagactcac acttgtccgc cgtgccccgc ccccgaactg      60
ctgggtggcc cctccgtgtt cctgttcccg cctaagccta aggacaccct tatgatcagc    120
cgcaccctg aagtgacctg tgtcgtcgtg gatgtgtcac acgaggaccc ggaggtcaag     180
ttcaattggt acgtggacgg cgtggaagtg cataacgcaa agaccaagcc tcgggaggaa    240
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc ccggaaaga tcgaaggacg cttcttaaac    720
```

| | |
|---|---|
| tcattattca accaagaagt tcaaattccc ttgaccgaaa gttactgtgg cccatgtcct | 780 |
| aaaaactgga tatgttacaa aaataactgc taccaatttt ttgatgagag taaaaactgg | 840 |
| tatgagagcc aggcttcttg tatgtctcaa aatgccagcc ttctgaaagt atacagcaaa | 900 |
| gaggaccagg atttacttaa actggtgaag tcagctcatt ggatgggact agtacacatt | 960 |
| ccaacaaatg gatcttggca gtgggaagat ggctccattc tctcacccaa cctactaaca | 1020 |
| ataattgaaa tgcagaaggg agactgtgca ctctatgcct cgagctttaa aggcttcata | 1080 |
| gaaaactgtt caactccaaa tacatacatc tgcatgcaaa ggactgtg | 1128 |

<210> SEQ ID NO 68
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152L/Y199F eNKG2D6 fusion

<400> SEQUENCE: 68

| | |
|---|---|
| atggacccga aaagctgcga caagactcac acttgtccgc cgtgccccgc ccccgaactg | 60 |
| ctgggtggcc cctccgtgtt cctgttcccg cctaagccta aggacaccct tatgatcagc | 120 |
| cgcacccctg aagtgacctg tgtcgtcgtg gatgtgtcac acgaggaccc ggaggtcaag | 180 |
| ttcaattggt acgtggacgg cgtggaagtg cataacgcaa agaccaagcc tcggaggaa | 240 |
| cagtacaact cgacctaccg cgtggtgtca gtcctgactg tgctgcacca ggactggctg | 300 |
| aacgggaagg agtacaagtg caaagtgtcg aacaaggccc tgccggctcc aattgaaaag | 360 |
| accatcagca aggccaaggg ccagccaagg gaaccacagg tgtacaccct ccctccttcc | 420 |
| cgggacgagc tgaccaaaaa ccaagtgtcc ctgacttgcc ttgtgaaggg gttctaccct | 480 |
| tctgacattg ccgtcgaatg ggaatcgaac ggacagcctg aaaacaacta taagactacc | 540 |
| ccgcccgtgc tggattccga cggaagcttc ttcctgtact ccaagctgac cgtggacaag | 600 |
| tcgagatggc agcagggaaa tgtgttcagc tgctccgtga tgcatgaggc gctgcacaac | 660 |
| cactacaccc agaagtcact gagcctctcc cccggaaaga tcgaaggacg cttcttaaac | 720 |
| tcattattca accaagaagt tcaaattccc ttgaccgaaa gttactgtgg cccatgtcct | 780 |
| aaaaactgga tatgttacaa aaataactgc taccaatttt ttgatgagag taaaaactgg | 840 |
| tatgagagcc aggcttcttg tatgtctcaa aatgccagcc ttctgaaagt atacagcaaa | 900 |
| gaggaccagg atttacttaa actggtgaag tcactgcatt ggatgggact agtacacatt | 960 |
| ccaacaaatg gatcttggca gtgggaagat ggctccattc tctcacccaa cctactaaca | 1020 |
| ataattgaaa tgcagaaggg agactgtgca ctctatgcct cgagctttaa aggcttcata | 1080 |
| gaaaactgtt caactccaaa tacatacatc tgcatgcaaa ggactgtg | 1128 |

<210> SEQ ID NO 69
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152S/Y199F eNKG2D7 fusion

<400> SEQUENCE: 69

| | |
|---|---|
| atggacccga aaagctgcga caagactcac acttgtccgc cgtgccccgc ccccgaactg | 60 |
| ctgggtggcc cctccgtgtt cctgttcccg cctaagccta aggacaccct tatgatcagc | 120 |
| cgcacccctg aagtgacctg tgtcgtcgtg gatgtgtcac acgaggaccc ggaggtcaag | 180 | ttcaattggt acgtggacgg cgtggaagtg cataacgcaa agaccaagcc tcgggaggaa     240 cagtacaact cgacctaccg cgtggtgtca gtcctgactg tgctgcacca ggactggctg     300 aacgggaagg agtacaagtg caaagtgtcg aacaaggccc tgccggctcc aattgaaaag     360 accatcagca aggccaaggg ccagccaagg gaaccacagg tgtacaccct ccctccttcc     420 cgggacgagc tgaccaaaaa ccaagtgtcc ctgacttgcc ttgtgaaggg gttctaccct     480 tctgacattg ccgtcgaatg ggaatcgaac ggacagcctg aaaacaacta taagactacc     540 ccgcccgtgc tggattccga cggaagcttc ttcctgtact ccaagctgac cgtggacaag     600 tcgagatggc agcagggaaa tgtgttcagc tgctccgtga tgcatgaggc gctgcacaac     660 cactacaccc agaagtcact gagcctctcc cccggaaaga tcgaaggacg cttcttaaac     720 tcattattca accaagaagt tcaaattccc ttgaccgaaa gttactgtgg cccatgtcct     780 aaaaactgga tatgttacaa aaataactgc taccaatttt ttgatgagag taaaaactgg     840 tatgagagcc aggcttcttg tatgtctcaa aatgccagcc ttctgaaagt atacagcaaa     900 gaggaccagg atttacttaa actggtgaag tcaagtcatt ggatgggact agtacacatt     960 ccaacaaatg gatcttggca gtgggaagat ggctccattc tctcacccaa cctactaaca    1020 ataattgaaa tgcagaaggg agactgtgca ctctatgcct cgagctttaa aggcttcata    1080 gaaaactgtt caactccaaa tacatacatc tgcatgcaaa ggactgtg               1128

<210> SEQ ID NO 70
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152T/Y199F eNKG2D8 fusion

<400> SEQUENCE: 70
atggacccga aaagctgcga caagactcac acttgtccgc cgtgccccgc ccccgaactg      60
ctgggtggcc cctccgtgtt cctgttcccg cctaagccta aggacaccct tatgatcagc     120 cgcaccctg aagtgacctg tgtcgtcgtg gatgtgtcac acgaggaccc ggaggtcaag     180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaatttt ttgatgagag taaaaactgg     840
tatgagagcc aggcttcttg tatgtctcaa aatgccagcc ttctgaaagt atacagcaaa     900
gaggaccagg atttacttaa actggtgaag tcaactcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggcttcata    1080

```
gaaaactgtt caactccaaa tacatacatc tgcatgcaaa ggactgtg          1128
```

<210> SEQ ID NO 71
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152V/Y199F eNKG2D9 fusion

<400> SEQUENCE: 71

```
atggacccga aaagctgcga caagactcac acttgtccgc cgtgccccgc ccccgaactg    60
ctgggtggcc cctccgtgtt cctgttcccg cctaagccta aggacaccct tatgatcagc   120
cgcacccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
tctgacattg ccgtcgaatg ggaatcgaac ggacagcctg aaaacaacta taagactacc   540
ccgcccgtgc tggattccga cggaagcttc ttcctgtact ccaagctgac cgtggacaag   600
tcgagatggc agcagggaaa tgtgttcagc tgctccgtga tgcatgaggc gctgcacaac   660
cactacaccc agaagtcact gagcctctcc cccggaaaga tcgaaggacg cttcttaaac   720
tcattattca accaagaagt tcaaattccc ttgaccgaaa gttactgtgg cccatgtcct   780
aaaaactgga tatgttacaa aaataactgc taccaatttt ttgatgagag taaaaactgg   840
tatgagagcc aggcttcttg tatgtctcaa aatgccagcc ttctgaaagt atacagcaaa   900
gaggaccagg atttacttaa actggtgaag tcagtgcatt ggatgggact agtacacatt   960
ccaacaaatg gatcttggca gtgggaagat ggctccattc tctcacccaa cctactaaca  1020
ataattgaaa tgcagaaggg agactgtgca ctctatgcct cgagctttaa aggcttcata  1080
gaaaactgtt caactccaaa tacatacatc tgcatgcaaa ggactgtg            1128
```

<210> SEQ ID NO 72
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y199D eNKG2D10 fusion

<400> SEQUENCE: 72

```
atggacccga aaagctgcga caagactcac acttgtccgc cgtgccccgc ccccgaactg    60
ctgggtggcc cctccgtgtt cctgttcccg cctaagccta aggacaccct tatgatcagc   120
cgcacccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
```
tctgacattg ccgtcgaatg ggaatcgaac ggacagcctg aaaacaacta taagactacc 540
ccgcccgtgc tggattccga cggaagcttc ttcctgtact ccaagctgac cgtggacaag 600
tcgagatggc agcagggaaa tgtgttcagc tgctccgtga tgcatgaggc gctgcacaac 660
cactacaccc agaagtcact gagcctctcc ccggaaaga tcgaaggacg cttcttaaac 720
tcattattca accaagaagt tcaaattccc ttgaccgaaa gttactgtgg cccatgtcct 780
aaaaactgga tatgttacaa aaataactgc taccaatttt tgatgagag taaaaactgg 840 tatgagagcc aggcttcttg tatgtctcaa aatgccagcc ttctgaaagt atacagcaaa 900
gaggaccagg atttacttaa actggtgaag tcatatcatt ggatgggact agtacacatt 960
ccaacaaatg gatcttggca gtgggaagat ggctccattc tctcacccaa cctactaaca 1020
ataattgaaa tgcagaaggg agactgtgca ctctatgcct cgagctttaa aggcgatata 1080
gaaaactgtt caactccaaa tacatacatc tgcatgcaaa ggactgtg 1128

<210> SEQ ID NO 73
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y199E eNKG2D11 fusion

<400> SEQUENCE: 73
atggacccga aaagctgcga caagactcac acttgtccgc cgtgccccgc cccgaactg 60 ctgggtggcc cctccgtgtt cctgttcccg cctaagccta aggacaccct tatgatcagc 120 cgcaccccctg aagtgacctg tgtcgtcgtg gatgtgtcac acgaggaccc ggaggtcaag 180
ttcaattggt acgtggacgg cgtggaagtg cataacgcaa agaccaagcc tcgggaggaa 240
cagtacaact cgacctaccg cgtggtgtca gtcctgactg tgctgcacca ggactggctg 300
aacgggaagg agtacaagtg caaagtgtcg aacaaggccc tgccggctcc aattgaaaag 360
accatcagca aggccaaggg ccagccaagg gaaccacagg tgtacaccct ccctccttcc 420
cgggacgagc tgaccaaaaa ccaagtgtcc ctgacttgcc ttgtgaaggg gttctacccc 480
tctgacattg ccgtcgaatg ggaatcgaac ggacagcctg aaaacaacta taagactacc 540
ccgcccgtgc tggattccga cggaagcttc ttcctgtact ccaagctgac cgtggacaag 600
tcgagatggc agcagggaaa tgtgttcagc tgctccgtga tgcatgaggc gctgcacaac 660
cactacaccc agaagtcact gagcctctcc ccggaaaga tcgaaggacg cttcttaaac 720
tcattattca accaagaagt tcaaattccc ttgaccgaaa gttactgtgg cccatgtcct 780
aaaaactgga tatgttacaa aaataactgc taccaatttt tgatgagag taaaaactgg 840 tatgagagcc aggcttcttg tatgtctcaa aatgccagcc ttctgaaagt atacagcaaa 900
gaggaccagg atttacttaa actggtgaag tcataccatt ggatgggact agtacacatt 960
ccaacaaatg gatcttggca gtgggaagat ggctccattc tctcacccaa cctactaaca 1020
ataattgaaa tgcagaaggg agactgtgca ctctatgcct cgagctttaa aggcgagata 1080
gaaaactgtt caactccaaa tacatacatc tgcatgcaaa ggactgtg 1128

<210> SEQ ID NO 74
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152D/Y199D eNKG2D12 fusion -continued

<400> SEQUENCE: 74

| | | | | | |
|---|---|---|---|---|---|
| atggacccga | aaagctgcga | caagactcac | acttgtccgc | cgtgccccgc | ccccgaactg | 60 |
| ctgggtggcc | cctccgtgtt | cctgttcccg | cctaagccta | aggacaccct | tatgatcagc | 120 |
| cgcaccctg | aagtgacctg | tgtcgtcgtg | gatgtgtcac | acgaggaccc | ggaggtcaag | 180 |
| ttcaattggt | acgtggacgg | cgtggaagtg | cataacgcaa | agaccaagcc | tcgggaggaa | 240 |
| cagtacaact | cgacctaccg | cgtggtgtca | gtcctgactg | tgctgcacca | ggactggctg | 300 |
| aacgggaagg | agtacaagtg | caaagtgtcg | aacaaggccc | tgccggctcc | aattgaaaag | 360 |
| accatcagca | aggccaaggg | ccagccaagg | gaaccacagg | tgtacaccct | ccctccttcc | 420 |
| cgggacgagc | tgaccaaaaa | ccaagtgtcc | ctgacttgcc | ttgtgaaggg | gttctaccct | 480 |
| tctgacattg | ccgtcgaatg | ggaatcgaac | ggacagcctg | aaaacaacta | taagactacc | 540 |
| ccgcccgtgc | tggattccga | cggaagcttc | ttcctgtact | ccaagctgac | cgtggacaag | 600 |
| tcgagatggc | agcagggaaa | tgtgttcagc | tgctccgtga | tgcatgaggc | gctgcacaac | 660 |
| cactacaccc | agaagtcact | gagcctctcc | cccggaaaga | tcgaaggacg | cttcttaaac | 720 |
| tcattattca | accaagaagt | tcaaattccc | ttgaccgaaa | gttactgtgg | cccatgtcct | 780 |
| aaaaactgga | tatgttacaa | aaataactgc | taccaatttt | ttgatgagag | taaaaactgg | 840 |
| tatgagagcc | aggcttcttg | tatgtctcaa | aatgccagcc | ttctgaaagt | atacagcaaa | 900 |
| gaggaccagg | atttacttaa | actggtgaag | tcagatcatt | ggatgggact | agtacacatt | 960 |
| ccaacaaatg | gatcttggca | gtgggaagat | ggctccattc | tctcacccaa | cctactaaca | 1020 |
| ataattgaaa | tgcagaaggg | agactgtgca | ctctatgcct | cgagctttaa | aggcgatata | 1080 |
| gaaaactgtt | caactccaaa | tacatacatc | tgcatgcaaa | ggactgtg | | 1128 |

<210> SEQ ID NO 75
<211> LENGTH: 1128
<212> TYPE: DNA
<213> ORGANISM: Artificial sequence
<220> FEATURE:
<223> OTHER INFORMATION: Synthetic polynucleotide, encoding human IgG1 Fc-NKG2D Y152E/Y199E eNKG2D13 fusion

<400> SEQUENCE: 75

| | | | | | |
|---|---|---|---|---|---|
| atggacccga | aaagctgcga | caagactcac | acttgtccgc | cgtgccccgc | ccccgaactg | 60 |
| ctgggtggcc | cctccgtgtt | cctgttcccg | cctaagccta | aggacaccct | tatgatcagc | 120 |
| cgcaccctg | aagtgacctg | tgtcgtcgtg | gatgtgtcac | acgaggaccc | ggaggtcaag | 180 |
| ttcaattggt | acgtggacgg | cgtggaagtg | cataacgcaa | agaccaagcc | tcgggaggaa | 240 |
| cagtacaact | cgacctaccg | cgtggtgtca | gtcctgactg | tgctgcacca | ggactggctg | 300 |
| aacgggaagg | agtacaagtg | caaagtgtcg | aacaaggccc | tgccggctcc | aattgaaaag | 360 |
| accatcagca | aggccaaggg | ccagccaagg | gaaccacagg | tgtacaccct | ccctccttcc | 420 |
| cgggacgagc | tgaccaaaaa | ccaagtgtcc | ctgacttgcc | ttgtgaaggg | gttctaccct | 480 |
| tctgacattg | ccgtcgaatg | ggaatcgaac | ggacagcctg | aaaacaacta | taagactacc | 540 |
| ccgcccgtgc | tggattccga | cggaagcttc | ttcctgtact | ccaagctgac | cgtggacaag | 600 |
| tcgagatggc | agcagggaaa | tgtgttcagc | tgctccgtga | tgcatgaggc | gctgcacaac | 660 |
| cactacaccc | agaagtcact | gagcctctcc | cccggaaaga | tcgaaggacg | cttcttaaac | 720 |
| tcattattca | accaagaagt | tcaaattccc | ttgaccgaaa | gttactgtgg | cccatgtcct | 780 |
| aaaaactgga | tatgttacaa | aaataactgc | taccaatttt | ttgatgagag | taaaaactgg | 840 |

```
tatgagagcc aggcttcttg tatgtctcaa aatgccagcc ttctgaaagt atacagcaaa      900
gaggaccagg atttacttaa actggtgaag tcagagcatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggcgagata     1080
gaaaactgtt caactccaaa tacatacatc tgcatgcaaa ggactgtg                  1128
```

<210> SEQ ID NO 76
<211> LENGTH: 1128
<212> TYPE: DNA
<213> ORGANISM: Artificial sequence
<220> FEATURE:
<223> OTHER INFORMATION: Synthetic polynucleotide, encoding human IgG1
     Fc-NKG2D Y152L eNKG2D14 fusion

<400> SEQUENCE: 76

```
atggaccccga aaagctgcga caagactcac acttgtccgc cgtgccccgc ccccgaactg       60
ctgggtggcc cctccgtgtt cctgttcccg cctaagccta aggacaccct tatgatcagc      120 cgcaccccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa      240
cagtacaact cgacctaccg cgtggtgtca gtcctgactg tgctgcacca ggactggctg      300
aacgggaagg agtacaagtg caaagtgtcg aacaaggccc tgccggctcc aattgaaaag      360
accatcagca aggccaaggg ccagccaagg gaaccacagg tgtacaccct ccctccttcc      420
cgggacgagc tgaccaaaaa ccaagtgtcc ctgacttgcc ttgtgaaggg gttctaccct      480
tctgacattg ccgtcgaatg ggaatcgaac ggacagcctg aaaacaacta taagactacc      540
ccgcccgtgc tggattccga cggaagcttc ttcctgtact ccaagctgac cgtggacaag      600
tcgagatggc agcagggaaa tgtgttcagc tgctccgtga tgcatgaggc gctgcacaac      660
cactacaccc agaagtcact gagcctctcc cccggaaaga tcgaaggacg cttcttaaac      720
tcattattca accaagaagt tcaaattccc ttgaccgaaa gttactgtgg cccatgtcct      780
aaaaactgga tatgttacaa aaataactgc taccaatttt ttgatgagag taaaaactgg      840
tatgagagcc aggcttcttg tatgtctcaa aatgccagcc ttctgaaagt atacagcaaa      900
gaggaccagg atttacttaa actggtgaag tcactgcatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggctatata     1080
gaaaactgtt caactccaaa tacatacatc tgcatgcaaa ggactgtg                  1128
```

<210> SEQ ID NO 77
<211> LENGTH: 1128
<212> TYPE: DNA
<213> ORGANISM: Artificial sequence
<220> FEATURE:
<223> OTHER INFORMATION: Synthetic polynucleotide, encoding human IgG1
     Fc-NKG2D Y152F/Y199F eNKG2D15 fusion

<400> SEQUENCE: 77

```
atggaccccga aaagctgcga caagactcac acttgtccgc cgtgccccgc ccccgaactg       60
ctgggtggcc cctccgtgtt cctgttcccg cctaagccta aggacaccct tatgatcagc      120 cgcaccccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa      240
```

| | | | | |
|---|---|---|---|---|
| cagtacaact | cgacctaccg | cgtggtgtca | gtcctgactg | tgctgcacca ggactggctg | 300 |
| aacgggaagg | agtacaagtg | caaagtgtcg | aacaaggccc | tgccggctcc aattgaaaag | 360 |
| accatcagca | aggccaaggg | ccagccaagg | gaaccacagg | tgtacaccct ccctccttcc | 420 |
| cgggacgagc | tgaccaaaaa | ccaagtgtcc | ctgacttgcc | ttgtgaaggg gttctaccct | 480 |
| tctgacattg | ccgtcgaatg | ggaatcgaac | ggacagcctg | aaaacaacta taagactacc | 540 |
| ccgcccgtgc | tggattccga | cggaagcttc | ttcctgtact | ccaagctgac cgtggacaag | 600 |
| tcgagatggc | agcagggaaa | tgtgttcagc | tgctccgtga | tgcatgaggc gctgcacaac | 660 |
| cactacaccc | cagaagtcact | gagcctctcc | cccggaaaga | tcgaaggacg cttcttaaac | 720 |
| tcattattca | accaagaagt | tcaaattccc | ttgaccgaaa | gttactgtgg cccatgtcct | 780 |
| aaaaactgga | tatgttacaa | aaataactgc | taccaatttt | ttgatgagag taaaaactgg | 840 |
| tatgagagcc | aggcttcttg | tatgtctcaa | aatgccagcc | ttctgaaagt atacagcaaa | 900 |
| gaggaccagg | atttacttaa | actggtgaag | tcattccatt | ggatgggact agtacacatt | 960 |
| ccaacaaatg | gatcttggca | gtgggaagat | ggctccattc | tctcacccaa cctactaaca | 1020 |
| ataattgaaa | tgcagaaggg | agactgtgca | ctctatgcct | cgagctttaa aggcttcata | 1080 |
| gaaaactgtt | caactccaaa | tacatacatc | tgcatgcaaa | ggactgtg | 1128 |

<210> SEQ ID NO 78
<211> LENGTH: 181
<212> TYPE: PRT
<213> ORGANISM: Artificial sequence
<220> FEATURE:
<223> OTHER INFORMATION: Synthetic peptide MICwed alpha1-alpha2

<400> SEQUENCE: 78

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr
            180

<210> SEQ ID NO 79
<211> LENGTH: 543

<212> TYPE: DNA
<213> ORGANISM: Artificial sequence
<220> FEATURE:
<223> OTHER INFORMATION: Synthetic polynucleotide, encoding MICwed alpha1-alpha2

<400> SEQUENCE: 79

```
gagcctcaca gcctccggta taatttgact gtactctctt gggatggctc cgtgcagtcc      60
ggctttctga ctgaagttca tctcgacggt caacctttcc tgcgctgcga ccgacaaaaa     120
tgccgcgcca agccccaagg cagtgggcc gaagatgtac tgggaaacaa gacctgggac      180
cgggagacac gagacctgac aggctggggc aaggacttgc gcatgacact cgcccatatc     240
aaggaccaga aggaaggatt gcactctttg caagagattc gcgtgtgtga aatccacgag     300
gacaattcaa cgaggagctc ccagcacttc tattacgatg gagaactctt cttgtcacag     360
aacttggaaa ccaaggaatg gactatgcct cagagctctc gggcacagac tctcgctatg     420
aacgttagaa acttccttaa ggaggatgct atggagaccg atactcacta ccacgccatg     480
cacgccgact gcctccagga actgcggaga tatctgaagt ccggcgtggt tttgagaaga     540
acc                                                                   543
```

<210> SEQ ID NO 80
<211> LENGTH: 181
<212> TYPE: PRT
<213> ORGANISM: Artificial sequence
<220> FEATURE:
<223> OTHER INFORMATION: Synthetic peptide MIC25 alpha1-alpha2

<400> SEQUENCE: 80

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr
            180
```

<210> SEQ ID NO 81
<211> LENGTH: 543
<212> TYPE: DNA
<213> ORGANISM: Artificial sequence
<220> FEATURE:
<223> OTHER INFORMATION: Synthetic polynucleotide, encoding MIC25
      alpha1-alpha2

<400> SEQUENCE: 81

```
gagcctcaca gcctccggta taatttgact gtactctctt gggatggctc cgtgcagtcc    60
ggctttctga ctgaagttca tctcgacggt caaccttcc tgcgctgcga ccgacaaaaa   120
tgccgcgcca agccccaagg gcagtgggcc gaagatgtac tgggaaacaa gacctgggac   180
cgggagacac gagacctgac aggctggggc aaggacttgc gcatgacact cgcccatatc   240
aaggaccaga aggaaggatt gcactctttg caagagattc gcgtgtgtga atccacgag    300
gacaattcaa cgaggagctc ccagcacttc tattacgatg gagaactctt cttgtcacag   360
aacttggaaa ccctcgaatg gactatgcct cagagctctc gggcacagac tctcgctatg   420
aacgttagaa acttccttaa ggaggatgct atggagaccg atactcacta ccacgccatg   480
cgcgccgact gcctctctga actgcggaga tatctgaagt ccggcgtggt tttgaagaa    540
acc                                                                 543
```

<210> SEQ ID NO 82
<211> LENGTH: 330
<212> TYPE: PRT
<213> ORGANISM: Artificial sequence
<220> FEATURE:
<223> OTHER INFORMATION: Synthetic peptide human IgG1 heavy chain
      CH1-CH2-CH3 D265A/N297A

<400> SEQUENCE: 82

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 83
<211> LENGTH: 990
<212> TYPE: DNA
<213> ORGANISM: Artificial sequence
<220> FEATURE:
<223> OTHER INFORMATION: human IgG1 heavy chain CH1-CH2-CH3 D265A/N297A

<400> SEQUENCE: 83
gcgtcgacca agggcccgtc agtgttcccg ctggccccgt catccaagtc cacgtctggg      60
ggcacagcag ccctgggatg cttggtcaag gactacttcc ccgagcccgt gactgtgtcc     120
tggaactccg gagcactgac ctccggagtg cacaccttcc cgcggtgct gcagtcctcc     180 ggactgtact ccctgtcgtc ggtcgtgacc gtgccgagct cctcgctcgg aacccagacc     240
tacatctgca acgtgaacca caagccctcg aacaccaaag tggacaagaa ggtcgagccc     300
aaaagctgcg acaagactca cacttgtccg ccgtgccccg cccccgaact gctgggtggc     360
ccctccgtgt tcctgttccc gcctaagcct aaggacaccc ttatgatcag ccgcaccct     420 gaagtgacct gtgtcgtcgt ggcagtgtca cacgaggacc cggaggtcaa gttcaattgg     480
tacgtggacg gcgtggaagt gcataacgca aagaccaagc ctcgggagga acagtacgcc     540
tcgacctacc gcgtggtgtc agtcctgact gtgctgcacc aggactggct gaacgggaag     600
gagtacaagt gcaaagtgtc gaacaaggcc ctgccggctc caattgaaaa gaccatcagc     660
aaggccaagg gccagccaag ggaaccacag gtgtacaccc tccctccttc ccgggacgag     720
ctgaccaaaa accaagtgtc cctgacttgc cttgtgaagg ggttctaccc ttctgacatt     780
gccgtcgaat gggaatcgaa cggacagcct gaaaacaact ataagactac cccgcccgtg     840
ctggattccg acggaagctt cttcctgtac tccaagctga ccgtggacaa gtcgagatgg     900
cagcagggaa atgtgttcag ctgctccgtg atgcatgagg cgctgcacaa ccactacacc     960
cagaagtcac tgagcctctc ccccggaaag                                      990

<210> SEQ ID NO 84
<211> LENGTH: 107
<212> TYPE: PRT
<213> ORGANISM: Artificial sequence
<220> FEATURE:
<223> OTHER INFORMATION: Synthetic peptide human kappa light chain

<400> SEQUENCE: 84

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
                20                  25                  30
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 85
<211> LENGTH: 321
<212> TYPE: DNA
<213> ORGANISM: Artificial sequence
<220> FEATURE:
<223> OTHER INFORMATION: Synthetic polynucleotide, encoding human kappa
      light chain

<400> SEQUENCE: 85
agaaccgtgg ccgccccgag cgtgttcatt ttccctccct ccgacgagca gttgaaatcg    60
ggcaccgcta gcgtggtctg ccttctcaac aatttctatc cacgggaagc caaagtgcag   120
tggaaggtcg acaacgcgct ccaatccggg aactcacagg aatccgtgac tgagcaggat   180
tccaaggact cgacctactc cctgtcatcc acgctgaccc tgagcaaggc agactacgag   240
aagcacaagg tctacgcctg cgaagtgaca caccagggac tgtccagccc cgtgaccaag   300
agcttcaaca gaggagaatg c                                              321

<210> SEQ ID NO 86
<211> LENGTH: 120
<212> TYPE: PRT
<213> ORGANISM: Artificial sequence
<220> FEATURE:
<223> OTHER INFORMATION: Synthetic peptide trastuzumab VH

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 87
<211> LENGTH: 360
<212> TYPE: DNA
<213> ORGANISM: Artificial sequence
```

```
<220> FEATURE:
<223> OTHER INFORMATION: Synthetic polynucleotide, encoding trastuzumab
      VH

<400> SEQUENCE: 87
gaagtccaat tggtcgaatc aggcggtgga ctcgtgcaac ctggaggttc gttacgctta      60
tcatgtgctg caagtggatt taatattaaa gatacctaca tccactgggt acgtcaagct     120
cccggcaagg gtctcgagtg ggtcgcacgc atttacccca ccaacggata cacgcgctac     180
gccgattcag tgaagggacg tttcacaatc tctgctgata ctagcaaaaa taccgcatac     240
ctccagatga actctcttag ggccgaggac acagctgtgt actactgtag ccgttgggga     300
ggagacggtt tttacgcaat ggattactgg ggccaaggaa ccctggtcac agtttcatcg     360

<210> SEQ ID NO 88
<211> LENGTH: 107
<212> TYPE: PRT
<213> ORGANISM: Artificial sequence
<220> FEATURE:
<223> OTHER INFORMATION: Synthetic peptide trastuzumab VL

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 89
<211> LENGTH: 321
<212> TYPE: DNA
<213> ORGANISM: Artificial sequence
<220> FEATURE:
<223> OTHER INFORMATION: Synthetic polynucleotide, encoding trastuzumab
      VL

<400> SEQUENCE: 89
gatatccaaa tgactcaatc accatcttca ctctccgcga gcgtgggtga tcgggtcacc      60
atcacatgta gggcgagcca agatgtgaat accgccgtcg cgtggtatca acaaaagccg     120
ggaaaagcac caaaactgct tatatactct gcatccttcc tgtactctgg ggtgccaagc     180
cggttctccg gtagtagatc tggtactgac tttacactca ctatcagcag tctgcaacct     240
gaggactttg cgacatacta ttgccagcag cactacacaa ccccacctac atttggtcag     300
gggacaaagg tggagatcaa g                                                321

<210> SEQ ID NO 90
<211> LENGTH: 121
<212> TYPE: PRT
<213> ORGANISM: Artificial sequence
<220> FEATURE:
<223> OTHER INFORMATION: Synthetic peptide rituximab VH
```

<400> SEQUENCE: 90

| Gln | Val | Gln | Leu | Gln | Gln | Pro | Gly | Ala | Glu | Leu | Val | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Met | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Asn | Met | His | Trp | Val | Lys | Gln | Thr | Pro | Gly | Arg | Gly | Leu | Glu | Trp | Ile |
|---|---|---|---|---|---|---|---|---|---|---|---|---|---|---|---|
| | | 35 | | | | | 40 | | | | | 45 | | | |

| Gly | Ala | Ile | Tyr | Pro | Gly | Asn | Gly | Asp | Thr | Ser | Tyr | Asn | Gln | Lys | Phe |
|---|---|---|---|---|---|---|---|---|---|---|---|---|---|---|---|
| 50 | | | | | 55 | | | | | 60 | | | | | |

| Lys | Gly | Lys | Ala | Thr | Leu | Thr | Ala | Asp | Lys | Ser | Ser | Thr | Ala | Tyr |
|---|---|---|---|---|---|---|---|---|---|---|---|---|---|---|
| 65 | | | | 70 | | | | | 75 | | | | | 80 |

| Met | Gln | Leu | Ser | Ser | Leu | Thr | Ser | Glu | Asp | Ser | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Ser | Thr | Tyr | Tyr | Gly | Gly | Asp | Trp | Tyr | Phe | Asn | Val | Trp | Gly |
|---|---|---|---|---|---|---|---|---|---|---|---|---|---|---|---|
| | | | 100 | | | | | 105 | | | | | 110 | | |

| Ala | Gly | Thr | Thr | Val | Thr | Val | Ser | Ala |
|---|---|---|---|---|---|---|---|---|
| | | | 115 | | | | | 120 |

<210> SEQ ID NO 91
<211> LENGTH: 363
<212> TYPE: DNA
<213> ORGANISM: Artificial sequence
<220> FEATURE:
<223> OTHER INFORMATION: Synthetic polynucleotide, encoding rituximab VH

<400> SEQUENCE: 91

```
caagttcagc ttcagcagcc gggggctgag ttggtgaaac ccggggccag tgtgaagatg    60
agctgtaaag cgagcggcta caccttcact tcttataata tgcattgggt taagcaaacg   120
ccaggaaggg ggctggagtg gatcggcgct atttacccag gtaacggtga cacatcatat   180
aaccaaaagt ttaagggaaa ggcaacccte acagcggaca agagtagctc aaccgcatac   240
atgcaactgt caagccttac ctccgaagac agcgcagtgt actactgcgc cagaagcacc   300
tactatgggg gtgattggta cttcaacgtc tggggggctg gcaccacagt gactgtaagc   360
gca                                                                 363
```

<210> SEQ ID NO 92
<211> LENGTH: 106
<212> TYPE: PRT
<213> ORGANISM: Artificial sequence
<220> FEATURE:
<223> OTHER INFORMATION: Synthetic peptide rituximab VL

<400> SEQUENCE: 92

| Gln | Ile | Val | Leu | Ser | Gln | Ser | Pro | Ala | Ile | Leu | Ser | Ala | Ser | Pro | Gly |
|---|---|---|---|---|---|---|---|---|---|---|---|---|---|---|---|
| 1 | | | | 5 | | | | | 10 | | | | | 15 | |

| Glu | Lys | Val | Thr | Met | Thr | Cys | Arg | Ala | Ser | Ser | Ser | Val | Ser | Tyr | Ile |
|---|---|---|---|---|---|---|---|---|---|---|---|---|---|---|---|
| | | | 20 | | | | | 25 | | | | | 30 | | |

| His | Trp | Phe | Gln | Gln | Lys | Pro | Gly | Ser | Ser | Pro | Lys | Pro | Trp | Ile | Tyr |
|---|---|---|---|---|---|---|---|---|---|---|---|---|---|---|---|
| | | 35 | | | | | 40 | | | | | 45 | | | |

| Ala | Thr | Ser | Asn | Leu | Ala | Ser | Gly | Val | Pro | Val | Arg | Phe | Ser | Gly | Ser |
|---|---|---|---|---|---|---|---|---|---|---|---|---|---|---|---|
| 50 | | | | | 55 | | | | | 60 | | | | | |

| Gly | Ser | Gly | Thr | Ser | Tyr | Ser | Leu | Thr | Ile | Ser | Arg | Val | Glu | Ala | Glu |
|---|---|---|---|---|---|---|---|---|---|---|---|---|---|---|---|
| 65 | | | | 70 | | | | | 75 | | | | | 80 | |

| Asp | Ala | Ala | Thr | Tyr | Tyr | Cys | Gln | Gln | Trp | Thr | Ser | Asn | Pro | Pro | Thr |
|---|---|---|---|---|---|---|---|---|---|---|---|---|---|---|---|
| | | | | 85 | | | | | 90 | | | | | 95 | |

Phe Gly Gly Gly Thr Lys Leu Glu Ile Lys
            100                 105

<210> SEQ ID NO 93
<211> LENGTH: 318
<212> TYPE: DNA
<213> ORGANISM: Artificial sequence
<220> FEATURE:
<223> OTHER INFORMATION: Synthetic polynucleotide, encoding rituximab VL

<400> SEQUENCE: 93
cagatcgtgt tgtcccaatc acccgcaatt ctctctgcga gcccagggga gaaggtgacc      60
atgacttgcc gcgcttcaag ttccgtatcc tacattcact ggttccagca gaagcccgga     120
agttccccta agccctggat ctatgctaca tccaatctgg caagcggtgt tcccgttaga     180 tttteecggaa geggtetgg aaccagttac agtetgacta ttteccaggget egaggeegaa     240 gatgcggcta cttattattg ccaacagtgg acctctaacc cacccacatt cggcggcggc     300
actaagttgg aaattaag                                                   318

<210> SEQ ID NO 94
<211> LENGTH: 450
<212> TYPE: PRT
<213> ORGANISM: Artificial sequence
<220> FEATURE:
<223> OTHER INFORMATION: Synthetic peptide trastuzumab heavy chain

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

```
Pro Ser Val Phe Leu Phe Pro Pro Lys Pro Lys Asp Thr Leu Met Ile
            245                 250                 255
Ser Arg Thr Pro Glu Val Thr Cys Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 95
<211> LENGTH: 1350
<212> TYPE: DNA
<213> ORGANISM: Artificial sequence
<220> FEATURE:
<223> OTHER INFORMATION: Synthetic polynucleotide, encoding trastuzumab
      heavy chain

<400> SEQUENCE: 95
gaagtccaat tggtcgaatc aggcggtgga ctcgtgcaac tggaggttc gttacgctta      60
tcatgtgctg caagtggatt taatattaaa gataccctaca tccactgggt acgtcaagct    120
cccggcaagg gtctcgagtg ggtcgcacgc atttacccca ccaacggata cacgcgctac    180
gccgattcag tgaagggacg tttcacaatc tctgctgata ctagcaaaaa taccgcatac    240
ctccagatga actctcttag ggccgaggac acagctgtgt actactgtag ccgttgggga   300
ggagacggtt tttacgcaat ggattactgg ggccaaggaa ccctggtcac agtttcatcg    360
gcgtcgacca agggcccgtc agtgttcccg ctggccccgt catccaagtc cacgtctggg    420
ggcacagcag ccctgggatg cttggtcaag gactacttcc ccgagcccgt gactgtgtcc    480
tggaactccg gagcactgac ctccggagtg cacaccttc ccgcggtgct gcagtcctcc    540
ggactgtact ccctgtcgtc ggtcgtgacc gtgccgagct cctcgctcgg aacccagacc    600
tacatctgca acgtgaacca caagccctcg aacaccaaag tggacaagaa ggtcgagccc    660
aaaagctgcg acaagactca cacttgtccg ccgtgccccg cccccgaact gctgggtggc    720
ccctccgtgt tcctgttccc gcctaagcct aaggacaccc ttatgatcag ccgcaccccct   780
```

```
gaagtgacct gtgtcgtcgt ggatgtgtca cacgaggacc cggaggtcaa gttcaattgg    840
tacgtggacg gcgtggaagt gcataacgca aagaccaagc ctcgggagga acagtacaac    900
tcgacctacc gcgtggtgtc agtcctgact gtgctgcacc aggactggct gaacgggaag    960
gagtacaagt gcaaagtgtc gaacaaggcc ctgccggctc caattgaaaa gaccatcagc   1020
aaggccaagg gccagccaag ggaaccacag gtgtacaccc tccctccttc ccgggacgag   1080
ctgaccaaaa accaagtgtc cctgacttgc cttgtgaagg ggttctaccc ttctgacatt   1140
gccgtcgaat gggaatcgaa cggacagcct gaaaacaact ataagactac cccgcccgtg   1200
ctggattccg acggaagctt cttcctgtac tccaagctga ccgtggacaa gtcgagatgg   1260
cagcagggaa atgtgttcag ctgctccgtg atgcatgagg cgctgcacaa ccactacacc   1320
cagaagtcac tgagcctctc ccccggaaag                                    1350
```

<210> SEQ ID NO 96
<211> LENGTH: 213
<212> TYPE: PRT
<213> ORGANISM: Artificial sequence
<220> FEATURE:
<223> OTHER INFORMATION: Synthetic peptide trastuzumab light chain

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 97
<211> LENGTH: 642
<212> TYPE: DNA
<213> ORGANISM: Artificial sequence
<220> FEATURE:

<223> OTHER INFORMATION: Synthetic polynucleotide, encoding trastuzumab
      light chain

<400> SEQUENCE: 97

```
gatatccaaa tgactcaatc accatcttca ctctccgcga gcgtgggtga tcgggtcacc    60
atcacatgta gggcgagcca agatgtgaat accgccgtcg cgtggtatca acaaaagccg   120
ggaaaagcac caaaactgct tatatactct gcatccttcc tgtactctgg ggtgccaagc   180
cggttctccg gtagtagatc tggtactgac tttacactca ctatcagcag tctgcaacct   240
gaggactttg cgacatacta ttgccagcag cactacacaa ccccacctac atttggtcag   300
gggacaaagg tggagatcaa gaccgtggcc gccccgagcg tgttcatttt ccctcccctcc   360
gacgagcagt tgaaatcggg caccgctagc gtggtctgcc ttctcaacaa tttctatcca   420
cgggaagcca aagtgcagtg gaaggtcgac aacgcgctcc aatccgggaa ctcacaggaa   480
tccgtgactg agcaggattc caaggactcg acctactccc tgtcatccac gctgaccctg   540
agcaaggcag actacgagaa gcacaaggtc tacgcctgcg aagtgacaca ccagggactg   600
tccagccccg tgaccaagag cttcaacaga ggagaatgct ag                     642
```

<210> SEQ ID NO 98
<211> LENGTH: 451
<212> TYPE: PRT
<213> ORGANISM: Artificial sequence
<220> FEATURE:
<223> OTHER INFORMATION: Synthetic peptide rituximab heavy chain

<400> SEQUENCE: 98

```
Gln Val Gln Leu Gln Gln Pro Gly Ala Glu Leu Val Lys Pro Gly Ala
1               5                   10                  15
Ser Val Lys Met Ser Cys Lys Ala Ser Gly Tyr Thr Phe Thr Ser Tyr
            20                  25                  30
Asn Met His Trp Val Lys Gln Thr Pro Gly Arg Gly Leu Glu Trp Ile
        35                  40                  45
Gly Ala Ile Tyr Pro Gly Asn Gly Asp Thr Ser Tyr Asn Gln Lys Phe
    50                  55                  60
Lys Gly Lys Ala Thr Leu Thr Ala Asp Lys Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Ser Thr Tyr Tyr Gly Gly Asp Trp Tyr Phe Asn Val Trp Gly
            100                 105                 110
Ala Gly Thr Thr Val Thr Val Ser Ala Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
```

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 99
<211> LENGTH: 1353
<212> TYPE: DNA
<213> ORGANISM: Artificial sequence
<220> FEATURE:
<223> OTHER INFORMATION: Synthetic polynucleotide, encoding rituximab
      heavy chain

<400> SEQUENCE: 99
caagttcagc ttcagcagcc gggggctgag ttggtgaaac ccggggccag tgtgaagatg      60
agctgtaaag cgagcggcta caccttcact tcttataata tgcattgggt taagcaaacg     120
ccaggaaggg ggctggagtg gatcggcgct atttacccag gtaacggtga cacatcatat     180
aaccaaaagt ttaagggaaa ggcaaccctc acagcggaca gagtagctc aaccgcatac      240 atgcaactgt caagccttac ctccgaagac agcgcagtgt actactgcgc cagaagcacc     300
tactatgggg gtgattggta cttcaacgtc tggggggctg gcaccacagt gactgtaagc     360
gcagcgtcga ccaagggccc gtcagtgttc ccgctggccc cgtcatccaa gtccacgtct     420
gggggcacag cagccctggg atgcttggtc aaggactact ccccgagcc cgtgactgtg      480 tcctggaact ccggagcact gacctccgga gtgcacacct ttcccgcggt gctgcagtcc     540
tccggactgt actccctgtc gtcggtcgtg accgtgccga gctcctcgct cggaacccag     600
acctacatct gcaacgtgaa ccacaagccc tcgaacacca agtggacaa gaaggtcgag      660 cccaaaagct gcgacaagac tcacacttgt ccgccgtgcc cgccccga actgctgggt      720

```
ggcccctccg tgttcctgtt cccgcctaag cctaaggaca cccttatgat cagccgcacc    780
cctgaagtga cctgtgtcgt cgtggatgtg tcacacgagg acccggaggt caagttcaat    840
tggtacgtgg acggcgtgga agtgcataac gcaaagacca agcctcggga ggaacagtac    900
aactcgacct accgcgtggt gtcagtcctg actgtgctgc accaggactg gctgaacggg    960
aaggagtaca agtgcaaagt gtcgaacaag gccctgccgg ctccaattga aaagaccatc   1020
agcaaggcca agggccagcc aagggaacca caggtgtaca ccctccctcc ttcccgggac   1080
gagctgacca aaaccaagt gtccctgact tgccttgtga aggggttcta cccttctgac   1140
attgccgtcg aatgggaatc gaacggacag cctgaaaaca actataagac taccccgccc   1200
gtgctggatt ccgacggaag cttcttcctg tactccaagc tgaccgtgga caagtcgaga   1260
tggcagcagg gaaatgtgtt cagctgctcc gtgatgcatg aggcgctgca caaccactac   1320
acccagaagt cactgagcct ctcccccgga aag                                 1353
```

<210> SEQ ID NO 100
<211> LENGTH: 212
<212> TYPE: PRT
<213> ORGANISM: Artificial sequence
<220> FEATURE:
<223> OTHER INFORMATION: Synthetic peptide rituximab light chain

<400> SEQUENCE: 100

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

<210> SEQ ID NO 101
<211> LENGTH: 639
<212> TYPE: DNA

-continued

<213> ORGANISM: Artificial sequence
<220> FEATURE:
<223> OTHER INFORMATION: Synthetic polynucleotide, encoding rituximab light chain

<400> SEQUENCE: 101

```
cagatcgtgt tgtcccaatc acccgcaatt ctctctgcga gcccagggga gaaggtgacc    60
atgacttgcc gcgcttcaag ttccgtatcc tacattcact ggttccagca gaagcccgga   120
agttccccta agccctggat ctatgctaca tccaatctgg caagcggtgt tcccgttaga   180
tttccggaa gcgggtctgg aaccagttac agtctgacta tttccagggt cgaggccgaa   240
gatgcggcta cttattattg ccaacagtgg acctctaacc cacccacatt cggcggcggc   300
actaagttgg aaattaagac cgtggccgcc ccgagcgtgt tcatttttcc tccctccgac   360
gagcagttga atcgggcac cgctagcgtg gtctgccttc tcaacaattt ctatccacgg   420
gaagccaaag tgcagtggaa ggtcgacaac gcgctccaat ccgggaactc acaggaatcc   480
gtgactgagc aggattccaa ggactcgacc tactccctgt catccacgct gaccctgagc   540
aaggcagact acgagaagca aggtctac gcctgcgaag tgacacacca gggactgtcc   600
agccccgtga ccaagagctt caacagagga gaatgctag                         639
```

<210> SEQ ID NO 102
<211> LENGTH: 634
<212> TYPE: PRT
<213> ORGANISM: Artificial sequence
<220> FEATURE:
<223> OTHER INFORMATION: Synthetic peptide trastuzumab HC_MICwed

<400> SEQUENCE: 102

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

```
                  210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Gly Gly Gly Ser Glu Pro His Ser Leu Arg Tyr Asn Leu Thr Val
        450                 455                 460

Leu Ser Trp Asp Gly Ser Val Gln Ser Gly Phe Leu Thr Glu Val His
465                 470                 475                 480

Leu Asp Gly Gln Pro Phe Leu Arg Cys Asp Arg Gln Lys Cys Arg Ala
                485                 490                 495

Lys Pro Gln Gly Gln Trp Ala Glu Asp Val Leu Gly Asn Lys Thr Trp
                500                 505                 510

Asp Arg Glu Thr Arg Asp Leu Thr Gly Trp Gly Lys Asp Leu Arg Met
            515                 520                 525

Thr Leu Ala His Ile Lys Asp Gln Lys Glu Gly Leu His Ser Leu Gln
        530                 535                 540

Glu Ile Arg Val Cys Glu Ile His Glu Asp Asn Ser Thr Arg Ser Ser
545                 550                 555                 560

Gln His Phe Tyr Tyr Asp Gly Glu Leu Phe Leu Ser Gln Asn Leu Glu
                565                 570                 575

Thr Lys Glu Trp Thr Met Pro Gln Ser Ser Arg Ala Gln Thr Leu Ala
                580                 585                 590

Met Asn Val Arg Asn Phe Leu Lys Glu Asp Ala Met Glu Thr Asp Thr
            595                 600                 605

His Tyr His Ala Met His Ala Asp Cys Leu Gln Glu Leu Arg Arg Tyr
        610                 615                 620

Leu Lys Ser Gly Val Val Leu Arg Arg Thr
625                 630
```

<210> SEQ ID NO 103
<211> LENGTH: 1902
<212> TYPE: DNA
<213> ORGANISM: Artificial sequence
<220> FEATURE:
<223> OTHER INFORMATION: Synthetic polynucleotide, encoding trastuzumab
      HC_MICwed

<400> SEQUENCE: 103

| | | |
|---|---|---|
| gaagtccaat tggtcgaatc aggcggtgga ctcgtgcaac ctggaggttc gttacgctta | 60 |
| tcatgtgctg caagtggatt taatattaaa gatacctaca tccactgggt acgtcaagct | 120 |
| cccggcaagg gtctcgagtg gtcgcacgc atttacccca ccaacggata cacgcgctac | 180 |
| gccgattcag tgaagggacg tttcacaatc tctgctgata ctagcaaaaa taccgcatac | 240 |
| ctccagatga actctcttag ggccgaggac acagctgtgt actactgtag ccgttgggga | 300 |
| ggagacggtt tttacgcaat ggattactgg ggccaaggaa ccctggtcac agtttcatcg | 360 |
| gcgtcgacca agggcccgtc agtgttccg ctggccccgt catccaagtc cacgtctggg | 420 |
| ggcacagcag ccctgggatg cttggtcaag gactacttcc ccgagcccgt gactgtgtcc | 480 |
| tggaactccg gagcactgac ctccggagtg cacacctttc ccgcggtgct gcagtcctcc | 540 |
| ggactgtact ccctgtcgtc ggtcgtgacc gtgccgagct cctcgctcgg aacccagacc | 600 |
| tacatctgca acgtgaacca caagccctcg aacaccaaag tggacaagaa ggtcgagccc | 660 |
| aaaagctgcg acaagactca cacttgtccg ccgtgccccg ccccgaact gctgggtggc | 720 |
| ccctccgtgt tcctgttccc gcctaagcct aaggacaccc ttatgatcag ccgcaccct | 780 |
| gaagtgacct gtgtcgtcgt ggcagtgtca cacgaggacc cggaggtcaa gttcaattgg | 840 |
| tacgtggacg gcgtggaagt gcataacgca agaccaagc ctcgggagga acagtacgcc | 900 |
| tcgacctacc gcgtggtgtc agtcctgact gtgctgcacc aggactggct gaacgggaag | 960 |
| gagtacaagt gcaaagtgtc gaacaaggcc ctgccggctc caattgaaaa gaccatcagc | 1020 |
| aaggccaagg gccagccaag ggaaccacag gtgtacaccc tccctccttc ccgggacgag | 1080 |
| ctgaccaaaa accaagtgtc cctgacttgc cttgtgaagg ggttctaccc ttctgacatt | 1140 |
| gccgtcgaat gggaatcgaa cggacagcct gaaaacaact ataagactac cccgcccgtg | 1200 |
| ctggattccg acggaagctt cttcctgtac tccaagctga ccgtggacaa gtcgagatgg | 1260 |
| cagcagggaa atgtgttcag ctgctccgtg atgcatgagg cgctgcacaa ccactacacc | 1320 |
| cagaagtcac tgagcctctc ccccggagga ggtggcagcg agcctcacag cctccggtat | 1380 |
| aatttgactg tactctcttg ggatggctcc gtgcagtccg gctttctgac tgaagttcat | 1440 |
| ctcgacggtc aacctttcct gcgctgcgac cgacaaaaat gccgcgccaa gccccaaggg | 1500 |
| cagtgggccg aagatgtact gggaaacaag acctgggacc gggagacacg agacctgaca | 1560 |
| ggctggggca aggacttgcg catgacactc gcccatatca aggaccagaa ggaaggattg | 1620 |
| cactctttgc aagagattcg cgtgtgtgaa atccacgagg acaattcaac gaggagctcc | 1680 |
| cagcacttct attacgatgg agaactcttc ttgtcacaga acttggaaac caaggaatgg | 1740 |
| actatgcctc agagctctcg ggcacagact ctcgctatga acgttagaaa cttccttaag | 1800 |
| gaggatgcta tggagaccga tactcactac cacgccatgc acgccgactg cctccaggaa | 1860 |
| ctgcggagat atctgaagtc cggcgtggtt ttgagaagaa cc | 1902 |

<210> SEQ ID NO 104
<211> LENGTH: 634

```
<212> TYPE: PRT
<213> ORGANISM: Artificial sequence
<220> FEATURE:
<223> OTHER INFORMATION: Synthetic peptide trastuzumab HC_MIC25

<400> SEQUENCE: 104
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 |

| Ser | Leu | Arg | Leu | Ser | Cys | Ala | Ala | Ser | Gly | Phe | Asn | Ile | Lys | Asp | Thr |
| | | | 20 | | | | | 25 | | | | | 30 | | |

| Tyr | Ile | His | Trp | Val | Arg | Gln | Ala | Pro | Gly | Lys | Gly | Leu | Glu | Trp | Val |
| | | 35 | | | | | 40 | | | | | 45 | | | |

| Ala | Arg | Ile | Tyr | Pro | Thr | Asn | Gly | Tyr | Thr | Arg | Tyr | Ala | Asp | Ser | Val |
| 50 | | | | | 55 | | | | | 60 | | | | | |

| Lys | Gly | Arg | Phe | Thr | Ile | Ser | Ala | Asp | Thr | Ser | Lys | Asn | Thr | Ala | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ser | Arg | Trp | Gly | Gly | Asp | Gly | Phe | Tyr | Ala | Met | Asp | Tyr | Trp | Gly | Gln |
| | | | 100 | | | | | 105 | | | | | 110 | | |

| Gly | Thr | Leu | Val | Thr | Val | Ser | Ser | Ala | Ser | Thr | Lys | Gly | Pro | Ser | Val |
| | | 115 | | | | | 120 | | | | | 125 | | | |

| Phe | Pro | Leu | Ala | Pro | Ser | Ser | Lys | Ser | Thr | Ser | Gly | Gly | Thr | Ala | Ala |
| 130 | | | | | 135 | | | | | 140 | | | | | |

| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |

| Trp | Asn | Ser | Gly | Ala | Leu | Thr | Ser | Gly | Val | His | Thr | Phe | Pro | Ala | Val |
| | | | | 165 | | | | | 170 | | | | | 175 | |

| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |

| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |

| Pro | Ser | Asn | Thr | Lys | Val | Asp | Lys | Lys | Val | Glu | Pro | Lys | Ser | Cys | Asp |
| 210 | | | | | 215 | | | | | 220 | | | | | |

| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |

| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |

| Ser | Arg | Thr | Pro | Glu | Val | Thr | Cys | Val | Val | Val | Ala | Val | Ser | His | Glu |
| | | | 260 | | | | | 265 | | | | | 270 | | |

| Asp | Pro | Glu | Val | Lys | Phe | Asn | Trp | Tyr | Val | Asp | Gly | Val | Glu | Val | His |
| | | 275 | | | | | 280 | | | | | 285 | | | |

| Asn | Ala | Lys | Thr | Lys | Pro | Arg | Glu | Glu | Gln | Tyr | Ala | Ser | Thr | Tyr | Arg |
| 290 | | | | | 295 | | | | | 300 | | | | | |

| Val | Val | Ser | Val | Leu | Thr | Val | Leu | His | Gln | Asp | Trp | Leu | Asn | Gly | Lys |
| 305 | | | | | 310 | | | | | 315 | | | | | 320 |

| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |

| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |

| Thr | Leu | Pro | Pro | Ser | Arg | Asp | Glu | Leu | Thr | Lys | Asn | Gln | Val | Ser | Leu |
| | | 355 | | | | | 360 | | | | | 365 | | | |

| Thr | Cys | Leu | Val | Lys | Gly | Phe | Tyr | Pro | Ser | Asp | Ile | Ala | Val | Glu | Trp |
| 370 | | | | | 375 | | | | | 380 | | | | | |

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Gly Gly Gly Ser Glu Pro His Ser Leu Arg Tyr Asn Leu Thr Val
450                 455                 460

Leu Ser Trp Asp Gly Ser Val Gln Ser Gly Phe Leu Thr Glu Val His
465                 470                 475                 480

Leu Asp Gly Gln Pro Phe Leu Arg Cys Asp Arg Gln Lys Cys Arg Ala
            485                 490                 495

Lys Pro Gln Gly Gln Trp Ala Glu Asp Val Leu Gly Asn Lys Thr Trp
            500                 505                 510

Asp Arg Glu Thr Arg Asp Leu Thr Gly Trp Gly Lys Asp Leu Arg Met
            515                 520                 525

Thr Leu Ala His Ile Lys Asp Gln Lys Glu Gly Leu His Ser Leu Gln
530                 535                 540

Glu Ile Arg Val Cys Glu Ile His Glu Asp Asn Ser Thr Arg Ser Ser
545                 550                 555                 560

Gln His Phe Tyr Tyr Asp Gly Glu Leu Phe Leu Ser Gln Asn Leu Glu
            565                 570                 575

Thr Leu Glu Trp Thr Met Pro Gln Ser Ser Arg Ala Gln Thr Leu Ala
            580                 585                 590

Met Asn Val Arg Asn Phe Leu Lys Glu Asp Ala Met Glu Thr Asp Thr
            595                 600                 605

His Tyr His Ala Met Arg Ala Asp Cys Leu Ser Glu Leu Arg Arg Tyr
610                 615                 620

Leu Lys Ser Gly Val Val Leu Arg Arg Thr
625                 630

<210> SEQ ID NO 105
<211> LENGTH: 1902
<212> TYPE: DNA
<213> ORGANISM: Artificial sequence
<220> FEATURE:
<223> OTHER INFORMATION: Synthetic polynucleotide, encoding trastuzumab
      HC_MIC25

<400> SEQUENCE: 105
gaagtccaat tggtcgaatc aggcggtgga ctcgtgcaac ctggaggttc gttacgctta      60
tcatgtgctg caagtggatt taatattaaa gataccctaca tccactgggt acgtcaagct   120
cccggcaagg gtctcgagtg ggtcgcacgc atttacccca ccaacggata cacgcgctac    180
gccgattcag tgaagggacg tttcacaatc tctgctgata ctagcaaaaa taccgcatac    240
ctccagatga actctcttag ggccgaggac acagctgtgt actactgtag ccgttgggga    300
ggagacggtt tttacgcaat ggattactgg ggccaaggaa ccctggtcac agtttcatcg    360
gcgtcgacca agggcccgtc agtgttcccg ctggccccgt catccaagtc acgtctgggg   420
ggcacagcag ccctgggatg cttggtcaag gactacttcc ccgagcccgt gactgtgtcc    480
tggaactccg gagcactgac ctccggagtg cacaccttc ccgcggtgct gcagtcctcc     540
ggactgtact ccctgtcgtc ggtcgtgacc gtgccgagct cctcgctcgg aacccagacc    600

```
tacatctgca acgtgaacca caagccctcg aacaccaaag tggacaagaa ggtcgagccc    660
aaaagctgcg acaagactca cacttgtccg ccgtgcccg cccccgaact gctgggtggc    720
ccctccgtgt tcctgttccc gcctaagcct aaggacaccc ttatgatcag ccgcaccct    780 gaagtgacct gtgtcgtcgt ggcagtgtca cacgaggacc cggaggtcaa gttcaattgg    840
tacgtggacg gcgtggaagt gcataacgca aagaccaagc ctcgggagga acagtacgcc    900
tcgacctacc gcgtggtgtc agtcctgact gtgctgcacc aggactggct gaacgggaag    960
gagtacaagt gcaaagtgtc gaacaaggcc ctgccggctc caattgaaaa gaccatcagc   1020
aaggccaagg gccagccaag ggaaccacag gtgtacaccc tccctccttc ccgggacgag   1080
ctgaccaaaa accaagtgtc cctgacttgc cttgtgaagg ggttctaccc ttctgacatt   1140
gccgtcgaat gggaatcgaa cggacagcct gaaaacaact ataagactac cccgcccgtg   1200
ctggattccg acggaagctt cttcctgtac tccaagctga ccgtggacaa gtcgagatgg   1260
cagcagggaa atgtgttcag ctgctccgtg atgcatgagg cgctgcacaa ccactacacc   1320
cagaagtcac tgagcctctc ccccggagga ggtggcagcg agcctcacag cctccggtat   1380
aatttgactg tactctcttg ggatggctcc gtgcagtccg gctttctgac tgaagttcat   1440
ctcgacggtc aaccttttcct gcgctgcgac cgacaaaaat gccgcgccaa gccccaaggg   1500
cagtgggccg aagatgtact gggaaacaag acctgggacc gggagacacg agacctgaca   1560
ggctggggca aggacttgcg catgacactc gcccatatca aggaccagaa ggaaggattg   1620
cactctttgc aagagattcg cgtgtgtgaa atccacgagg acaattcaac gaggagctcc   1680
cagcacttct attacgatgg agaactcttc ttgtcacaga acttggaaac cctcgaatgg   1740
actatgcctc agagctctcg ggcacagact ctcgctatga acgttagaaa cttccttaag   1800
gaggatgcta tggagaccga tactcactac cacgccatgc gcgccgactg cctctctgaa   1860
ctgcggagat atctgaagtc cggcgtggtt ttgagaagaa cc                      1902
```

<210> SEQ ID NO 106
<211> LENGTH: 404
<212> TYPE: PRT
<213> ORGANISM: Artificial sequence
<220> FEATURE:
<223> OTHER INFORMATION: Synthetic peptide rituximab LC_ULBP2.wt

<400> SEQUENCE: 106

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
```

|     |     |     |     | 130 |     |     |     |     | 135 |     |     |     |     | 140 |     |
| --- | --- | --- | --- | --- | --- | --- | --- | --- | --- | --- | --- | --- | --- | --- | --- |

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270

Leu Gly Lys Lys Leu Asn Val Thr Thr Ala Trp Lys Ala Gln Asn Pro
        275                 280                 285

Val Leu Arg Glu Val Val Asp Ile Leu Thr Glu Gln Leu Arg Asp Ile
    290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Met Ser Phe His Tyr Phe Ser Met Gly
    370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 107
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.wt

<400> SEQUENCE: 107
cagatcgtgt tgtcccaatc acccgcaatt ctctctgcga gcccagggga gaaggtgacc     60
atgacttgcc gcgcttcaag ttccgtatcc tacattcact ggttccagca gaagcccgga    120
agttccccta agccctggat ctatgctaca tccaatctgg caagcggtgt tcccgttaga    180
tttttccgga agcgggtctgg aaccagttac agtctgacta tttccagggt cgaggccgaa    240
gatgcggcta cttattattg ccaacagtgg acctctaacc cacccacatt cggcggcggc    300
actaagttgg aaattaagcg gaccgtggcc gccccgagcg tgttcatttt ccctcccctcc    360 gacgagcagt tgaaatcggg caccgctagc gtggtctgcc ttctcaacaa tttctatcca    420
cgggaagcca agtgcagtg gaaggtcgac aacgcgctcc aatccgggaa ctcacaggaa    480

```
tccgtgactg agcaggattc caaggactcg acctactccc tgtcatccac gctgaccctg    540
agcaaggcag actacgagaa gcacaaggtc tacgcctgcg aagtgacaca ccagggactg    600
tccagccccg tgaccaagag cttcaacaga ggagaatgcg cacctacctc aagctctgga    660
ggaggtggca gcgagcccca tagtctgagc tacgacatca cagttattcc caagttcagg    720
cccggaccgc gctggtgtgc cgtgcaagga caagtcgacg aaaaaacctt tcttcattac    780
gattgcggaa ataagactgt aacgccagtc tctcctttag gtaagaagtt aaacgtcact    840
acggcgtgga aggcacaaaa ccccgtcctg cgcgaggtcg tcgacatcct gactgaacaa    900
tgcgcgacca tccagctcga gaattacact ccaaaggagc ctcttaccct gcaggctaga    960
atgtcttgcg agcaaaaggc agagggccac tcctccggca gctggcagtt cagtttcgac    1020
ggacaaatct ttctgttatt cgattcagag aagagaatgt ggactacagt tcaccccggt    1080
gcccgtaaaa tgaaggagaa gtgggaaaac gacaaagtgg tggcgatgtc attccactat    1140
ttctcgatgg gagactgcat cggttggctg gaagatttcc tcatgggtat ggactccact    1200
ttggagccat cg                                                        1212
```

<210> SEQ ID NO 108
<211> LENGTH: 187
<212> TYPE: PRT
<213> ORGANISM: Artificial sequence
<220> FEATURE:
<223> OTHER INFORMATION: Synthetic peptide ULPB2 alpha1-alpha2 variant R80W

<400> SEQUENCE: 108

```
Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Met Ser Phe His Tyr Phe Ser Met Gly
145                 150                 155                 160

Asp Cys Ile Gly Trp Leu Glu Asp Phe Leu Met Gly Met Asp Ser Thr
                165                 170                 175

Leu Glu Pro Ser Ala Gly Ala Pro Pro Met Val
            180                 185
```

<210> SEQ ID NO 109
<211> LENGTH: 540
<212> TYPE: DNA
<213> ORGANISM: Artificial sequence
<220> FEATURE:

<223> OTHER INFORMATION: Synthetic polynucleotide, encoding ULPB2
       alpha1-alpha2 variant R80W

<400> SEQUENCE: 109

```
gagcccata gtctgagcta cgacatcaca gttattccca agttcaggcc cggaccgcgc    60
tggtgtgccg tgcaaggaca gtcgacgaa aaaacctttc ttcattacga ttgcggaaat   120
aagactgtaa cgccagtctc tcctttaggt aagaagttaa acgtcactac ggcgtggaag   180
gcacaaaacc ccgtcctgcg cgaggtcgtc gacatcctga ctgaacaatt gtgggacatc   240
cagctcgaga attacactcc aaaggagcct cttaccctgc aggctagaat gtcttgcgag   300
caaaaggcag agggccactc ctccggcagc tggcagttca gtttcgacgg acaaatcttt   360
ctgttattcg attcagagaa gagaatgtgg actacagttc accccggtgc cgtaaaatg   420 aaggagaagt gggaaaacga caaagtggtg gcgatgtcat tccactattt ctcgatggga   480
gactgcatcg gttggctgga agatttcctc atgggtatgg actccacttt ggagccatcg   540
```

<210> SEQ ID NO 110
<211> LENGTH: 513
<212> TYPE: DNA
<213> ORGANISM: Artificial sequence
<220> FEATURE:
<223> OTHER INFORMATION: Synthetic polynucleotide, encoding ULPB2
       alpha1-alpha2 variant R80W NNK library
<220> FEATURE:
<221> NAME/KEY: misc_feature
<222> LOCATION: (457)..(458)
<223> OTHER INFORMATION: n is a, c, g, or t
<220> FEATURE:
<221> NAME/KEY: misc_feature
<222> LOCATION: (460)..(461)
<223> OTHER INFORMATION: n is a, c, g, or t
<220> FEATURE:
<221> NAME/KEY: misc_feature
<222> LOCATION: (463)..(464)
<223> OTHER INFORMATION: n is a, c, g, or t
<220> FEATURE:
<221> NAME/KEY: misc_feature
<222> LOCATION: (466)..(467)
<223> OTHER INFORMATION: n is a, c, g, or t
<220> FEATURE:
<221> NAME/KEY: misc_feature
<222> LOCATION: (469)..(470)
<223> OTHER INFORMATION: n is a, c, g, or t

<400> SEQUENCE: 110

```
gagcccata gcctcagcta tgacattacg gtgattccca aatttcgccc aggaccacgt    60
tggtgcgccg tccagggtca ggtagatgaa aagactttcc tgcattatga ttgcggcaat   120
aaaaccgtga cgccggtatc gccgttaggc aaaaaattga atgtcacgac agcgtggaaa   180
gcacagaacc cggtgttgcg cgaggtagtc gatattttga cggaacaact ctgggacatt   240
cagctcgaga attacacccc aaaagaaccg ctgacgctgc aagcgcgtat gtcgtgcgaa   300
caaaaagcag aaggtcactc tagcggggagt tggcagtttt ccttcgatgg gcagattttt   360
ctgctgtttg attcggagaa acgcatgtgg actacagtcc acccgggtgc ccggaaaatg   420
aaagagaagt gggagaatga taaagtggtg gccactnnkn nknnknnknn ktccatgggc   480
gattgcattg gctggttaga ggattttctc atg                                513
```

<210> SEQ ID NO 111
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant

ULBP2.C

<400> SEQUENCE: 111

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Thr Ile Leu Trp Gln Thr Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 112
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.C

<400> SEQUENCE: 112
gagccccata gtctgagcta cgacatcaca gttattccca agttcaggcc cggaccgcgc     60
tggtgtgccg tgcaaggaca gtcgacgaa aaaacctttc ttcattacga ttgcggaaat    120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa gagaatgtgg actacagttc accccggtgc ccgtaaaatg    420
aaggagaagt gggaaaacga caaagtggtg gcgactattc tgtggcagac ttcgatggga    480
gactgcatcg gttggctgga agatttcctc atgggtatgg actccacttt ggagccatcg    540

<210> SEQ ID NO 113
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.R

<400> SEQUENCE: 113

Glu Pro His Ser Leu Ser Tyr Asp Ile Thr Val Ile Pro Lys Phe Arg
1               5                   10                  15

Pro Gly Pro Arg Trp Cys Ala Val Gln Gly Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
130                 135                 140

Glu Asn Asp Lys Val Val Ala Thr Leu Leu Trp Gly Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 114
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.R

<400> SEQUENCE: 114
gagccccata gtctgagcta cgacatcaca gttattccca gttcaggcc cggaccgcgc    60 tggtgtgccg tgcaaggaca gtcgacgaa aaaacctttc ttcattacga ttgcggaaat   120
aagactgtaa cgccagtctc tcctttaggt aagaagttaa acgtcactac ggcgtggaag   180
gcacaaaacc ccgtcctgcg cgaggtcgtc gacatcctga ctgaacaatt gtgggacatc   240
cagctcgaga attacactcc aaaggagcct cttaccctgc aggctagaat gtcttgcgag   300
caaaaggcag agggccactc ctccggcagc tggcagttca gtttcgacgg acaaatcttt   360
ctgttattcg attcagagaa gagaatgtgg actacagttc accccggtgc cgtaaaatg   420 aaggagaagt gggaaaacga caaagtggtg gcgactttgt tgtgggggtg gtcgatggga   480
gactgcatcg gttggctgga agatttcctc atgggtatgg actccacttt ggagccatcg   540

<210> SEQ ID NO 115
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.AA

<400> SEQUENCE: 115

Glu Pro His Ser Leu Ser Tyr Asp Ile Thr Val Ile Pro Lys Phe Arg
1               5                   10                  15

| Pro | Gly | Pro | Arg | Trp | Cys | Ala | Val | Gln | Gly | Gln | Val | Asp | Glu | Lys | Thr |
| | | 20 | | | | | 25 | | | | | 30 | | | |

Phe Leu His Tyr Asp Cys Gly Asn Lys Thr Val Thr Pro Val Ser Pro
          35                  40                  45

Leu Gly Lys Lys Leu Asn Val Thr Thr Ala Trp Lys Ala Gln Asn Pro
 50                  55                  60

Val Leu Arg Glu Val Val Asp Ile Leu Thr Glu Gln Leu Trp Asp Ile
 65                  70                  75                  80

Gln Leu Glu Asn Tyr Thr Pro Lys Gly Pro Leu Thr Leu Gln Ala Arg
                 85                  90                  95

Met Ser Cys Glu Gln Lys Ala Glu Gly His Ser Ser Gly Ser Trp Gln
                100                 105                 110

Phe Ser Phe Asp Gly Gln Ile Phe Leu Leu Phe Asp Ser Glu Lys Arg
            115                 120                 125

Met Trp Thr Thr Val His Pro Gly Ala Arg Lys Met Lys Glu Lys Trp
130                 135                 140

Glu Asn Asp Lys Val Val Ala Thr Met Phe Trp Ser Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 116
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.AA

<400> SEQUENCE: 116
gagccccata gtctgagcta cgacatcaca gttattccca agttcaggcc cggaccgcgc      60
tggtgtgccg tgcaaggaca gtcgacgaa aaaacctttc ttcattacga ttgcggaaat      120
aagactgtaa cgccagtctc tcctttaggt aagaagttaa acgtcactac ggcgtggaag     180
gcacaaaacc ccgtcctgcg cgaggtcgtc gacatcctga ctgaacaatt gtgggacatc     240
cagctcgaga attacactcc aaaggagcct cttaccctgc aggctagaat gtcttgcgag     300
caaaaggcag agggccactc ctccggcagc tggcagttca gtttcgacgg acaaatcttt     360
ctgttattcg attcagagaa agaatgtgg actacagttc accccggtgc cgtaaaatg      420 aaggagaagt gggaaaacga caaagtggtg gcgactatgt tttggagttg gtcgatggga     480
gactgcatcg gttggctgga agatttcctc atgggtatgg actccacttt ggagccatcg     540

<210> SEQ ID NO 117
<211> LENGTH: 180
<212> TYPE: PRT
<213> ORGANISM: Artificial sequence
<220> FEATURE:
<223> OTHER INFORMATION: Synthetic peptide, ULBP alpha1-alpha2 variant
      ULBP2.AB

<400> SEQUENCE: 117

Glu Pro His Ser Leu Ser Tyr Asp Ile Thr Val Ile Pro Lys Phe Arg
1               5                  10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
                35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
            115                 120                 125

Met Trp Thr Thr Val His Pro Gly Ala Arg Lys Met Lys Glu Lys Trp
130                 135                 140

Glu Asn Asp Lys Val Val Ala Thr Leu Met Trp Gln Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 118
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.AB

<400> SEQUENCE: 118 gagcccata gtctgagcta cgacatcaca gttattccca gttcaggcc cggaccgcgc      60 tggtgtgccg tgcaaggaca gtcgacgaa aaaacctttc ttcattacga ttgcggaaat    120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa gagaatgtgg actacagttc accccggtgc ccgtaaaatg    420
aaggagaagt gggaaaacga caaagtggtg gcgactctta tgtggcagtg gtcgatggga    480
gactgcatcg gttggctgga agatttcctc atgggtatgg actccacttt ggagccatcg    540

<210> SEQ ID NO 119
<211> LENGTH: 404
<212> TYPE: PRT
<213> ORGANISM: Artificial sequence
<220> FEATURE:
<223> OTHER INFORMATION: Synthetic peptide rituximab LC_ULBP2.C

<400> SEQUENCE: 119

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
                35                  40                  45

```
Ala Thr Ser Asn Leu Ala Ser Gly Val Pro Val Arg Phe Ser Gly Ser
 50                  55                  60
Gly Ser Gly Thr Ser Tyr Ser Leu Thr Ile Ser Arg Val Glu Ala Glu
 65                  70                  75                  80
Asp Ala Ala Thr Tyr Tyr Cys Gln Gln Trp Thr Ser Asn Pro Pro Thr
                 85                  90                  95
Phe Gly Gly Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys Ala Pro Thr Ser Ser Gly Gly Gly Gly Ser
210                 215                 220
Glu Pro His Ser Leu Ser Tyr Asp Ile Thr Val Ile Pro Lys Phe Arg
225                 230                 235                 240
Pro Gly Pro Arg Trp Cys Ala Val Gln Gly Gln Val Asp Glu Lys Thr
                245                 250                 255
Phe Leu His Tyr Asp Cys Gly Asn Lys Thr Val Thr Pro Val Ser Pro
            260                 265                 270
Leu Gly Lys Lys Leu Asn Val Thr Thr Ala Trp Lys Ala Gln Asn Pro
        275                 280                 285
Val Leu Arg Glu Val Val Asp Ile Leu Thr Glu Gln Leu Trp Asp Ile
290                 295                 300
Gln Leu Glu Asn Tyr Thr Pro Lys Glu Pro Leu Thr Leu Gln Ala Arg
305                 310                 315                 320
Met Ser Cys Glu Gln Lys Ala Glu Gly His Ser Ser Gly Ser Trp Gln
                325                 330                 335
Phe Ser Phe Asp Gly Gln Ile Phe Leu Leu Phe Asp Ser Glu Lys Arg
            340                 345                 350
Met Trp Thr Thr Val His Pro Gly Ala Arg Lys Met Lys Glu Lys Trp
        355                 360                 365
Glu Asn Asp Lys Val Val Ala Thr Ile Leu Trp Gln Thr Ser Met Gly
370                 375                 380
Asp Cys Ile Gly Trp Leu Glu Asp Phe Leu Met Gly Met Asp Ser Thr
385                 390                 395                 400
Leu Glu Pro Ser
```

<210> SEQ ID NO 120
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.C

<400> SEQUENCE: 120

```
cagatcgtgt tgtcccaatc acccgcaatt ctctctgcga gcccagggga gaaggtgacc      60
atgacttgcc gcgcttcaag ttccgtatcc tacattcact ggttccagca gaagcccgga     120
agttccccta agccctggat ctatgctaca tccaatctgg caagcggtgt tcccgttaga     180
ttttccggaa gcgggtctgg aaccagttac agtctgacta tttccagggt cgaggccgaa     240
gatgcggcta cttattattg ccaacagtgg acctctaacc cacccacatt cggcggcggc     300
actaagttgg aaattaagcg gaccgtggcc gccccgagcg tgttcatttt ccctcccctcc    360
gacgagcagt tgaaatcggg caccgctagc gtggtctgcc ttctcaacaa tttctatcca     420
cgggaagcca agtgcagtg gaaggtcgac aacgcgctcc aatccgggaa ctcacaggaa      480
tccgtgactg agcaggattc caaggactcg acctactccc tgtcatccac gctgaccctg     540
agcaaggcag actacgagaa gcacaaggtc tacgcctgcg aagtgacaca ccagggactg     600
tccagccccg tgaccaagag cttcaacaga ggagaatgcg cacctacctc aagctctgga     660
ggaggtggca gcgagcccca tagtctgagc tacgacatca cagttattcc caagttcagg     720
cccggaccgc gctggtgtgc cgtgcaagga caagtcgacg aaaaaacctt tcttcattac     780
gattgcggaa ataagactgt aacgccagtc tctcctttag gtaagaagtt aaacgtcact     840
acggcgtgga aggcacaaaa ccccgtcctg cgcgaggtca tcgacatcct gactgaacaa     900
ttgtgggaca tccagctcga gaattacact ccaaaggagc tcttaccct gcaggctaga      960
atgtcttgcg agcaaaaggc agagggccac tcctccggca gctggcagtt cagtttcgac    1020
ggacaaatct ttctgttatt cgattcagag aagagaatgt ggactacagt tcaccccggt    1080
gcccgtaaaa tgaaggagaa gtgggaaaac gacaaagtgg tggcgactat tctgtggcag    1140
acttcgatgg agactgcat cggttggctg gaagatttcc tcatgggtat ggactccact    1200
ttggagccat cg                                                       1212
```

<210> SEQ ID NO 121
<211> LENGTH: 404
<212> TYPE: PRT
<213> ORGANISM: Artificial sequence
<220> FEATURE:
<223> OTHER INFORMATION: Synthetic peptide rituximab LC_ULBP2.R

<400> SEQUENCE: 121

```
Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270

Leu Gly Lys Lys Leu Asn Val Thr Thr Ala Trp Lys Ala Gln Asn Pro
        275                 280                 285

Val Leu Arg Glu Val Val Asp Ile Leu Thr Glu Gln Leu Trp Asp Ile
    290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Thr Leu Leu Trp Gly Trp Ser Met Gly
    370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 122
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.R

<400> SEQUENCE: 122
cagatcgtgt tgtcccaatc acccgcaatt ctctctgcga gcccagggga gaaggtgacc    60
atgacttgcc gcgcttcaag ttccgtatcc tacattcact ggttccagca gaagcccgga   120
agttccccta agccctggat ctatgctaca tccaatctgg caagcggtgt tcccgttaga   180
ttttccggaa gcgggtctgg aaccagttac agtctgacta tttccagggt cgaggccgaa   240
gatgcggcta cttattattg ccaacagtgg acctctaacc cacccacatt cggcggcggc   300
actaagttgg aaattaagcg gaccgtggcc gccccgagcg tgttcatttt ccctccctcc   360
gacgagcagt tgaaatcggg caccgctagc gtggtctgcc ttctcaacaa tttctatcca   420
cgggaagcca agtgcagtg gaaggtcgac aacgcgctcc aatccgggaa ctcacaggaa   480
tccgtgactg agcaggattc caaggactcg acctactccc tgtcatccac gctgaccctg   540

-continued

```
agcaaggcag actacgagaa gcacaaggtc tacgcctgcg aagtgacaca ccagggactg      600
tccagccccg tgaccaagag cttcaacaga ggagaatgcg cacctacctc aagctctgga      660
ggaggtggca gcgagcccca tagtctgagc tacgacatca cagttattcc caagttcagg      720
cccggaccgc gctggtgtgc cgtgcaagga caagtcgacg aaaaaacctt tcttcattac      780
gattgcggaa ataagactgt aacgccagtc tctcctttag gtaagaagtt aaacgtcact      840
acggcgtgga aggcacaaaa ccccgtcctg cgcgaggtcg tcgacatcct gactgaacaa      900
ttgtgggaca tccagctcga gaattacact ccaaaggagc tcttaccct gcaggctaga      960 atgtcttgcg agcaaaaggc agagggccac tcctccggca gctggcagtt cagtttcgac     1020
ggacaaatct ttctgttatt cgattcagag aagagaatgt ggactacagt tcaccccggt     1080
gcccgtaaaa tgaaggagaa gtgggaaaac gacaaagtgg tggcgacttt gttgtggggg     1140
tggtcgatgg gagactgcat cggttggctg gaagatttcc tcatgggtat ggactccact     1200
ttggagccat cg                                                         1212
```

<210> SEQ ID NO 123
<211> LENGTH: 404
<212> TYPE: PRT
<213> ORGANISM: Artificial sequence
<220> FEATURE:
<223> OTHER INFORMATION: Synthetic peptide rituximab LC_ULBP2.AA

<400> SEQUENCE: 123

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Ser Gly Gly Gly Gly Ser
    210                 215                 220

Glu Pro His Ser Leu Ser Tyr Asp Ile Thr Val Ile Pro Lys Phe Arg
225                 230                 235                 240
```

Pro Gly Pro Arg Trp Cys Ala Val Gln Gly Gln Val Asp Glu Lys Thr
            245                 250                 255

Phe Leu His Tyr Asp Cys Gly Asn Lys Thr Val Thr Pro Val Ser Pro
        260                 265                 270

Leu Gly Lys Lys Leu Asn Val Thr Thr Ala Trp Lys Ala Gln Asn Pro
    275                 280                 285

Val Leu Arg Glu Val Val Asp Ile Leu Thr Glu Gln Leu Trp Asp Ile
290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Thr Met Phe Trp Ser Trp Ser Met Gly
    370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 124
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.AA

<400> SEQUENCE: 124
cagatcgtgt tgtcccaatc acccgcaatt ctctctgcga gcccagggga gaaggtgacc        60
atgacttgcc gcgcttcaag ttccgtatcc tacattcact ggttccagca gaagcccgga       120
agttccccta gccctggat ctatgctaca tccaatctgg caagcggtgt tcccgttaga        180
ttttccggaa gcgggtctgg aaccagttac agtctgacta tttccagggt cgaggccgaa       240
gatgcggcta cttattattg ccaacagtgg acctctaacc cacccacatt cggcggcggc       300
actaagttgg aaattaagcg gaccgtggcc gccccgagcg tgttcatttt ccctccctcc       360
gacgagcagt tgaaatcggg caccgctagc gtggtctgcc ttctcaacaa tttctatcca       420
cgggaagcca agtgcagtg gaaggtcgac aacgcgctcc aatccgggaa ctcacaggaa        480
tccgtgactg agcaggattc caaggactcg acctactccc tgtcatccac gctgacctg        540 agcaaggcag actacgagaa gcacaaggtc tacgcctgcg aagtgacaca ccagggactg       600
tccagccccg tgaccaagag cttcaacaga ggagaatgcg cacctacctc aagctctgga       660
ggaggtggca gcgagcccca tagtctgagc tacgacatca cagttattcc caagttcagg       720
cccggaccgc gctggtgtgc cgtgcaagga caagtcgacg aaaaaacctt tcttcattac       780
gattgcggaa ataagactgt aacgccagtc tctcctttag gtaagaagtt aaacgtcact       840
acggcgtgga aggcacaaaa ccccgtcctg cgcgaggtcg tcgacatcct gactgaacaa       900
ttgtgggaca tccagctcga gaattacact ccaaaggagc ctcttaccct gcaggctaga       960
atgtcttgcg agcaaaaggc agagggccac tcctccggca gctggcagtt cagtttcgac      1020
ggacaaatct ttctgttatt cgattcagag aagagaatgt ggactacagt tcaccccggt      1080

-continued

```
gcccgtaaaa tgaaggagaa gtgggaaaac gacaaagtgg tggcgactat gttttggagt    1140
tggtcgatgg gagactgcat cggttggctg gaagatttcc tcatgggtat ggactccact    1200
ttggagccat cg                                                         1212
```

<210> SEQ ID NO 125
<211> LENGTH: 404
<212> TYPE: PRT
<213> ORGANISM: Artificial sequence
<220> FEATURE:
<223> OTHER INFORMATION: Synthetic peptide rituximab LC_ULBP2.AB

<400> SEQUENCE: 125

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270

Leu Gly Lys Lys Leu Asn Val Thr Thr Ala Trp Lys Ala Gln Asn Pro
        275                 280                 285

Val Leu Arg Glu Val Val Asp Ile Leu Thr Glu Gln Leu Trp Asp Ile
    290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335
```

```
Phe Ser Phe Asp Gly Gln Ile Phe Leu Leu Phe Asp Ser Glu Lys Arg
                340                 345                 350

Met Trp Thr Thr Val His Pro Gly Ala Arg Lys Met Lys Glu Lys Trp
        355                 360                 365

Glu Asn Asp Lys Val Val Ala Thr Leu Met Trp Gln Trp Ser Met Gly
    370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 126
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.AB

<400> SEQUENCE: 126
cagatcgtgt tgtcccaatc acccgcaatt ctctctgcga gcccagggga gaaggtgacc       60
atgacttgcc gcgcttcaag ttccgtatcc tacattcact ggttccagca gaagcccgga      120
agttccccta gccctggat ctatgctaca tccaatctgg caagcggtgt tcccgttaga       180
ttttccggaa gcgggtctgg aaccagttac agtctgacta tttccagggt cgaggccgaa      240
gatgcggcta cttattattg ccaacagtgg acctctaacc cacccacatt cggcggcggc      300
actaagttgg aaattaagcg gaccgtggcc gccccgagcg tgttcatttt ccctcccctcc     360 gacgagcagt tgaaatcggg caccgctagc gtggtctgcc ttctcaacaa tttctatcca     420
cgggaagcca agtgcagtg gaaggtcgac aacgcgctcc aatccgggaa ctcacaggaa      480
tccgtgactg agcaggattc caaggactcg acctactccc tgtcatccac gctgaccctg     540
agcaaggcag actacgagaa gcacaaggtc tacgcctgcg aagtgacaca ccagggactg      600
tccagccccg tgaccaagag cttcaacaga ggagaatgcg cacctacctc aagctctgga      660
ggaggtggca gcgagcccca tagtctgagc tacgacatca cagttattcc aagttcagg     720 cccggaccgc gctggtgtgc cgtgcaagga caagtcgacg aaaaaacctt tcttcattac      780
gattgcggaa ataagactgt aacgccagtc tctcctttag gtaagaagtt aaacgtcact      840
acggcgtgga aggcacaaaa ccccgtcctg cgcgaggtcg tcgacatcct gactgaacaa      900
ttgtgggaca tccagctcga gaattacact ccaaaggagc tcttacccct gcaggctaga      960
atgtcttgcg agcaaaaggc agagggccac tcctccggca gctggcagtt cagtttcgac     1020
ggacaaatct ttctgttatt cgattcagag aagagaatgt ggactacagt tcaccccggt     1080
gcccgtaaaa tgaaggagaa gtgggaaaac gacaaagtgg tggcgactct tatgtggcag     1140
tggtcgatgg gagactgcat cggttggctg gaagatttcc tcatgggtat ggactccact     1200
ttggagccat cg                                                           1212

<210> SEQ ID NO 127
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.S3

<400> SEQUENCE: 127

Glu Pro His Ser Leu Ser Tyr Asp Ile Thr Val Ile Pro Lys Phe Arg
```

```
  1               5                  10                 15
Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
            35                  40                  45

Leu Gly Lys Lys Leu Asn Val Thr Thr Ala Trp Lys Ala Gln Asn Pro
        50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
            115                 120                 125

Met Trp Thr Thr Val His Pro Gly Ala Arg Lys Met Lys Glu Lys Trp
            130                 135                 140

Glu Asn Asp Lys Val Val Ala Thr Lys Leu Tyr Leu Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 128
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.S3

<400> SEQUENCE: 128 gagcccata gtctgagcta cgacatcaca gttattccca agttcaggcc cggaccgcgc    60
tggtgtgccg tgcaaggaca gtcgacgaa aaaacctttc ttcattacga ttgcggaaat   120
aagactgtaa cgccagtctc tcctttaggt aagaagttaa acgtcactac ggcgtggaag   180
gcacaaaacc ccgtcctgcg cgaggtcgtc gacatcctga ctgaacaatt gtgggacatc   240
cagctcgaga attacactcc aaaggagcct cttaccctgc aggctagaat gtcttgcgag   300
caaaaggcag agggccactc ctccggcagc tggcagttca gtttcgacgg acaaatcttt   360
ctgttattcg attcagagaa gagaatgtgg actacagttc accccggtgc ccgtaaaatg   420
aaggagaagt gggaaaacga caaagtggtg gcgactaagc tttatctttg gtcgatggga   480
gactgcatcg gttggctgga agatttcctc atgggtatgg actccacttt ggagccatcg   540

<210> SEQ ID NO 129
<211> LENGTH: 404
<212> TYPE: PRT
<213> ORGANISM: Artificial sequence
<220> FEATURE:
<223> OTHER INFORMATION: Synthetic peptide rituximab LC_ULBP2.S3

<400> SEQUENCE: 129

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30
```

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Val Ala Ala Pro
             100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
     130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270

Leu Gly Lys Lys Leu Asn Val Thr Thr Ala Trp Lys Ala Gln Asn Pro
        275                 280                 285

Val Leu Arg Glu Val Val Asp Ile Leu Thr Glu Gln Leu Trp Asp Ile
    290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Thr Lys Leu Tyr Leu Trp Ser Met Gly
    370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 130
<211> LENGTH: 1212
<212> TYPE: DNA
<213> ORGANISM: Artificial sequence
<220> FEATURE:
<223> OTHER INFORMATION: Synthetic polynucleotide, encoding rituximab

LC_ULBP2.S3

<400> SEQUENCE: 130

```
cagatcgtgt tgtcccaatc acccgcaatt ctctctgcga gcccagggga gaaggtgacc     60
atgacttgcc gcgcttcaag ttccgtatcc tacattcact ggttccagca gaagcccgga    120
agttccccta agccctggat ctatgctaca tccaatctgg caagcggtgt tcccgttaga    180
ttttccggaa gcgggtctgg aaccagttac agtctgacta tttccagggt cgaggccgaa    240
gatgcggcta cttattattg ccaacagtgg acctctaacc cacccacatt cggcggcggc    300
actaagttgg aaattaagcg gaccgtggcc gccccgagcg tgttcatttt ccctccctcc    360
gacgagcagt tgaaatcggg caccgctagc gtggtctgcc ttctcaacaa tttctatcca    420
cgggaagcca aagtgcagtg gaaggtcgac aacgcgctcc aatccgggaa ctcacaggaa    480
tccgtgactg agcaggattc caaggactcg acctactccc tgtcatccac gctgaccctg    540
agcaaggcag actacgagaa gcacaaggtc tacgcctgcg aagtgacaca ccagggactg    600
tccagccccg tgaccaagag cttcaacaga ggagaatgcg cacctacctc aagctctgga    660
ggaggtggca gcgagcccca tagtctgagc tacgacatca cagttattcc caagttcagg    720
cccggaccgc gctggtgtgc cgtgcaagga caagtcgacg aaaaaacctt tcttcattac    780
gattgcggaa ataagactgt aacgccagtc tctcctttag gtaagaagtt aaacgtcact    840
acggcgtgga aggcacaaaa ccccgtcctg cgcgaggtcg tcgacatcct gactgaacaa    900
ttgtgggaca tccagctcga gaattacact ccaaaggagc ctcttaccct gcaggctaga    960
atgtcttgcg agcaaaaggc agagggccac tcctccggca gctggcagtt cagtttcgac   1020
ggacaaatct ttctgttatt cgattcagag aagagaatgt ggactacagt tcaccccggt   1080
gcccgtaaaa tgaaggagaa gtgggaaaac gacaaagtgg tggcgactaa gctttatctt   1140
tggtcgatgg gagactgcat cggttggctg gaagatttcc tcatgggtat ggactccact   1200
ttggagccat cg                                                       1212
```

<210> SEQ ID NO 131
<211> LENGTH: 634
<212> TYPE: PRT
<213> ORGANISM: Artificial sequence
<220> FEATURE:
<223> OTHER INFORMATION: Synthetic peptide rituximab HC_ULBP2.R80W

<400> SEQUENCE: 131

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
                435                 440                 445

Pro Gly Gly Gly Gly Ser Glu Pro His Ser Leu Ser Tyr Asp Ile Thr
    450                 455                 460

Val Ile Pro Lys Phe Arg Pro Gly Pro Arg Trp Cys Ala Val Gln Gly
465                 470                 475                 480

Gln Val Asp Glu Lys Thr Phe Leu His Tyr Asp Cys Gly Asn Lys Thr
                485                 490                 495

Val Thr Pro Val Ser Pro Leu Gly Lys Lys Leu Asn Val Thr Thr Ala
            500                 505                 510

Trp Lys Ala Gln Asn Pro Val Leu Arg Glu Val Val Asp Ile Leu Thr
    515                 520                 525

Glu Gln Leu Trp Asp Ile Gln Leu Glu Asn Tyr Thr Pro Lys Glu Pro
530                 535                 540
```

```
Leu Thr Leu Gln Ala Arg Met Ser Cys Glu Gln Lys Ala Glu Gly His
545                 550                 555                 560

Ser Ser Gly Ser Trp Gln Phe Ser Phe Asp Gly Gln Ile Phe Leu Leu
                565                 570                 575

Phe Asp Ser Glu Lys Arg Met Trp Thr Thr Val His Pro Gly Ala Arg
            580                 585                 590

Lys Met Lys Glu Lys Trp Glu Asn Asp Lys Val Val Ala Met Ser Phe
        595                 600                 605

His Tyr Phe Ser Met Gly Asp Cys Ile Gly Trp Leu Glu Asp Phe Leu
    610                 615                 620

Met Gly Met Asp Ser Thr Leu Glu Pro Ser
625                 630
```

<210> SEQ ID NO 132
<211> LENGTH: 1902
<212> TYPE: DNA
<213> ORGANISM: Artificial sequence
<220> FEATURE:
<223> OTHER INFORMATION: Synthetic polynucleotide, encoding rituximab
      HC_ULBP2.R80W

<400> SEQUENCE: 132

```
caagttcagc ttcagcagcc gggggctgag ttggtgaaac ccggggccag tgtgaagatg    60
agctgtaaag cgagcggcta caccttcact tcttataata tgcattgggt taagcaaacg    120
ccaggaaggg ggctggagtg gatcggcgct atttacccag gtaacggtga cacatcatat    180
aaccaaaagt ttaagggaaa ggcaacccct cacagcggac agagtagctc aaccgcatac    240
atgcaactgt caagccttac ctccgaagac agcgcagtgt actactgcgc cagaagcacc    300
tactatgggg gtgattggta cttcaacgtc tgggggggctg gcaccacagt gactgtaagc    360
gcagcgtcga ccaagggccc gtcagtgttc ccgctggccc cgtcatccaa gtccacgtct    420 ggggcacag cagccctggg atgcttggtc aaggactact ccccgagcc cgtgactgtg    480 tcctggaact ccggagcact gacctccgga gtgcacacct ttcccgcggt gctgcagtcc    540
tccggactgt actccctgtc gtcggtcgtg accgtgccga gctcctcgct cggaacccag    600
acctacatct gcaacgtgaa ccacaagccc tcgaacacca agtggacaa gaaggtcgag    660 cccaaaagct gcgacaagac tcacacttgt ccgccgtgcc cgcccccga actgctgggt    720 ggcccctccg tgttcctgtt cccgcctaag cctaaggaca cccttatgat cagccgcacc    780
cctgaagtga cctgtgtcgt cgtggcagtg tcacacgagg acccggaggt caagttcaat    840
tggtacgtga cggcgtgga agtgcataac gcaaagacca gcctcggga ggaacagtac    900 gcctcgacct accgcgtggt gtcagtcctg actgtgctgc accaggactg gctgaacggg    960
aaggagtaca agtgcaaagt gtcgaacaag gccctgccgg ctccaattga aaagaccatc    1020
agcaaggcca agggccagcc aagggaacca caggtgtaca ccctccctcc ttcccgggac    1080
gagctgacca aaaaccaagt gtccctgact tgccttgtga aggggttcta cccttctgac    1140
attgccgtcg aatgggaatc gaacggacag cctgaaaaca actataagac taccccgccc    1200
gtgctggatt ccgacggaag cttcttcctg tactccaagc tgaccgtgga caagtcgaga    1260
tggcagcagg gaaatgtgtt cagctgctcc gtgatgcatg aggcgctgca caaccactac    1320
acccagaagt cactgagcct ctcccccgga ggaggtggca gcgagcccca tagtctgagc    1380
tacgacatca cagttattcc caagttcagg cccggaccgc gctggtgtgc cgtgcaagga    1440
caagtcgacg aaaaaacctt tcttcattac gattgcggaa ataagactgt aacgccagtc    1500
```

```
tctcctttag gtaagaagtt aaacgtcact acggcgtgga aggcacaaaa ccccgtcctg   1560
cgcgaggtcg tcgacatcct gactgaacaa ttgtgggaca tccagctcga gaattacact   1620
ccaaaggagc tcttaccct gcaggctaga atgtcttgcg agcaaaaggc agagggccac    1680
tcctccggca gctggcagtt cagtttcgac ggacaaatct ttctgttatt cgattcagag   1740
aagagaatgt ggactacagt tcaccccggt gcccgtaaaa tgaaggagaa gtgggaaaac   1800
gacaaagtgg tggcgatgtc attccactat ttctcgatgg gagactgcat cggttggctg   1860
gaagatttcc tcatgggtat ggactccact ttggagccat cg                     1902
```

<210> SEQ ID NO 133
<211> LENGTH: 405
<212> TYPE: PRT
<213> ORGANISM: Artificial sequence
<220> FEATURE:
<223> OTHER INFORMATION: Synthetic peptide trastuzumab LC_ULBP2.R

<400> SEQUENCE: 133

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Pro Thr Ser Ser Gly Gly Gly Gly
    210                 215                 220

Ser Glu Pro His Ser Leu Ser Tyr Asp Ile Thr Val Ile Pro Lys Phe
225                 230                 235                 240

Arg Pro Gly Pro Arg Trp Cys Ala Val Gln Gly Gln Val Asp Glu Lys
                245                 250                 255

Thr Phe Leu His Tyr Asp Cys Gly Asn Lys Thr Val Thr Pro Val Ser
            260                 265                 270

Pro Leu Gly Lys Lys Leu Asn Val Thr Thr Ala Trp Lys Ala Gln Asn
        275                 280                 285

Pro Val Leu Arg Glu Val Val Asp Ile Leu Thr Glu Gln Leu Trp Asp
```

Ile Gln Leu Glu Asn Tyr Thr Pro Lys Glu Pro Leu Thr Leu Gln Ala
305                 310                 315                 320

Arg Met Ser Cys Glu Gln Lys Ala Glu Gly His Ser Ser Gly Ser Trp
            325                 330                 335

Gln Phe Ser Phe Asp Gly Gln Ile Phe Leu Leu Phe Asp Ser Glu Lys
                340                 345                 350

Arg Met Trp Thr Thr Val His Pro Gly Ala Arg Lys Met Lys Glu Lys
            355                 360                 365

Trp Glu Asn Asp Lys Val Val Ala Thr Leu Leu Trp Gly Trp Ser Met
        370                 375                 380

Gly Asp Cys Ile Gly Trp Leu Glu Asp Phe Leu Met Gly Met Asp Ser
385                 390                 395                 400

Thr Leu Glu Pro Ser
            405

<210> SEQ ID NO 134
<211> LENGTH: 1215
<212> TYPE: DNA
<213> ORGANISM: Artificial sequence
<220> FEATURE:
<223> OTHER INFORMATION: Synthetic polynucleotide, encoding trastuzumab
      LC_ULBP2.R

<400> SEQUENCE: 134
gatatccaaa tgactcaatc accatcttca ctctccgcga gcgtgggtga tcgggtcacc     60
atcacatgta gggcgagcca agatgtgaat accgccgtcg cgtggtatca acaaaagccg    120
ggaaaagcac caaaactgct tatatactct gcatccttcc tgtactctgg ggtgccaagc    180
cggttctccg gtagtagatc tggtactgac tttacactca ctatcagcag tctgcaacct    240
gaggactttg cgacatacta ttgccagcag cactacacaa ccccacctac atttggtcag    300
gggacaaagg tggagatcaa gcggaccgtg gccgccccga gcgtgttcat tttcccctcc    360
tccgacgagc agttgaaatc gggcaccgct agcgtggtct gccttctcaa caatttctat    420
ccacgggaag ccaaagtgca gtggaaggtc gacaacgcgc tccaatccgg gaactcacag    480
gaatccgtga ctgagcagga ttccaaggac tcgacctact ccctgtcatc cacgctgacc    540
ctgagcaagg cagactacga aagcacaag gtctacgcct gcgaagtgac acaccaggga    600
ctgtccagcc ccgtgaccaa gagcttcaac agaggagaat gcgcacctac ctcaagctct    660
ggaggaggtg gcagcgagcc ccatagtctg agctacgaca tcacagttat tcccaagttc    720
aggcccggac cgcgctggtg tgccgtgcaa ggacaagtcg acgaaaaaac ctttcttcat    780
tacgattgcg gaaataagac tgtaacgcca gtctctcctt taggtaagaa gttaaacgtc    840
actacggcgt ggaaggcaca aaaccccgtc ctgcgcgagg tcgtcgacat cctgactgaa    900
caattgtggg acatccagct cgagaattac actccaaagg agcctcttac cctgcaggct    960
agaatgtctt gcgagcaaaa ggcagagggc cactcctccg gcagctggca gttcagtttc   1020
gacggacaaa tctttctgtt attcgattca gagaagagaa tgtggactac agttcacccc   1080
ggtgcccgta aaatgaagga aagtgggaa acgacaaag tggtggcgac tttgttgtgg   1140
gggtggtcga tgggagactg catcggttgg ctggaagatt tcctcatggg tatggactcc   1200
actttggagc catcg                                                   1215

<210> SEQ ID NO 135
<211> LENGTH: 156

```
<212> TYPE: PRT
<213> ORGANISM: Artificial sequence
<220> FEATURE:
<223> OTHER INFORMATION: Synthetic peptide NKG2D.wt ectodomain

<400> SEQUENCE: 135

Met Ala Leu Pro Val Thr Ala Leu Leu Pro Leu Ala Leu Leu Leu
1               5                   10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val
145                 150                 155

<210> SEQ ID NO 136
<211> LENGTH: 468
<212> TYPE: DNA
<213> ORGANISM: Artificial sequence
<220> FEATURE:
<223> OTHER INFORMATION: Synthetic polynucleotide, encoding NKG2D.wt
      ectodomain

<400> SEQUENCE: 136
atggcattgc ctgttacagc tctgctgctg cccctggctc tgcttctgca tgctgccaga      60
cctctgttca atcaagaggt gcagatccct ctgaccgaga gctactgtgg ccctgtcct     120 aagaactgga tctgctacaa gaacaactgc taccagttct tcgacgagag caagaattgg    180
tacgagagcc aggccagctg catgagccag aatgccagcc tgctgaaggt gtacagcaaa    240
gaggaccagg atctgctgaa gctggtcaag agctaccact ggatgggact cgtgcacatc    300
cctacaaacg gcagctggca gtgggaggac ggctctatcc tgtctcctaa cctgctgacc    360
atcatcgaga tgcagaaggg cgactgcgcc ctgtacgcca gcagctttaa gggctacatc    420
gagaactgca gcaccccctaa cacctacatc tgtatgcagc ggaccgtg               468

<210> SEQ ID NO 137
<211> LENGTH: 156
<212> TYPE: PRT
<213> ORGANISM: Artificial sequence
<220> FEATURE:
<223> OTHER INFORMATION: Synthetic peptide NKG2D.YA ectodomain

<400> SEQUENCE: 137

Met Ala Leu Pro Val Thr Ala Leu Leu Pro Leu Ala Leu Leu Leu
1               5                   10                  15

His Ala Ala Arg Pro Leu Phe Asn Gln Glu Val Gln Ile Pro Leu Thr
                20                  25                  30
```

```
Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
 50                  55                  60

Ala Ser Cys Met Ser Gln Asn Ala Ser Leu Leu Lys Val Tyr Ser Lys
 65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
            115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val
145                 150                 155
```

<210> SEQ ID NO 138
<211> LENGTH: 468
<212> TYPE: DNA
<213> ORGANISM: Artificial sequence
<220> FEATURE:
<223> OTHER INFORMATION: Synthetic polynucleotide, encoding NKG2D.YA ectodomain

<400> SEQUENCE: 138

```
atggcattgc ctgttacagc tctgctgctg cccctggctc tgcttctgca tgctgccaga      60
cctctgttca atcaagaggt gcagatccct ctgaccgaga gctactgtgg ccctgtcct     120 aagaactgga tctgctacaa gaacaactgc taccagttct tcgacgagag caagaattgg     180
tacgagagcc aggccagctg catgagccag aatgccagcc tgctgaaggt gtacagcaaa     240
gaggaccagg atctgctgaa gctggtcaag agcgcccact ggatgggact cgtgcacatc     300
cctacaaacg gcagctggca gtgggaggac ggctctatcc tgtctcctaa cctgctgacc     360
atcatcgaga tgcagaaggg cgactgcgcc ctgtacgcca gcagctttaa gggctacatc     420
gagaactgca gcacccctaa cacctacatc tgtatgcagc ggaccgtg                  468
```

<210> SEQ ID NO 139
<211> LENGTH: 156
<212> TYPE: PRT
<213> ORGANISM: Artificial sequence
<220> FEATURE:
<223> OTHER INFORMATION: Synthetic peptide NKG2D.AF ectodomain

<400> SEQUENCE: 139

```
Met Ala Leu Pro Val Thr Ala Leu Leu Leu Pro Leu Ala Leu Leu Leu
 1               5                  10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
 50                  55                  60

Ala Ser Cys Met Ser Gln Asn Ala Ser Leu Leu Lys Val Tyr Ser Lys
 65                  70                  75                  80

Glu Asp Gln Asp Leu Leu Lys Leu Val Lys Ser Ala His Trp Met Gly
                85                  90                  95
```

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Phe Ile Glu Asn Cys Ser
130                 135                 140

Thr Pro Asn Thr Tyr Ile Cys Met Gln Arg Thr Val
145                 150                 155

<210> SEQ ID NO 140
<211> LENGTH: 468
<212> TYPE: DNA
<213> ORGANISM: Artificial sequence
<220> FEATURE:
<223> OTHER INFORMATION: Synthetic polynucleotide, encoding NKG2D.AF
      ectodomain

<400> SEQUENCE: 140
atggcattgc ctgttacagc tctgctgctg cccctggctc tgcttctgca tgctgccaga      60
cctctgttca atcaagaggt gcagatccct ctgaccgaga gctactgtgg ccctgtcct     120 aagaactgga tctgctacaa gaacaactgc taccagttct tcgacgagag caagaattgg     180
tacgagagcc aggccagctg catgagccag aatgccagcc tgctgaaggt gtacagcaaa     240
gaggaccagg atctgctgaa gctggtcaag agcgcccact ggatgggact cgtgcacatc     300
cctacaaacg gcagctggca gtgggaggac ggctctatcc tgtctcctaa cctgctgacc     360
atcatcgaga tgcagaaggg cgactgcgcc ctgtacgcca gcagctttaa gggcttcatc     420
gagaactgca gcacccctaa cacctacatc tgtatgcagc ggaccgtg               468

<210> SEQ ID NO 141
<211> LENGTH: 69
<212> TYPE: PRT
<213> ORGANISM: Artificial sequence
<220> FEATURE:
<223> OTHER INFORMATION: Synthetic peptide CD8alpha hinge and
      transmembrane domain

<400> SEQUENCE: 141

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 142
<211> LENGTH: 207
<212> TYPE: DNA
<213> ORGANISM: Artificial sequence
<220> FEATURE:
<223> OTHER INFORMATION: Synthetic polynucleotide, encoding CD8alpha
      hinge and transmembrane domain

<400> SEQUENCE: 142
accaccacac cagctcctag acctccaact cctgctccta caatcgccag ccagcctctg      60
tctctgaggc cagaagcttg tagacctgct gcaggcggag ccgtgcatac aagaggactg    120
gatttcgcct gcgacatcta catctgggcc cctctggctg aacatgtgg cgtgctgctg    180 ctgagcctgg tcatcaccct gtactgc                                        207

<210> SEQ ID NO 143
<211> LENGTH: 42
<212> TYPE: PRT
<213> ORGANISM: Artificial sequence
<220> FEATURE:
<223> OTHER INFORMATION: Synthetic peptide 4-1BB

<400> SEQUENCE: 143

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 144
<211> LENGTH: 126
<212> TYPE: DNA
<213> ORGANISM: Artificial sequence
<220> FEATURE:
<223> OTHER INFORMATION: Synthetic polynucleotide, encoding 4-1BB

<400> SEQUENCE: 144
aagcggggca gaaagaagct gctgtacatc tttaagcagc ccttcatgcg gcccgtgcag     60
accacacaag aggaagatgg ctgctcctgc agattccccg aggaagaaga aggcggctgc    120
gagctg                                                               126

<210> SEQ ID NO 145
<211> LENGTH: 112
<212> TYPE: PRT
<213> ORGANISM: Artificial sequence
<220> FEATURE:
<223> OTHER INFORMATION: Synthetic peptide CD3zeta

<400> SEQUENCE: 145

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 146
<211> LENGTH: 336
<212> TYPE: DNA
<213> ORGANISM: Artificial sequence
<220> FEATURE:
<223> OTHER INFORMATION: Synthetic polynucleotide, encoding CD3zeta

<400> SEQUENCE: 146

```
agagtgaagt tcagccgttc tgccgacgct cccgcctata agcagggaca gaaccagctg      60
tacaacgagc tgaacctggg gagaagagaa gagtacgacg tgctggacaa gcggagaggc     120
agagatcctg agatgggcgg caagcccaga cggaagaatc ctcaagaggg cctgtataat     180
gagctgcaga agacaagat ggccgaggcc tacagcgaga tcggaatgaa gggcgagcgc     240
agaagaggca agggacacga tggactgtac cagggcctga gcaccgccac caaggatacc     300
tatgatgccc tgcacatgca ggccctgcct ccaaga                               336
```

<210> SEQ ID NO 147
<211> LENGTH: 239
<212> TYPE: PRT
<213> ORGANISM: Artificial sequence
<220> FEATURE:
<223> OTHER INFORMATION: Synthetic peptide EGFP

<400> SEQUENCE: 147

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 148
<211> LENGTH: 717
<212> TYPE: DNA
<213> ORGANISM: Artificial sequence
<220> FEATURE:
<223> OTHER INFORMATION: Synthetic polynucleotide, encoding EGFP

<400> SEQUENCE: 148

```
atggtgtcta aaggcgagga actgttcacc ggcgtggtgc ccattctggt ggaactggac    60
ggggatgtga acggccacaa gtttagcgtt agcggcgaag gcgaagggga tgccacatac   120
ggaaagctga ccctgaagtt catctgcacc accggcaagc tgcctgtgcc ttggcctaca   180
ctggtcacca cactgacata cggcgtgcag tgctttagca gataccccga ccatatgaag   240
cagcacgact tcttcaagtc cgccatgcct gagggctacg tgcaagagcg accatcttc    300 tttaaggacg acggcaacta caagaccagg gccgaagtga agtttgaggg cgacaccctg   360
gtcaaccgga tcgagctgaa gggcatcgac ttcaaagagg atggcaacat cctgggccac   420
aagctcgagt acaactacaa cagccacaac gtgtacatca tggccgacaa gcagaagaac   480
ggcatcaagg ccaacttcaa gatccggcac aacatcgagg acggcagcgt cagctggcc    540 gatcactacc agcagaacac ccctatcgga gatggccctg tgctgctccc cgacaatcac   600
tacctgagca cacagagcgc cctgagcaag accccaacg agaagaggga tcacatggtg    660
ctgctggaat ttgtgaccgc cgcaggcatc accctcggca tggacgaact gtacaaa      717
```

<210> SEQ ID NO 149
<211> LENGTH: 473
<212> TYPE: PRT
<213> ORGANISM: Artificial sequence
<220> FEATURE:
<223> OTHER INFORMATION: Synthetic peptide CD8hingeTM_4-1BB_CD3zeta_EGFP

<400> SEQUENCE: 149

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys Ser Leu Lys Arg Gly Arg Lys Lys Leu Leu Tyr
65                  70                  75                  80

Ile Phe Lys Gln Pro Phe Met Arg Pro Val Gln Thr Thr Gln Glu Glu
                85                  90                  95

Asp Gly Cys Ser Cys Arg Phe Pro Glu Glu Glu Glu Gly Gly Cys Glu
            100                 105                 110

Leu Arg Val Lys Phe Ser Arg Ser Ala Asp Ala Pro Ala Tyr Lys Gln
        115                 120                 125

Gly Gln Asn Gln Leu Tyr Asn Glu Leu Asn Leu Gly Arg Arg Glu Glu
    130                 135                 140

Tyr Asp Val Leu Asp Lys Arg Arg Gly Arg Asp Pro Glu Met Gly Gly
145                 150                 155                 160

Lys Pro Arg Arg Lys Asn Pro Gln Glu Gly Leu Tyr Asn Glu Leu Gln
                165                 170                 175

Lys Asp Lys Met Ala Glu Ala Tyr Ser Glu Ile Gly Met Lys Gly Glu
            180                 185                 190

Arg Arg Arg Gly Lys Gly His Asp Gly Leu Tyr Gln Gly Leu Ser Thr
        195                 200                 205

Ala Thr Lys Asp Thr Tyr Asp Ala Leu His Met Gln Ala Leu Pro Pro
    210                 215                 220

Arg Ser Gly Ser Gly Ser Gly Ser Gly Ser Met Val Ser Lys Gly Glu
225                 230                 235                 240
```

```
Glu Leu Phe Thr Gly Val Val Pro Ile Leu Val Leu Asp Gly Asp
                245                 250                 255

Val Asn Gly His Lys Phe Ser Val Ser Gly Glu Gly Glu Gly Asp Ala
            260                 265                 270

Thr Tyr Gly Lys Leu Thr Leu Lys Phe Ile Cys Thr Thr Gly Lys Leu
        275                 280                 285

Pro Val Pro Trp Pro Thr Leu Val Thr Thr Leu Thr Tyr Gly Val Gln
    290                 295                 300

Cys Phe Ser Arg Tyr Pro Asp His Met Lys Gln His Asp Phe Phe Lys
305                 310                 315                 320

Ser Ala Met Pro Glu Gly Tyr Val Gln Glu Arg Thr Ile Phe Phe Lys
                325                 330                 335

Asp Asp Gly Asn Tyr Lys Thr Arg Ala Glu Val Lys Phe Glu Gly Asp
            340                 345                 350

Thr Leu Val Asn Arg Ile Glu Leu Lys Gly Ile Asp Phe Lys Glu Asp
        355                 360                 365

Gly Asn Ile Leu Gly His Lys Leu Glu Tyr Asn Tyr Asn Ser His Asn
    370                 375                 380

Val Tyr Ile Met Ala Asp Lys Gln Lys Asn Gly Ile Lys Ala Asn Phe
385                 390                 395                 400

Lys Ile Arg His Asn Ile Glu Asp Gly Ser Val Gln Leu Ala Asp His
                405                 410                 415

Tyr Gln Gln Asn Thr Pro Ile Gly Asp Gly Pro Val Leu Leu Pro Asp
            420                 425                 430

Asn His Tyr Leu Ser Thr Gln Ser Ala Leu Ser Lys Asp Pro Asn Glu
        435                 440                 445

Lys Arg Asp His Met Val Leu Leu Glu Phe Val Thr Ala Ala Gly Ile
    450                 455                 460

Thr Leu Gly Met Asp Glu Leu Tyr Lys
465                 470
```

<210> SEQ ID NO 150
<211> LENGTH: 1419
<212> TYPE: DNA
<213> ORGANISM: Artificial sequence
<220> FEATURE:
<223> OTHER INFORMATION: Synthetic polynucleotide, encoding
      CD8hingeTM_4-1BB_CD3zeta_EGFP

<400> SEQUENCE: 150

```
accaccacac cagctcctag acctccaact cctgctccta caatcgccag ccagcctctg      60
tctctgaggc cagaagcttg tagacctgct gcaggcggag ccgtgcatac aagaggactg     120
gatttcgcct cgacatctca catctgggcc cctctggctg aacatgtgg cgtgctgctg     180
ctgagcctgg tcatcaccct gtactgcagc ctgaagcggg cagaaagaa gctgctgtac     240
atctttaagc agcccttcat gcggcccgtg cagaccacac aagaggaaga tggctgctcc     300
tgcagattcc ccgaggaaga agaaggcggc tgcgagctga gtgaagtt cagccgttct     360
gccgacgctc ccgcctataa gcagggacag aaccagctgt acaacgagct gaacctgggg     420
agaagagaag agtacgacgt gctggacaag cggagaggca gagatcctga gatggcggc     480
aagcccagac ggaagaatcc tcaagagggc ctgtataatg agctgcagaa agacaagatg     540
gccgaggcct acagcgagat cggaatgaag ggcgagcgca agaggcaa gggacacgat     600
ggactgtacc agggcctgag caccgccacc aaggatacct atgatgccct gcacatgcag     660
```

-continued

```
gccctgcctc caagatcagg ctctggttct ggcagcggca gcatggtgtc taaaggcgag   720
gaactgttca ccggcgtggt gcccattctg gtggaactgg acggggatgt gaacggccac   780
aagtttagcg ttagcggcga aggcgaaggg gatgccacat acggaaagct gaccctgaag   840
ttcatctgca ccaccggcaa gctgcctgtg ccttggccta cactggtcac cacactgaca   900
tacggcgtgc agtgctttag cagataccc gaccatatga agcagcacga cttcttcaag   960
tccgccatgc ctgagggcta cgtgcaagag cggaccatct tctttaagga cgacggcaac  1020
tacaagacca gggccgaagt gaagtttgag ggcgacaccc tggtcaaccg gatcgagctg  1080
aagggcatcg acttcaaaga ggatggcaac atcctgggcc acaagctcga gtacaactac  1140
aacagccaca acgtgtacat catggccgac aagcagaaga cggcatcaa ggccaacttc  1200 aagatccggc acaacatcga ggacggcagc gttcagctgg ccgatcacta ccagcagaac  1260 accctatcg gagatggccc tgtgctgctc cccgacaatc actacctgag cacacagagc  1320
gccctgagca aggaccccaa cgagaagagg gatcacatgg tgctgctgga atttgtgacc  1380
gccgcaggca tcaccctcgg catggacgaa ctgtacaaa                          1419
```

<210> SEQ ID NO 151
<211> LENGTH: 629
<212> TYPE: PRT
<213> ORGANISM: Artificial sequence
<220> FEATURE:
<223> OTHER INFORMATION: Synthetic peptide NKG2D.wt_CD8hingeTM_4-
      1BB_CD3zeta_EGFP complete chimeric antigen receptor

<400> SEQUENCE: 151

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220
```

-continued

```
Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
            245                 250                 255

Cys Arg Phe Pro Glu Glu Glu Gly Gly Cys Glu Leu Arg Val Lys
            260                 265                 270

Phe Ser Arg Ser Ala Asp Ala Pro Ala Tyr Lys Gln Gly Gln Asn Gln
        275                 280                 285

Leu Tyr Asn Glu Leu Asn Leu Gly Arg Arg Glu Glu Tyr Asp Val Leu
    290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
                325                 330                 335

Ala Glu Ala Tyr Ser Glu Ile Gly Met Lys Gly Glu Arg Arg Arg Gly
            340                 345                 350

Lys Gly His Asp Gly Leu Tyr Gln Gly Leu Ser Thr Ala Thr Lys Asp
        355                 360                 365

Thr Tyr Asp Ala Leu His Met Gln Ala Leu Pro Pro Arg Ser Gly Ser
    370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
                405                 410                 415

Lys Phe Ser Val Ser Gly Glu Gly Glu Gly Asp Ala Thr Tyr Gly Lys
            420                 425                 430

Leu Thr Leu Lys Phe Ile Cys Thr Thr Gly Lys Leu Pro Val Pro Trp
        435                 440                 445

Pro Thr Leu Val Thr Thr Leu Thr Tyr Gly Val Gln Cys Phe Ser Arg
    450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
        515                 520                 525

Gly His Lys Leu Glu Tyr Asn Tyr Asn Ser His Asn Val Tyr Ile Met
    530                 535                 540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
                565                 570                 575

Thr Pro Ile Gly Asp Gly Pro Val Leu Leu Pro Asp Asn His Tyr Leu
            580                 585                 590

Ser Thr Gln Ser Ala Leu Ser Lys Asp Pro Asn Glu Lys Arg Asp His
        595                 600                 605

Met Val Leu Leu Glu Phe Val Thr Ala Ala Gly Ile Thr Leu Gly Met
    610                 615                 620

Asp Glu Leu Tyr Lys
625
```

<210> SEQ ID NO 152
<211> LENGTH: 1887
<212> TYPE: DNA
<213> ORGANISM: Artificial sequence
<220> FEATURE:
<223> OTHER INFORMATION: Synthetic polynucleotide, encoding
NKG2D.wt_CD8hingeTM_4-1BB_CD3zeta_EGFP complete chimeric antigen
receptor

<400> SEQUENCE: 152

| | | | | |
|---|---|---|---|---|
| atggcattgc | ctgttacagc | tctgctgctg | ccctggctc | tgcttctgca tgctgccaga | 60 |
| cctctgttca | atcaagaggt | gcagatccct | ctgaccgaga | gctactgtgg ccctgtcct | 120 |
| aagaactgga | tctgctacaa | gaacaactgc | taccagttct | tcgacgagag caagaattgg | 180 |
| tacgagagcc | aggccagctg | catgagccag | aatgccagcc | tgctgaaggt gtacagcaaa | 240 |
| gaggaccagg | atctgctgaa | gctggtcaag | agctaccact | ggatgggact cgtgcacatc | 300 |
| cctacaaacg | gcagctggca | gtgggaggac | ggctctatcc | tgtctcctaa cctgctgacc | 360 |
| atcatcgaga | tgcagaaggg | cgactgcgcc | ctgtacgcca | gcagctttaa ggctacatc | 420 |
| gagaactgca | gcacccctaa | cacctacatc | tgtatgcagc | ggaccgtgac caccacacca | 480 |
| gctcctagac | ctccaactcc | tgctcctaca | atcgccagcc | agcctctgtc tctgaggcca | 540 |
| gaagcttgta | gacctgctgc | aggcggagcc | gtgcatacaa | gaggactgga tttcgcctgc | 600 |
| gacatctaca | tctgggcccc | tctggctgga | acatgtggcg | tgctgctgct gagcctggtc | 660 |
| atcaccctgt | actgcagcct | gaagcggggc | agaaagaagc | tgctgtacat ctttaagcag | 720 |
| cccttcatgc | ggcccgtgca | gaccacacaa | gaggaagatg | ctgctcctg cagattcccc | 780 |
| gaggaagaag | aaggcggctg | cgagctgaga | gtgaagttca | gccgttctgc cgacgctccc | 840 |
| gcctataagc | agggacagaa | ccagctgtac | aacgagctga | acctggggag aagagaagag | 900 |
| tacgacgtgc | tggacaagcg | gagaggcaga | gatcctgaga | tgggcggcaa gcccagacgg | 960 |
| aagaatcctc | aagagggcct | gtataatgag | ctgcagaaag | acaagatggc cgaggcctac | 1020 |
| agcgagatcg | gaatgaaggg | cgagcgcaga | agaggcaagg | acacgatgg actgtaccag | 1080 |
| ggcctgagca | ccgccaccaa | ggatacctat | gatgccctgc | acatgcaggc cctgcctcca | 1140 |
| agatcaggct | ctggttctgg | cagcggcagc | atggtgtcta | aggcgagga actgttcacc | 1200 |
| ggcgtggtgc | ccattctggt | ggaactggac | ggggatgtga | acggccacaa gtttagcgtt | 1260 |
| agcggcgaag | gcgaagggga | tgccacatac | ggaaagctga | ccctgaagtt catctgcacc | 1320 |
| accggcaagc | tgcctgtgcc | ttggcctaca | ctggtcacca | cactgacata cggcgtgcag | 1380 |
| tgctttagca | ataccccga | ccatatgaag | cagcacgact | tcttcaagtc cgccatgcct | 1440 |
| gagggctacg | tgcaagagcg | gaccatcttc | tttaaggacg | acggcaacta caagaccagg | 1500 |
| gccgaagtga | agtttgaggg | cgacacctg | gtcaaccgga | tcgagctgaa gggcatcgac | 1560 |
| ttcaaagagg | atggcaacat | cctgggccac | aagctcgagt | acaactacaa cagccacaac | 1620 |
| gtgtacatca | tggccgacaa | gcagaagaac | ggcatcaagg | ccaacttcaa gatccggcac | 1680 |
| aacatcgagg | acggcagcgt | tcagctggcc | gatcactacc | agcagaacac ccctatcgga | 1740 |
| gatggccctg | tgctgctccc | cgacaatcac | tacctgagca | cacagagcgc cctgagcaag | 1800 |
| gaccccaacg | agaagaggga | tcacatggtg | ctgctggaat | tgtgaccgc cgcaggcatc | 1860 |
| accctcggca | tggacgaact | gtacaaa | | | 1887 |

<210> SEQ ID NO 153
<211> LENGTH: 629
<212> TYPE: PRT

<213> ORGANISM: Artificial sequence
<220> FEATURE:
<223> OTHER INFORMATION: Synthetic peptide NKG2D.YA_CD8hingeTM_4-
1BB_CD3zeta_EGFP complete chimeric antigen receptor

<400> SEQUENCE: 153

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu Arg Val Lys
            260                 265                 270

Phe Ser Arg Ser Ala Asp Ala Pro Ala Tyr Lys Gln Gly Gln Asn Gln
        275                 280                 285

Leu Tyr Asn Glu Leu Asn Leu Gly Arg Arg Glu Glu Tyr Asp Val Leu
    290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
                325                 330                 335

Ala Glu Ala Tyr Ser Glu Ile Gly Met Lys Gly Glu Arg Arg Arg Gly
            340                 345                 350

Lys Gly His Asp Gly Leu Tyr Gln Gly Leu Ser Thr Ala Thr Lys Asp
        355                 360                 365

Thr Tyr Asp Ala Leu His Met Gln Ala Leu Pro Pro Arg Ser Gly Ser
    370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
            405                 410                 415

Lys Phe Ser Val Ser Gly Glu Gly Glu Gly Asp Ala Thr Tyr Gly Lys
        420                 425                 430

Leu Thr Leu Lys Phe Ile Cys Thr Thr Gly Lys Leu Pro Val Pro Trp
    435                 440                 445

Pro Thr Leu Val Thr Thr Leu Thr Tyr Gly Val Gln Cys Phe Ser Arg
450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
            485                 490                 495

Tyr Lys Thr Arg Ala Glu Val Lys Phe Glu Gly Asp Thr Leu Val Asn
        500                 505                 510

Arg Ile Glu Leu Lys Gly Ile Asp Phe Lys Glu Asp Gly Asn Ile Leu
    515                 520                 525

Gly His Lys Leu Glu Tyr Asn Tyr Asn Ser His Asn Val Tyr Ile Met
530                 535                 540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
            565                 570                 575

Thr Pro Ile Gly Asp Gly Pro Val Leu Leu Pro Asp Asn His Tyr Leu
        580                 585                 590

Ser Thr Gln Ser Ala Leu Ser Lys Asp Pro Asn Glu Lys Arg Asp His
    595                 600                 605

Met Val Leu Leu Glu Phe Val Thr Ala Ala Gly Ile Thr Leu Gly Met
610                 615                 620

Asp Glu Leu Tyr Lys
625

<210> SEQ ID NO 154
<211> LENGTH: 1887
<212> TYPE: DNA
<213> ORGANISM: Artificial sequence
<220> FEATURE:
<223> OTHER INFORMATION: Synthetic polynucleotide, encoding
      NKG2D.YA_CD8hingeTM_4-1BB_CD3zeta_EGFP complete chimeric antigen
      receptor

<400> SEQUENCE: 154
atggcattgc ctgttacagc tctgctgctg cccctggctc tgcttctgca tgctgccaga       60
cctctgttca atcaagaggt gcagatccct ctgaccgaga gctactgtgg ccctgtcct       120 aagaactgga tctgctacaa gaacaactgc taccagttct tcgacgagag caagaattgg      180
tacgagagcc aggccagctg catgagccag aatgccagcc tgctgaaggt gtacagcaaa      240
gaggaccagg atctgctgaa gctggtcaag agcgcccact ggatgggact cgtgcacatc      300
cctacaaacg gcagctggca gtgggaggac ggctctatcc tgtctcctaa cctgctgacc      360
atcatcgaga tgcagaaggg cgactgcgcc ctgtacgcca gcagctttaa gggctacatc      420
gagaactgca gcacccctaa cacctacatc tgtatgcagc ggaccgtgac caccacacca      480
gctcctagac ctccaactcc tgctcctaca atcgccagcc agcctctgtc tctgaggcca      540
gaagcttgta gacctgctgc aggcggagcc gtgcatacaa gaggactgga tttcgcctgc      600

```
gacatctaca tctgggcccc tctggctgga acatgtggcg tgctgctgct gagcctggtc      660
atcaccctgt actgcagcct gaagcggggc agaaagaagc tgctgtacat ctttaagcag      720
cccttcatgc ggcccgtgca gaccacacaa gaggaagatg gctgctcctg cagattcccc      780
gaggaagaag aaggcggctg cgagctgaga gtgaagttca gccgttctgc cgacgctccc      840
gcctataagc agggacagaa ccagctgtac aacgagctga acctggggag aagagaagag      900
tacgacgtgc tggacaagcg agagggcaga gatcctgaga tgggcggcaa gcccagacgg      960
aagaatcctc aagagggcct gtataatgag ctgcagaaag acaagatggc cgaggcctac     1020
agcgagatcg aatgaaggg cgagcgcaga agaggcaagg acacgatgg actgtaccag     1080 ggcctgagca ccgccaccaa ggatacctat gatgccctgc acatgcaggc cctgcctcca     1140
agatcaggct ctggttctgg cagcggcagc atggtgtcta aaggcgagga actgttcacc     1200
ggcgtggtgc ccattctggt ggaactggac ggggatgtga acggccacaa gtttagcgtt     1260
agcggcgaag gcgaagggga tgccacatac ggaaagctga ccctgaagtt catctgcacc     1320
accggcaagc tgcctgtgcc ttggcctaca ctggtcacca cactgacata cggcgtgcag     1380
tgctttagca gatacccga ccatatgaag cagcacgact tcttcaagtc cgccatgcct     1440
gagggctacg tgcaagagcg gaccatcttc tttaaggacg acggcaacta caagaccagg     1500
gccgaagtga gtttgaggg cgacacctg gtcaaccgga tcgagctgaa gggcatcgac     1560
ttcaaagagg atggcaacat cctgggccac aagctcgagt acaactacaa cagccacaac     1620
gtgtacatca tggccgacaa gcagaagaac ggcatcaagg ccaacttcaa gatccggcac     1680
aacatcgagg acggcagcgt tcagctggcc gatcactacc agcagaacac ccctatcgga     1740
gatggccctg tgctgctccc cgacaatcac tacctgagca cacagagcgc cctgagcaag     1800
gaccccaacg agaagaggga tcacatggtg ctgctggaat ttgtgaccgc cgcaggcatc     1860
accctcggca tggacgaact gtacaaa                                         1887
```

<210> SEQ ID NO 155
<211> LENGTH: 629
<212> TYPE: PRT
<213> ORGANISM: Artificial sequence
<220> FEATURE:
<223> OTHER INFORMATION: Synthetic peptide NKG2D.AF_CD8hingeTM_4-
      1BB_CD3zeta_EGFP complete chimeric antigen receptor

<400> SEQUENCE: 155

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125
```

```
Cys Ala Leu Tyr Ala Ser Ser Phe Lys Gly Phe Ile Glu Asn Cys Ser
            130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu Arg Val Lys
            260                 265                 270

Phe Ser Arg Ser Ala Asp Ala Pro Ala Tyr Lys Gln Gly Gln Asn Gln
        275                 280                 285

Leu Tyr Asn Glu Leu Asn Leu Gly Arg Arg Glu Glu Tyr Asp Val Leu
    290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
                325                 330                 335

Ala Glu Ala Tyr Ser Glu Ile Gly Met Lys Gly Glu Arg Arg Arg Gly
            340                 345                 350

Lys Gly His Asp Gly Leu Tyr Gln Gly Leu Ser Thr Ala Thr Lys Asp
        355                 360                 365

Thr Tyr Asp Ala Leu His Met Gln Ala Leu Pro Pro Arg Ser Gly Ser
370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
                405                 410                 415

Lys Phe Ser Val Ser Gly Glu Gly Glu Gly Asp Ala Thr Tyr Gly Lys
            420                 425                 430

Leu Thr Leu Lys Phe Ile Cys Thr Thr Gly Lys Leu Pro Val Pro Trp
        435                 440                 445

Pro Thr Leu Val Thr Thr Leu Thr Tyr Gly Val Gln Cys Phe Ser Arg
    450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
        515                 520                 525

Gly His Lys Leu Glu Tyr Asn Tyr Asn Ser His Asn Val Tyr Ile Met
530                 535                 540
```

```
Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
                565                 570                 575

Thr Pro Ile Gly Asp Gly Pro Val Leu Leu Pro Asp Asn His Tyr Leu
            580                 585                 590

Ser Thr Gln Ser Ala Leu Ser Lys Asp Pro Asn Glu Lys Arg Asp His
        595                 600                 605

Met Val Leu Leu Glu Phe Val Thr Ala Ala Gly Ile Thr Leu Gly Met
    610                 615                 620

Asp Glu Leu Tyr Lys
625

<210> SEQ ID NO 156
<211> LENGTH: 1887
<212> TYPE: DNA
<213> ORGANISM: Artificial sequence
<220> FEATURE:
<223> OTHER INFORMATION: Synthetic polynucleotide, encoding
      NKG2D.AF_CD8hingeTM_4-1BB_CD3zeta_EGFP complete chimeric antigen
      receptor

<400> SEQUENCE: 156
atggcattgc ctgttacagc tctgctgctg cccctggctc tgcttctgca tgctgccaga     60
cctctgttca atcaagaggt gcagatccct ctgaccgaga gctactgtgg ccctgtcct    120 aagaactgga tctgctacaa gaacaactgc taccagttct tcgacgagag caagaattgg    180
tacgagagcc aggccagctg catgagccag aatgccagcc tgctgaaggt gtacagcaaa    240
gaggaccagg atctgctgaa gctggtcaag agcgcccact ggatgggact cgtgcacatc    300
cctacaaacg gcagctggca gtgggaggac ggctctatcc tgtctcctaa cctgctgacc    360
atcatcgaga tgcagaaggg cgactgcgcc ctgtacgcca gcagctttaa gggcttcatc    420
gagaactgca gcaccctaa cacctacatc tgtatgcagc ggaccgtgac caccacacca    480
gctcctagac ctccaactcc tgctcctaca atcgccagcc agcctctgtc tctgaggcca    540
gaagcttgta gacctgctgc aggcggagcc gtgcatacaa aggactgga tttcgcctgc    600 gacatctaca tctgggcccc tctggctgga acatgtggcg tgctgctgct gagcctggtc    660
atcaccctgt actgcagcct gaagcggggc agaaagaagc tgctgtacat ctttaagcag    720
cccttcatgc ggcccgtgca gaccacacaa gaggaagatg gctgctcctg cagattcccc    780
gaggaagaag aaggcggctg cgagctgaga gtgaagttca gccgttctgc cgacgctccc    840
gcctataagc agggacagaa ccagctgtac aacgagctga acctggggag aagagaagag    900
tacgacgtgc tggacaagcg cgagaggcaga atcctgaga tgggcggcaa gcccagacgg    960
aagaatcctc aagagggcct gtataatgag ctgcagaaag acaagatggc cgaggcctac   1020
agcgagatcg gaatgaaggg cgagcgcaga gaggcaagg acacgatgg actgtaccag   1080 ggcctgagca ccgccaccaa ggatacctat gatgccctgc acatgcaggc cctgcctcca   1140
agatcaggct ctggttctgg cagcggcagc atggtgtcta aggcgagga actgttcacc   1200 ggcgtggtgc ccattctggt ggaactggac ggggatgtga acggccacaa gtttagcgtt   1260
agcggcgaag gcgaagggga tgccacatac ggaaagctga ccctgaagtt catctgcacc   1320
accggcaagc tgcctgtgcc ttggcctaca ctggtcacca cactgacata cggcgtgcag   1380
tgctttagca gataccccga ccatatgaag cagcacgact tcttcaagtc cgccatgcct   1440
gagggctacg tgcaagagcg gaccatcttc tttaaggacg acggcaacta caagaccagg   1500
```

```
gccgaagtga agtttgaggg cgacaccctg tcaaccgga tcgagctgaa gggcatcgac    1560
ttcaaagagg atggcaacat cctgggccac aagctcgagt acaactacaa cagccacaac    1620
gtgtacatca tggccgacaa gcagaagaac ggcatcaagg ccaacttcaa gatccggcac    1680
aacatcgagg acggcagcgt tcagctggcc gatcactacc agcagaacac ccctatcgga    1740
gatggccctg tgctgctccc cgacaatcac tacctgagca cacagagcgc cctgagcaag    1800
gaccccaacg agaagaggga tcacatggtg ctgctggaat tgtgaccgc cgcaggcatc    1860 accctcggca tggacgaact gtacaaa                                        1887
```

<210> SEQ ID NO 157
<211> LENGTH: 473
<212> TYPE: PRT
<213> ORGANISM: Artificial sequence
<220> FEATURE:
<223> OTHER INFORMATION: Synthetic peptide NKG2D.YA_CD8hingeTM_EGFP
      silent chimeric antigen receptor

<400> SEQUENCE: 157

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Ser Gly Ser Gly Ser Gly Ser Gly Ser Met Val Ser Lys Gly Glu
225                 230                 235                 240

Glu Leu Phe Thr Gly Val Val Pro Ile Leu Val Glu Leu Asp Gly Asp
                245                 250                 255

Val Asn Gly His Lys Phe Ser Val Ser Gly Glu Gly Glu Gly Asp Ala
            260                 265                 270

Thr Tyr Gly Lys Leu Thr Leu Lys Phe Ile Cys Thr Thr Gly Lys Leu
        275                 280                 285
```

```
Pro Val Pro Trp Pro Thr Leu Val Thr Thr Leu Thr Tyr Gly Val Gln
    290                 295                 300
Cys Phe Ser Arg Tyr Pro Asp His Met Lys Gln His Asp Phe Phe Lys
305                 310                 315                 320
Ser Ala Met Pro Glu Gly Tyr Val Gln Glu Arg Thr Ile Phe Phe Lys
                325                 330                 335
Asp Asp Gly Asn Tyr Lys Thr Arg Ala Glu Val Lys Phe Glu Gly Asp
            340                 345                 350
Thr Leu Val Asn Arg Ile Glu Leu Lys Gly Ile Asp Phe Lys Glu Asp
        355                 360                 365
Gly Asn Ile Leu Gly His Lys Leu Glu Tyr Asn Tyr Asn Ser His Asn
    370                 375                 380
Val Tyr Ile Met Ala Asp Lys Gln Lys Asn Gly Ile Lys Ala Asn Phe
385                 390                 395                 400
Lys Ile Arg His Asn Ile Glu Asp Gly Ser Val Gln Leu Ala Asp His
                405                 410                 415
Tyr Gln Gln Asn Thr Pro Ile Gly Asp Gly Pro Val Leu Leu Pro Asp
            420                 425                 430
Asn His Tyr Leu Ser Thr Gln Ser Ala Leu Ser Lys Asp Pro Asn Glu
        435                 440                 445
Lys Arg Asp His Met Val Leu Leu Glu Phe Val Thr Ala Ala Gly Ile
    450                 455                 460
Thr Leu Gly Met Asp Glu Leu Tyr Lys
465                 470
```

```
<210> SEQ ID NO 158
<211> LENGTH: 1419
<212> TYPE: DNA
<213> ORGANISM: Artificial sequence
<220> FEATURE:
<223> OTHER INFORMATION: Synthetic polynucleotide, encoding
      NKG2D.YA_CD8hingeTM_EGFP silent chimeric antigen receptor

<400> SEQUENCE: 158
atggcattgc ctgttacagc tctgctgctg cccctggctc tgcttctgca tgctgccaga      60
cctctgttca tcaagaggt gcagatccct ctgaccgaga gctactgtgg ccccctgtcct     120 aagaactgga tctgctacaa gaacaactgc taccagttct tcgacgagag caagaattgg     180
tacgagagcc aggccagctg catgagccag aatgccagcc tgctgaaggt gtacagcaaa     240
gaggaccagg atctgctgaa gctggtcaag agcgcccact ggatgggact cgtgcacatc     300
cctacaaacg gcagctggca gtgggaggac ggctctatcc tgtctcctaa cctgctgacc     360
atcatcgaga tgcagaaggg cgactgcgcc ctgtacgcca gcagctttaa ggctacatc     420 gagaactgca gcacccctaa cacctacatc tgtatgcagc ggaccgtgac caccacacca     480
gctcctagac ctccaactcc tgctcctaca atcgccagcc agcctctgtc tctgaggcca     540
gaagcttgta gacctgctgc aggcggagcc gtgcatacaa gaggactgga tttcgcctgc     600
gacatctaca tctgggcccc tctggctgga acatgtggcg tgctgctgct gagcctggtc     660
atcaccctgt actgctcagg ctctggttct ggcagcggca gcatggtgtc taaaggcgag     720
gaactgttca ccggcgtggt gcccattctg gtggaactgg acgggatgt gaacggccac     780 aagtttagcg ttagcggcga aggcgaaggg gatgccacat acggaaagct gaccctgaag     840
ttcatctgca ccaccggcaa gctgcctgtg ccttggccta cactggtcac cacactgaca     900
tacggcgtgc agtgctttag cagataccc gaccatatga agcagcacga cttcttcaag     960
```

```
tccgccatgc ctgagggcta cgtgcaagag cggaccatct tctttaagga cgacggcaac    1020
tacaagacca gggccgaagt gaagtttgag ggcgacaccc tggtcaaccg gatcgagctg    1080
aagggcatcg acttcaaaga ggatggcaac atcctgggcc acaagctcga gtacaactac    1140
aacagccaca acgtgtacat catggccgac aagcagaaga acggcatcaa ggccaacttc    1200
aagatccggc acaacatcga ggacggcagc gttcagctgg ccgatcacta ccagcagaac    1260
acccctatcg agatggccc tgtgctgctc cccgacaatc actacctgag cacacagagc    1320
gccctgagca aggaccccaa cgagaagagg gatcacatgg tgctgctgga atttgtgacc    1380
gccgcaggca tcaccctcgg catggacgaa ctgtacaaa                           1419
```

<210> SEQ ID NO 159
<211> LENGTH: 225
<212> TYPE: PRT
<213> ORGANISM: Artificial sequence
<220> FEATURE:
<223> OTHER INFORMATION: Synthetic peptide NKG2D.YA_CD8hingeTM silent
      chimeric antigen receptor

<400> SEQUENCE: 159

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
        50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
210                 215                 220

Cys
225

<210> SEQ ID NO 160
<211> LENGTH: 675
<212> TYPE: DNA
<213> ORGANISM: Artificial sequence
<220> FEATURE:

<223> OTHER INFORMATION: Synthetic polynucleotide, encoding
       NKG2D.YA_CD8hingeTM silent chimeric antigen receptor

<400> SEQUENCE: 160

```
atggcattgc ctgttacagc tctgctgctg cccctggctc tgcttctgca tgctgccaga      60
cctctgttca atcaagaggt gcagatccct ctgaccgaga gctactgtgg ccctgtcct     120
aagaactgga tctgctacaa gaacaactgc taccagttct tcgacgagag caagaattgg    180
tacgagagcc aggccagctg catgagccag aatgccagcc tgctgaaggt gtacagcaaa    240
gaggaccagg atctgctgaa gctggtcaag agcgcccact ggatgggact cgtgcacatc    300
cctacaaacg gcagctggca gtgggaggac ggctctatcc tgtctcctaa cctgctgacc    360
atcatcgaga tgcagaaggg cgactgcgcc ctgtacgcca gcagctttaa gggctacatc    420
gagaactgca gcacccctaa cacctacatc tgtatgcagc ggaccgtgac caccacacca    480
gctcctagac ctccaactcc tgctcctaca atcgccagcc agcctctgtc tctgaggcca    540
gaagcttgta gacctgctgc aggcggagcc gtgcatacaa aggactgga tttcgcctgc    600
gacatctaca tctgggcccc tctggctgga acatgtggcg tgctgctgct gagcctggtc    660
atcaccctgt actgc                                                     675
```

<210> SEQ ID NO 161
<211> LENGTH: 629
<212> TYPE: PRT
<213> ORGANISM: Artificial sequence
<220> FEATURE:
<223> OTHER INFORMATION: Synthetic peptide NKG2D.YA_CD8hingeTM_4-
       1BBtraf2_CD3zeta_EGFP complete chimeric antigen receptor

<400> SEQUENCE: 161

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205
```

```
Ala Gly Thr Cys Gly Val Leu Leu Ser Leu Val Ile Thr Leu Tyr
    210                 215                 220

Cys Ser Leu Lys Arg Gly Arg Lys Leu Leu Tyr Ile Phe Lys Gln
225                 230                 235                 240

Pro Phe Met Arg Pro Val Gln Thr Thr Gln Ala Ala Gly Cys Ser
            245                 250                 255

Cys Arg Phe Pro Glu Ala Ala Gly Gly Cys Glu Leu Arg Val Lys
            260                 265                 270

Phe Ser Arg Ser Ala Asp Ala Pro Ala Tyr Lys Gln Gly Gln Asn Gln
        275                 280                 285

Leu Tyr Asn Glu Leu Asn Leu Gly Arg Arg Glu Glu Tyr Asp Val Leu
    290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
                325                 330                 335

Ala Glu Ala Tyr Ser Glu Ile Gly Met Lys Gly Glu Arg Arg Arg Gly
            340                 345                 350

Lys Gly His Asp Gly Leu Tyr Gln Gly Leu Ser Thr Ala Thr Lys Asp
            355                 360                 365

Thr Tyr Asp Ala Leu His Met Gln Ala Leu Pro Pro Arg Ser Gly Ser
    370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
            405                 410                 415

Lys Phe Ser Val Ser Gly Glu Gly Glu Gly Asp Ala Thr Tyr Gly Lys
            420                 425                 430

Leu Thr Leu Lys Phe Ile Cys Thr Thr Gly Lys Leu Pro Val Pro Trp
    435                 440                 445

Pro Thr Leu Val Thr Thr Leu Thr Tyr Gly Val Gln Cys Phe Ser Arg
450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
            485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
    515                 520                 525

Gly His Lys Leu Glu Tyr Asn Tyr Asn Ser His Asn Val Tyr Ile Met
530                 535                 540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
            565                 570                 575

Thr Pro Ile Gly Asp Gly Pro Val Leu Leu Pro Asp Asn His Tyr Leu
            580                 585                 590

Ser Thr Gln Ser Ala Leu Ser Lys Asp Pro Asn Glu Lys Arg Asp His
    595                 600                 605

Met Val Leu Leu Glu Phe Val Thr Ala Ala Gly Ile Thr Leu Gly Met
610                 615                 620

Asp Glu Leu Tyr Lys
```

<210> SEQ ID NO 162
<211> LENGTH: 1887
<212> TYPE: DNA
<213> ORGANISM: Artificial sequence
<220> FEATURE:
<223> OTHER INFORMATION: Synthetic polynucleotide, encoding NKG2D.YA_CD8hingeTM_4-1BBtraf2_CD3zeta_EGFP complete chimeric antigen receptor

<400> SEQUENCE: 162

| | |
|---|---|
| atggcattgc ctgttacagc tctgctgctg cccctggctc tgcttctgca tgctgccaga | 60 |
| cctctgttca atcaagaggt gcagatccct ctgaccgaga gctactgtgg ccctgtcct | 120 |
| aagaactgga tctgctacaa gaacaactgc taccagttct tcgacgagag caagaattgg | 180 |
| tacgagagcc aggccagctg catgagccag aatgccagcc tgctgaaggt gtacagcaaa | 240 |
| gaggaccagg atctgctgaa gctggtcaag agcgcccact ggatgggact cgtgcacatc | 300 |
| cctacaaacg gcagctggca gtgggaggac ggctctatcc tgtctcctaa cctgctgacc | 360 |
| atcatcgaga tgcagaaggg cgactgcgcc ctgtacgcca gcagctttaa gggctacatc | 420 |
| gagaactgca gcacccctaa cacctacatc tgtatgcagc ggaccgtgac caccacacca | 480 |
| gctcctagac ctccaactcc tgctcctaca atcgccagcc agcctctgtc tctgaggcca | 540 |
| gaagcttgta gacctgctgc aggcggagcc gtgcatacaa aggactgga tttcgcctgc | 600 |
| gacatctaca tctgggcccc tctggctgga acatgtggcg tgctgctgct gagcctggtc | 660 |
| atcaccctgt actgcagcct gaagcggggc agaaagaagc tgctgtacat ctttaagcag | 720 |
| cccttcatgc ggcccgtgca gaccacacaa gccgctgcag gctgctcctg cagattcccc | 780 |
| gaggctgccg caggcggctg cgagctgaga gtgaagttca gccgttctgc cgacgctccc | 840 |
| gcctataagc agggacagaa ccagctgtac aacgagctga acctggggag aagagaagag | 900 |
| tacgacgtgc tggacaagcg agagggcaga gatcctgaga tgggcggcaa gcccagacgg | 960 |
| aagaatcctc aagagggcct gtataatgag ctgcagaaag acaagatggc cgaggcctac | 1020 |
| agcgagatcg gaatgaaggg cgagcgcaga gaggcaagg acacgatgg actgtaccag | 1080 |
| ggcctgagca ccgccaccaa ggatacctat gatgccctgc acatgcaggc cctgcctcca | 1140 |
| agatcaggct ctggttctgg cagcggcagc atggtgtcta aaggcgagga actgttcacc | 1200 |
| ggcgtggtgc ccattctggt ggaactggac ggggatgtga acggccacaa gtttagcgtt | 1260 |
| agcggcgaag gcgaagggga tgccacatac ggaaagctga ccctgaagtt catctgcacc | 1320 |
| accggcaagc tgcctgtgcc ttggcctaca ctggtcacca cactgacata cggcgtgcag | 1380 |
| tgctttagca gatacccga ccatatgaag cagcacgact tcttcaagtc cgccatgcct | 1440 |
| gagggctacg tgcaagagcg gaccatcttc tttaaggacg acggcaacta caagaccagg | 1500 |
| gccgaagtga gtttgaggg cgacaccctg gtcaaccgga tcgagctgaa gggcatcgac | 1560 |
| ttcaaagagg atggcaacat cctgggccac aagctcgagt acaactacaa cagccacaac | 1620 |
| gtgtacatca tggccgacaa gcagaagaac ggcatcaagg ccaacttcaa gatccggcac | 1680 |
| aacatcgagg acggcagcgt tcagctggcc gatcactacc agcagaacac ccctatcgga | 1740 |
| gatggccctg tgctgctccc cgacaatcac tacctgagca cacagagcgc cctgagcaag | 1800 |
| gaccccaacg agaagaggga tcacatggtg ctgctggaat tgtgaccgc cgcaggcatc | 1860 |
| accctcggca tggacgaact gtacaaa | 1887 |

```
<210> SEQ ID NO 163
<211> LENGTH: 629
<212> TYPE: PRT
<213> ORGANISM: Artificial sequence
<220> FEATURE:
<223> OTHER INFORMATION: Synthetic peptide NKG2D.YA_CD8hingeTM_4-
      1BB_CD3itam_EGFP complete chimeric antigen receptor

<400> SEQUENCE: 163

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu Arg Val Lys
            260                 265                 270

Phe Ser Arg Ser Ala Asp Ala Pro Ala Tyr Lys Gln Gly Gln Asn Gln
        275                 280                 285

Leu Phe Asn Glu Leu Asn Leu Gly Arg Arg Glu Glu Phe Asp Val Leu
290                 295                 300

Asp Lys Arg Arg Gly Arg Asp Pro Glu Met Gly Gly Lys Pro Arg Arg
305                 310                 315                 320

Lys Asn Pro Gln Glu Gly Leu Phe Asn Glu Leu Gln Lys Asp Lys Met
                325                 330                 335

Ala Glu Ala Phe Ser Glu Ile Gly Met Lys Gly Glu Arg Arg Arg Gly
            340                 345                 350

Lys Gly His Asp Gly Leu Phe Gln Gly Leu Ser Thr Ala Thr Lys Asp
        355                 360                 365
```

```
Thr Phe Asp Ala Leu His Met Gln Ala Leu Pro Pro Arg Ser Gly Ser
    370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
                405                 410                 415

Lys Phe Ser Val Ser Gly Glu Gly Glu Gly Asp Ala Thr Tyr Gly Lys
                420                 425                 430

Leu Thr Leu Lys Phe Ile Cys Thr Thr Gly Lys Leu Pro Val Pro Trp
        435                 440                 445

Pro Thr Leu Val Thr Thr Leu Thr Tyr Gly Val Gln Cys Phe Ser Arg
450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
                500                 505                 510

Arg Ile Glu Leu Lys Gly Ile Asp Phe Lys Glu Asp Gly Asn Ile Leu
            515                 520                 525

Gly His Lys Leu Glu Tyr Asn Tyr Asn Ser His Asn Val Tyr Ile Met
    530                 535                 540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
                565                 570                 575

Thr Pro Ile Gly Asp Gly Pro Val Leu Leu Pro Asp Asn His Tyr Leu
                580                 585                 590

Ser Thr Gln Ser Ala Leu Ser Lys Asp Pro Asn Glu Lys Arg Asp His
            595                 600                 605

Met Val Leu Leu Glu Phe Val Thr Ala Ala Gly Ile Thr Leu Gly Met
    610                 615                 620

Asp Glu Leu Tyr Lys
625

<210> SEQ ID NO 164
<211> LENGTH: 1887
<212> TYPE: DNA
<213> ORGANISM: Artificial sequence
<220> FEATURE:
<223> OTHER INFORMATION: Synthetic polynucleotide, encoding
      NKG2D.YA_CD8hingeTM_4-1BB_CD3itam_EGFP complete chimeric antigen
      receptor

<400> SEQUENCE: 164
atggcattgc ctgttacagc tctgctgctg cccctggctc tgcttctgca tgctgccaga     60
cctctgttca tcaagaggt  gcagatccct ctgaccgaga gctactgtgg ccctgtcct    120 aagaactgga tctgctacaa gaacaactgc taccagttct tcgacgagag caagaattgg    180
tacgagagcc aggccagctg catgagccag aatgccagcc tgctgaaggt gtacagcaaa    240
gaggaccagg atctgctgaa gctggtcaag agcgcccact ggatgggact cgtgcacatc    300
cctacaaacg gcagctggca gtgggaggac ggctctatcc tgtctcctaa cctgctgacc    360
atcatcgaga tgcagaaggg cgactgcgcc ctgtacgcca gcagctttaa ggctacatc     420 gagaactgca gcacccctaa cacctacatc tgtatgcagc ggaccgtgac caccacacca    480
```

```
gctcctagac ctccaactcc tgctcctaca atcgccagcc agcctctgtc tctgaggcca   540
gaagcttgta gacctgctgc aggcggagcc gtgcatacaa gaggactgga tttcgcctgc   600
gacatctaca tctgggcccc tctggctgga acatgtggcg tgctgctgct gagcctggtc   660
atcaccctgt actgcagcct gaagcggggc agaaagaagc tgctgtacat ctttaagcag   720
cccttcatgc ggcccgtgca gaccacacaa gaggaagatg gctgctcctg cagattcccc   780
gaggaagaag aaggcggctg cgagctgaga gtgaagttca gccgttctgc cgacgctccc   840
gcctataagc agggacagaa ccagctgttc aacgagctga actggggag aagagaagag   900 ttcgacgtgc tggacaagcg agagggcaga gatcctgaga tgggcggcaa gcccagacgg   960
aagaatcctc aagagggcct gtttaatgag ctgcagaaag acaagatggc cgaggccttc  1020
agcgagatcg aatgaaggg cgagcgcaga gaggcaagg acacgatgg actgttccag  1080 ggcctgagca ccgccaccaa ggatacccttt gatgccctgc acatgcaggc cctgcctcca  1140
agatcaggct ctggttctgg cagcggcagc atggtgtcta aaggcgagga actgttcacc  1200
ggcgtggtgc ccattctggt ggaactggac ggggatgtga acggccacaa gtttagcgtt  1260
agcggcgaag gcgaagggga tgccacatac ggaaagctga ccctgaagtt catctgcacc  1320
accggcaagc tgcctgtgcc ttggcctaca ctggtcacca cactgacata cggcgtgcag  1380
tgctttagca gataccccga ccatatgaag cagcacgact tcttcaagtc cgccatgcct  1440
gagggctacg tgcaagagcg gaccatcttc tttaaggacg acggcaacta caagaccagg  1500
gccgaagtga agtttgaggg cgacaccctg gtcaaccgga tcgagctgaa gggcatcgac  1560
ttcaaagagg atggcaacat cctgggccac aagctcgagt acaactacaa cagccacaac  1620
gtgtacatca tggccgacaa gcagaagaac ggcatcaagg ccaacttcaa gatccggcac  1680
aacatcgagg acggcagcgt tcagctggcc gatcactacc agcagaacac ccctatcgga  1740
gatggccctg tgctgctccc cgacaatcac tacctgagca cacagagcgc cctgagcaag  1800
gaccccaacg agaagaggga tcacatggtg ctgctggaat ttgtgaccgc cgcaggcatc  1860
accctcggca tggacgaact gtacaaa                                      1887
```

<210> SEQ ID NO 165
<211> LENGTH: 629
<212> TYPE: PRT
<213> ORGANISM: Artificial sequence
<220> FEATURE:
<223> OTHER INFORMATION: Synthetic peptide NKG2D.YA_CD8hingeTM_4-
     1BBtraf2_CD3itam_EGFP complete chimeric antigen receptor

<400> SEQUENCE: 165

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110
```

```
Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
                180                 185                 190

Thr Arg Gly Leu Asp Phe Ala Cys Asp Ile Tyr Ile Trp Ala Pro Leu
            195                 200                 205

Ala Gly Thr Cys Gly Val Leu Leu Leu Ser Leu Val Ile Thr Leu Tyr
        210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Ala Ala Gly Cys Ser
                245                 250                 255

Cys Arg Phe Pro Glu Ala Ala Gly Gly Cys Glu Leu Arg Val Lys
                260                 265                 270

Phe Ser Arg Ser Ala Asp Ala Pro Ala Tyr Lys Gln Gly Gln Asn Gln
            275                 280                 285

Leu Phe Asn Glu Leu Asn Leu Gly Arg Arg Glu Glu Phe Asp Val Leu
        290                 295                 300

Asp Lys Arg Arg Gly Arg Asp Pro Glu Met Gly Gly Lys Pro Arg Arg
305                 310                 315                 320

Lys Asn Pro Gln Glu Gly Leu Phe Asn Glu Leu Gln Lys Asp Lys Met
                325                 330                 335

Ala Glu Ala Phe Ser Glu Ile Gly Met Lys Gly Glu Arg Arg Arg Gly
            340                 345                 350

Lys Gly His Asp Gly Leu Phe Gln Gly Leu Ser Thr Ala Thr Lys Asp
        355                 360                 365

Thr Phe Asp Ala Leu His Met Gln Ala Leu Pro Pro Arg Ser Gly Ser
    370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
                405                 410                 415

Lys Phe Ser Val Ser Gly Glu Gly Glu Gly Asp Ala Thr Tyr Gly Lys
                420                 425                 430

Leu Thr Leu Lys Phe Ile Cys Thr Thr Gly Lys Leu Pro Val Pro Trp
            435                 440                 445

Pro Thr Leu Val Thr Thr Leu Thr Tyr Gly Val Gln Cys Phe Ser Arg
    450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
        515                 520                 525
```

Gly His Lys Leu Glu Tyr Asn Tyr Asn Ser His Asn Val Tyr Ile Met
         530                 535                 540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
                565                 570                 575

Thr Pro Ile Gly Asp Gly Pro Val Leu Leu Pro Asp Asn His Tyr Leu
            580                 585                 590

Ser Thr Gln Ser Ala Leu Ser Lys Asp Pro Asn Glu Lys Arg Asp His
                595                 600                 605

Met Val Leu Leu Glu Phe Val Thr Ala Ala Gly Ile Thr Leu Gly Met
610                 615                 620

Asp Glu Leu Tyr Lys
625

<210> SEQ ID NO 166
<211> LENGTH: 1887
<212> TYPE: DNA
<213> ORGANISM: Artificial sequence
<220> FEATURE:
<223> OTHER INFORMATION: Synthetic polynucleotide, encoding
      NKG2D.YA_CD8hingeTM_4-1BBtraf2_CD3itam_EGFP complete chimeric
      antigen receptor

<400> SEQUENCE: 166
atggcattgc tgttacagc tctgctgctg ccctggctc tgcttctgca tgctgccaga      60
cctctgttca atcaagaggt gcagatccct ctgaccgaga gctactgtgg ccctgtcct   120 aagaactgga tctgctacaa gaacaactgc taccagttct tcgacgagag caagaattgg   180
tacgagagcc aggccagctg catgagccag aatgccagcc tgctgaaggt gtacagcaaa   240
gaggaccagg atctgctgaa gctggtcaag agcgcccact ggatgggact cgtgcacatc   300
cctacaaacg gcagctggca gtgggaggac ggctctatcc tgtctcctaa cctgctgacc   360
atcatcgaga tgcagaaggg cgactgcgcc ctgtacgcca gcagctttaa gggctacatc   420
gagaactgca gcaccctaa cacctacatc tgtatgcagc ggaccgtgac caccacacca   480
gctcctagac ctccaactcc tgctcctaca atcgccagc agcctctgtc tctgaggcca   540
gaagcttgta acctgctgc aggcggagcc gtgcatacaa aggactgga tttcgcctgc   600 gacatctaca tctgggcccc tctggctgga acatgtggcg tgctgctgct gagcctggtc   660
atcaccctgt actgcagcct gaagcgggc agaaagaagc tgctgtacat ctttaagcag   720
cccttcatgc ggcccgtgca gaccacacaa gccgctgcag ctgctcctg cagattcccc   780 gaggctgccg caggcggctg cgagctgaga gtgaagttca gccgttctgc cgacgctccc   840
gcctataagc gggacagaa ccagctgttc aacgagctga acctggggag aagagaagag   900
ttcgacgtgc tggacaagcg agaggcaga gatcctgaga tgggcggcaa gcccagacgg   960
aagaatcctc aagaggcct gtttaatgag ctgcagaaag acaagatggc cgaggccttc  1020
agcgagatcg aatgaagggc cgagcgcaga agaggcaagg acacgatgg actgttccag  1080 ggcctgagca ccgccaccaa ggataccttt gatgccctgc acatgcaggc cctgcctcca  1140
agatcaggct ctggttctgg cagcggcagc atggtgtcta aaggcgagga actgttcacc  1200
ggcgtggtgc ccattctggt ggaactggac gggatgtgta acggccacaa gtttagcgtt  1260
agcggcgaag gcgaagggga tgccacatac ggaaagctga ccctgaagtt catctgcacc  1320
accggcaagc tgcctgtgcc ttggcctaca ctggtcacca cactgacata cggcgtgcag  1380

```
tgctttagca gatacccega ccatatgaag cagcacgact tcttcaagtc cgccatgcct    1440
gagggctacg tgcaagagcg gaccatcttc tttaaggacg acggcaacta caagaccagg    1500
gccgaagtga agtttgaggg cgacaccctg gtcaaccgga tcgagctgaa gggcatcgac    1560
ttcaaagagg atggcaacat cctgggccac aagctcgagt acaactacaa cagccacaac    1620
gtgtacatca tggccgacaa gcagaagaac ggcatcaagg ccaacttcaa gatccggcac    1680
aacatcgagg acggcagcgt tcagctggcc gatcactacc agcagaacac ccctatcgga    1740
gatggccctg tgctgctccc cgacaatcac tacctgagca cacagagcgc cctgagcaag    1800
gaccccaacg agaagaggga tcacatggtg ctgctggaat ttgtgaccgc cgcaggcatc    1860
accctcggca tggacgaact gtacaaa                                        1887
```

<210> SEQ ID NO 167
<211> LENGTH: 517
<212> TYPE: PRT
<213> ORGANISM: Artificial sequence
<220> FEATURE:
<223> OTHER INFORMATION: Synthetic peptide NKG2D.YA_CD8hingeTM_4-
      1BB_EGFP complete chimeric antigen receptor

<400> SEQUENCE: 167

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu Ser Gly Ser
            260                 265                 270
```

Gly Ser Gly Ser Gly Ser Met Val Ser Lys Gly Glu Glu Leu Phe Thr
            275                 280                 285
Gly Val Val Pro Ile Leu Val Glu Leu Asp Gly Asp Val Asn Gly His
        290                 295                 300
Lys Phe Ser Val Ser Gly Glu Gly Glu Gly Asp Ala Thr Tyr Gly Lys
305                 310                 315                 320
Leu Thr Leu Lys Phe Ile Cys Thr Thr Gly Lys Leu Pro Val Pro Trp
                325                 330                 335
Pro Thr Leu Val Thr Thr Leu Thr Tyr Gly Val Gln Cys Phe Ser Arg
            340                 345                 350
Tyr Pro Asp His Met Lys Gln His Asp Phe Phe Lys Ser Ala Met Pro
        355                 360                 365
Glu Gly Tyr Val Gln Glu Arg Thr Ile Phe Phe Lys Asp Asp Gly Asn
    370                 375                 380
Tyr Lys Thr Arg Ala Glu Val Lys Phe Glu Gly Asp Thr Leu Val Asn
385                 390                 395                 400
Arg Ile Glu Leu Lys Gly Ile Asp Phe Lys Glu Asp Gly Asn Ile Leu
                405                 410                 415
Gly His Lys Leu Glu Tyr Asn Tyr Asn Ser His Asn Val Tyr Ile Met
            420                 425                 430
Ala Asp Lys Gln Lys Asn Gly Ile Lys Ala Asn Phe Lys Ile Arg His
        435                 440                 445
Asn Ile Glu Asp Gly Ser Val Gln Leu Ala Asp His Tyr Gln Gln Asn
    450                 455                 460
Thr Pro Ile Gly Asp Gly Pro Val Leu Leu Pro Asp Asn His Tyr Leu
465                 470                 475                 480
Ser Thr Gln Ser Ala Leu Ser Lys Asp Pro Asn Glu Lys Arg Asp His
                485                 490                 495
Met Val Leu Leu Glu Phe Val Thr Ala Ala Gly Ile Thr Leu Gly Met
            500                 505                 510
Asp Glu Leu Tyr Lys
        515

<210> SEQ ID NO 168
<211> LENGTH: 1551
<212> TYPE: DNA
<213> ORGANISM: Artificial sequence
<220> FEATURE:
<223> OTHER INFORMATION: Synthetic polynucleotide, encoding
      NKG2D.YA_CD8hingeTM_4-1BB_EGFP complete chimeric antigen receptor

<400> SEQUENCE: 168
atggcattgc ctgttacagc tctgctgctg cccctggctc tgcttctgca tgctgccaga      60
cctctgttca atcaagaggt gcagatccct ctgaccgaga gctactgtgg ccctgtcct     120 aagaactgga tctgctacaa gaacaactgc taccagttct tcgacgagag caagaattgg     180
tacgagagcc aggccagctg catgagccag aatgccagcc tgctgaaggt gtacagcaaa     240
gaggaccagg atctgctgaa gctggtcaag agcgcccact ggatgggact cgtgcacatc     300
cctacaaacg gcagctggca gtgggaggac ggctctatcc tgtctcctaa cctgctgacc     360
atcatcgaga tgcagaaggg cgactgcgcc ctgtacgcca gcagctttaa gggctacatc     420
gagaactgca gcacccctaa cacctacatc tgtatgcagc ggaccgtgac caccacacca     480
gctcctagac ctccaactcc tgctcctaca atcgccagcc agcctctgtc tctgaggcca     540
gaagcttgta gacctgctgc aggcggagcc gtgcatacaa gaggactgga tttcgcctgc     600

-continued

```
gacatctaca tctgggcccc tctggctgga acatgtggcg tgctgctgct gagcctggtc      660
atcaccctgt actgcagcct gaagcggggc agaaagaagc tgctgtacat ctttaagcag      720
cccttcatgc ggcccgtgca gaccacacaa gaggaagatg ctgctcctg cagattcccc       780
gaggaagaag aaggcggctg cgagctgtca ggctctggtt ctggcagcgg cagcatggtg      840
tctaaaggcg aggaactgtt caccggcgtg gtgcccattc tggtggaact ggacggggat      900
gtgaacggcc acaagtttag cgttagcggc gaaggcgaag gggatgccac atacggaaag      960
ctgacccctga agttcatctg caccaccggc aagctgcctg tgccttggcc tacactggtc     1020
accacactga catacggcgt gcagtgcttt agcagatacc ccgaccatat gaagcagcac      1080
gacttcttca gtccgccat gcctgagggc tacgtgcaag agcggaccat cttctttaag       1140
gacgacggca actacaagac cagggccgaa gtgaagtttg agggcgacac cctggtcaac      1200
cggatcgagc tgaagggcat cgacttcaaa gaggatggca acatcctggg ccacaagctc      1260
gagtacaact acaacagcca caacgtgtac atcatggccg acaagcagaa gaacggcatc      1320
aaggccaact tcaagatccg cacaacatc gaggacggca cgttcagct ggccgatcac        1380
taccagcaga acacccctat cggagatggc cctgtgctgc tccccgacaa tcactacctg     1440
agcacacaga gcgccctgag caaggacccc aacgagaaga gggatcacat ggtgctgctg      1500
gaatttgtga ccgccgcagg catcaccctc ggcatggacg aactgtacaa a              1551
```

<210> SEQ ID NO 169
<211> LENGTH: 269
<212> TYPE: PRT
<213> ORGANISM: Artificial sequence
<220> FEATURE:
<223> OTHER INFORMATION: Synthetic peptide NKG2D.YA_CD8hingeTM_4-1BB
     complete chimeric antigen receptor

<400> SEQUENCE: 169

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190
```

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
        210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu
                260                 265

<210> SEQ ID NO 170
<211> LENGTH: 807
<212> TYPE: DNA
<213> ORGANISM: Artificial sequence
<220> FEATURE:
<223> OTHER INFORMATION: Synthetic polynucleotide, encoding
      NKG2D.YA_CD8hingeTM_4-1BB complete chimeric antigen receptor

<400> SEQUENCE: 170
atggcattgc ctgttacagc tctgctgctg cccctggctc tgcttctgca tgctgccaga      60
cctctgttca atcaagaggt gcagatccct ctgaccgaga gctactgtgg ccctgtcct     120 aagaactgga tctgctacaa gaacaactgc taccagttct tcgacgagag caagaattgg     180
tacgagagcc aggccagctg catgagccag aatgccagcc tgctgaaggt gtacagcaaa     240
gaggaccagg atctgctgaa gctggtcaag agcgcccact ggatgggact cgtgcacatc     300
cctacaaacg gcagctggca gtgggaggac ggctctatcc tgtctcctaa cctgctgacc     360
atcatcgaga tgcagaaggg cgactgcgcc ctgtacgcca gcagctttaa gggctacatc     420
gagaactgca gcacccctaa cacctacatc tgtatgcagc ggaccgtgac caccacacca     480
gctcctagac tccaactcc tgctcctaca atcgccagcc agcctctgtc tctgaggcca     540
gaagcttgta gacctgctgc aggcggagcc gtgcatacaa gaggactgga tttcgcctgc     600
gacatctaca tctgggcccc tctggctgga acatgtggcg tgctgctgct gagcctggtc     660
atcaccctgt actgcagcct gaagcggggc agaaagaagc tgctgtacat ctttaagcag     720
cccttcatgc ggcccgtgca gaccacacaa gaggaagatg gctgctcctg cagattcccc     780
gaggaagaag aaggcggctg cgagctg                                         807

<210> SEQ ID NO 171
<211> LENGTH: 736
<212> TYPE: PRT
<213> ORGANISM: Artificial sequence
<220> FEATURE:
<223> OTHER INFORMATION: Synthetic peptide CD19scFv_CD8hingeTM_4-
      1BB_CD3zeta_EGFP complete chimeric antigen receptor

<400> SEQUENCE: 171

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro

```
             65                  70                  75                  80
        Ser Arg Phe Ser Gly Ser Gly Ser Gly Thr Asp Tyr Ser Leu Thr Ile
                         85                  90                  95

Ser Asn Leu Glu Gln Glu Asp Ile Ala Thr Tyr Phe Cys Gln Gln Gly
                        100                 105                 110

Asn Thr Leu Pro Tyr Thr Phe Gly Gly Gly Thr Lys Leu Glu Ile Thr
                        115                 120                 125

Gly Gly Gly Gly Ser Gly Gly Gly Ser Gly Gly Gly Ser Glu
                        130                 135                 140

Val Lys Leu Gln Glu Ser Gly Pro Gly Leu Val Ala Pro Ser Gln Ser
        145                 150                 155                 160

Leu Ser Val Thr Cys Thr Val Ser Gly Val Ser Leu Pro Asp Tyr Gly
                        165                 170                 175

Val Ser Trp Ile Arg Gln Pro Pro Arg Lys Gly Leu Glu Trp Leu Gly
                        180                 185                 190

Val Ile Trp Gly Ser Glu Thr Thr Tyr Tyr Asn Ser Ala Leu Lys Ser
                        195                 200                 205

Arg Leu Thr Ile Ile Lys Asp Asn Ser Lys Ser Gln Val Phe Leu Lys
        210                 215                 220

Met Asn Ser Leu Gln Thr Asp Asp Thr Ala Ile Tyr Tyr Cys Ala Lys
        225                 230                 235                 240

His Tyr Tyr Tyr Gly Gly Ser Tyr Ala Met Asp Tyr Trp Gly Gln Gly
                        245                 250                 255

Thr Ser Val Thr Val Ser Ser Thr Thr Thr Pro Ala Pro Arg Pro Pro
                        260                 265                 270

Thr Pro Ala Pro Thr Ile Ala Ser Gln Pro Leu Ser Leu Arg Pro Glu
                        275                 280                 285

Ala Cys Arg Pro Ala Ala Gly Gly Ala Val His Thr Arg Gly Leu Asp
                        290                 295                 300

Phe Ala Cys Asp Ile Tyr Ile Trp Ala Pro Leu Ala Gly Thr Cys Gly
        305                 310                 315                 320

Val Leu Leu Leu Ser Leu Val Ile Thr Leu Tyr Cys Ser Leu Lys Arg
                        325                 330                 335

Gly Arg Lys Lys Leu Leu Tyr Ile Phe Lys Gln Pro Phe Met Arg Pro
                        340                 345                 350

Val Gln Thr Thr Gln Glu Glu Asp Gly Cys Ser Cys Arg Phe Pro Glu
                        355                 360                 365

Glu Glu Glu Gly Gly Cys Glu Leu Arg Val Lys Phe Ser Arg Ser Ala
                        370                 375                 380

Asp Ala Pro Ala Tyr Lys Gln Gly Gln Asn Gln Leu Tyr Asn Glu Leu
        385                 390                 395                 400

Asn Leu Gly Arg Arg Glu Glu Tyr Asp Val Leu Asp Lys Arg Arg Gly
                        405                 410                 415

Arg Asp Pro Glu Met Gly Gly Lys Pro Arg Arg Lys Asn Pro Gln Glu
                        420                 425                 430

Gly Leu Tyr Asn Glu Leu Gln Lys Asp Lys Met Ala Glu Ala Tyr Ser
                        435                 440                 445

Glu Ile Gly Met Lys Gly Glu Arg Arg Arg Gly Lys Gly His Asp Gly
                        450                 455                 460

Leu Tyr Gln Gly Leu Ser Thr Ala Thr Lys Asp Thr Tyr Asp Ala Leu
        465                 470                 475                 480

His Met Gln Ala Leu Pro Pro Arg Ser Gly Ser Gly Ser Gly Ser Gly
                        485                 490                 495
```

```
Ser Met Val Ser Lys Gly Glu Glu Leu Phe Thr Gly Val Val Pro Ile
            500                 505                 510

Leu Val Glu Leu Asp Gly Asp Val Asn Gly His Lys Phe Ser Val Ser
        515                 520                 525

Gly Glu Gly Glu Gly Asp Ala Thr Tyr Gly Lys Leu Thr Leu Lys Phe
    530                 535                 540

Ile Cys Thr Thr Gly Lys Leu Pro Val Pro Trp Pro Thr Leu Val Thr
545                 550                 555                 560

Thr Leu Thr Tyr Gly Val Gln Cys Phe Ser Arg Tyr Pro Asp His Met
            565                 570                 575

Lys Gln His Asp Phe Phe Lys Ser Ala Met Pro Glu Gly Tyr Val Gln
        580                 585                 590

Glu Arg Thr Ile Phe Phe Lys Asp Asp Gly Asn Tyr Lys Thr Arg Ala
    595                 600                 605

Glu Val Lys Phe Glu Gly Asp Thr Leu Val Asn Arg Ile Glu Leu Lys
610                 615                 620

Gly Ile Asp Phe Lys Glu Asp Gly Asn Ile Leu Gly His Lys Leu Glu
625                 630                 635                 640

Tyr Asn Tyr Asn Ser His Asn Val Tyr Ile Met Ala Asp Lys Gln Lys
            645                 650                 655

Asn Gly Ile Lys Ala Asn Phe Lys Ile Arg His Asn Ile Glu Asp Gly
        660                 665                 670

Ser Val Gln Leu Ala Asp His Tyr Gln Gln Asn Thr Pro Ile Gly Asp
    675                 680                 685

Gly Pro Val Leu Leu Pro Asp Asn His Tyr Leu Ser Thr Gln Ser Ala
690                 695                 700

Leu Ser Lys Asp Pro Asn Glu Lys Arg Asp His Met Val Leu Leu Glu
705                 710                 715                 720

Phe Val Thr Ala Ala Gly Ile Thr Leu Gly Met Asp Glu Leu Tyr Lys
            725                 730                 735

<210> SEQ ID NO 172
<211> LENGTH: 2208
<212> TYPE: DNA
<213> ORGANISM: Artificial sequence
<220> FEATURE:
<223> OTHER INFORMATION: Synthetic polynucleotide, encoding
      CD19scFv_CD8hingeTM_4-1BB_CD3zeta_EGFP complete chimeric antigen
      receptor

<400> SEQUENCE: 172
atggcattgc tgttacagc tctgctgctg cccctggctc tgcttctgca tgctgccaga      60
cctgacatcc agatgaccca gacaaccagc agcctgtctg ccagcctggg cgatagagtg     120
accatcagct gtagagccag ccaggacatc agcaagtacc tgaactggta tcagcagaaa    180
cccgacggca ccgtgaagct gctgatctac cacaccagca gactgcacag cggcgtgcca    240
agcagatttt ctggcagcgg ctctggcacc gactacagcc tgacaatcag caacctggaa    300
caagaggata tcgctaccta cttctgccag caaggcaaca ccctgcctta cacctttggc    360
ggaggcacca gctggaaat cacaggcggc ggaggaagcg gaggcggagg atctggtggt    420
ggtggatctg aagtgaaact gcaagagtct ggccctggcc tggtggcccc atctcaatct    480
ctgagcgtga cctgtaccgt cagcggagtg tccctgcctg attatggcgt gtcctggatc    540
cggcagcctc ctagaaaagg cctggaatgg ctggcgtga tctggggcag cgagacaacc    600
tactacaaca gcgccctgaa gtcccggctg accatcatca ggacaactc caagagccag    660
```

-continued

```
gtgttcctga agatgaacag cctgcagacc gacgacaccg ccatctacta ttgcgccaag    720
cactactact acggcggcag ctacgccatg gattattggg gccagggcac cagcgtgacc    780
gtttcttcta ccaccacacc agctcctaga cctccaactc ctgctcctac aatcgccagc    840
cagcctctgt ctctgaggcc agaagcttgt agacctgctg caggcggagc cgtgcataca    900
agaggactgg atttcgcctg cgacatctac atctgggccc tctggctgga acatgtggc    960 gtgctgctgc tgagcctggt catcaccctg tactgcagcc tgaagcgggg cagaaagaag    1020
ctgctgtaca tctttaagca gcccttcatg cggcccgtgc agaccacaca gaggaagat   1080 ggctgctcct gcagattccc cgaggaagaa gaaggcggct cgagctgag agtgaagttc    1140 agccgttctg ccgacgctcc cgcctataag cagggacaga accagctgta caacgagctg    1200
aacctgggga agagaagaa gtacgacgtg ctggacaagc ggagaggcag agatcctgag    1260
atgggcggca agcccagacg gaagaatcct caagagggcc tgtataatga gctgcagaaa    1320
gacaagatgg ccgaggccta cagcgagatc ggaatgaagg gcgagcgcag aagaggcaag    1380
ggacacgatg gactgtacca gggcctgagc accgccacca aggataccta tgatgccctg    1440
cacatgcagg ccctgcctcc aagatcaggc tctggttctg gcagcggcag catggtgtct    1500
aaaggcgagg aactgttcac cggcgtggtg cccattctgg tggaactgga cggggatgtg    1560 aacgccaca agtttagcgt tagcggcgaa ggcgaagggg atgccacata cggaaagctg    1620
accctgaagt tcatctgcac caccggcaag ctgcctgtgc cttggcctac actggtcacc    1680
acactgacat acggcgtgca gtgctttagc agataccccg accatatgaa gcagcacgac    1740
ttcttcaagt ccgccatgcc tgagggctac gtgcaagagc ggaccatctt ctttaaggac    1800
gacggcaact acaagaccag gccgaagtg aagtttgagg cgacaccct ggtcaaccgg    1860 atcgagctga agggcatcga cttcaaagag gatggcaaca tcctgggcca caagctcgag    1920
tacaactaca cagccacaa cgtgtacatc atggccgaca gcagaagaa cggcatcaag    1980 gccaacttca agatccggca caacatcgag gacggcagcg ttcagctggc cgatcactac    2040
cagcagaaca cccctatcgg agatggcccc gtgctgctcc ccgacaatca ctacctgagc    2100
acacagagcg ccctgagcaa ggaccccaac gagaagaggg atcacatggt gctgctggaa    2160
tttgtgaccg ccgcaggcat cacccttggc atggacgaac tgtacaaa            2208
```

<210> SEQ ID NO 173
<211> LENGTH: 1115
<212> TYPE: PRT
<213> ORGANISM: Artificial sequence
<220> FEATURE:
<223> OTHER INFORMATION: Synthetic peptide
    CD19scFv_CD8hingeTM_4-1BB_CD3zeta_EGFP-T2A-NKG2D.YA_CD8hingeTM

<400> SEQUENCE: 173

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80
```

```
Ser Arg Phe Ser Gly Ser Gly Ser Gly Thr Asp Tyr Ser Leu Thr Ile
                85              90                  95
Ser Asn Leu Glu Gln Glu Asp Ile Ala Thr Tyr Phe Cys Gln Gln Gly
            100                 105                 110
Asn Thr Leu Pro Tyr Thr Phe Gly Gly Gly Thr Lys Leu Glu Ile Thr
            115                 120                 125
Gly Gly Gly Gly Ser Gly Gly Gly Ser Gly Gly Gly Ser Glu
130             135                 140
Val Lys Leu Gln Glu Ser Gly Pro Gly Leu Val Ala Pro Ser Gln Ser
145             150                 155                 160
Leu Ser Val Thr Cys Thr Val Ser Gly Val Ser Leu Pro Asp Tyr Gly
                165                 170                 175
Val Ser Trp Ile Arg Gln Pro Pro Arg Lys Gly Leu Glu Trp Leu Gly
                180                 185                 190
Val Ile Trp Gly Ser Glu Thr Thr Tyr Tyr Asn Ser Ala Leu Lys Ser
                195                 200                 205
Arg Leu Thr Ile Ile Lys Asp Asn Ser Lys Ser Gln Val Phe Leu Lys
        210                 215                 220
Met Asn Ser Leu Gln Thr Asp Asp Thr Ala Ile Tyr Tyr Cys Ala Lys
225             230                 235                 240
His Tyr Tyr Tyr Gly Gly Ser Tyr Ala Met Asp Tyr Trp Gly Gln Gly
                245                 250                 255
Thr Ser Val Thr Val Ser Ser Thr Thr Thr Pro Ala Pro Arg Pro Pro
                260                 265                 270
Thr Pro Ala Pro Thr Ile Ala Ser Gln Pro Leu Ser Leu Arg Pro Glu
            275                 280                 285
Ala Cys Arg Pro Ala Ala Gly Gly Ala Val His Thr Arg Gly Leu Asp
            290                 295                 300
Phe Ala Cys Asp Ile Tyr Ile Trp Ala Pro Leu Ala Gly Thr Cys Gly
305             310                 315                 320
Val Leu Leu Leu Ser Leu Val Ile Thr Leu Tyr Cys Ser Leu Lys Arg
                325                 330                 335
Gly Arg Lys Lys Leu Leu Tyr Ile Phe Lys Gln Pro Phe Met Arg Pro
            340                 345                 350
Val Gln Thr Thr Gln Glu Glu Asp Gly Cys Ser Cys Arg Phe Pro Glu
            355                 360                 365
Glu Glu Glu Gly Gly Cys Glu Leu Arg Val Lys Phe Ser Arg Ser Ala
            370                 375                 380
Asp Ala Pro Ala Tyr Lys Gln Gly Gln Asn Gln Leu Tyr Asn Glu Leu
385             390                 395                 400
Asn Leu Gly Arg Arg Glu Glu Tyr Asp Val Leu Asp Lys Arg Arg Gly
            405                 410                 415
Arg Asp Pro Glu Met Gly Gly Lys Pro Arg Arg Lys Asn Pro Gln Glu
            420                 425                 430
Gly Leu Tyr Asn Glu Leu Gln Lys Asp Lys Met Ala Glu Ala Tyr Ser
            435                 440                 445
Glu Ile Gly Met Lys Gly Glu Arg Arg Arg Gly Lys Gly His Asp Gly
            450                 455                 460
Leu Tyr Gln Gly Leu Ser Thr Ala Thr Lys Asp Thr Tyr Asp Ala Leu
465             470                 475                 480
His Met Gln Ala Leu Pro Pro Arg Ser Gly Ser Gly Ser Gly Ser Gly
            485                 490                 495
Ser Met Val Ser Lys Gly Glu Glu Leu Phe Thr Gly Val Val Pro Ile
```

```
                500             505             510
Leu Val Glu Leu Asp Gly Asp Val Asn Gly His Lys Phe Ser Val Ser
            515                 520             525
Gly Glu Gly Glu Gly Asp Ala Thr Tyr Gly Lys Leu Thr Leu Lys Phe
            530                 535             540
Ile Cys Thr Thr Gly Lys Leu Pro Val Pro Trp Pro Thr Leu Val Thr
545                 550             555                 560
Thr Leu Thr Tyr Gly Val Gln Cys Phe Ser Arg Tyr Pro Asp His Met
                565             570             575
Lys Gln His Asp Phe Phe Lys Ser Ala Met Pro Glu Gly Tyr Val Gln
            580                 585             590
Glu Arg Thr Ile Phe Phe Lys Asp Asp Gly Asn Tyr Lys Thr Arg Ala
            595                 600             605
Glu Val Lys Phe Glu Gly Asp Thr Leu Val Asn Arg Ile Glu Leu Lys
            610                 615             620
Gly Ile Asp Phe Lys Glu Asp Gly Asn Ile Leu Gly His Lys Leu Glu
625                 630             635                 640
Tyr Asn Tyr Asn Ser His Asn Val Tyr Ile Met Ala Asp Lys Gln Lys
                645             650             655
Asn Gly Ile Lys Ala Asn Phe Lys Ile Arg His Asn Ile Glu Asp Gly
            660                 665             670
Ser Val Gln Leu Ala Asp His Tyr Gln Gln Asn Thr Pro Ile Gly Asp
            675                 680             685
Gly Pro Val Leu Leu Pro Asp Asn His Tyr Leu Ser Thr Gln Ser Ala
            690                 695             700
Leu Ser Lys Asp Pro Asn Glu Lys Arg Asp His Met Val Leu Leu Glu
705                 710             715                 720
Phe Val Thr Ala Ala Gly Ile Thr Leu Gly Met Asp Glu Leu Tyr Lys
                725             730             735
Leu Glu Gly Gly Gly Glu Gly Arg Gly Ser Leu Leu Thr Cys Gly Asp
            740                 745             750
Val Glu Glu Asn Pro Gly Pro Arg Met Leu Leu Val Thr Ser Leu
            755                 760             765
Leu Leu Cys Glu Leu Pro His Pro Ala Phe Leu Leu Ile Pro Leu Phe
            770                 775             780
Asn Gln Glu Val Gln Ile Pro Leu Thr Glu Ser Tyr Cys Gly Pro Cys
785                 790             795                 800
Pro Lys Asn Trp Ile Cys Tyr Lys Asn Asn Cys Tyr Gln Phe Phe Asp
            805                 810             815
Glu Ser Lys Asn Trp Tyr Glu Ser Gln Ala Ser Cys Met Ser Gln Asn
            820                 825             830
Ala Ser Leu Leu Lys Val Tyr Ser Lys Glu Asp Gln Asp Leu Leu Lys
            835                 840             845
Leu Val Lys Ser Ala His Trp Met Gly Leu Val His Ile Pro Thr Asn
            850                 855             860
Gly Ser Trp Gln Trp Glu Asp Gly Ser Ile Leu Ser Pro Asn Leu Leu
865                 870             875                 880
Thr Ile Ile Glu Met Gln Lys Gly Asp Cys Ala Leu Tyr Ala Ser Ser
                885             890             895
Phe Lys Gly Tyr Ile Glu Asn Cys Ser Thr Pro Asn Thr Tyr Ile Cys
            900                 905             910
Met Gln Arg Thr Val Gln Ile Pro Leu Thr Glu Ser Tyr Cys Gly Pro
            915                 920             925
```

```
Cys Pro Lys Asn Trp Ile Cys Tyr Lys Asn Asn Cys Tyr Gln Phe Phe
        930                 935                 940

Asp Glu Ser Lys Asn Trp Tyr Glu Ser Gln Ala Ser Cys Met Ser Gln
945                 950                 955                 960

Asn Ala Ser Leu Leu Lys Val Tyr Ser Lys Glu Asp Gln Asp Leu Leu
                965                 970                 975

Lys Leu Val Lys Ser Ala His Trp Met Gly Leu Val His Ile Pro Thr
            980                 985                 990

Asn Gly Ser Trp Gln Trp Glu Asp Gly Ser Ile Leu Ser Pro Asn Leu
        995                 1000                1005

Leu Thr Ile Ile Glu Met Gln Lys Gly Asp Cys Ala Leu Tyr Ala
    1010                1015                1020

Ser Ser Phe Lys Gly Tyr Ile Glu Asn Cys Ser Thr Pro Asn Thr
    1025                1030                1035

Tyr Ile Cys Met Gln Arg Thr Val Thr Thr Pro Ala Pro Arg
    1040                1045                1050

Pro Pro Thr Pro Ala Pro Thr Ile Ala Ser Gln Pro Leu Ser Leu
    1055                1060                1065

Arg Pro Glu Ala Cys Arg Pro Ala Ala Gly Gly Ala Val His Thr
    1070                1075                1080

Arg Gly Leu Asp Phe Ala Cys Asp Ile Tyr Ile Trp Ala Pro Leu
    1085                1090                1095

Ala Gly Thr Cys Gly Val Leu Leu Leu Ser Leu Val Ile Thr Leu
    1100                1105                1110

Tyr Cys
    1115
```

```
<210> SEQ ID NO 174
<211> LENGTH: 3345
<212> TYPE: DNA
<213> ORGANISM: Artificial sequence
<220> FEATURE:
<223> OTHER INFORMATION: Synthetic polynucleotide, encoding
      CD19scFv_CD8hingeTM_4-1BB_CD3zeta_EGFP-T2A-NKG2D.YA_CD8hingeTM

<400> SEQUENCE: 174
atggcattgc ctgttacagc tctgctgctg cccctggctc tgcttctgca tgctgccaga      60
cctgacatcc agatgaccca gacaaccagc agcctgtctg ccagcctggg cgatagagtg     120
accatcagct gtagagccag ccaggacatc agcaagtacc tgaactggta tcagcagaaa     180
cccgacggca ccgtgaagct gctgatctac cacaccagca gactgcacag cggcgtgcca     240
agcagatttt ctggcagcgg ctctggcacc gactacagcc tgacaatcag caacctggaa     300
caagaggata tcgctaccta cttctgccag caagcaaca cctgcctta cacctttggc      360
ggaggcacca agctggaaat cacaggcggc ggaggaagcg aggcggagg atctggtggt      420
ggtggatctg aagtgaaact gcaagagtct ggccctggcc tggtggcccc atctcaatct     480
ctgagcgtga cctgtaccgt cagcggagtg tccctgcctg attatggcgt gtcctggatc     540
cggcagcctc ctagaaaagg cctggaatgg ctgggcgtga tctggggcag cgagacaacc     600
tactacaaca gcgccctgaa gtcccggctg accatcatca ggacaactc caagagccag      660
gtgttcctga agatgaacag cctgcagacc gacgacaccg ccatctacta ttgcgccaag     720
cactactact acggcggcag ctacgccatg gattattggg gccagggcac cagcgtgacc     780
gtttcttcta ccaccacacc agctcctaga cctccaactc tgctcctac aatcgccagc     840
```

```
cagcctctgt ctctgaggcc agaagcttgt agacctgctg caggcggagc cgtgcataca    900
agaggactgg atttcgcctg cgacatctac atctgggccc ctctggctgg aacatgtggc    960
gtgctgctgc tgagcctggt catcaccctg tactgcagcc tgaagcgggg cagaaagaag   1020
ctgctgtaca tctttaagca gcccttcatg cggcccgtgc agaccacaca agaggaagat   1080
ggctgctcct gcagattccc cgaggaagaa gaaggcggct gcgagctgag agtgaagttc   1140
agccgttctg ccgacgctcc cgcctataag cagggacaga accagctgta caacgagctg   1200
aacctgggga agagaagaa gtacgacgtg ctggacaagc ggagaggcag agatcctgag   1260
atgggcggca gcccagacg gaagaatcct caagagggcc tgtataatga gctgcagaaa   1320
gacaagatgg ccgaggccta cagcgagatc ggaatgaagg gcgagcgcag aagaggcaag   1380
ggacacgatg gactgtacca gggcctgagc accgccacca aggataccta tgatgccctg   1440
cacatgcagg ccctgcctcc aagatcaggc tctggttctg gcagcggcag catggtgtct   1500
aaaggcgagg aactgttcac cggcgtggtg cccattctgg tggaactgga cggggatgtg   1560
aacggccaca gtttagcgt tagcggcgaa ggcgaagggg atgccacata cggaaagctg   1620
accctgaagt tcatctgcac caccggcaag ctgcctgtgc cttggcctac actggtcacc   1680
acactgacat acggcgtgca gtgctttagc agataccccg accatatgaa gcagcacgac   1740
ttcttcaagt ccgccatgcc tgagggctac gtgcaagagc ggaccatctt ctttaaggac   1800
gacggcaact acaagaccag ggccgaagtg aagtttgagg gcgacaccct ggtcaaccgg   1860
atcgagctga agggcatcga cttcaaagag gatggcaaca tcctgggcca caagctcgag   1920
tacaactaca cagccacaa cgtgtacatc atggccgaca gcagaagaa cggcatcaag   1980
gccaacttca agatccggca caacatcgag gacggcagcg ttcagctggc cgatcactac   2040
cagcagaaca cccctatcgg agatggcccct gtgctgctcc ccgacaatca ctacctgagc   2100
acacagagcg ccctgagcaa ggaccccaac gagaagaggg atcacatggt gctgctggaa   2160
tttgtgaccg ccgcaggcat caccctcggc atggacgaac tgtacaaact cgagggcggc   2220
ggagagggca gaggaagtct tctaacatgc ggtgacgtgg aggagaatcc cggccctagg   2280
atgcttctcc tggtgacaag ccttctgctc tgtgagttac acacccagc attcctcctg   2340
atcccactgt tcaaccagga ggttcagatt ccgctgaccg aaagctactg tggaccatgt   2400
cccaagaact ggatctgcta caaaacaat tgttatcaat ttttcgacga aagcaagaat   2460
tggtacgaaa gccaggcttc atgcatgagc caaaatgcat ccctgctgaa ggtgtacagc   2520
aaggaggacc aggacctgct gaaacttgtc aaatccgctc actggatggg actggtccat   2580
attcctacaa atggatcctg gcagtgggag gatggctcta tcctgtctcc caatctcctg   2640
actatcatag agatgcagaa gggagattgt gcattgtatg ctagttcatt caagggatac   2700
attgaaaact gctcaacacc taatacctac atatgtatgc agcgcacagt gcagatccct   2760
ctgaccgaga gctactgtgg ccctgtcct aagaactgga tctgctacaa gaacaactgc   2820
taccagttct tcgacgagag caagaattgg tacgagagcc aggccagctg catgagccag   2880
aatgccagcc tgctgaaggt gtacagcaaa gaggaccagg atctgctgaa gctggtcaag   2940
agcgcccact ggatgggact cgtgcacatc cctacaaacg gcagctggca gtgggaggac   3000
ggctctatcc tgtctcctaa cctgctgacc atcatcgaga tgcagaaggg cgactgcgcc   3060
ctgtacgcca gcagctttaa gggctacatc gagaactgca gcaccctaa cacctacatc   3120
tgtatgcagc ggaccgtgac cacgacgcca gcgccgcgac caccaacacc ggcgcccacc   3180
atcgcgtcgc agcccctgtc cctgcgccca gaggcgtgcc ggccagcggc ggggggcgca   3240
```

```
gtgcacacga gggggctgga cttcgcctgt gatatctaca tctgggcgcc cttggccggg    3300
acttgtgggg tccttctcct gtcactggtt atcaccettt actgc                   3345
```

<210> SEQ ID NO 175
<211> LENGTH: 161
<212> TYPE: PRT
<213> ORGANISM: Artificial sequence
<220> FEATURE:
<223> OTHER INFORMATION: Synthetic peptide FLAG_6xHis_mutIL2

<400> SEQUENCE: 175

```
Gly Ser Ser Gly Ser Ser Asp Tyr Lys Asp Asp Asp Lys His His
1               5                   10                  15

His His His His His His Gly Ser Ser Gly Ser Ser Ala Pro Thr Ser
            20                  25                  30

Ser Ser Thr Lys Lys Thr Gln Leu Gln Leu Glu His Leu Leu Leu Asp
        35                  40                  45

Leu Gln Met Ile Leu Asn Gly Ile Asn Asn Tyr Lys Asn Pro Lys Leu
    50                  55                  60

Thr Ala Met Leu Thr Lys Lys Phe Tyr Met Pro Lys Lys Ala Thr Glu
65                  70                  75                  80

Leu Lys His Leu Gln Cys Leu Glu Glu Glu Leu Lys Pro Leu Glu Glu
                85                  90                  95

Val Leu Asn Leu Ala Gln Ser Lys Asn Phe His Leu Arg Pro Arg Asp
            100                 105                 110

Leu Ile Ser Asn Ile Asn Val Ile Val Leu Glu Leu Lys Gly Ser Glu
        115                 120                 125

Thr Thr Phe Met Cys Glu Tyr Ala Asp Glu Thr Ala Thr Ile Val Glu
    130                 135                 140

Phe Leu Asn Arg Trp Ile Thr Phe Ser Gln Ser Ile Ile Ser Thr Leu
145                 150                 155                 160

Thr
```

<210> SEQ ID NO 176
<211> LENGTH: 483
<212> TYPE: DNA
<213> ORGANISM: Artificial sequence
<220> FEATURE:
<223> OTHER INFORMATION: Synthetic polynucleotide, encoding
      FLAG_6xHis_mutIL2

<400> SEQUENCE: 176

```
ggaagtagcg gtagtagtga ttacaaggac gatgacgaca agcaccacca tcatcatcat    60
caccacggta gcagcggcag cagtgccccc acctctagca gcacaaagaa gacccagctg   120
caactggaac acctcctgct ggacctgcag atgatcctga acggcatcaa caactacaag   180
aaccccaagc tgaccgccat gctgaccaaa aagttttaca tgcccaagaa ggccaccgag   240
cttaaacacc tgcaatgcct tgaggaggag ctgaagcccc tggaggaggt actgaacctg   300
gcccagagca agaactttca tctgaggccc agggacctga ttagcaacat caacgtgatc   360
gtgttggagt tgaagggcag cgagaccacg ttcatgtgcg agtacgccga cgagacggcc   420
accatagtgg agtttcttaa caggtggatc accttctcac agtctatcat cagcacccctg   480 acc                                                                  483
```

<210> SEQ ID NO 177
<211> LENGTH: 343

<212> TYPE: PRT
<213> ORGANISM: Artificial sequence
<220> FEATURE:
<223> OTHER INFORMATION: Synthetic peptide ULBP2.R80W_FLAG_6xHis_mutIL2

<400> SEQUENCE: 177

```
Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Met Ser Phe His Tyr Phe Ser Met Gly
145                 150                 155                 160

Asp Cys Ile Gly Trp Leu Glu Asp Phe Leu Met Gly Met Asp Ser Thr
                165                 170                 175

Leu Glu Pro Ser Gly Thr Gly Ser Ser Gly Ser Ser Asp Tyr Lys Asp
            180                 185                 190

Asp Asp Asp Lys His His His His His His Gly Ser Ser Gly
        195                 200                 205

Ser Ser Ala Pro Thr Ser Ser Ser Thr Lys Lys Thr Gln Leu Gln Leu
    210                 215                 220

Glu His Leu Leu Leu Asp Leu Gln Met Ile Leu Asn Gly Ile Asn Asn
225                 230                 235                 240

Tyr Lys Asn Pro Lys Leu Thr Ala Met Leu Thr Lys Lys Phe Tyr Met
                245                 250                 255

Pro Lys Lys Ala Thr Glu Leu Lys His Leu Gln Cys Leu Glu Glu Glu
            260                 265                 270

Leu Lys Pro Leu Glu Glu Val Leu Asn Leu Ala Gln Ser Lys Asn Phe
        275                 280                 285

His Leu Arg Pro Arg Asp Leu Ile Ser Asn Ile Asn Val Ile Val Leu
    290                 295                 300

Glu Leu Lys Gly Ser Glu Thr Thr Phe Met Cys Glu Tyr Ala Asp Glu
305                 310                 315                 320

Thr Ala Thr Ile Val Glu Phe Leu Asn Arg Trp Ile Thr Phe Ser Gln
                325                 330                 335

Ser Ile Ile Ser Thr Leu Thr
            340
```

<210> SEQ ID NO 178
<211> LENGTH: 1029
<212> TYPE: DNA
<213> ORGANISM: Artificial sequence
<220> FEATURE:

-continued

<223> OTHER INFORMATION: Synthetic polynucleotide, encoding
ULBP2.R80W_FLAG_6xHis_mutIL2

<400> SEQUENCE: 178

```
gagcccata gtctgagcta cgacatcaca gttattccca agttcaggcc cggaccgcgc    60
tggtgtgccg tgcaaggaca gtcgacgaa aaaaccttc ttcattacga ttgcggaaat   120
aagactgtaa cgccagtctc tcctttaggt aagaagttaa cgtcactac ggcgtggaag   180
gcacaaaacc ccgtcctgcg cgaggtcgtc gacatcctga ctgaacaatt gtgggacatc   240
cagctcgaga attacactcc aaaggagcct cttaccctgc aggctagaat gtcttgcgag   300
caaaaggcag agggccactc ctccggcagc tggcagttca gtttcgacgg acaaatcttt   360
ctgttattcg attcagagaa gagaatgtgg actacagttc accccggtgc ccgtaaaatg   420
aaggagaagt gggaaaacga caaagtggtg gcgatgtcat ccactatttt ctcgatggga   480
gactgcatcg gttggctgga agatttcctc atgggtatgg actccacttt ggagccatcg   540
ggtaccggta gtagcggtag tagtgattac aaggacgatg acgacaagca ccaccatcat   600
catcatcacc acggtagcag cggcagcagt gcccccacct ctagcagcac aaagaagacc   660
cagctgcaac tggaacacct cctgctggac ctgcagatga tcctgaacgg catcaacaac   720
tacaagaacc ccaagctgac cgccatgctg accaaaaagt tttacatgcc aagaaggcc   780
accgagctta acacctgca atgccttgag gaggagctga agcccctgga ggaggtactg   840
aacctggccc agagcaagaa ctttcatctg aggcccaggg acctgattag caacatcaac   900
gtgatcgtgt tggagttgaa gggcagcgag accacgttca gtgcgagta cgccgacgag   960
acggccacca tagtggagtt tcttaacagg tggatcacct tctcacagtc tatcatcagc  1020
accctgacc                                                         1029
```

<210> SEQ ID NO 179
<211> LENGTH: 343
<212> TYPE: PRT
<213> ORGANISM: Artificial sequence
<220> FEATURE:
<223> OTHER INFORMATION: Synthetic peptide ULBP2.S2_FLAG_6xHis_mutIL2

<400> SEQUENCE: 179

```
Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Thr Leu Met Arg Ile Trp Ser Met Gly
```

```
                145                 150                 155                 160
Asp Cys Ile Gly Trp Leu Glu Asp Phe Leu Met Gly Met Asp Ser Thr
                165                 170                 175
Leu Glu Pro Ser Gly Thr Gly Ser Ser Gly Ser Ser Asp Tyr Lys Asp
                180                 185                 190
Asp Asp Asp Lys His His His His His His Gly Ser Ser Gly
                195                 200                 205
Ser Ser Ala Pro Thr Ser Ser Ser Thr Lys Lys Thr Gln Leu Gln Leu
    210                 215                 220
Glu His Leu Leu Leu Asp Leu Gln Met Ile Leu Asn Gly Ile Asn Asn
225                 230                 235                 240
Tyr Lys Asn Pro Lys Leu Thr Ala Met Leu Thr Lys Lys Phe Tyr Met
                245                 250                 255
Pro Lys Lys Ala Thr Glu Leu Lys His Leu Gln Cys Leu Glu Glu Glu
                260                 265                 270
Leu Lys Pro Leu Glu Glu Val Leu Asn Leu Ala Gln Ser Lys Asn Phe
                275                 280                 285
His Leu Arg Pro Arg Asp Leu Ile Ser Asn Ile Asn Val Ile Val Leu
                290                 295                 300
Glu Leu Lys Gly Ser Glu Thr Thr Phe Met Cys Glu Tyr Ala Asp Glu
305                 310                 315                 320
Thr Ala Thr Ile Val Glu Phe Leu Asn Arg Trp Ile Thr Phe Ser Gln
                325                 330                 335
Ser Ile Ile Ser Thr Leu Thr
                340
```

<210> SEQ ID NO 180
<211> LENGTH: 1029
<212> TYPE: DNA
<213> ORGANISM: Artificial sequence
<220> FEATURE:
<223> OTHER INFORMATION: Synthetic polynucleotide, encoding
      ULBP2.S2_FLAG_6xHis_mutIL2

<400> SEQUENCE: 180

```
gagccccata gtctgagcta cgacatcaca gttattccca agttcaggcc cggaccgcgc      60
tggtgtgccg tgcaaggaca gtcgacgaa  aaaaccttc  ttcattacga ttgcggaaat     120
aagactgtaa cgccagtctc tcctttaggt aagaagttaa acgtcactac ggcgtggaag     180
gcacaaaacc ccgtcctgcg cgaggtcgtc gacatcctga ctgaacaatt gtgggacatc     240
cagctcgaga attacactcc aaaggagcct cttaccctgc aggctagaat gtcttgcgag     300
caaaaggcag agggccactc ctccggcagc tggcagttca gtttcgacgg acaaatctt t    360
ctgttattcg attcagagaa gagaatgtgg actacagttc accccggtgc cgtaaaatg      420
aaggagaagt gggaaaacga caaagtggtg gcgactctga tgaggatttg gtcgatggga     480
gactgcatcg gttggctgga agatttcctc atgggtatgg actccacttt ggagccatcg     540
ggtaccggta gtagcggtag tagtgattac aaggacgatg acgacaagca ccaccatcat     600
catcatcacc acggtagcag cggcagcagt gccccccacct ctagcagcac aaagaagacc    660
cagctgcaac tggaacacct cctgctggac ctgcagatga tcctgaacgg catcaacaac    720
tacaagaacc ccaagctgac cgccatgctg accaaaaagt ttacatgcc  caagaaggcc    780
accgagctta acaccctgca atgccttgag gaggagctga agcccctgga ggaggtactg    840
aacctggccc agagcaagaa ctttcatctg aggcccaggg acctgattag caacatcaac    900
```

```
gtgatcgtgt tggagttgaa gggcagcgag accacgttca tgtgcgagta cgccgacgag    960
acggccacca tagtggagtt tcttaacagg tggatcacct tctcacagtc tatcatcagc   1020
accctgacc                                                           1029
```

<210> SEQ ID NO 181
<211> LENGTH: 412
<212> TYPE: PRT
<213> ORGANISM: Artificial sequence
<220> FEATURE:
<223> OTHER INFORMATION: Synthetic peptide ULBP2.R80W_Fc1

<400> SEQUENCE: 181

```
Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Met Ser Phe His Tyr Phe Ser Met Gly
145                 150                 155                 160

Asp Cys Ile Gly Trp Leu Glu Asp Phe Leu Met Gly Met Asp Ser Thr
                165                 170                 175

Leu Glu Pro Ser Glu Pro Lys Ser Cys Asp Lys Thr His Thr Cys Pro
            180                 185                 190

Pro Cys Pro Ala Pro Glu Leu Leu Gly Gly Pro Ser Val Phe Leu Phe
        195                 200                 205

Pro Pro Lys Pro Lys Asp Thr Leu Met Ile Ser Arg Thr Pro Glu Val
    210                 215                 220

Thr Cys Val Val Val Ala Val Ser His Glu Asp Pro Glu Val Lys Phe
225                 230                 235                 240

Asn Trp Tyr Val Asp Gly Val Glu Val His Asn Ala Lys Thr Lys Pro
                245                 250                 255

Arg Glu Glu Gln Tyr Ala Ser Thr Tyr Arg Val Val Ser Val Leu Thr
            260                 265                 270

Val Leu His Gln Asp Trp Leu Asn Gly Lys Glu Tyr Lys Cys Lys Val
        275                 280                 285

Ser Asn Lys Ala Leu Pro Ala Pro Ile Glu Lys Thr Ile Ser Lys Ala
    290                 295                 300

Lys Gly Gln Pro Arg Glu Pro Gln Val Tyr Thr Leu Pro Pro Ser Arg
305                 310                 315                 320

Asp Glu Leu Thr Lys Asn Gln Val Ser Leu Thr Cys Leu Val Lys Gly
                325                 330                 335
```

Phe Tyr Pro Ser Asp Ile Ala Val Glu Trp Glu Ser Asn Gly Gln Pro
                340                 345                 350

Glu Asn Asn Tyr Asp Thr Thr Pro Pro Val Leu Asp Ser Asp Gly Ser
            355                 360                 365

Phe Phe Leu Tyr Ser Asp Leu Thr Val Asp Lys Ser Arg Trp Gln Gln
370                 375                 380

Gly Asn Val Phe Ser Cys Ser Val Met His Glu Ala Leu His Asn His
385                 390                 395                 400

Tyr Thr Gln Lys Ser Leu Ser Leu Ser Pro Gly Lys
            405                 410

<210> SEQ ID NO 182
<211> LENGTH: 1236
<212> TYPE: DNA
<213> ORGANISM: Artificial sequence
<220> FEATURE:
<223> OTHER INFORMATION: Synthetic polynucleotide, encoding
      ULBP2.R80W_Fc1

<400> SEQUENCE: 182

```
gagccccata gtctgagcta cgacatcaca gttattccca agttcaggcc cggaccgcgc    60
tggtgtgccg tgcaaggaca gtcgacgaa aaaacctttc ttcattacga ttgcggaaat   120
aagactgtaa cgccagtctc tcctttaggt aagaagttaa cgtcactac ggcgtggaag   180
gcacaaaacc ccgtcctgcg cgaggtcgtc gacatcctga ctgaacaatt gtgggacatc   240
cagctcgaga attacactcc aaaggagcct cttaccctgc aggctagaat gtcttgcgag   300
caaaaggcag agggccactc ctccggcagc tggcagttca gtttcgacgg acaaatcttt   360
ctgttattcg attcagagaa gagaatgtgg actacagttc accccggtgc cgtaaaatg    420
aaggagaagt gggaaaacga caaagtggtg gcgatgtcat ccactatttt ctcgatggga   480
gactgcatcg gttggctgga agatttcctc atgggtatgg actccacttt ggagccatcg   540
gagcccaaaa gctgcgacaa gactcacact tgtccgccgt gccccgcccc cgaactgctg   600
ggtggcccct ccgtgttcct gttcccgcct aagcctaagg acacccttat gatcagccgc   660
accccctgaag tgacctgtgt cgtcgtggca gtgtcacacg aggaccccga ggtcaagttc   720
aattggtacg tggacggcgt ggaagtgcat aacgcaaaga ccaagcctcg ggaggaacag   780
tacgcctcga cctaccgcgt ggtgtcagtc ctgactgtgc tgcaccagga ctggctgaac   840
gggaaggagt acaagtgcaa agtgtcgaac aaggccctgc cggctccaat tgaaaagacc   900
atcagcaagg ccaagggcca gccaagggaa ccacaggtgt acaccctccc tcctccccgg   960
gacgagctga ccaaaaacca gtgtccctg acttgccttg tgaagggtt ctacccttct   1020
gacattgccg tcgaatggga atcgaacgga cagcctgaaa acaactatga cactaccccg   1080
cccgtgctgg attccgacgg aagcttcttc ctgtactccg acctgaccgt ggacaagtcg   1140
agatggcagc agggaaatgt gttcagctgc tccgtgatgc atgaggcgct gcacaaccac   1200
tacacccaga gtcactgag cctctccccc ggaaag                             1236
```

<210> SEQ ID NO 183
<211> LENGTH: 368
<212> TYPE: PRT
<213> ORGANISM: Artificial sequence
<220> FEATURE:
<223> OTHER INFORMATION: Synthetic peptide Fc2_mutIL2

<400> SEQUENCE: 183

Glu Pro Lys Ser Cys Asp Lys Thr His Thr Cys Pro Pro Cys Pro Ala

```
            1               5                  10                 15
          Pro Glu Leu Leu Gly Gly Pro Ser Val Phe Leu Phe Pro Pro Lys Pro
                          20                  25                 30

Lys Asp Thr Leu Met Ile Ser Arg Thr Pro Glu Val Thr Cys Val Val
                          35                  40                 45

Val Ala Val Ser His Glu Asp Pro Glu Val Lys Phe Asn Trp Tyr Val
                      50                  55                  60

Asp Gly Val Glu Val His Asn Ala Lys Thr Lys Pro Arg Glu Glu Gln
          65                  70                  75                  80

Tyr Ala Ser Thr Tyr Arg Val Val Ser Val Leu Thr Val Leu His Gln
                              85                  90                  95

Asp Trp Leu Asn Gly Lys Glu Tyr Lys Cys Lys Val Ser Asn Lys Ala
                          100                 105                110

Leu Pro Ala Pro Ile Glu Lys Thr Ile Ser Lys Ala Lys Gly Gln Pro
                          115                 120                 125

Arg Glu Pro Gln Val Tyr Thr Leu Pro Pro Ser Arg Lys Glu Leu Thr
                      130                 135                 140

Lys Asn Gln Val Ser Leu Thr Cys Leu Val Lys Gly Phe Tyr Pro Ser
          145                 150                 155                 160

Asp Ile Ala Val Glu Trp Glu Ser Asn Gly Gln Pro Glu Asn Asn Tyr
                              165                 170                 175

Lys Thr Thr Pro Pro Val Leu Lys Ser Asp Gly Ser Phe Phe Leu Tyr
                          180                 185                 190

Ser Lys Leu Thr Val Asp Lys Ser Arg Trp Gln Gln Gly Asn Val Phe
                          195                 200                 205

Ser Cys Ser Val Met His Glu Ala Leu His Asn His Tyr Thr Gln Lys
          210                 215                 220

Ser Leu Ser Leu Ser Pro Gly Gly Gly Ser Ala Pro Thr Ser Ser
          225                 230                 235                 240

Ser Thr Lys Lys Thr Gln Leu Gln Leu Glu His Leu Leu Asp Leu
                          245                 250                 255

Gln Met Ile Leu Asn Gly Ile Asn Asn Tyr Lys Asn Pro Lys Leu Thr
                          260                 265                 270

Ala Met Leu Thr Lys Lys Phe Tyr Met Pro Lys Lys Ala Thr Glu Leu
                          275                 280                 285

Lys His Leu Gln Cys Leu Glu Glu Glu Leu Lys Pro Leu Glu Glu Val
                          290                 295                 300

Leu Asn Leu Ala Gln Ser Lys Asn Phe His Leu Arg Pro Arg Asp Leu
          305                 310                 315                 320

Ile Ser Asn Ile Asn Val Ile Val Leu Glu Leu Lys Gly Ser Glu Thr
                          325                 330                 335

Thr Phe Met Cys Glu Tyr Ala Asp Glu Thr Ala Thr Ile Val Glu Phe
                          340                 345                 350

Leu Asn Arg Trp Ile Thr Phe Ser Gln Ser Ile Ile Ser Thr Leu Thr
                          355                 360                 365
```

<210> SEQ ID NO 184
<211> LENGTH: 1104
<212> TYPE: DNA
<213> ORGANISM: Artificial sequence
<220> FEATURE:
<223> OTHER INFORMATION: Synthetic polynucleotide, encoding Fc2_mutIL2

<400> SEQUENCE: 184
gagcccaaaa gctgcgacaa gactcacact tgtccgccgt gccccgcccc cgaactgctg     60

```
ggtggcccct ccgtgttcct gttcccgcct aagcctaagg acacccttat gatcagccgc    120
acccctgaag tgacctgtgt cgtcgtggca gtgtcacacg aggacccgga ggtcaagttc    180
aattggtacg tggacggcgt ggaagtgcat aacgcaaaga ccaagcctcg ggaggaacag    240
tacgcctcga cctaccgcgt ggtgtcagtc ctgactgtgc tgcaccagga ctggctgaac    300
gggaaggagt acaagtgcaa agtgtcgaac aaggccctgc cggctccaat tgaaaagacc    360
atcagcaagg ccaagggcca gccaagggaa ccacaggtgt acaccctccc tccttcccgg    420
aaggagctga ccaaaaacca gtgtccctg acttgccttg tgaaggggtt ctacccttct    480
gacattgccg tcgaatggga atcgaacgga cagcctgaaa acaactataa gactacccca    540
cccgtgctga agtccgacgg aagcttcttc ctgtactcca agctgaccgt ggacaagtcg    600
agatggcagc agggaaatgt gttcagctgc tccgtgatgc atgaggcgct gcacaaccac    660
tacacccaga agtcactgag cctctccccc ggaggaggtg gcagcgcccc cacctctagc    720
agcacaaaga agacccagct gcaactggaa cactcctgc tggacctgca gatgatcctg    780
aacggcatca acaactacaa gaaccccaag ctgaccgcca tgctgaccaa aaagttttac    840
atgcccaaga aggccaccga gcttaaacac ctgcaatgcc ttgaggagga gctgaagccc    900
ctggaggagg tactgaacct ggcccagagc aagaactttc atctgaggcc cagggacctg    960
attagcaaca tcaacgtgat cgtgttggag ttgaagggca gcgagaccac gttcatgtgc   1020
gagtacgccg acgagacggc caccatagtg gagtttctta acaggtggat caccttctca   1080
cagtctatca tcagcaccct gacc                                          1104
```

<210> SEQ ID NO 185
<211> LENGTH: 349
<212> TYPE: PRT
<213> ORGANISM: Artificial sequence
<220> FEATURE:
<223> OTHER INFORMATION: Synthetic peptide Fc2_mutIL15

<400> SEQUENCE: 185

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Lys Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Ser Asn Trp Val Asn Val
225                 230                 235                 240

Ile Ser Asp Leu Lys Lys Ile Glu Asp Leu Ile Gln Ser Met His Ile
                245                 250                 255

Asp Ala Thr Leu Tyr Thr Glu Ser Asp Val His Pro Ser Cys Lys Val
            260                 265                 270

Thr Ala Met Lys Cys Phe Leu Leu Glu Leu Gln Val Ile Ser Leu Glu
        275                 280                 285

Ser Gly Asp Ala Ser Ile His Asp Thr Val Glu Asn Leu Ile Ile Leu
    290                 295                 300

Ala Asn Asn Ser Leu Ser Ser Asn Gly Asn Val Thr Glu Ser Gly Cys
305                 310                 315                 320

Lys Glu Cys Glu Glu Leu Glu Glu Lys Asn Ile Lys Glu Phe Leu Gln
                325                 330                 335

Ser Phe Val His Ile Val Gln Met Phe Ile Asn Thr Ser
            340                 345
```

<210> SEQ ID NO 186
<211> LENGTH: 1047
<212> TYPE: DNA
<213> ORGANISM: Artificial sequence
<220> FEATURE:
<223> OTHER INFORMATION: Synthetic polynucleotide, encoding Fc2_mutIL15

<400> SEQUENCE: 186

```
gagcccaaaa gctgcgacaa gactcacact tgtccgccgt gccccgcccc cgaactgctg      60
ggtggcccct ccgtgttcct gttcccgcct aagcctaagg acacccttat gatcagccgc     120
acccctgaag tgacctgtgt cgtcgtggca gtgtcacacg aggacccgga ggtcaagttc     180
aattggtacg tggacggcgt ggaagtgcat aacgcaaaga ccaagcctcg ggaggaacag     240
tacgcctcga cctaccgcgt ggtgtcagtc ctgactgtgc tgcaccagga ctggctgaac     300
gggaaggagt acaagtgcaa agtgtcgaac aaggccctgc cggctccaat tgaaaagacc     360
atcagcaagg ccaagggcca gccaagggaa ccacaggtgt acaccctccc tccttcccgg     420
aaggagctga ccaaaaacca gtgtccctg acttgccttg tgaaggggtt ctacccttct     480
gacattgccg tcgaatggga atcgaacgga cagcctgaaa acaactataa gactaccccg     540
cccgtgctga agtccgacgg aagcttcttc ctgtactcca agctgaccgt ggacaagtcg     600
agatggcagc agggaaatgt gttcagctgc tccgtgatgc atgaggcgct gcacaaccac     660
tacacccaga agtcactgag cctctccccc ggaggaggtg gcagcaattg ggtgaacgtg     720
atttctgact tgaagaaaat cgaggacttg attcaaagta tgcacataga cgcaacgctc     780
tatactgaga gtgatgttca tccctcttgt aaagttaccg ctatgaagtg tttcttgctc     840
gaactccaag ttatcagtct ggagagcggt gatgcctcca tacacgatac agtcgaaaac     900
cttatcattc tcgcaaataa ctcattgagt agcaatggca atgttacaga gtctgggtgt     960
aaggaatgcg aagaacttga agagaaaaac ataaaggagt tcctccaatc attcgtgcat    1020
attgtccaga tgtttatcaa cactagc                                        1047
```

<210> SEQ ID NO 187
<211> LENGTH: 412
<212> TYPE: PRT
<213> ORGANISM: Artificial sequence
<220> FEATURE:
<223> OTHER INFORMATION: Synthetic peptide ULBP2.S2_Fc1

<400> SEQUENCE: 187

```
Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Thr Leu Met Arg Ile Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser Glu Pro Lys Ser Cys Asp Lys Thr His Thr Cys Pro
            180                 185                 190

Pro Cys Pro Ala Pro Glu Leu Leu Gly Gly Pro Ser Val Phe Leu Phe
        195                 200                 205

Pro Pro Lys Pro Lys Asp Thr Leu Met Ile Ser Arg Thr Pro Glu Val
    210                 215                 220

Thr Cys Val Val Val Ala Val Ser His Glu Asp Pro Glu Val Lys Phe
225                 230                 235                 240

Asn Trp Tyr Val Asp Gly Val Glu Val His Asn Ala Lys Thr Lys Pro
                245                 250                 255

Arg Glu Glu Gln Tyr Ala Ser Thr Tyr Arg Val Val Ser Val Leu Thr
            260                 265                 270

Val Leu His Gln Asp Trp Leu Asn Gly Lys Glu Tyr Lys Cys Lys Val
        275                 280                 285

Ser Asn Lys Ala Leu Pro Ala Pro Ile Glu Lys Thr Ile Ser Lys Ala
    290                 295                 300

Lys Gly Gln Pro Arg Glu Pro Gln Val Tyr Thr Leu Pro Pro Ser Arg
305                 310                 315                 320

Asp Glu Leu Thr Lys Asn Gln Val Ser Leu Thr Cys Leu Val Lys Gly
                325                 330                 335

Phe Tyr Pro Ser Asp Ile Ala Val Glu Trp Glu Ser Asn Gly Gln Pro
            340                 345                 350

Glu Asn Asn Tyr Asp Thr Thr Pro Pro Val Leu Asp Ser Asp Gly Ser
        355                 360                 365
```

Phe Phe Leu Tyr Ser Asp Leu Thr Val Asp Lys Ser Arg Trp Gln Gln
            370                 375                 380

Gly Asn Val Phe Ser Cys Ser Val Met His Glu Ala Leu His Asn His
385                 390                 395                 400

Tyr Thr Gln Lys Ser Leu Ser Leu Ser Pro Gly Lys
                405                 410

<210> SEQ ID NO 188
<211> LENGTH: 1236
<212> TYPE: DNA
<213> ORGANISM: Artificial sequence
<220> FEATURE:
<223> OTHER INFORMATION: Synthetic polynucleotide, encoding ULBP2.S2_Fc1

<400> SEQUENCE: 188
gagccccata gtctgagcta cgacatcaca gttattccca gttcaggcc cggaccgcgc       60 tggtgtgccg tgcaaggaca gtcgacgaa aaaccttc ttcattacga ttgcggaaat       120
aagactgtaa cgccagtctc tcctttaggt aagaagttaa cgtcactac ggcgtggaag       180 gcacaaaacc ccgtcctgcg cgaggtcgtc gacatcctga ctgaacaatt gtgggacatc      240
cagctcgaga attacactcc aaaggagcct cttaccctgc aggctagaat gtcttgcgag      300
caaaaggcag agggccactc ctccggcagc tggcagttca gtttcgacgg acaaatcttt      360
ctgttattcg attcagagaa gagaatgtgg actacagttc accccggtgc ccgtaaaatg      420
aaggagaagt gggaaaacga caaagtggtg gcgactctga tgaggatttg gtcgatggga      480
gactgcatcg gttggctgga agatttcctc atgggtatgg actccacttt ggagccatcg      540
gagcccaaaa gctgcgacaa gactcacact tgtccgccgt gccccgcccc cgaactgctg      600
ggtggcccct ccgtgttcct gttcccgcct aagcctaagg acacccttat gatcagccgc      660 accctgaag tgacctgtgt cgtcgtggca gtgtcacacg aggacccgga ggtcaagttc      720
aattggtacg tggacggcgt ggaagtgcat aacgcaaaga ccaagcctcg ggaggaacag      780
tacgcctcga cctaccgcgt ggtgtcagtc ctgactgtgc tgcaccagga ctggctgaac      840
gggaaggagt acaagtgcaa agtgtcgaac aaggccctgc cggctccaat tgaaaagacc      900
atcagcaagg ccaagggcca gccaagggaa ccacaggtgt acaccctccc tccttcccgg      960
gacgagctga ccaaaaacca gtgtccctg acttgccttg tgaagggggtt ctacccttct     1020 gacattgccg tcgaatggga atcgaacgga cagcctgaaa acaactatga cactaccccg     1080
cccgtgctgg attccgacgg aagcttcttc ctgtactccg acctgaccgt ggacaagtcg     1140
agatggcagc agggaaatgt gttcagctgc tccgtgatgc atgaggcgct gcacaaccac     1200
tacacccaga agtcactgag cctctccccc ggaaag                               1236

<210> SEQ ID NO 189
<211> LENGTH: 412
<212> TYPE: PRT
<213> ORGANISM: Artificial sequence
<220> FEATURE:
<223> OTHER INFORMATION: Synthetic peptide ULBP2.S3_Fc1

<400> SEQUENCE: 189

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro

```
            35                  40                  45
Leu Gly Lys Lys Leu Asn Val Thr Thr Ala Trp Lys Ala Gln Asn Pro
 50                  55                  60
Val Leu Arg Glu Val Val Asp Ile Leu Thr Glu Gln Leu Trp Asp Ile
 65                  70                  75                  80
Gln Leu Glu Asn Tyr Thr Pro Lys Glu Pro Leu Thr Leu Gln Ala Arg
                 85                  90                  95
Met Ser Cys Glu Gln Lys Ala Glu Gly His Ser Ser Gly Ser Trp Gln
                100                 105                 110
Phe Ser Phe Asp Gly Gln Ile Phe Leu Leu Phe Asp Ser Glu Lys Arg
                115                 120                 125
Met Trp Thr Thr Val His Pro Gly Ala Arg Lys Met Lys Glu Lys Trp
                130                 135                 140
Glu Asn Asp Lys Val Val Ala Thr Lys Leu Tyr Leu Trp Ser Met Gly
145                 150                 155                 160
Asp Cys Ile Gly Trp Leu Glu Asp Phe Leu Met Gly Met Asp Ser Thr
                165                 170                 175
Leu Glu Pro Ser Glu Pro Lys Ser Cys Asp Lys Thr His Thr Cys Pro
                180                 185                 190
Pro Cys Pro Ala Pro Glu Leu Leu Gly Gly Pro Ser Val Phe Leu Phe
                195                 200                 205
Pro Pro Lys Pro Lys Asp Thr Leu Met Ile Ser Arg Thr Pro Glu Val
210                 215                 220
Thr Cys Val Val Val Ala Val Ser His Glu Asp Pro Glu Val Lys Phe
225                 230                 235                 240
Asn Trp Tyr Val Asp Gly Val Glu Val His Asn Ala Lys Thr Lys Pro
                245                 250                 255
Arg Glu Glu Gln Tyr Ala Ser Thr Tyr Arg Val Val Ser Val Leu Thr
                260                 265                 270
Val Leu His Gln Asp Trp Leu Asn Gly Lys Glu Tyr Lys Cys Lys Val
                275                 280                 285
Ser Asn Lys Ala Leu Pro Ala Pro Ile Glu Lys Thr Ile Ser Lys Ala
290                 295                 300
Lys Gly Gln Pro Arg Glu Pro Gln Val Tyr Thr Leu Pro Pro Ser Arg
305                 310                 315                 320
Asp Glu Leu Thr Lys Asn Gln Val Ser Leu Thr Cys Leu Val Lys Gly
                325                 330                 335
Phe Tyr Pro Ser Asp Ile Ala Val Glu Trp Glu Ser Asn Gly Gln Pro
                340                 345                 350
Glu Asn Asn Tyr Asp Thr Thr Pro Pro Val Leu Asp Ser Asp Gly Ser
                355                 360                 365
Phe Phe Leu Tyr Ser Asp Leu Thr Val Asp Lys Ser Arg Trp Gln Gln
                370                 375                 380
Gly Asn Val Phe Ser Cys Ser Val Met His Glu Ala Leu His Asn His
385                 390                 395                 400
Tyr Thr Gln Lys Ser Leu Ser Leu Ser Pro Gly Lys
                405                 410

<210> SEQ ID NO 190
<211> LENGTH: 1236
<212> TYPE: DNA
<213> ORGANISM: Artificial sequence
<220> FEATURE:
<223> OTHER INFORMATION: Synthetic polynucleotide, encoding ULBP2.S3_Fc1
```

<400> SEQUENCE: 190

```
gagccccata gtctgagcta cgacatcaca gttattccca agttcaggcc cggaccgcgc    60
tggtgtgccg tgcaaggaca agtcgacgaa aaaacctttc ttcattacga ttgcggaaat   120
aagactgtaa cgccagtctc tcctttaggt aagaagttaa acgtcactac ggcgtggaag   180
gcacaaaacc ccgtcctgcg cgaggtcgtc gacatcctga ctgaacaatt gtgggacatc   240
cagctcgaga attacactcc aaaggagcct cttaccctgc aggctagaat gtcttgcgag   300
caaaaggcag agggccactc ctccggcagc tggcagttca gtttcgacgg acaaatcttt   360
ctgttattcg attcagagaa gagaatgtgg actacagttc accccggtgc cgtaaaaatg   420
aaggagaagt gggaaaacga caaagtggtg gcgactaagc tttatctttg gtcgatggga   480
gactgcatcg gttggctgga agatttcctc atgggtatgg actccacttt ggagccatcg   540
gagcccaaaa gctgcgacaa gactcacact tgtccgccgt gccccgcccc cgaactgctg   600
ggtggcccct ccgtgttcct gttcccgcct aagcctaagg acacccttat gatcagccgc   660
acccctgaag tgacctgtgt cgtcgtggca gtgtcacacg aggacccgga ggtcaagttc   720
aattggtacg tggacggcgt ggaagtgcat aacgcaaaga ccaagcctcg ggaggaacag   780
tacgcctcga cctaccgcgt ggtgtcagtc ctgactgtgc tgcaccagga ctggctgaac   840
gggaaggagt acaagtgcaa agtgtcgaac aaggccctgc cggctccaat tgaaaagacc   900
atcagcaagg ccaagggcca gccaaggaaa ccacaggtgt acaccctccc tccttcccgg   960
gacgagctga ccaaaaacca gtgtccctg acttgccttg tgaaggggtt ctacccttct  1020
gacattgccg tcgaatggga atcgaacgga cagcctgaaa acaactatga cactacccgg  1080
cccgtgctgg attccgacgg aagcttcttc ctgtactccg acctgaccgt ggacaagtcg  1140
agatggcagc agggaaatgt gttcagctgc tccgtgatgc atgaggcgct gcacaaccac  1200
tacacccaga agtcactgag cctctccccc ggaaag                              1236
```

<210> SEQ ID NO 191
<211> LENGTH: 368
<212> TYPE: PRT
<213> ORGANISM: Artificial sequence
<220> FEATURE:
<223> OTHER INFORMATION: Synthetic peptide Fc2_wtIL2 (wild-type)

<400> SEQUENCE: 191

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Glu Leu Thr
```

```
                130              135               140
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Lys Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
210                 215                 220

Ser Leu Ser Leu Ser Pro Gly Gly Gly Gly Ser Ala Pro Thr Ser Ser
225                 230                 235                 240

Ser Thr Lys Lys Thr Gln Leu Gln Leu Glu His Leu Leu Leu Asp Leu
                245                 250                 255

Gln Met Ile Leu Asn Gly Ile Asn Asn Tyr Lys Asn Pro Lys Leu Thr
                260                 265                 270

Arg Met Leu Thr Phe Lys Phe Tyr Met Pro Lys Lys Ala Thr Glu Leu
                275                 280                 285

Lys His Leu Gln Cys Leu Glu Glu Leu Lys Pro Leu Glu Glu Val
                290                 295                 300

Leu Asn Leu Ala Gln Ser Lys Asn Phe His Leu Arg Pro Arg Asp Leu
305                 310                 315                 320

Ile Ser Asn Ile Asn Val Ile Val Leu Glu Leu Lys Gly Ser Glu Thr
                325                 330                 335

Thr Phe Met Cys Glu Tyr Ala Asp Glu Thr Ala Thr Ile Val Glu Phe
                340                 345                 350

Leu Asn Arg Trp Ile Thr Phe Ala Gln Ser Ile Ile Ser Thr Leu Thr
                355                 360                 365

<210> SEQ ID NO 192
<211> LENGTH: 1104
<212> TYPE: DNA
<213> ORGANISM: Artificial sequence
<220> FEATURE:
<223> OTHER INFORMATION: Synthetic polynucleotide, encoding Fc2_wtIL2

<400> SEQUENCE: 192
gagcccaaaa gctgcgacaa gactcacact tgtccgccgt gccccgcccc cgaactgctg     60
ggtggcccct ccgtgttcct gttcccgcct aagcctaagg acacccttat gatcagccgc    120 accccctgaag tgacctgtgt cgtcgtggca gtgtcacacg aggacccgga ggtcaagttc    180
aattggtacg tggacggcgt ggaagtgcat aacgcaaaga ccaagcctcg ggaggaacag    240
tacgcctcga cctaccgcgt ggtgtcagtc ctgactgtgc tgcaccagga ctggctgaac    300
gggaaggagt acaagtgcaa agtgtcgaac aaggccctgc cggctccaat tgaaaagacc    360
atcagcaagg ccaagggcca gccaagggaa ccacaggtgt acaccctccc tccttcccgg    420
aaggagctga ccaaaaacca gtgtccctg acttgccttg tgaaggggtt ctaccctcct    480
gacattgccg tcgaatggga atcgaacgga cagcctgaaa acaactataa gactaccccg    540
cccgtgctga gtccgacgg aagcttcttc ctgtactcca agctgaccgt ggacaagtcg    600
agatggcagc agggaaatgt gttcagctgc tccgtgatgc atgaggcgct gcacaaccac    660
tacacccaga gtcactgag cctctccccc ggaggaggtg gcagcgctcc aacctctagc    720
tctacgaaga aaactcaact ccagcttgag catttgcttt tggaccttca aatgatattg    780
```

```
aacgggatta acaattacaa gaacccaaa ctgacgcgaa tgcttacatt caaattttac    840
atgccaaaga aggccaccga gctgaaacac ttgcaatgtc ttgaggaaga gctgaagcca    900
ttggaggagg tcctgaattt ggctcaaagt aagaacttcc acctgcggcc aagggatctc    960
ataagcaaca taaatgtcat tgtattggaa ctgaaaggga gcgaaaccac ctttatgtgc   1020
gagtatgcag atgaaactgc aaccatagtc gagttcctca atcgctggat aactttcgcg   1080
cagtcaatta tatcaacact cacc                                         1104
```

<210> SEQ ID NO 193
<211> LENGTH: 368
<212> TYPE: PRT
<213> ORGANISM: Artificial sequence
<220> FEATURE:
<223> OTHER INFORMATION: Synthetic peptide Fc2_IL21.wt (wild-type)

<400> SEQUENCE: 193

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Lys Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Gln Gly Gln Asp Arg
225                 230                 235                 240

His Met Ile Arg Met Arg Gln Leu Ile Asp Ile Val Asp Gln Leu Lys
                245                 250                 255

Asn Tyr Val Asn Asp Leu Val Pro Glu Phe Leu Pro Ala Pro Glu Asp
            260                 265                 270

Val Glu Thr Asn Cys Glu Trp Ser Ala Phe Ser Cys Phe Gln Lys Ala
        275                 280                 285

Gln Leu Lys Ser Ala Asn Thr Gly Asn Asn Glu Arg Ile Ile Asn Val
    290                 295                 300
```

```
Leu Ile Lys Lys Leu Lys Arg Lys Pro Pro Ser Thr Asn Ala Gly Arg
305                 310                 315                 320

Arg Gln Lys His Arg Leu Thr Cys Pro Ser Cys Asp Ser Tyr Glu Lys
            325                 330                 335

Lys Pro Pro Lys Glu Phe Leu Glu Arg Phe Lys Ser Leu Leu Gln Lys
        340                 345                 350

Met Ile His Gln His Leu Ser Ser Arg Thr His Gly Ser Glu Asp Ser
    355                 360                 365
```

<210> SEQ ID NO 194
<211> LENGTH: 1104
<212> TYPE: DNA
<213> ORGANISM: Artificial sequence
<220> FEATURE:
<223> OTHER INFORMATION: Synthetic polynucleotide, encoding Fc2_IL21.wt (wild-type)

<400> SEQUENCE: 194

```
gagcccaaaa gctgcgacaa gactcacact tgtccgccgt gccccgcccc cgaactgctg      60
ggtggcccct ccgtgttcct gttcccgcct aagcctaagg acacccttat gatcagccgc     120
acccctgaag tgacctgtgt cgtcgtggca gtgtcacacg aggacccgga ggtcaagttc     180
aattggtacg tggacggcgt ggaagtgcat aacgcaaaga ccaagcctcg ggaggaacag     240
tacgcctcga cctaccgcgt ggtgtcagtc ctgactgtgc tgcaccagga ctggctgaac     300
gggaaggagt acaagtgcaa agtgtcgaac aaggccctgc cggctccaat tgaaaagacc     360
atcagcaagg ccaagggcca gccaagggaa ccacaggtgt acaccctccc tccttcccgg     420
aaggagctga ccaaaaacca gtgtccctg acttgccttg tgaaggggtt ctaccctct     480
gacattgccg tcgaatggga atcgaacgga cagcctgaaa acaactataa gactacccg     540
cccgtgctga gtccgacgg aagcttcttc ctgtactcca agctgaccgt ggacaagtcg     600
agatggcagc agggaaatgt gttcagctgc tccgtgatgc atgaggcgct gcacaaccac     660
tacacccaga agtcactgag cctctccccc ggaggaggtg gcagccaggg tcaagaccgc     720
catatgatcc gaatgcgaca gctcattgat attgtcgatc aattgaaaaa ttacgtgaat     780
gatcttgtac cggagttcct ccccgcaccg gaggacgttg aaacgaattg tgagtggtca     840
gcatttctt gctttcagaa ggctcaactc aagagtgcaa acacgggtaa caacgagcgc     900
attatcaatg ttctcatcaa aaagctgaaa cgaaaaccgc ctagcaccaa cgcaggcaga     960
cgacagaagc accggctcac gtgcccaagt tgcgattctt atgagaaaaa gccaccgaaa    1020
gaattcctgg agcggttcaa gtccctcttg cagaaaatga ttcatcagca tctctccagc    1080
aggacacacg gctccgagga ctcc                                          1104
```

<210> SEQ ID NO 195
<211> LENGTH: 368
<212> TYPE: PRT
<213> ORGANISM: Artificial sequence
<220> FEATURE:
<223> OTHER INFORMATION: Synthetic peptide Fc2_IL21.D18A

<400> SEQUENCE: 195

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
```

```
              35                  40                  45
Val Ala Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Ala Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Lys Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Ser Gln Gly Gln Asp Arg
225                 230                 235                 240

His Met Ile Arg Met Arg Gln Leu Ile Asp Ile Val Ala Gln Leu Lys
                245                 250                 255

Asn Tyr Val Asn Asp Leu Val Pro Glu Phe Leu Pro Ala Pro Glu Asp
            260                 265                 270

Val Glu Thr Asn Cys Glu Trp Ser Ala Phe Ser Cys Phe Gln Lys Ala
        275                 280                 285

Gln Leu Lys Ser Ala Asn Thr Gly Asn Asn Glu Arg Ile Ile Asn Val
    290                 295                 300

Leu Ile Lys Lys Leu Lys Arg Lys Pro Pro Ser Thr Asn Ala Gly Arg
305                 310                 315                 320

Arg Gln Lys His Arg Leu Thr Cys Pro Ser Cys Asp Ser Tyr Glu Lys
                325                 330                 335

Lys Pro Pro Lys Glu Phe Leu Glu Arg Phe Lys Ser Leu Leu Gln Lys
            340                 345                 350

Met Ile His Gln His Leu Ser Ser Arg Thr His Gly Ser Glu Asp Ser
        355                 360                 365
```

<210> SEQ ID NO 196
<211> LENGTH: 1104
<212> TYPE: DNA
<213> ORGANISM: Artificial sequence
<220> FEATURE:
<223> OTHER INFORMATION: Synthetic polynucleotide, encoding
      Fc2_IL21.D18A

<400> SEQUENCE: 196
gagcccaaaa gctgcgacaa gactcacact tgtccgccgt gccccgcccc cgaactgctg      60
ggtggcccct ccgtgttcct gttcccgcct aagcctaagg acacccttat gatcagccgc     120
acccctgaag tgacctgtgt cgtcgtggca gtgtcacacg aggacccgga ggtcaagttc     180

-continued

```
aattggtacg tggacggcgt ggaagtgcat aacgcaaaga ccaagcctcg ggaggaacag    240
tacgcctcga cctaccgcgt ggtgtcagtc ctgactgtgc tgcaccagga ctggctgaac    300
gggaaggagt acaagtgcaa agtgtcgaac aaggccctgc cggctccaat tgaaaagacc    360
atcagcaagg ccaagggcca gccaagggaa ccacaggtgt acaccctccc tccttcccgg    420
aaggagctga ccaaaaacca gtgtccctg acttgccttg tgaaggggtt ctacccttct    480
gacattgccg tcgaatggga atcgaacgga cagcctgaaa acaactataa gactaccccg    540
cccgtgctga agtccgacgg aagcttcttc ctgtactcca agctgaccgt ggacaagtcg    600
agatggcagc agggaaatgt gttcagctgc tccgtgatgc atgaggcgct gcacaaccac    660
tacacccaga agtcactgag cctctccccc ggaggaggtg gcagccaggg tcaagaccgc    720
catatgatcc gaatgcgaca gctcattgat attgtcgcac aattgaaaaa ttacgtgaat    780
gatcttgtac cggagttcct ccccgcaccg gaggacgttg aaacgaattg tgagtggtca    840
gcattttctt gctttcagaa ggctcaactc aagagtgcaa acacgggtaa caacgagcgc    900
attatcaatg ttctcatcaa aaagctgaaa cgaaaaccgc ctagcaccaa cgcaggcaga    960
cgacagaagc accggctcac gtgcccaagt tgcgattctt atgagaaaaa gccaccgaaa   1020
gaattcctgg agcggttcaa gtccctcttg cagaaaatga ttcatcagca tctctccagc   1080
aggacacacg gctccgagga ctcc                                         1104
```

<210> SEQ ID NO 197
<211> LENGTH: 368
<212> TYPE: PRT
<213> ORGANISM: Artificial sequence
<220> FEATURE:
<223> OTHER INFORMATION: Synthetic peptide Fc2_IL21.E109R

<400> SEQUENCE: 197

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Lys Ser Asp Gly Ser Phe Phe Leu Tyr
            180                 185                 190

Ser Lys Leu Thr Val Asp Lys Ser Arg Trp Gln Gln Gly Asn Val Phe
```

```
                195                 200                 205
Ser Cys Ser Val Met His Glu Ala Leu His Asn His Tyr Thr Gln Lys
    210                 215                 220
Ser Leu Ser Leu Ser Pro Gly Gly Gly Ser Gln Gly Gln Asp Arg
225                 230                 235                 240
His Met Ile Arg Met Arg Gln Leu Ile Asp Ile Val Asp Gln Leu Lys
                245                 250                 255
Asn Tyr Val Asn Asp Leu Val Pro Glu Phe Leu Pro Ala Pro Glu Asp
            260                 265                 270
Val Glu Thr Asn Cys Glu Trp Ser Ala Phe Ser Cys Phe Gln Lys Ala
        275                 280                 285
Gln Leu Lys Ser Ala Asn Thr Gly Asn Asn Glu Arg Ile Ile Asn Val
    290                 295                 300
Leu Ile Lys Lys Leu Lys Arg Lys Pro Pro Ser Thr Asn Ala Gly Arg
305                 310                 315                 320
Arg Gln Lys His Arg Leu Thr Cys Pro Ser Cys Asp Ser Tyr Glu Lys
                325                 330                 335
Lys Pro Pro Lys Glu Phe Leu Arg Arg Phe Lys Ser Leu Leu Gln Lys
                340                 345                 350
Met Ile His Gln His Leu Ser Ser Arg Thr His Gly Ser Glu Asp Ser
            355                 360                 365
```

<210> SEQ ID NO 198
<211> LENGTH: 1104
<212> TYPE: DNA
<213> ORGANISM: Artificial sequence
<220> FEATURE:
<223> OTHER INFORMATION: Synthetic polynucleotide, encoding
      Fc2_IL21.E109R

<400> SEQUENCE: 198

```
gagcccaaaa gctgcgacaa gactcacact tgtccgccgt gccccgcccc cgaactgctg    60
ggtggcccct ccgtgttcct gttcccgcct aagcctaagg acacccttat gatcagccgc   120
acccctgaag tgacctgtgt cgtcgtggca gtgtcacacg aggacccgga ggtcaagttc   180
aattggtacg tggacggcgt ggaagtgcat aacgcaaaga ccaagcctcg ggaggaacag   240
tacgcctcga cctaccgcgt ggtgtcagtc ctgactgtgc tgcaccagga ctggctgaac   300
gggaaggagt acaagtgcaa agtgtcgaac aaggccctgc cggctccaat tgaaaagacc   360
atcagcaagg ccaagggcca gccaagggaa ccacaggtgt acaccctccc tccttcccgg   420
aaggagctga ccaaaaacca gtgtccctg acttgccttg tgaagggggtt ctacccttct   480
gacattgccg tcgaatggga atcgaacgga cagcctgaaa acaactataa gactaccccg   540
cccgtgctga agtccgacgg aagcttcttc ctgtactcca agctgaccgt ggacaagtcg   600
agatggcagc agggaaatgt gttcagctgc tccgtgatgc atgaggcgct gcacaaccac   660
tacacccaga agtcactgag cctctccccc ggaggaggtg gcagccaggg tcaagaccgc   720
catatgatcc gaatgcgaca gctcattgat attgtcgatc aattgaaaaa ttacgtgaat   780
gatcttgtac cggagttcct ccccgcaccg gaggacgttg aaacgaattg tgagtggtca   840
gcatttctt gctttcagaa ggctcaactc aagagtgcaa acacgggtaa caacgagcgc   900
attatcaatg ttctcatcaa aaagctgaaa cgaaaaccgc ctagcaccaa cgcaggcaga   960
cgacagaagc accggctcac gtgcccaagt tgcgattctt atgagaaaaa gccaccgaaa  1020
gaattcctgc ggcggttcaa gtccctcttg cagaaaatga ttcatcagca tctctccagc  1080
```
aggacacacg gctccgagga ctcc                                                      1104

<210> SEQ ID NO 199
<211> LENGTH: 368
<212> TYPE: PRT
<213> ORGANISM: Artificial sequence
<220> FEATURE:
<223> OTHER INFORMATION: Synthetic peptide Fc2_IL21.D18A.E109R

<400> SEQUENCE: 199

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Gly Gln Asp Arg
225                 230                 235                 240

His Met Ile Arg Met Arg Gln Leu Ile Asp Ile Val Ala Gln Leu Lys
                245                 250                 255

Asn Tyr Val Asn Asp Leu Val Pro Glu Phe Leu Pro Ala Pro Glu Asp
            260                 265                 270

Val Glu Thr Asn Cys Glu Trp Ser Ala Phe Ser Cys Phe Gln Lys Ala
        275                 280                 285

Gln Leu Lys Ser Ala Asn Thr Gly Asn Asn Glu Arg Ile Ile Asn Val
    290                 295                 300

Leu Ile Lys Lys Leu Lys Arg Lys Pro Pro Ser Thr Asn Ala Gly Arg
305                 310                 315                 320

Arg Gln Lys His Arg Leu Thr Cys Pro Ser Cys Asp Ser Tyr Glu Lys
                325                 330                 335

Lys Pro Pro Lys Glu Phe Leu Arg Arg Phe Lys Ser Leu Leu Gln Lys
            340                 345                 350

Met Ile His Gln His Leu Ser Ser Arg Thr His Gly Ser Glu Asp Ser
```

<210> SEQ ID NO 200
<211> LENGTH: 1104
<212> TYPE: DNA
<213> ORGANISM: Artificial sequence
<220> FEATURE:
<223> OTHER INFORMATION: Synthetic polynucleotide, encoding
    Fc2_IL21.D18A.E109R

<400> SEQUENCE: 200

```
gagcccaaaa gctgcgacaa gactcacact tgtccgccgt gccccgcccc cgaactgctg      60
ggtggcccct ccgtgttcct gttcccgcct aagcctaagg acacccttat gatcagccgc     120
accccctgaag tgacctgtgt cgtcgtggca gtgtcacacg aggacccgga ggtcaagttc     180
aattggtacg tggacggcgt ggaagtgcat aacgcaaaga ccaagcctcg ggaggaacag     240
tacgcctcga cctaccgcgt ggtgtcagtc ctgactgtgc tgcaccagga ctggctgaac     300
gggaaggagt acaagtgcaa agtgtcgaac aaggccctgc cggctccaat tgaaaagacc     360
atcagcaagg ccaagggcca gccaagggaa ccacaggtgt acaccctccc tccttcccgg     420
gacgagctga ccaaaaacca gtgtccctg acttgccttg tgaaggggtt ctacccttct     480
gacattgccg tcgaatggga atcgaacgga cagcctgaaa acaactataa gactaccccg     540
cccgtgctgg attccgacgg aagcttcttc ctgtactcca agctgaccgt ggacaagtcg     600
agatggcagc agggaaatgt gttcagctgc tccgtgatgc atgaggcgct gcacaaccac     660
tacacccaga gtcactgag cctctccccc ggaggaggtg gcagccaggg tcaagaccgc     720
catatgatcc gaatgcgaca gctcattgat attgtcgcac aattgaaaaa ttacgtgaat     780
gatcttgtac cggagttcct ccccgcaccg gaggacgttg aaacgaattg tgagtggtca     840
gcatttttctt gctttcagaa ggctcaactc aagagtgcaa acacgggtaa caacgagcgc     900
attatcaatg ttctcatcaa aaagctgaaa cgaaaaccgc ctagcaccaa cgcaggcaga     960
cgacagaagc accggctcac gtgcccaagt tgcgattctt atgagaaaaa gccaccgaaa    1020
gaattcctgc ggcggttcaa gtccctcttg cagaaaatga ttcatcagca tctctccagc    1080
aggacacacg gctccgagga ctcc                                            1104
```

<210> SEQ ID NO 201
<211> LENGTH: 233
<212> TYPE: PRT
<213> ORGANISM: Artificial sequence
<220> FEATURE:
<223> OTHER INFORMATION: Synthetic peptide Fc2

<400> SEQUENCE: 201

```
Met Asp Pro Lys Ser Cys Asp Lys Thr His Thr Cys Pro Pro Cys Pro
1               5                   10                  15
Ala Pro Glu Leu Leu Gly Gly Pro Ser Val Phe Leu Phe Pro Pro Lys
            20                  25                  30
Pro Lys Asp Thr Leu Met Ile Ser Arg Thr Pro Glu Val Thr Cys Val
        35                  40                  45
Val Val Ala Val Ser His Glu Asp Pro Glu Val Lys Phe Asn Trp Tyr
    50                  55                  60
Val Asp Gly Val Glu Val His Asn Ala Lys Thr Lys Pro Arg Glu Glu
65                  70                  75                  80
Gln Tyr Ala Ser Thr Tyr Arg Val Val Ser Val Leu Thr Val Leu His
                85                  90                  95
```

-continued

```
Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Lys Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Lys Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 202
<211> LENGTH: 699
<212> TYPE: DNA
<213> ORGANISM: Artificial sequence
<220> FEATURE:
<223> OTHER INFORMATION: Synthetic polynucleotide, encoding Fc2

<400> SEQUENCE: 202
atggacccca aaagctgcga caagactcac acttgtccgc cgtgccccgc ccccgaactg      60
ctgggtggcc cctccgtgtt cctgttcccg cctaagccta aggacaccct tatgatcagc     120
cgcacccctg aagtgacctg tgtcgtcgtg gcagtgtcac acgaggaccc ggaggtcaag     180
ttcaattggt acgtggacgg cgtggaagtg cataacgcaa agaccaagcc tcgggaggaa     240
cagtacgcct cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cggaaggagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tgaagtccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaag                            699
```